US012723040B2

(12) United States Patent
Parhi et al.

(10) Patent No.: US 12,723,040 B2
(45) Date of Patent: Sep. 1, 2026

(54) BACTERIAL EFFLUX PUMP INHIBITORS

(71) Applicants: Ajit K. Parhi, Monmouth Junction, NJ (US); Yi Yuan, Monmouth Junction, NJ (US); Yongzheng Zhang, Monmouth Junction, NJ (US); Jesus Rosado, Monmouth Junction, NJ (US); Lu Jun, Monmouth Junction, NJ (US); TAXIS PHARMACEUTICALS, INC., Monmouth Junction, NJ (US)

(72) Inventors: Ajit K. Parhi, Monmouth Junction, NJ (US); Yi Yuan, Monmouth Junction, NJ (US); Yongzheng Zhang, Monmouth Junction, NJ (US); Jesus Rosado, Monmouth Junction, NJ (US); Lu Jun, Monmouth Junction, NJ (US)

(73) Assignee: TAXIS PHARMACEUTICALS, INC., Monmouth Junction, NJ (US)

( * ) Notice: Subject to any disclaimer, the term of this patent is extended or adjusted under 35 U.S.C. 154(b) by 346 days.

(21) Appl. No.: 17/927,645

(22) PCT Filed: May 28, 2021

(86) PCT No.: PCT/US2021/034963
§ 371 (c)(1),
(2) Date: Nov. 23, 2022

(87) PCT Pub. No.: WO2021/243273
PCT Pub. Date: Dec. 2, 2021

(65) Prior Publication Data
US 2024/0239771 A1 Jul. 18, 2024

Related U.S. Application Data

(60) Provisional application No. 63/032,160, filed on May 29, 2020.

(51) Int. Cl.
*C07D 403/12* (2006.01)
*A61K 31/4045* (2006.01)
*A61P 31/04* (2006.01)
*C07D 209/42* (2006.01)

(52) U.S. Cl.
CPC ........ *C07D 403/12* (2013.01); *A61K 31/4045* (2013.01); *A61P 31/04* (2018.01); *C07D 209/42* (2013.01)

(58) Field of Classification Search
CPC . C07D 403/12; C07D 209/42; A61K 31/4045
See application file for complete search history.

(56) References Cited

U.S. PATENT DOCUMENTS

| | | | |
|---|---|---|---|
| 3,238,215 | A | 3/1966 | Zenitz |
| 3,465,080 | A | 9/1969 | Wright |
| 3,978,224 | A | 8/1976 | Steinman et al. |
| 4,910,193 | A | 3/1990 | Buchheit |
| 4,938,949 | A | 7/1990 | Borch et al. |
| 5,663,152 | A | 9/1997 | Hayano et al. |
| 5,864,039 | A | 1/1999 | Kawakita et al. |
| 6,204,279 | B1 | 3/2001 | Leger et al. |
| 6,326,391 | B1 | 12/2001 | Markham et al. |
| 6,506,339 | B1 | 1/2003 | Girardot et al. |
| 6,555,569 | B2 | 4/2003 | Sutcliffe et al. |
| 6,730,684 | B1 | 5/2004 | Miller et al. |
| 7,855,228 | B2 | 12/2010 | Gitai et al. |
| 7,893,020 | B2 | 2/2011 | Glinka et al. |
| 8,642,076 | B2 | 2/2014 | Manoharan et al. |
| 9,907,807 | B2 | 3/2018 | Evers et al. |
| 9,926,261 | B2 | 3/2018 | Lavoie et al. |
| 9,950,993 | B2 | 4/2018 | Lavoie et al. |
| 11,458,121 | B2 | 10/2022 | Lavoie et al. |
| 11,826,357 | B2 * | 11/2023 | LaVoie .................... A61P 31/04 |
| 11,993,571 | B2 | 5/2024 | Lavoie et al. |
| 2003/0199689 | A1 | 10/2003 | Nazaréet al. |
| 2004/0204378 | A1 | 10/2004 | Nelson et al. |
| 2005/0084506 | A1 | 4/2005 | Tachdjian et al. |

(Continued)

FOREIGN PATENT DOCUMENTS

| | | |
|---|---|---|
| WO | 1992004017 | 3/1992 |
| WO | 1999037667 | 7/1999 |

(Continued)

OTHER PUBLICATIONS

Pubchem Database , "N-Cyclohexyl-3-methylbenzamide", Compound Summary for CID 236099, 14 pages (create date: Mar. 26, 2005).

(Continued)

*Primary Examiner* — Kamal A Saeed
(74) *Attorney, Agent, or Firm* — Viksnins Harris Padys Malen LLP

(57) ABSTRACT

Disclosed herein are compounds of formula I: (formula I) and salts thereof. Also disclosed are compositions comprising compounds of formula I and methods using compounds of formula I.

formula I:

I

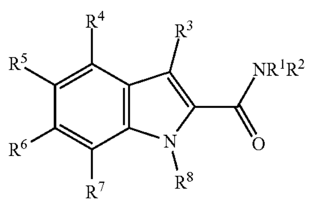

20 Claims, No Drawings

(56) References Cited

U.S. PATENT DOCUMENTS

| | | | |
|---|---|---|---|
| 2007/0155721 | A1 | 7/2007 | Hersperger et al. |
| 2008/0132457 | A1 | 6/2008 | Bostian et al. |
| 2009/0042866 | A1 | 2/2009 | Lennox et al. |
| 2009/0215828 | A1 | 8/2009 | Schunk et al. |
| 2010/0143299 | A1 | 6/2010 | Gao et al. |
| 2010/0256112 | A1 | 10/2010 | Bradbury et al. |
| 2013/0296228 | A1 | 11/2013 | Patel et al. |
| 2014/0323532 | A1 | 10/2014 | Wei et al. |
| 2015/0175539 | A1 | 6/2015 | Jiricek et al. |
| 2015/0291565 | A1 | 10/2015 | Djaballah et al. |
| 2016/0271081 | A1 | 9/2016 | Lavoie et al. |
| 2016/0271082 | A1 | 9/2016 | Lavoie et al. |
| 2018/0036283 | A1 | 2/2018 | North et al. |
| 2018/0179158 | A1 | 6/2018 | Dreier et al. |
| 2019/0031624 | A1 | 1/2019 | Lavoie et al. |
| 2019/0055188 | A1 | 2/2019 | Lavoie et al. |
| 2019/0084919 | A1 | 3/2019 | Lavoie et al. |
| 2020/0270211 | A1 | 8/2020 | Burnett et al. |

FOREIGN PATENT DOCUMENTS

| | | |
|---|---|---|
| WO | 2001026652 | 4/2001 |
| WO | 2003000657 | 3/2003 |
| WO | 2003028725 | 4/2003 |
| WO | 2005113579 | 12/2005 |
| WO | 2007053131 | 5/2007 |
| WO | 2007115231 | 10/2007 |
| WO | 2008012782 | 1/2008 |
| WO | 2009103552 | 8/2009 |
| WO | 2009110002 | 9/2009 |
| WO | 2009111547 | 9/2009 |
| WO | 2012084971 | 6/2012 |
| WO | 2014078294 | 5/2014 |
| WO | 2015164482 | 10/2015 |
| WO | 2016040505 | 3/2016 |
| WO | 2017023894 | 2/2017 |
| WO | 2018119395 | 6/2018 |
| WO | 2018165611 | 9/2018 |
| WO | 2018165612 | 9/2018 |
| WO | 2018165614 | 9/2018 |
| WO | 2018218192 | 11/2018 |
| WO | 2019005841 | 1/2019 |
| WO | 2019099402 | 5/2019 |
| WO | 2020168017 | 8/2020 |

OTHER PUBLICATIONS

Robertson, GT , et al., "A Novel Indole Compound That Inhibits Pseudomonas aeruginosa Growth by Targeting MreB is a Substrate for MexAB-OprM", Journal of Bacteriology 189 (19), 6870-6881 (2007).

Rodrigues, L , et al., "Antituberculosis drugs: reducing efflux = increasing activity", Drug Discovery Today 22(3), 592-599 (2017).

Samosorn, S , et al., "Synthesis of functionalised 2-aryl-5-nitro-1H-indoles and their activity as bacterial NorA efflux pump inhibitors", Bioorganic & Medicinal Chemistry 14, 857-865 (2006).

Shi, H, et al., "Chiral twisting in a bacterial cytoskeletal polymer affects filament size and orientation", Nature Communications 11, 1408, 1-12 (2020).

STN CAS Registry No. , Registry File No. 1026060-58-1, 1 page (2008).

STN CAS Registry No., Registry File No. 788216-67-0, 1 page (2004).

STN CAS Registry No. , Registry File No. 860554-34-3, 1 page (2005).

Tambat, R , et al., "Microbe-Derived Indole Metabolite Demonstrates Potent Multidrug Efflux Pump Inhibition in *Staphylococcus aureus*", Frontiers in Microbiology 10, 2153, 13 pages (2019).

Taylor, P , et al., "A Forward Chemical Screen Identifies Antibiotic Adjuvants in *Escherichia coli*", ACS Chem Biol 7, 1547-1555 (2012).

Tsuyuguchi, K , "Diagnosis, treatment and prevention of infectious diseases. Topics: III. Various problems in antimicrobial agents; 3. Advances in antituberculosis drugs", Journal of Japanese Society of Internal Medicine 102 (11); Nihon Naika Gakkai Zasshi. ; 102(11):2922-2927, Japanese. doi: 10.2169/naika.102.2922 (2013).

Wenzler, T, et al., "A new approach to chemotherapy: drug-induced differentiation kills African trypanosomes", Scientific Reports 6 (22451), 1-10 (2016).

Woods, R , et al., "Current Guidelines for Antibiotic Prophylaxis of Surgical Wounds", Am Fam Physician 57, 2731-2740 (1998).

Yamachika, S , et al., "Anti-Pseudomonas aeruginosa Compound, 1,2,3,4-Tetrahydro-1,3,5-triazine Derivative, Exerts Its Action by Primarily Targeting MreB", Biol Pharm Bull 35(10), 1740-1744 (2012).

Yang, X, et al., "A tobramycin vector enhances synergy and efficacy of efflux pump inhibitors against multidrug-resistant Gram-negative bacteria", J. Med. Chem 60, 3913-1932 (2017).

Yaqub, G, et al., "Conventional-Microwave Mediated Synthesis and In Vitro Antimicrobial Activity of Novel Carbazole-Efflux Pump Inhibitor Hybrid Antibacterials", Hindawi J. Chemistry, doi: 10.1155/2017/7243279, Article ID 724329, 5 pages (2017).

Alanazi, A, et al., "Synthesis, antitumor and antimicrobial activity of some new 6-methyl-3-phenyl-4(3H)-quinazolinone analogues: in silico studies", Journal of Enzyme Inhibition and Medicinal Chemistry 31(5), 721-735 (2016).

Almeida Da Silva PE , et al., "Molecular basis and mechanisms of drug resistance in *Mycobacterium tuberculosis*: classical and new drugs", J Antimicrob Chemother 66(7), 1417-1430 (2011).

Astolfi, A, et al., "Pharmacophore-Based Repositioning of Approved Drugs as Novel *Staphylococcus aureus* NorA Efflux Pump Inhibitors", J Med Chem 60(4), 1598-1604 (2017).

Awuni, E , et al., "Effect of A22 on the Conformation of Bacterial Actin MreB", International Journal of Molecular Sciences 20, 1304 (2019).

Awuni, Y , et al., "Exploring the A22-Bacterial Actin MreB Interaction through Molecular Dynamics Simulations", J. Phys. Chem, B 120(37), 4867-4874 (2016).

Barker, C , et al., "Degradation of MAC13243 and studies of the interaction of resulting thiourea compounds with the lipoprotein targeting chaperone LolA", Bioorganic & Medicinal Chemistry Letters 23, 2426-2431 (2013).

Bean, G, et al., "A22 disrupts the bacterial actin cytoskeleton by directly binding and inducing a low-affinity state in MreB", Biochemistry 48 (22), 4852-7 (2009).

Bellemin, R , et al., "New indole derivatives as ACAT inhibitors: synthesis and structure-activity relationships", Eur J Med Chem 31, 123-132 (1996).

Bohnert, J , et al., "Efflux inhibition by selective serotonin reuptake inhibitors in *Escherichia coli*", J Antimicrob Chemother 66, 2057-2060 (2011).

Bonez, P , et al., "Antibacterial, cyto and genotoxic activities of A22 compound ((S-3,4-dichlorobenzyl) Isothiourea hydrochloride)", Microbial Pathogenesis 99, 14-18 (2016).

Bonez, P , et al., "Anti-biofilm activity of A22 ((S-3,4-dichlorobenzyl) isothiourea hydrochloride) against Pseudomonas aeruginosa: Influence on biofilm formation, motility and bioadhesion", Microbial Pathogenesis 111, 6-13 (2017).

Buonerba, F , et al., "Improved Potency of Indole-Based NorA Efflux Pump Inhibitors: From Serendipity toward Rational Design and Development", J. Med. Chem DOI:10.1021/acs.jmedchem.6b01281, 8 pages (Dec. 2, 2016).

CAS Registry , No. 2110778-37-3, 1 page (2017).

CAS Registry , No. 1978423-07-2, 1 page (Aug. 24, 2016).

CAS Registry , RN 1566604-70-3, 1 page (Mar. 11, 2014).

CAS Registry , RN 1626576-60-0, 1 page (Sep. 26, 2014).

CAS Registry , RN 1788589-70-7, 1 page (Jun. 25, 2015).

CAS Registry , RN 1957085-66-3m 1 page (Jul. 21, 2016).

CAS Registry , RN 2058714-02-4, 1 page (Jan. 25, 2017).

Charles, E , "Inhibition of MreB and ftsZ proteins to minimize *E. coli* biofilms formation", doi: https://doi.org/10.1101/523167, 20 pages (2019).

(56) References Cited

OTHER PUBLICATIONS

Fleeman, R , et al., "Identification of a Novel Polyamine Scaffold With Potent Efflux Pump Inhibition Activity Toward Multi-Drug Resistant Bacterial Pathogens", Frontiers in Microbiology 9, 1301, 16 pages (2018).
Grossman, T. , et al., "The Efflux Pump Inhibitor Timcodar Improves the Potency of Antimycobacterial Agents", Antimicrobial Agents and Chemotherapy 59(3), 1534-1541 (2015).
Gupta, S , et al., "Acceleration of Tuberculosis Treatment by Adjunctive Therapy with Verapamil as an Efflux Inhibitor", American Journal of respiratory and Critical Care Medicince 188, 600-607 (2013).
Handzlik, J , et al., "Recent Advances in Multi-Drug Resistance (MDR) Efflux Pump Inhibitors of Gram-Positive Bacteria *S. aureus*", Antibiotics 2, 28-45 (2013).
Iwai, N , et al., "Novel S-Benzylisothiourea Compound That Induces Spherical Cells in Escherichia coli Probably by Acting on a Rod-shape-determining Protein(s) Other Than Penicillin-binding Protein 2", Biosci Biotechnol Biochem 66 (12), 2658-2662 (2002).
Iwai, N , et al., "Structure-Activity Relationship of S-Benzylisothiourea Derivatives to Induce Spherical Cells in *Escherichia coli*", Biosci Biotechnol Biochem 68(11), 2265-2269 (2004).
Iwai, N , et al., "Structure-Activity Relationship Study of the Bacterial Actin-Like Protein MreB Inhibitors: Effects of Substitution of Benzyl Group in S-Benzylisothiourea", Biosci. Biotechnol. Biochem 71 (1), 246-248 (2007).
Japanese Office Action , for JP Application No. 2019-549454, 7 pages, dated Sep. 29, 2022. [English Translation].
Lee, J , et al., "Roles of Indole as an Interspecies and Interkingdom Signaling Molecule", Trends in Microbiology 23 (11), 707-718 (2015).
Louw, G , et al., "A balancing act: efflux/influx in mycobacterial drug resistance", Antimicrobial Agents and Chemotherapy 53(8), 3181-3189 (2009).
Lv, X , et al., "Synthesis and antimicrobial activities of novel quinazoliln-4(3H)-one derivatives containing a 1,2,4-triazolo[3,4-b][1,3,4]thiadiazole moiety", Journal of Saudi Chemical Society 22, 101-109 (2018).
Martos, J , et al., "Antimicrobial Activity of Essential Oils and Chloroform Alone and Combinated With Cetrimide Against Enterococcus Faecalis Biofilm", European Journal of Microbiology and Immunology 3 (1), 44-48 (2013).
Merriam-Webster , "Carbocyclic", Merriam-Webster.com Dictionary, http://www.merriam-webster.com/dictionary/carbocyclic, accessed Oct. 13, 2022 (2022).
Merriam-Webster , "Cycloalkyl", Merriam-Webster.com Dictionary, https://www.merriam-webster.com/dictionary/cycloalkyl, accessed Oct. 13, 2022 (2022).
Meyer, B, et al., "Antimicrobial Preservative Use in Parenteral Products: Past and Present", Journal of Pharmaceutical Sciences 96 (12), 3155-3167 (2007).
Millson, D, et al., "Migraine pharmacotherapy with oral triptans: a rational approach to clinical management", Exp Opin Pharmacother I(3), 391-404 (2000).
Mistry, S, et al., "Discovery of a Novel Class of Negative Allosteric Modulator of the Dopamine D2 Receptor Through Fragmentation of a Bitopic Ligand", Journal of Medicinal Chemistry 58, 6819-6843 (2015).
Nagarajan, G , et al., "Effect of H4R antagonist N-(2-aminoethyl)-5-chloro-1H-indol-2-carboxamides and 5-chloro-2-(piperazin-1-ylmethyl)-1H-benzimidazole on histamine and 4-methylhistamine-induced mast cell response", Journal of Receptors and Signal Transduction 37(3), 304-313 (2017).
Noguchi, N , et al., "Anti-infectious Effect of S-Benzylisothiourea Compound A22, Which Inhibits the Actin-Like Protein, MreB, in Shigella flexneri", Biol. Pharm. Bull 31 (7), 1327-1332 (2008).
Olgen, S, et al., "Synthesis of new indole-2-carboxamide and 3-acetamide derivatives and evaluation their antioxidant properties", Journal of Enzyme Inhibition and Medicinal Chemistry 28 (1), 58-64 (2013).
Patent Cooperation Treaty , International Search Report and Written Opinion for PCT/US2021/034963, 10 pages, dated Oct. 14, 2021.
Perry, J , et al., "In vitro activity of S-(3,4-dichlorobenzyl)isothiourea hydrochloride and novel structurally related compounds against multidrug-resistant bacteria, including *Pseudomonas aeruginosa* and *Burkholderia cepacian* complex", International Journal of Antimicrobial Agents, 39 (1), 27-32 (2012).
Pubchem , "101437777", CID 101437777, 9 pages, Create Date Dec. 18, 2015.
Pubchem , "10954401", CID 10954401, 14 pages, Create Date Oct. 26, 2006.
Pubchem , "67894517", CID 67894517, 10 pages, Create Date Nov. 30, 2012.
Pubchem , "6-Chloro-2,3,4, 9-tetrahydro-1H-carbazol-1-amine", Compound Summary for CID 17743497, 15 pages (Create Date Nov. 13, 2007).
Pubchem , "LLVYCKNUAXLGFC-UHFFFAOYSA-N", Compound Summary for CID 67376113, 11 pages (create date Nov. 30, 2012).
Pubchem , "SCHEMBL9670581", Substance Record for SID 235049721, 7 pages, Feb. 13, 2015.
Pubchem Database , "Acetamide, N-cyclohexyl-2-phenyl-", Compound Summary for CID 82500, 16 pages (Create Date: Mar. 26, 2005).
Pubchem Database , "Cyclohexyloxybenzene", CID 137492, 17 pages (Create date: Mar. 27, 2005).

* cited by examiner

BACTERIAL EFFLUX PUMP INHIBITORS

PRIORITY OF INVENTION

This application claims priority from U.S. Provisional Patent Application No. 63/032,160 filed May 29, 2020, which is hereby incorporated by reference in its entirety.

BACKGROUND OF THE INVENTION

Antibiotics have been effective tools in the treatment of infectious diseases. However, bacteria have developed several different mechanisms to overcome the action of antibiotics.

These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with an antibiotic, lower the minimum inhibitory concentration of the antibiotic to inhibit bacterial cell growth. Not to be bound by theory the compounds are believed to exert this effect by the inhibition of a bacterial efflux pump(s).

Accordingly, one embodiment provides a compound of formula I:

I

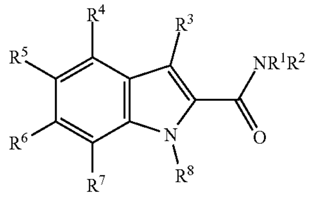

wherein:

$R^1$ is:

(a) $(C_1\text{-}C_{14})$alkyl wherein the $(C_1\text{-}C_{14})$alkyl is substituted with one or more (e.g., 1, 2, or 3) —$NR^{a1}R^{b1}$ groups, and wherein the $(C_1\text{-}C_{14})$alkyl is substituted with one or more (e.g., 1, 2, or 3) groups independently selected from the group consisting of —OH, —$OR^c$, —CN, $NO_2$, $B(OH)_2$, —$SO_2R^d$, —$CO_2R^e$, —OC(=O)—$NR^{a2}R^{b2}$, and —O(C=O)—$(C_1\text{-}C_6)$alkyl-$NR^{a2}R^{b2}$, and wherein the $(C_1\text{-}C_{14})$alkyl is optionally substituted independently with one or more (e.g., 1, 2, 3, 4, or 5) halo, $(C_1\text{-}C_4)$alkyl or $(C_3\text{-}C_7)$carbocyclyl; or (b) 4-7 membered monocyclic heterocyclyl-$(C_1\text{-}C_6)$alkyl- wherein the 4-7 membered monocyclic heterocyclyl-$(C_1\text{-}C_6)$alkyl- is substituted independently with one or more (e.g., 1, 2, or 3) $Z^1$ or $Z^2$, and wherein the 4-7 membered monocyclic heterocyclyl-$(C_1\text{-}C_6)$alkyl- is substituted independently with one or more (e.g., 1, 2, or 3) oxo, $Z^3$, or $Z^4$, and wherein the 4-7 membered monocyclic heterocyclyl-$(C_1\text{-}C_6)$alkyl- is optionally substituted independently with one or more (e.g., 1, 2, 3, 4, or 5) halo, $(C_1\text{-}C_4)$alkyl, or $(C_3\text{-}C_7)$carbocyclyl;

$R^2$ is hydrogen, $(C_1\text{-}C_4)$alkyl, or $(C_3\text{-}C_7)$carbocyclyl;

$R^3$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, OH, —X—$(C_3\text{-}C_7)$carbocyclyl, —X-aryl, —X-heterocyclyl, or —X-heteroaryl, wherein the —X—$(C_3\text{-}C_7)$carbocyclyl, —X-aryl, —X-heterocyclyl, or —X-heteroaryl is independently optionally substituted with one or more (e.g., 1, 2, 3, 4, or 5) groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^4$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, OH, X-aryl, —X-heterocyclyl, or —X-heteroaryl, wherein the —X—$(C_3\text{-}C_7)$carbocyclyl, —X-aryl, —X— heterocyclyl, or —X-heteroaryl is independently optionally substituted with one or more (e.g., 1, 2, 3, 4, or 5) groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^5$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, —OH, X-aryl, —X-heterocyclyl, or —X-heteroaryl, wherein the —X—$(C_3\text{-}C_7)$carbocyclyl, —X-aryl, —X— heterocyclyl, or —X-heteroaryl is independently optionally substituted with one or more (e.g., 1, 2, 3, 4, or 5) groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^6$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, OH, X-aryl, —X-heterocyclyl, or —X-heteroaryl, wherein the —X—$(C_3\text{-}C_7)$carbocyclyl, —X-aryl, —X— heterocyclyl, or —X-heteroaryl is independently optionally substituted with one or more (e.g., 1, 2, 3, 4, or 5) groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^7$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, OH, X-aryl, —X-heterocyclyl, or —X-heteroaryl, wherein the —X—$(C_3\text{-}C_7)$carbocyclyl, —X-aryl, —X— heterocyclyl, or —X-heteroaryl is independently optionally substituted with one or more (e.g., 1, 2, 3, 4, or 5) groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^8$ is hydrogen, ($C_1$-$C_4$)alkyl, or ($C_3$-$C_7$)carbocyclyl;

each X is independently absent, —($C_1$-$C_6$)alkyl-, —O—, —S—, —S(═O)—, —S(═O)$_2$—, or —NR—;

$Z^1$ is —$NR^{a1}R^{b1}$;

each $Z^2$ is independently —($C_1$-$C_6$)alkyl substituted with one or more (e.g., 1, 2, or 3) $Z^1$, wherein the —($C_1$-$C_6$)alkyl is optionally substituted independently with one or more (e.g., 1, 2, 3, 4, or 5) halo or ($C_3$-$C_7$)carbocyclyl;

each $Z^3$ is independently —OH, —$OR^c$, —CN, $NO_2$, —$B(OH)_2$, —$SO_2R^d$, —$CO_2R^e$, —OC(═O)—$NR^{a2}R^{b2}$ and —O(C═O)—($C_1$-$C_6$)alkyl-$NR^{a2}R^{b2}$, each $Z^4$ is independently —($C_1$-$C_6$)alkyl substituted with one or more (e.g., 1, 2, or 3) $Z^3$, wherein the —($C_1$-$C_6$)alkyl is optionally substituted independently with one or more (e.g., 1, 2, 3, 4, or 5) halo or ($C_3$-$C_7$)carbocyclyl;

each $R^{a1}$ and $R^{b1}$ is independently hydrogen, ($C_1$-$C_6$)alkyl or ($C_3$-$C_7$)carbocyclyl;

each $R^{a2}$ and $R^{b2}$ is independently hydrogen, ($C_1$-$C_6$)alkyl, or ($C_3$-$C_7$)carbocyclyl; and each $R^{a3}$ and $R^{b3}$ is independently hydrogen, ($C_1$-$C_6$)alkyl, or ($C_3$-$C_7$)carbocyclyl;

each $R^c$ is independently ($C_1$-$C_6$)alkyl, wherein the ($C_1$-$C_6$)alkyl is optionally substituted independently with one or more (e.g., 1, 2, 3, 4, or 5) —$NR^{a3}R^{b3}$ OH, ($C_1$-$C_6$)alkoxy, or ($C_1$-$C_6$)haloalkoxy;

each $R^d$ is independently ($C_1$-$C_6$)alkyl or ($C_3$-$C_7$)carbocyclyl;

each $R^e$ is independently hydrogen, ($C_1$-$C_6$)alkyl, or ($C_3$-$C_7$)carbocyclyl; and each $R^f$ is independently hydrogen, ($C_1$-$C_6$)alkyl, or ($C_3$-$C_7$)carbocyclyl;

or a salt thereof.

One embodiment provides a compound of formula I:

I

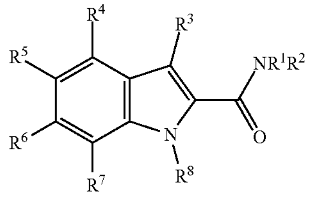

wherein:

$R^1$ is:

(a) ($C_1$-$C_{14}$)alkyl wherein the ($C_1$-$C_{14}$)alkyl is substituted with one or more (e.g., 1, 2, or 3) —$NR^{a1}R^{b1}$ groups, and wherein the ($C_1$-$C_{14}$)alkyl is substituted with one or more (e.g., 1, 2, or 3) groups independently selected from the group consisting of —OH, —$OR^c$, —CN, —$B(OH)_2$, —$SO_2R^d$, —$CO_2R$, —OC(═O)—$NR^{a2}R^{b2}$, and —O(C═O)—($C_1$-$C_6$)alkyl-$NR^{a2}R^{b2}$, and wherein the ($C_1$-$C_{14}$)alkyl is optionally substituted independently with one or more (e.g., 1, 2, 3, 4, or 5) halo, ($C_1$-$C_4$)alkyl or ($C_3$-$C_7$)carbocyclyl; or (b) 4-7 membered monocyclic heterocyclyl-($C_1$-$C_6$)alkyl- wherein the 4-7 membered monocyclic heterocyclyl-($C_1$-$C_6$)alkyl- is substituted independently with one or more (e.g., 1, 2, or 3) $Z^1$ or $Z^2$, and wherein the 4-7 membered monocyclic heterocyclyl-($C_1$-$C_6$)alkyl- is substituted independently with one or more (e.g., 1, 2, or 3) oxo, $Z^3$, or $Z^4$, and wherein the 4-7 membered monocyclic heterocyclyl-($C_1$-$C_6$)alkyl- is optionally substituted independently with one or more (e.g., 1, 2, 3, 4, or 5) halo, ($C_1$-$C_4$)alkyl, or ($C_3$-$C_7$)carbocyclyl;

$R^2$ is hydrogen, ($C_1$-$C_4$)alkyl, or ($C_3$-$C_7$)carbocyclyl;

$R^3$ is —X—($C_3$-$C_7$)carbocyclyl, —X-aryl, —X-heterocyclyl, or —X-heteroaryl wherein the —X—($C_3$-$C_7$)carbocyclyl, —X-aryl, —X-heterocyclyl, or —X-heteroaryl is independently optionally substituted with one or more (e.g., 1, 2, 3, 4, or 5) groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^7$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^8$ is hydrogen, ($C_1$-$C_4$)alkyl, or ($C_3$-$C_7$)carbocyclyl;

each X is independently absent, —($C_1$-$C_6$)alkyl-, —O—, —S—, —S(═O)—, —S(═O)$_2$—, or —$NR^f$—;

$Z^1$ is —$NR^{a1}R^{b1}$;

each $Z^2$ is independently —($C_1$-$C_6$)alkyl substituted with one or more (e.g., 1, 2, or 3) $Z^1$, wherein the —($C_1$-$C_6$)alkyl is optionally substituted independently with one or more (e.g., 1, 2, 3, 4, or 5) halo or ($C_3$-$C_7$)carbocyclyl;

each $Z^3$ is independently —OH, —$OR^c$, —CN, —$B(OH)_2$, —$SO_2R^d$, —$CO_2R^e$, —OC(═O)—$NR^{a2}R^{b2}$ and —O(C═O)—($C_1$-$C_6$)alkyl-$NR^{a2}R^{b2}$, each $Z^4$ is independently —($C_1$-$C_6$)alkyl substituted with one or more (e.g., 1, 2, or 3) $Z^3$, wherein the —($C_1$-$C_6$)alkyl is optionally substituted independently with one or more (e.g., 1, 2, 3, 4, or 5) halo or ($C_3$-$C_7$)carbocyclyl;

each $R^{a1}$ and $R^{b1}$ is independently hydrogen, ($C_1$-$C_6$)alkyl or ($C_3$-$C_7$)carbocyclyl;

each $R^{a2}$ and $R^{b2}$ is independently hydrogen, ($C_1$-$C_6$)alkyl, or ($C_3$-$C_7$)carbocyclyl; and each $R^{a3}$ and $R^{b3}$ is independently hydrogen, ($C_1$-$C_6$)alkyl, or ($C_3$-$C_7$)carbocyclyl;

each $R^c$ is independently ($C_1$-$C_6$)alkyl, wherein the ($C_1$-$C_6$)alkyl is optionally substituted independently with one or more (e.g., 1, 2, 3, 4, or 5) —$NR^{a3}R^{b3}$ OH, ($C_1$-$C_6$)alkoxy, or ($C_1$-$C_6$)haloalkoxy;

each $R^d$ is independently ($C_1$-$C_6$)alkyl or ($C_3$-$C_7$)carbocyclyl;

each $R^e$ is independently hydrogen, ($C_1$-$C_6$)alkyl, or ($C_3$-$C_7$)carbocyclyl; and each $R^f$ is independently hydrogen, ($C_1$-$C_6$)alkyl, or ($C_3$-$C_7$)carbocyclyl;

or a salt thereof.

One embodiment provides a pharmaceutical composition comprising a compound of formula I or a pharmaceutically acceptable salt thereof as described herein, and a pharmaceutically acceptable vehicle.

One embodiment provides pharmaceutical composition comprising a compound of formula I or a pharmaceutically acceptable salt thereof as described herein, one or more antibacterial agents and a pharmaceutically acceptable vehicle.

One embodiment provides a method of inhibiting a bacterial efflux pump in an animal (e.g., a mammal such as a human) comprising administering to the animal a compound of formula I or a pharmaceutically acceptable salt thereof as described herein.

One embodiment provides a method of inhibiting a bacterial efflux pump in an animal (e.g., a mammal such as a human) comprising administering to the animal in need thereof a compound of formula I or a pharmaceutically acceptable salt thereof as described herein.

One embodiment provides a method of treating or preventing a bacterial infection in an animal (e.g., a mammal such as a human) comprising co-administering to the animal a compound of formula I or a pharmaceutically acceptable salt thereof as described herein and one or more antibacterial agents.

One embodiment provides a method of treating or preventing a bacterial infection in an animal (e.g., a mammal such as a human) comprising co-administering to the animal in need thereof a compound of formula I or a pharmaceutically acceptable salt thereof as described herein and one or more antibacterial agents.

One embodiment provides a method of inhibiting a bacterial efflux pump in an animal (e.g., a mammal such as a human) with a bacterial infection comprising administering to the animal a compound of formula I or a pharmaceutically acceptable salt thereof as described herein.

One embodiment provides a method of treating or preventing a bacterial infection in an animal (e.g., a mammal such as a human) infected with bacteria comprising co-administering to the animal a compound of formula I or a pharmaceutically acceptable salt thereof as described herein and one or more antibacterial agents.

One embodiment provides a compound of formula I or a pharmaceutically acceptable salt thereof as described herein for use in medical treatment.

One embodiment provides a compound of formula I or a pharmaceutically acceptable salt thereof as described herein for the prophylactic or therapeutic inhibition of a bacterial efflux pump for the treatment of a bacterial infection.

One embodiment provides a compound of formula I or a pharmaceutically acceptable salt thereof as described herein which is used in combination with one or more antibacterial agents for the prophylactic or therapeutic treatment of a bacterial infection.

One embodiment provides the use of a compound of formula I or a pharmaceutically acceptable salt thereof as described herein for the preparation of a medicament for inhibiting a bacterial efflux pump.

One embodiment provides the use of a compound of formula I or a pharmaceutically acceptable salt thereof as described herein for the preparation of a medicament for treating a bacterial infection in an animal (e.g., a mammal such as a human).

One embodiment provides the use of a compound of formula I or a pharmaceutically acceptable salt thereof as described herein for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$ haloalkyl".

The term cycloalkyl, carbocycle, or carbocyclyl includes saturated and partially unsaturated carbocyclic ring systems. In one embodiment the cycloalkyl is a monocyclic carbocyclic ring. Such cycloalkyls include "$(C_3-C_7)$carbocyclyl" and "$(C_3-C_8)$cycloalkyl"

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; $(C_1-C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be fury, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is understood that the embodiments provided below are for compounds of formula I and all sub-formulas thereof (e.g., formulas Ia, Ib). It is to be understood the two or more embodiments may be combined.

In one embodiment $R^2$ is hydrogen.

In one embodiment $R^8$ is hydrogen.

In one embodiment a compound of formula I is a compound of formula Ia:

Ia

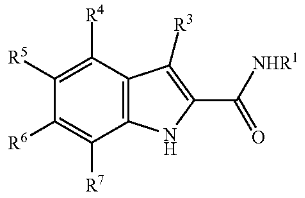

or a salt thereof.

In one embodiment $R^4$ is hydrogen or halo.

In one embodiment $R^4$ is hydrogen.

In one embodiment $R^4$ is hydrogen, halo, or aryl, wherein the aryl is optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^4$ is hydrogen, halo or phenyl, wherein the phenyl is substituted with halo.

In one embodiment $R^4$ is hydrogen or 4-fluorophenyl.

In one embodiment $R^6$ is hydrogen or halo.

In one embodiment $R^6$ is hydrogen.

In one embodiment $R^6$ is hydrogen, halo, or aryl wherein the aryl is optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy;

In one embodiment $R^6$ is hydrogen, halo, or phenyl, wherein the phenyl is substituted with halo.

In one embodiment $R^6$ is hydrogen, phenyl, or 4-fluorophenyl.

In one embodiment a compound of formula I is a compound of formula Ib:

Ib

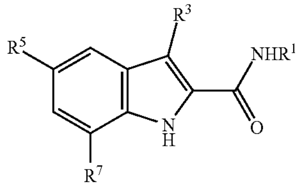

or a salt thereof.

In one embodiment $R^5$ is hydrogen or halo.

In one embodiment $R^5$ is hydrogen or fluoro.

In one embodiment $R^7$ is hydrogen or halo.

In one embodiment $R^7$ is hydrogen or fluoro.

In one embodiment $R^7$ is hydrogen, halo, or aryl wherein the aryl is optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^7$ is hydrogen, halo, or phenyl, wherein the phenyl is substituted with halo.

In one embodiment $R^7$ is hydrogen, fluoro, or 4-fluorophenyl.

In one embodiment $R^3$ is —X—$(C_3-C_7)$carbocyclyl or —X-aryl, wherein the —X—$(C_3-C_7)$carbocyclyl or —X-aryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^3$ is $(C_3-C_7)$carbocyclyl or aryl, wherein the $(C_3-C_7)$carbocyclyl or aryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$ alkoxy, and $(C_1-C_4)$haloalkoxy.

In one embodiment $R^3$ is $(C_3-C_7)$carbocyclyl or phenyl, wherein the $(C_3-C_7)$carbocyclyl or phenyl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$ alkoxy, and $(C_1-C_4)$haloalkoxy.

In one embodiment $R^3$ is $(C_4-C_7)$carbocyclyl or phenyl, wherein the $(C_3-C_7)$carbocyclyl or phenyl is independently optionally substituted with one or more groups independently selected from the group consisting of halo and —CN.

In one embodiment $R^3$ is:

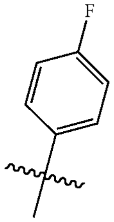 , 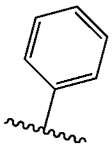 , 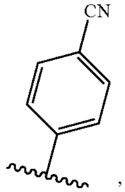 , 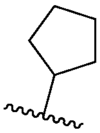 ,

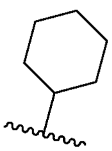 , 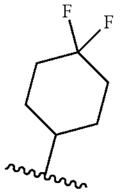 , 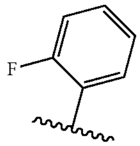 , or

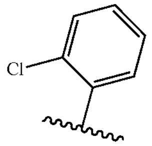 .

In one embodiment $R^3$ is hydrogen, $(C_1-C_4)$alkyl, —X—$(C_3-C_7)$carbocyclyl or —X-aryl, wherein the —X—$(C_3-C_7)$carbocyclyl or —X-aryl is independently optionally substituted with one or more groups independently selected from the group consisting of halo, —OH, $—NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^3$ is hydrogen, $(C_1-C_4)$alkyl, $(C_3-C_7)$carbocyclyl or —X-aryl, wherein the or —X-aryl is independently optionally substituted with one or more groups independently selected from the group consisting of halo, —OH, $—NO_2$, —CN, $(C_1-C_4)$alkyl, $(C_1-C_4)$haloalkyl, $(C_1-C_4)$alkoxy, and $(C_1-C_4)$haloalkoxy.

In one embodiment X is absent or —S—.

In one embodiment $R^3$ is hydrogen, $(C_1-C_4)$alkyl, $(C_3-C_7)$carbocyclyl or aryl, wherein the $(C_3-C_7)$carbocyclyl or aryl is independently optionally substituted with one or more groups independently selected from the group consisting of halo, —OH, $—NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^3$ is hydrogen, $(C_1-C_4)$alkyl, $(C_3-C_7)$carbocyclyl or phenyl, wherein the $(C_3-C_7)$carbocyclyl or phenyl is independently optionally substituted with one or more groups independently selected from the group consisting of halo, —OH, $—NO_2$, —CN, $(C_1-C_4)$alkyl, $(C_1-C_4)$haloalkyl, $(C_1-C_4)$alkoxy, and $(C_1-C_4)$haloalkoxy.

In one embodiment $R^3$ is hydrogen, $(C_1-C_4)$alkyl, $(C_4-C_7)$carbocyclyl or phenyl, wherein the $(C_3-C_7)$carbocyclyl or phenyl is independently optionally substituted with one or more groups independently selected from the group consisting of halo and —CN.

In one embodiment $R^3$ is: hydrogen, $(C_1-C_4)$alkyl,

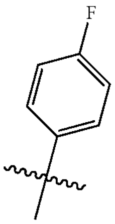 , 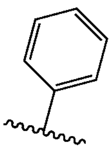 , 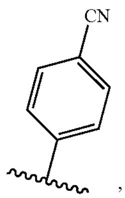 , 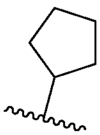 ,

-continued

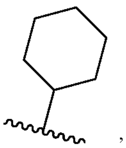 , 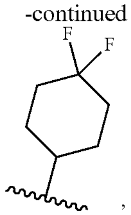 , 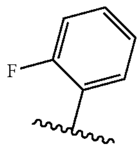 ,

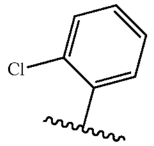 , 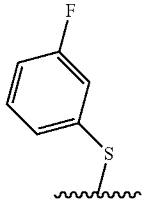 .

In one embodiment $R^1$ is:

(a) $(C_2-C_7)$alkyl wherein the $(C_2-C_7)$alkyl is substituted with one or more $—NR^{a1}R^{b1}$ groups, and wherein the $(C_2-C_7)$alkyl is substituted with one or more groups independently selected from the group consisting of —OH, $—OR^c$, —CN, $—B(OH)_2$, $—SO_2R^d$, $—CO_2R^e$, —OC(═O)—$NR^{a2}R^{b2}$, and —O(C═O)—$(C_1-C_6)$alkyl-$NR^{a2}R^{b2}$, and wherein the $(C_2-C_7)$alkyl is optionally substituted independently with one or more halo, $(C_1-C_4)$alkyl or $(C_3-C_7)$carbocyclyl;

or (b) 4-7 membered monocyclic heterocyclyl-$(C_1-C_2)$alkyl- wherein the 4-7 membered monocyclic heterocyclyl-$(C_1-C_2)$alkyl- is substituted independently with one or more $Z^1$ or $Z^2$, and wherein the 4-7 membered monocyclic heterocyclyl-$(C_1-C_1)$alkyl- is substituted independently with one or more oxo, $Z^3$, or $Z^4$, and wherein the 4-7 membered monocyclic heterocyclyl-$(C_1-C_6)$alkyl- is optionally substituted independently with one or more halo, $(C_1-C_4)$alkyl, or $(C_3-C_7)$carbocyclyl.

In one embodiment $R^1$ is:

(a) $(C_2-C_7)$alkyl wherein the $(C_2-C_7)$alkyl is substituted with one or more $—NR^{a1}R^{b1}$ groups, and wherein the $(C_2-C_7)$alkyl is substituted with one or more groups independently selected from the group consisting of —OH and $—OR^c$ and wherein the $(C_2-C_7)$alkyl is optionally substituted independently with one or more halo, $(C_1-C_4)$alkyl or $(C_3-C_7)$carbocyclyl; or (b) 4-7 membered monocyclic heterocyclyl-$(C_1-C_2)$alkyl- wherein the 4-7 membered monocyclic heterocyclyl-$(C_1-C_2)$alkyl- is substituted independently with one or more $—NR^{a1}R^{b1}$ or —$(C_1-C_6)$alkyl substituted with one or more $—NR^{a1}R^{b1}$ and wherein the 4-7 membered monocyclic heterocyclyl-$(C_1-C_2)$alkyl- is substituted independently with one or more oxo or —OH, and wherein the 4-7 membered monocyclic heterocyclyl-$(C_1-C_6)$alkyl- is optionally substituted independently with one or more halo, $(C_1-C_4)$alkyl, or $(C_3-C_7)$carbocyclyl.

In one embodiment $R^1$ is:

(a) $(C_2-C_7)$alkyl wherein the $(C_2-C_7)$alkyl is substituted with one or more $—NR^{a1}R^{b1}$ groups, and wherein the $(C_2-C_7)$alkyl is substituted with one or more groups independently selected from the group consisting of —OH and $—OR^c$; or (b) 4-7 membered monocyclic heterocyclyl-$(C_1-C_2)$alkyl- wherein the 4-7 membered monocyclic heterocyclyl-$(C_1-C_2)$alkyl- is substituted independently with one or more $—NR^{a1}R^{b1}$ or —$(C_1-C_6)$alkyl-$NR^{a1}R^{b1}$ and wherein the 4-7 membered monocyclic heterocyclyl-($C_1$-$C_2$)alkyl- is substituted independently with one or more oxo or —OH.

In one embodiment $R^1$ is:

(a) ($C_2$-$C_7$)alkyl wherein the ($C_2$-$C_7$)alkyl is substituted with one or more —$NH_2$, and wherein the ($C_2$-$C_7$)alkyl is substituted with one or more groups independently selected from the group consisting of —OH and —O($C_1$-$C_6$)alkyl-$NH_2$; or (b) 4-7 membered monocyclic heterocyclyl-($C_1$-$C_2$)alkyl- wherein the 4-7 membered monocyclic heterocyclyl-($C_1$-$C_2$)alkyl- is substituted independently with one or more —($C_1$-$C_6$)alkyl-$NH_2$, and wherein the 4-7 membered monocyclic heterocyclyl-($C_1$-$C_2$)alkyl- is substituted independently with one or more oxo or —OH.

In one embodiment $R^1$ is ($C_2$-$C_7$)alkyl wherein the ($C_2$-$C_7$)alkyl is substituted with one or more —$NR^{a1}R^{b1}$ groups, and wherein the ($C_2$-$C_7$)alkyl is substituted with one or more groups independently selected from the group consisting of —OH, —$OR^c$, —CN, —$B(OH)_2$, —$SO_2R^d$, —$CO_2R^e$, —OC(=O)—$NR^{a2}R^{b2}$, and —O(C=O)—($C_1$-$C_6$)alkyl-$NR^{a2}R^{b2}$, and wherein the ($C_2$-$C_7$)alkyl is optionally substituted independently with one or more halo, ($C_1$-$C_4$)alkyl or ($C_3$-$C_7$)carbocyclyl.

In one embodiment $R^1$ is ($C_2$-$C_7$)alkyl wherein the ($C_2$-$C_7$)alkyl is substituted with one or more —$NR^{a1}R^{b1}$ groups, and wherein the ($C_2$-$C_7$)alkyl is substituted with one or more groups independently selected from the group consisting of —OH and —$OR^c$ and wherein the ($C_2$-$C_7$)alkyl is optionally substituted independently with one or more halo, ($C_1$-$C_4$) alkyl or ($C_3$-$C_7$)carbocyclyl.

In one embodiment $R^1$ is ($C_2$-$C_7$)alkyl wherein the ($C_2$-$C_7$)alkyl is substituted with one or more —$NR^{a1}R^{b1}$ groups, and wherein the ($C_2$-$C_7$)alkyl is substituted with one or more groups independently selected from the group consisting of —OH and —$OR^c$.

In one embodiment $R^1$ is ($C_2$-$C_7$)alkyl wherein the ($C_2$-$C_7$)alkyl is substituted with one or more —$NH_2$, and wherein the ($C_2$-$C_7$)alkyl is substituted with one or more groups independently selected from the group consisting of —OH and —O($C_1$-$C_6$)alkyl-$NH_2$.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with one or more $Z^1$ or $Z^2$, and wherein the 4-7 membered monocyclic heterocyclyl-($C_1$-$C_1$)alkyl- is substituted independently with one or more oxo, $Z^3$, or $Z^4$, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with one or more —$NR^{a1}R^{b1}$ or —($C_1$-$C_6$)alkyl substituted with one or more —$NR^{a1}R^{b1}$ and wherein the 4-7 membered monocyclic heterocyclyl-($C_1$-$C_2$)alkyl- is substituted independently with one or more oxo or —OH, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with one or more —$NR^{a1}R^{b1}$ or —($C_1$-$C_6$)alkyl-$NR^{a1}R^{b1}$ and wherein the 4-7 membered monocyclic heterocyclyl-($C_1$-$C_2$)alkyl- is substituted independently with one or more oxo or —OH.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with one or more —($C_1$-$C_6$)alkyl-$NH_2$, and wherein the 4-7 membered monocyclic heterocyclyl-($C_1$-$C_2$)alkyl- is substituted independently with one or more oxo or —OH.

In one embodiment $R^1$ is:

(a) ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH, —$OR^c$, —CN, —$B(OH)_2$, —$SO_2R^d$, —$CO_2R^e$, —OC(=O)—$NR^{a2}R^{b2}$, and —O(C=O)—($C_1$-$C_6$)alkyl-$NR^{a2}R^{b2}$, and wherein the ($C_2$-$C_7$)alkyl is optionally substituted independently with one or more halo, ($C_1$-$C_4$)alkyl or ($C_3$-$C_7$)carbocyclyl;

or (b) 4-7 membered monocyclic heterocyclyl-($C_1$-$C_2$)alkyl- wherein the 4-7 membered monocyclic heterocyclyl-($C_1$-$C_2$)alkyl- is substituted independently with one or more $Z^1$ or $Z^2$, and wherein the 4-7 membered monocyclic heterocyclyl-($C_1$-$C_1$)alkyl- is substituted independently with one or more oxo, $Z^3$, or $Z^4$, and wherein the 4-7 membered monocyclic heterocyclyl-($C_1$-$C_6$) alkyl- is optionally substituted independently with one or more halo, ($C_1$-$C_4$)alkyl, or ($C_3$-$C_7$)carbocyclyl.

In one embodiment $R^1$ is:

(a) ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH and —$OR^c$ and wherein the ($C_2$-$C_7$)alkyl is optionally substituted independently with one or more halo, ($C_1$-$C_4$)alkyl or ($C_3$-$C_7$)carbocyclyl; or (b) 4-7 membered monocyclic heterocyclyl-($C_1$-$C_2$)alkyl- wherein the 4-7 membered monocyclic heterocyclyl-($C_1$-$C_2$)alkyl- is substituted independently with one or more —$NR^{a1}R^{b1}$ or —($C_1$-$C_6$)alkyl substituted with one or more —$NR^{a1}R^{b1}$ and wherein the 4-7 membered monocyclic heterocyclyl-($C_1$-$C_2$)alkyl- is substituted independently with one or more oxo or —OH, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

In one embodiment $R^1$ is:

(a) ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH and —$OR^c$; or (b) 4-7 membered monocyclic heterocyclyl-($C_1$-$C_2$)alkyl- wherein the 4-7 membered monocyclic heterocyclyl-($C_1$-$C_2$)alkyl- is substituted independently with one or more —$NR^{a1}R^{b1}$ or —($C_1$-$C_6$)alkyl-$NR^{a1}R^{b1}$ and wherein the 4-7 membered monocyclic heterocyclyl-($C_1$-$C_2$)alkyl- is substituted independently with one or more oxo or —OH.

In one embodiment $R^1$ is:

(a) ($C_2$-$C_7$)alkyl wherein the ($C_2$-$C_7$)alkyl is substituted with two or more —$NH_2$, and wherein the ($C_2$-$C_7$)alkyl is substituted with one or more groups independently selected from the group consisting of —OH and —O($C_1$-$C_6$)alkyl-$NH_2$; or (b) 4-7 membered monocyclic heterocyclyl-($C_1$-$C_2$)alkyl- wherein the 4-7 membered monocyclic heterocyclyl- ($C_1$-$C_2$)alkyl- is substituted independently with one or more —($C_1$-$C_6$)alkyl-$NH_2$, and wherein the 4-7 membered monocyclic heterocyclyl-($C_1$-$C_2$)alkyl- is substituted independently with one or more oxo or —OH.

In one embodiment $R^1$ is ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH, —$OR^c$, —CN, —$B(OH)_2$, —$SO_2R^d$, —$CO_2R^e$, —OC(═O)—$NR^{a2}R^{b2}$, and —O(C═O)—($C_1$-$C_6$)alkyl-$NR^{a2}R^{b2}$, and wherein the ($C_2$-$C_7$)alkyl is optionally substituted independently with one or more halo, ($C_1$-$C_4$)alkyl or ($C_3$-$C_7$)carbocyclyl.

In one embodiment $R^1$ is ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH and —$OR^c$ and wherein the ($C_2$-$C_7$)alkyl is optionally substituted independently with one or more halo, ($C_1$-$C_4$) alkyl or ($C_3$-$C_7$)carbocyclyl.

In one embodiment $R^1$ is ($C_2$-$C_7$)alkyl wherein the ($C_2$-$C_7$)alkyl is substituted with two or more —$NR^{a1}R^{b1}$ groups, and wherein the ($C_2$-$C_7$)alkyl is substituted with one or more groups independently selected from the group consisting of —OH and —$OR^c$.

In one embodiment $R^1$ is ($C_2$-$C_7$)alkyl wherein the ($C_2$-$C_7$)alkyl is substituted with two or more —$NH_2$, and wherein the ($C_2$-$C_7$)alkyl is substituted with one or more groups independently selected from the group consisting of —OH and —O($C_1$-$C_6$)alkyl-$NH_2$.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with two or more $Z^1$ or $Z^2$, and wherein the 4-7 membered monocyclic heterocyclyl-($C_1$-$C_1$)alkyl- is substituted independently with one or more oxo, $Z^3$, or $Z^4$, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with two or more —$NR^{a1}R^{b1}$ or —($C_1$-$C_6$)alkyl substituted with one or more —$NR^{a1}R^{b1}$ and wherein the 4-7 membered monocyclic heterocyclyl-($C_1$-$C_2$)alkyl- is substituted independently with one or more oxo or —OH, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with two or more —$NR^{a1}R^{b1}$ or —($C_1$-$C_6$)alkyl-$NR^{a1}R^{b1}$ and wherein the 4-7 membered monocyclic heterocyclyl-($C_1$-$C_2$)alkyl- is substituted independently with one or more oxo or —OH.

In one embodiment $R^1$ is 4-7 membered monocyclic heterocyclyl-($C_1$-$C_2$)alkyl- wherein the 4-7 membered monocyclic heterocyclyl-($C_1$-$C_2$)alkyl- is substituted independently with two or more —($C_1$-$C_6$)alkyl-$NH_2$, and wherein the 4-7 membered monocyclic heterocyclyl-($C_1$-$C_2$)alkyl- is substituted independently with one or more oxo or —OH.

In one embodiment $R^1$ is:

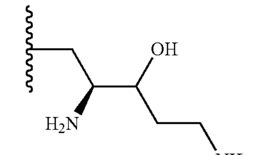 , 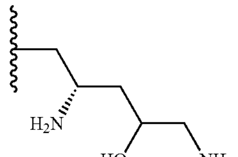 ,

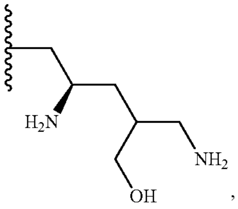 , 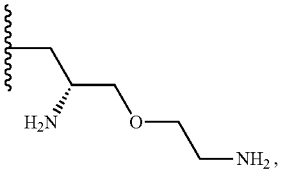 ,

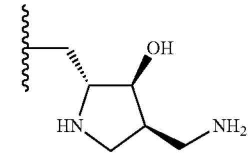 , 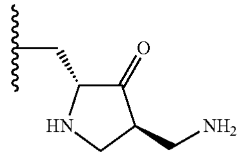 ,

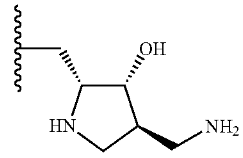 , or 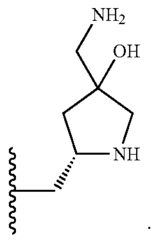 .

In one embodiment $R^1$ is:

(a) ($C_2$-$C_7$)alkyl wherein the ($C_2$-$C_7$)alkyl is substituted with one or more —$NH_2$, and wherein the ($C_2$-$C_7$)alkyl is substituted with one or more groups independently selected from the group consisting of —OH and —O($C_1$-$C_6$)alkyl, wherein the —O($C_1$-$C_6$)alkyl is substituted with one or two —$NH_2$; or (b) 4-7 membered monocyclic heterocyclyl-($C_1$-$C_2$)alkyl- wherein the 4-7 membered monocyclic heterocyclyl-($C_1$-$C_2$)alkyl- is substituted independently with one or more —($C_1$-$C_6$)alkyl-$NH_2$, and wherein the 4-7 membered monocyclic heterocyclyl-($C_1$-$C_2$)alkyl- is substituted independently with one or more oxo or —OH.

In one embodiment $R^1$ is ($C_2$-$C_7$)alkyl wherein the ($C_2$-$C_7$)alkyl is substituted with one or more —$NH_2$, and wherein the ($C_2$-$C_7$)alkyl is substituted with one or more groups independently selected from the group consisting of —OH and —O($C_1$-$C_6$)alkyl, wherein the —O($C_1$-$C_6$)alkyl is substituted with one or two —$NH_2$.

In one embodiment $R^1$ is:

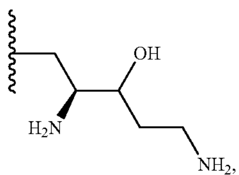 , 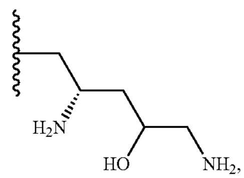 ,

-continued
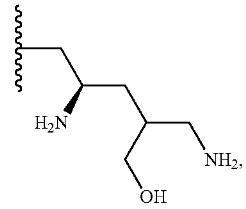,
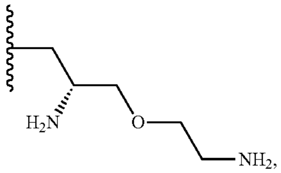,
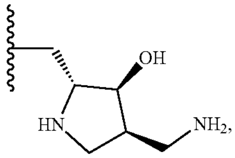,
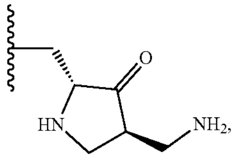,
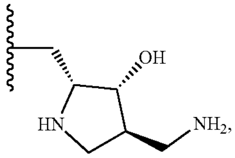,
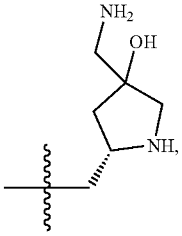,
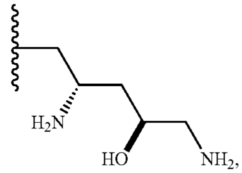,
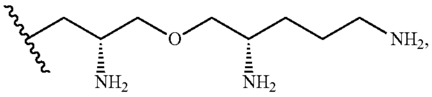,
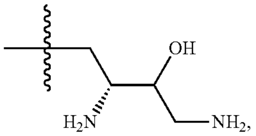, or
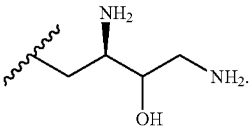.
One embodiment provides a compound that is:
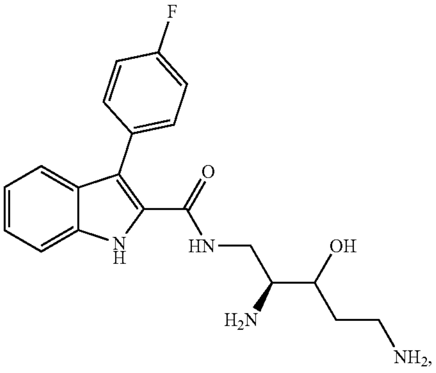,
-continued
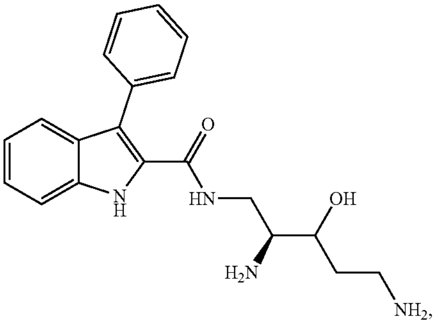,
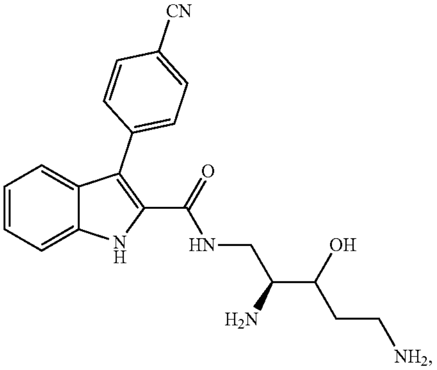,
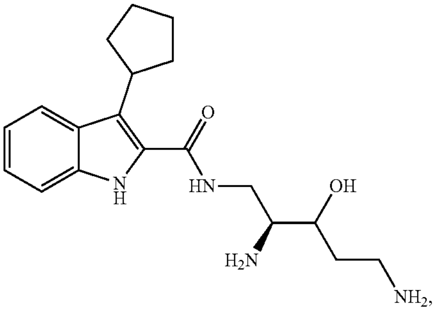,
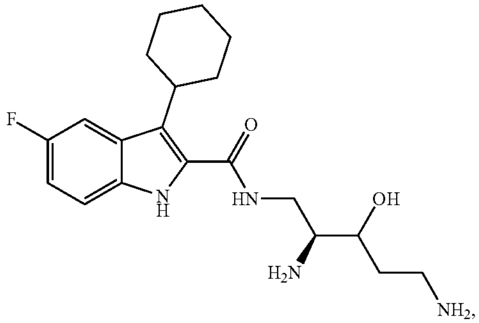,
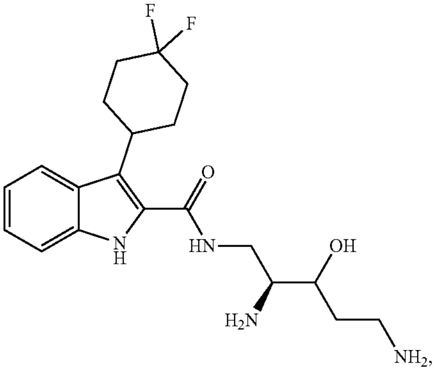, -continued
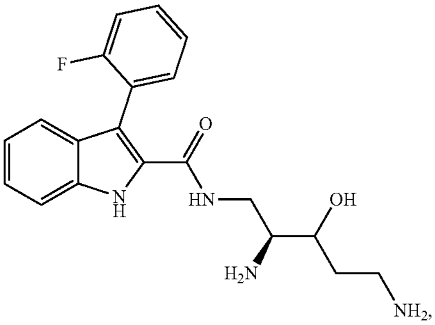
,
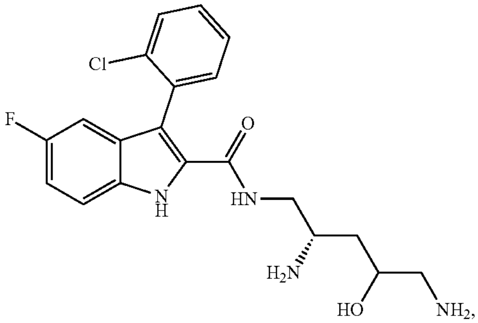
,
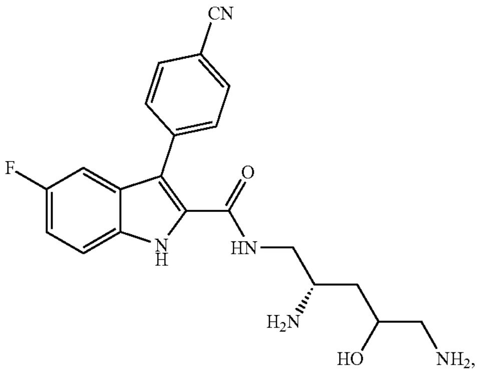
,
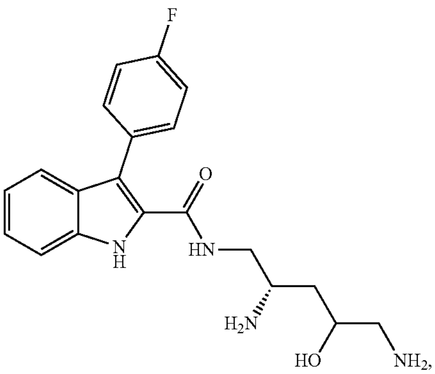
,
-continued
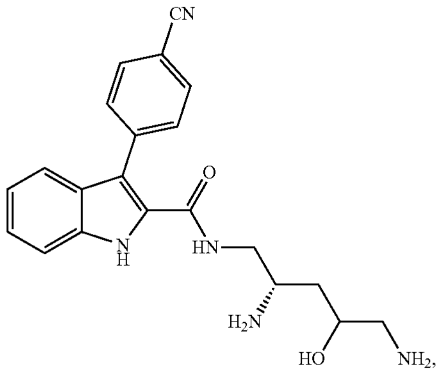
,
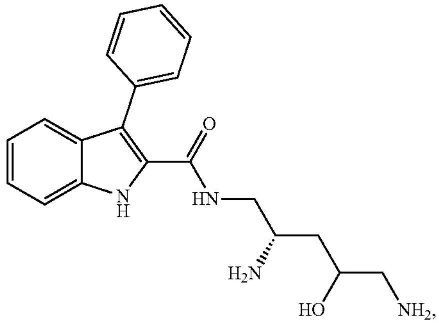
,
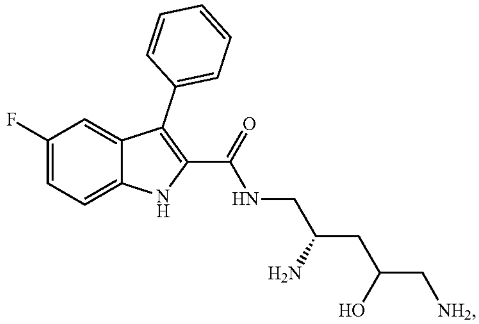
,
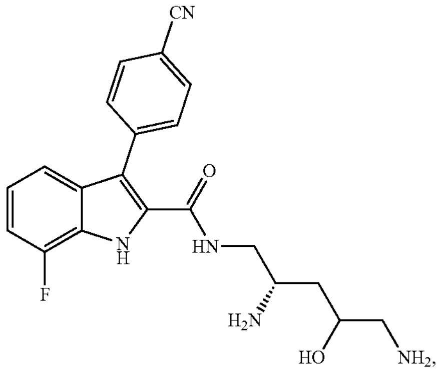
,
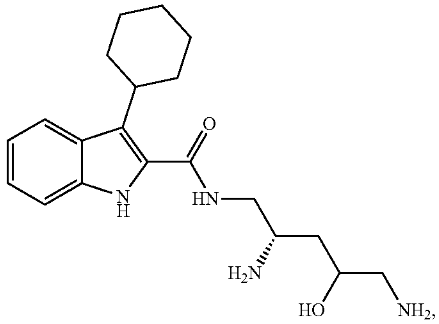
, -continued
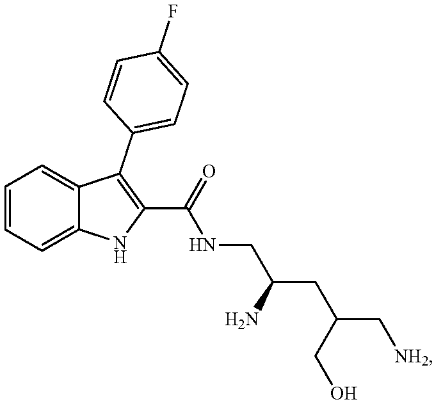
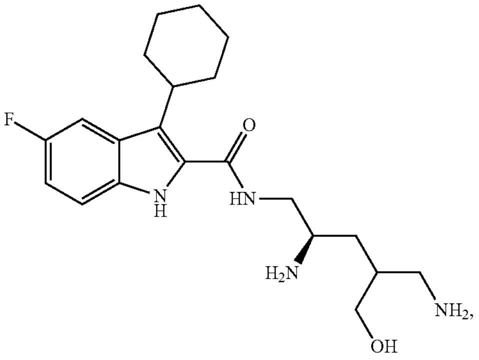
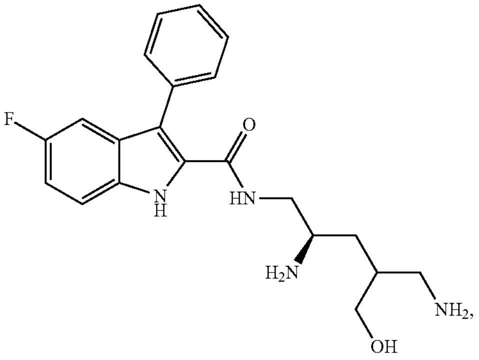
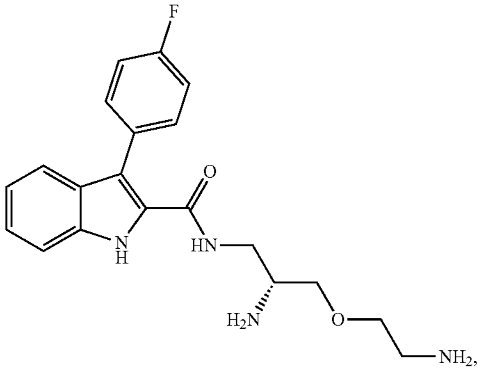
-continued
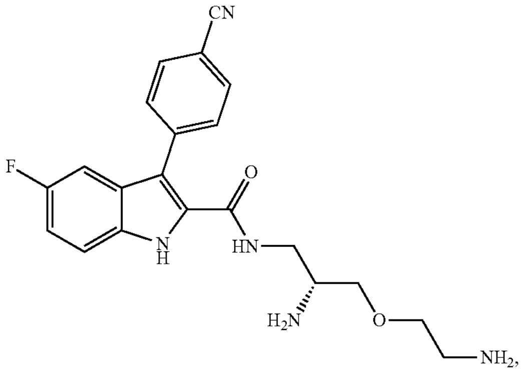
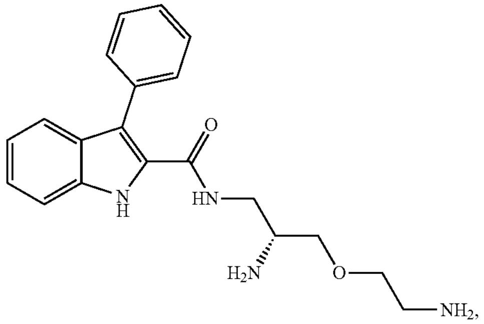
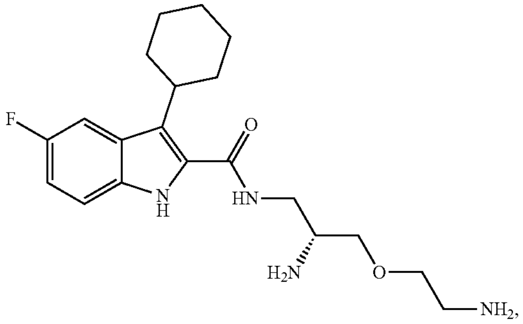
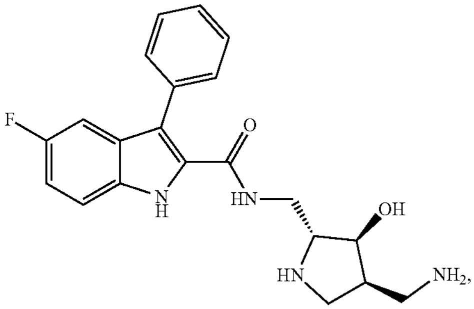
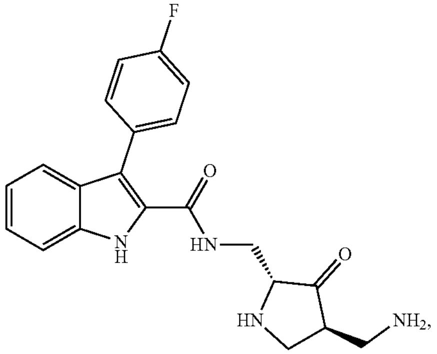

-continued
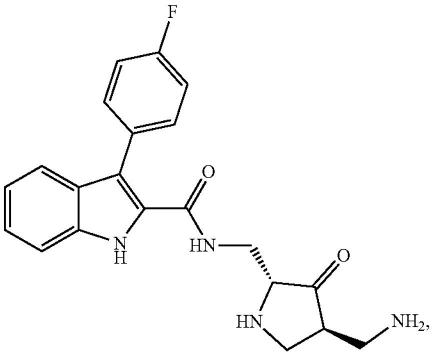
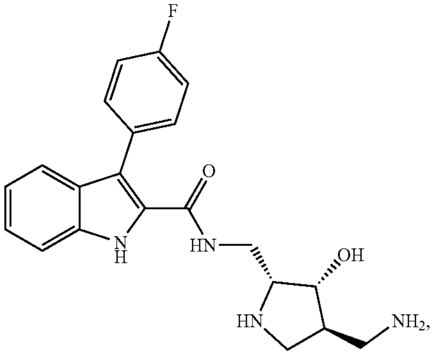
or
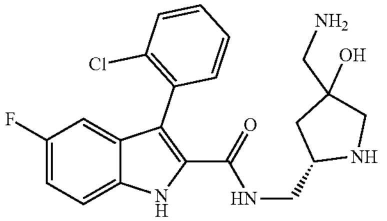
or a salt thereof.
One embodiment provides a compound that is:
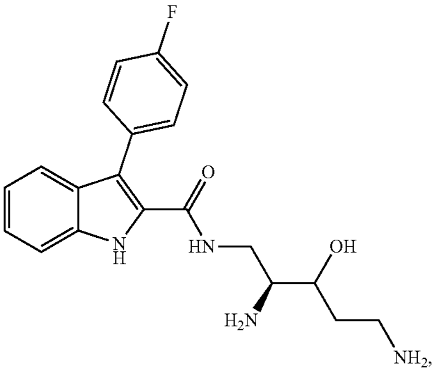
-continued
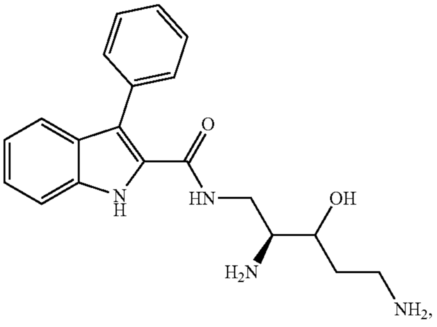
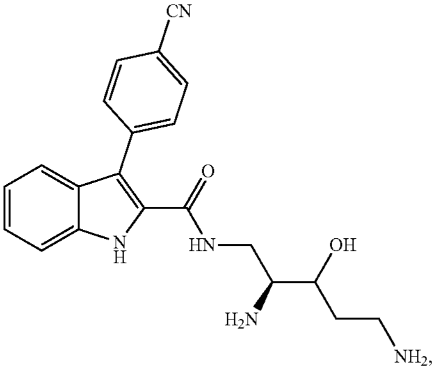
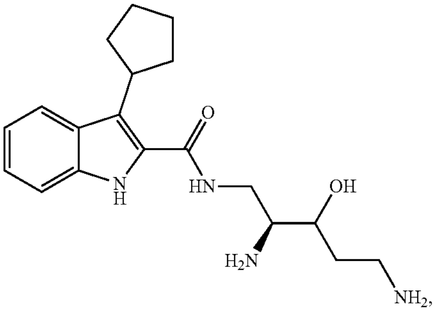
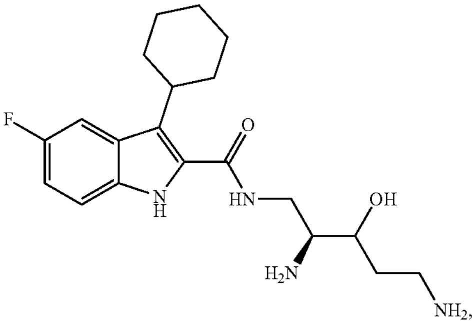
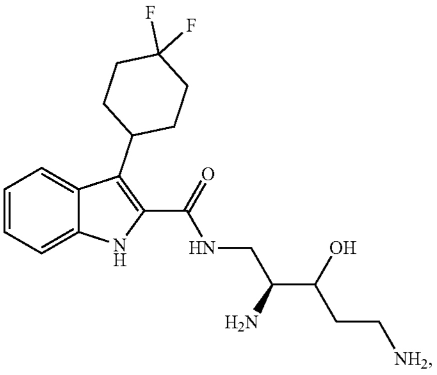

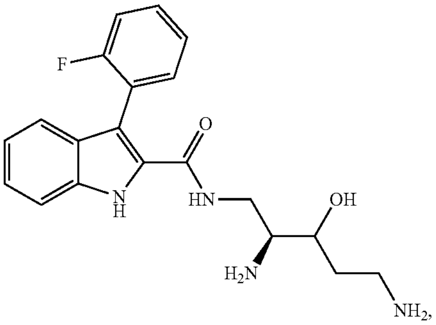
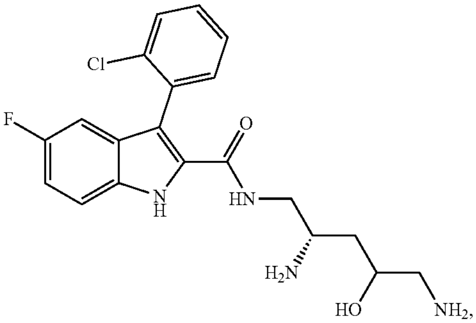
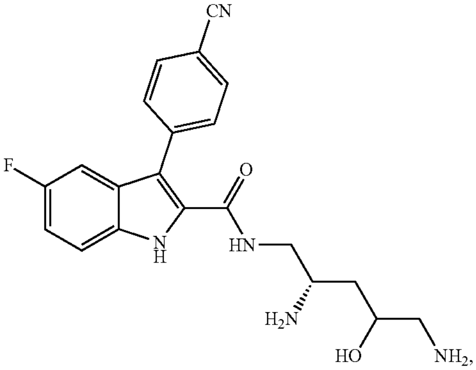
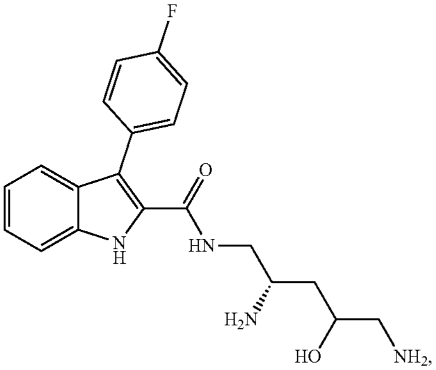
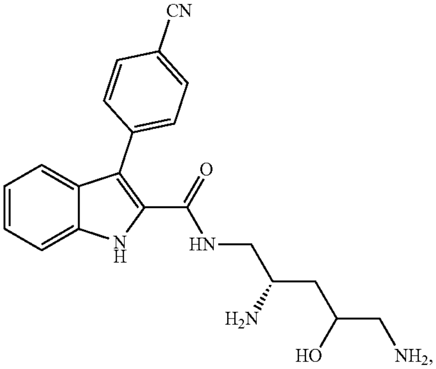
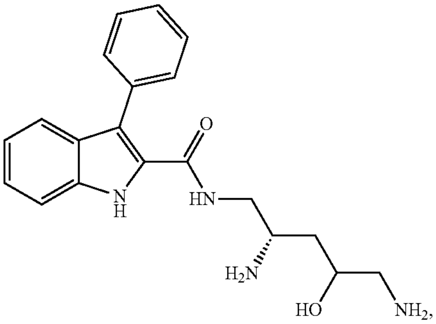
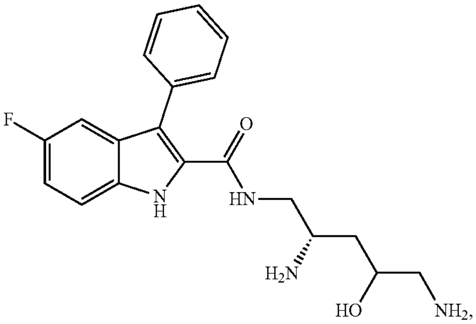
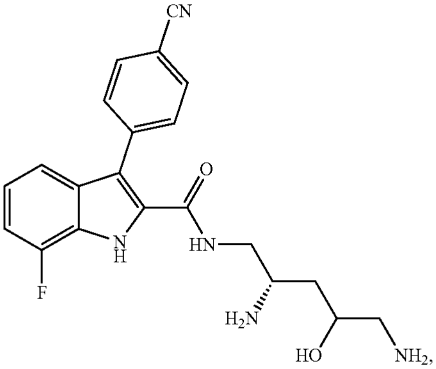
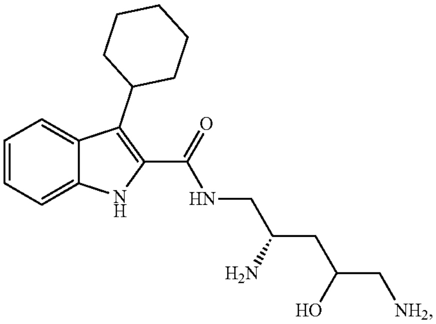

-continued
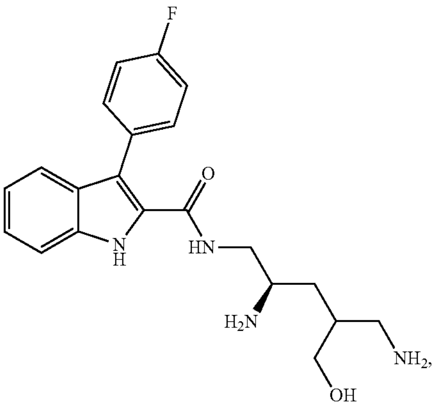
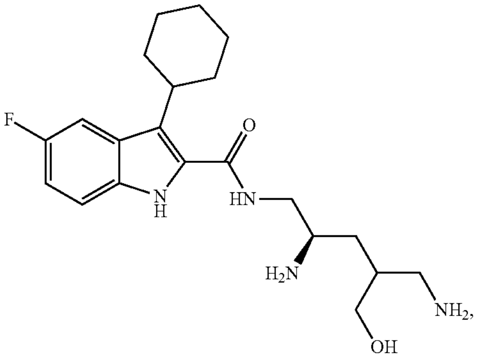
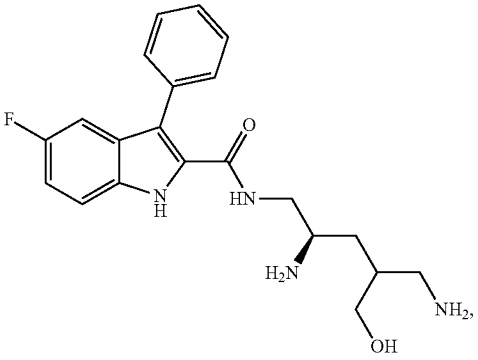
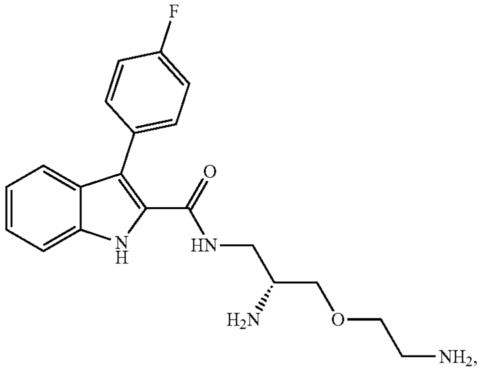
-continued
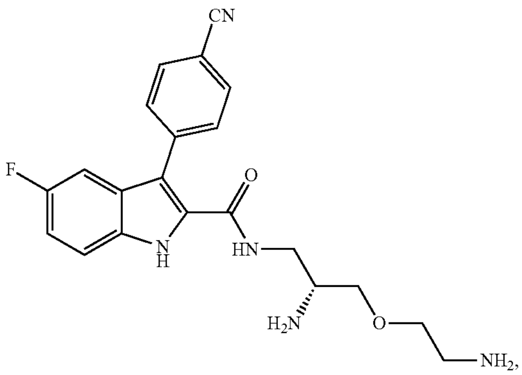
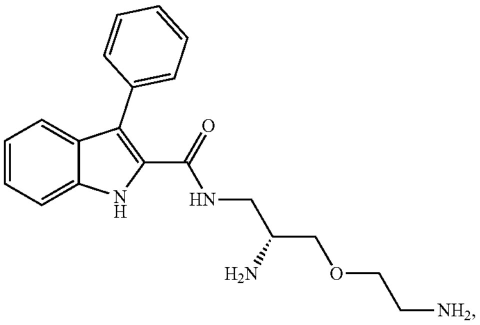
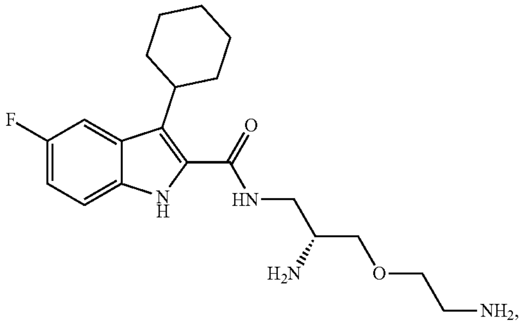
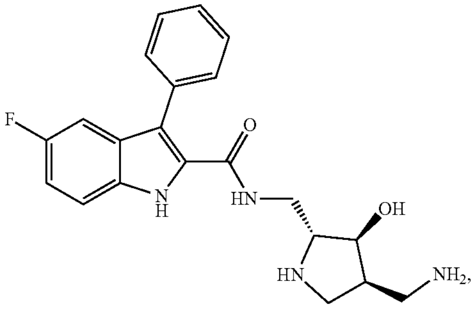
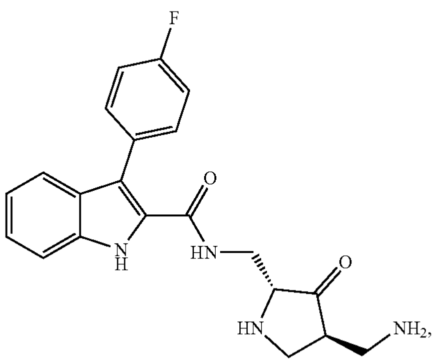

-continued
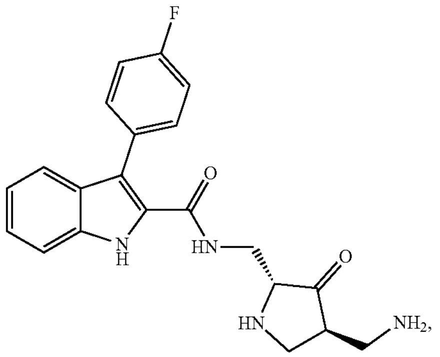
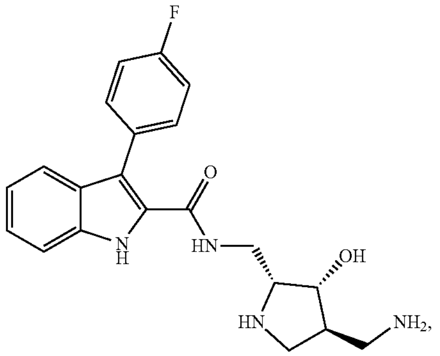
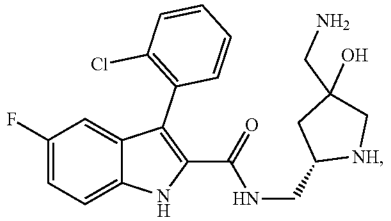
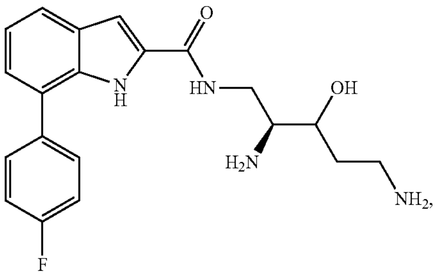
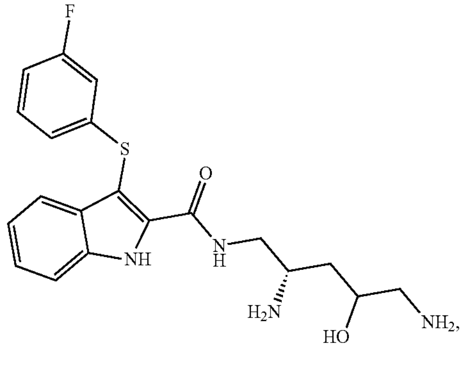
-continued
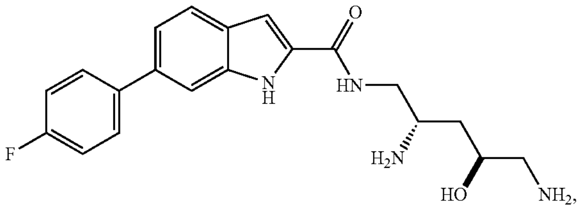
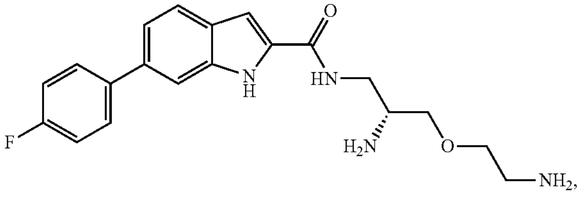
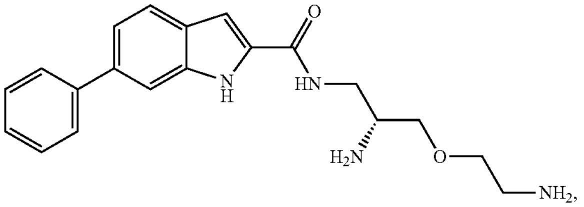
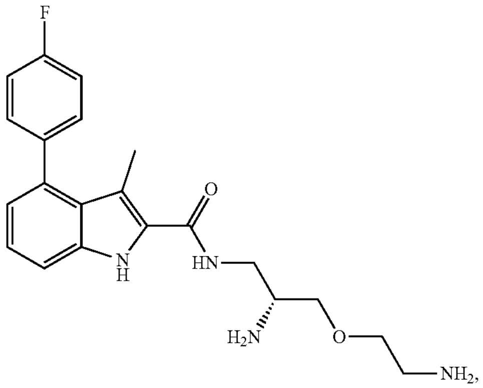
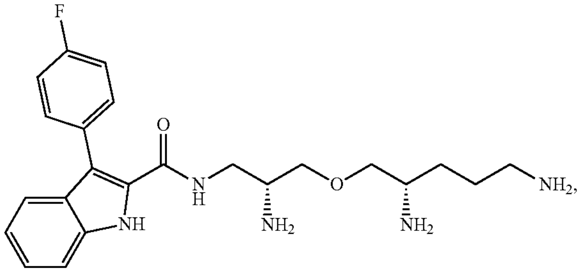
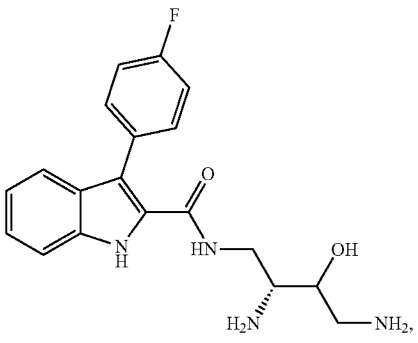
or -continued

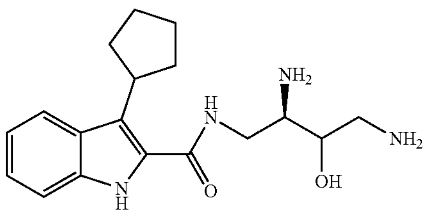

or a salt thereof.

Generally, compounds of formula I as well as synthetic intermediates that can be used for preparing compounds of formula I can be prepared as illustrated in the following general schemes. It is understood that variable groups shown below (e.g., $R^1$, $R^2$, $R^3$, $R^4$, $R^5$, $R^6$. $R^7$, $R^8$) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I. Schemes 1-5 illustrate general methods for the preparation of compounds of formula I.

Scheme 1

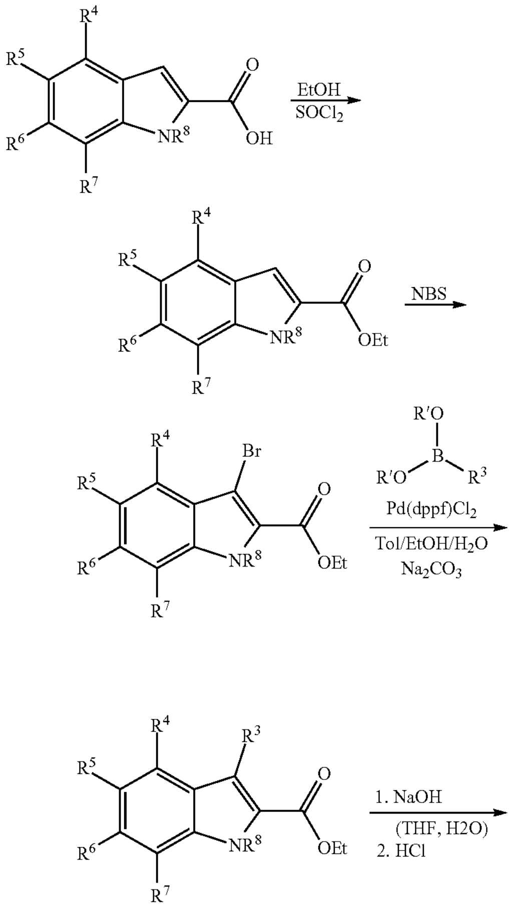

-continued

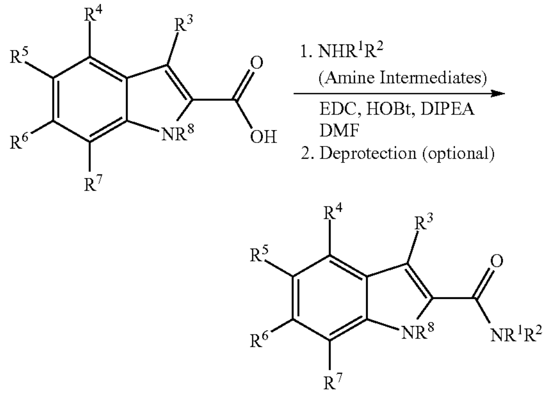

Scheme 2

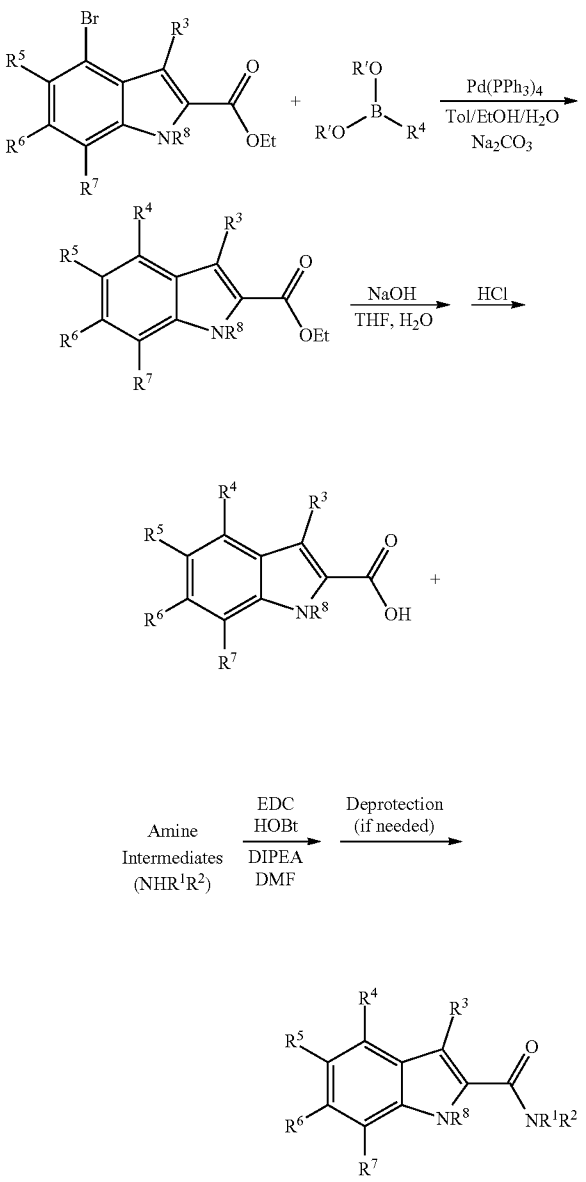

Scheme 3

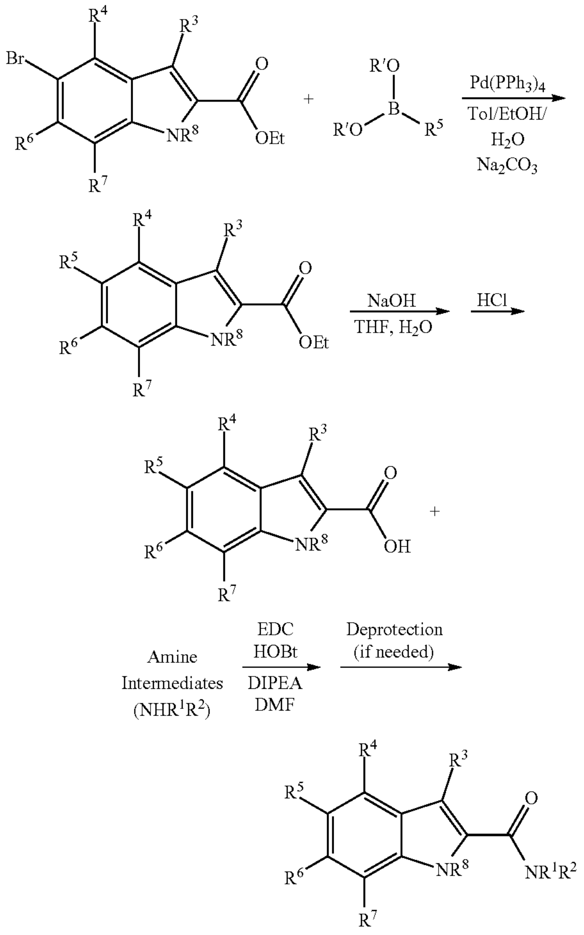

Scheme 4

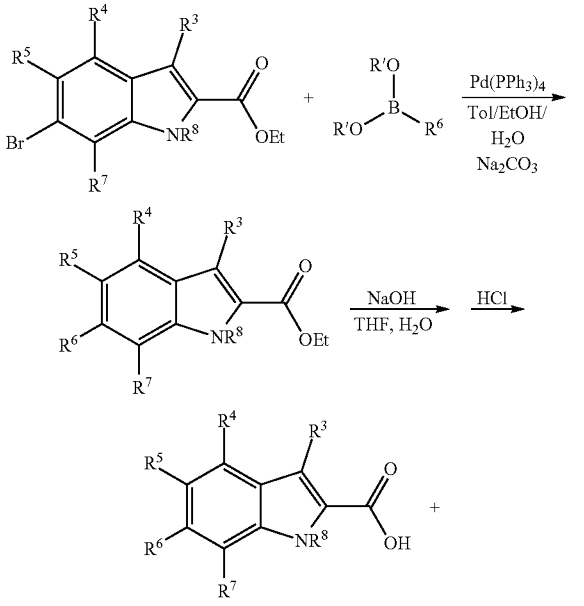

-continued

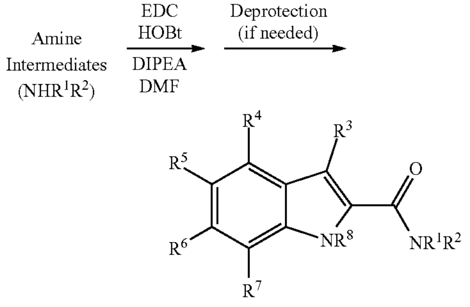

Scheme 5

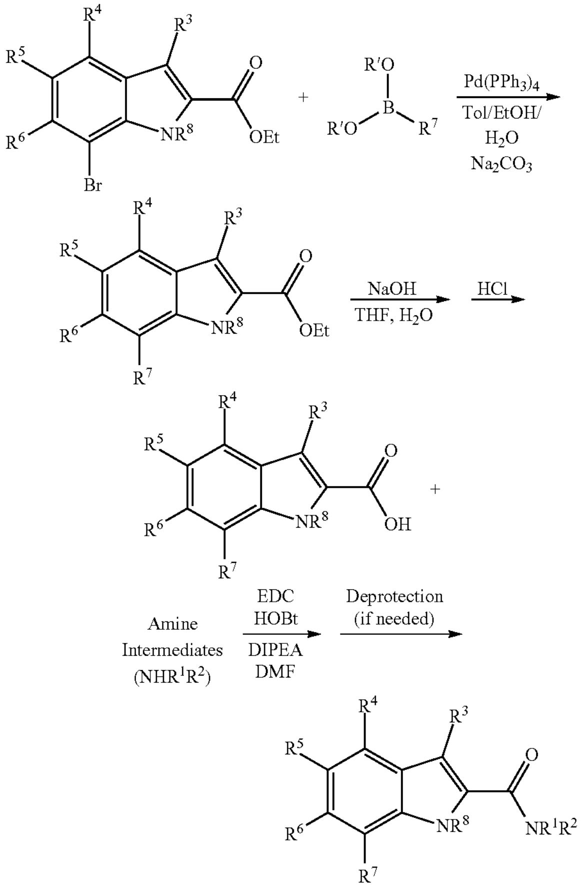

The compounds disclosed herein are bacterial efflux pump inhibitors. An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas*

*hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitides, Pantoea agglomerans, Pasteurella canes, Pasteurella haemolytica, Pasteurella multocida, Pasteurella tularensis, Porphyromonas gingivalis, Proteus mirabilis, Proteus* vu/gar/s, *Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthraces, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis.*

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin (e.g., cefepime), a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, rifamycins, macrolides, ketolides, oxazolidinones, coumermycins, and chloramphenicol.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound (or composition thereof) may be at least 51% the absolute stereoisomer depicted. In another embodiment, the compound (or composition thereof) may be at least 60% the absolute stereoisomer depicted. In another embodiment, the compound (or composition thereof) may be at least 80% the absolute stereoisomer depicted. In another embodiment, the compound (or composition thereof) may be at least 90% the absolute stereoisomer depicted. In another embodiment, the compound (or composition thereof) may be at least 95 the absolute stereoisomer depicted. In another embodiment, the compound (or composition thereof) may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, p-$CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration, the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method as described in Example 29 and as shown in Table 1.

TABLE 1

| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 1 | 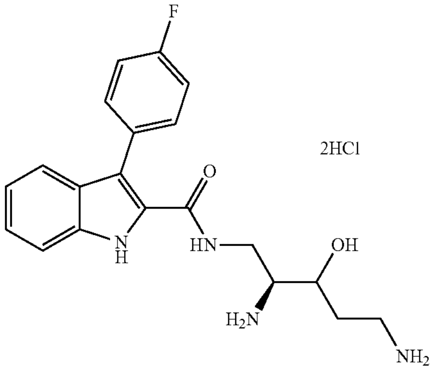 [SMILES: NCCC(O)[C@@H](N)CNC(=O)c1[nH]c2ccccc2c1-c1ccc(F)cc1] 2HCl | >100 | 0.125 (8) | 2 (1) | 2 (16) |
| 2 | 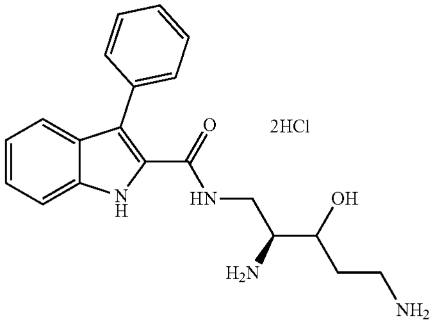 [SMILES: NCCC(O)[C@@H](N)CNC(=O)c1[nH]c2ccccc2c1-c1ccccc1] 2HCl | >100 | 0.125 (8) | 1 (2) | 2 (16) |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 2 | 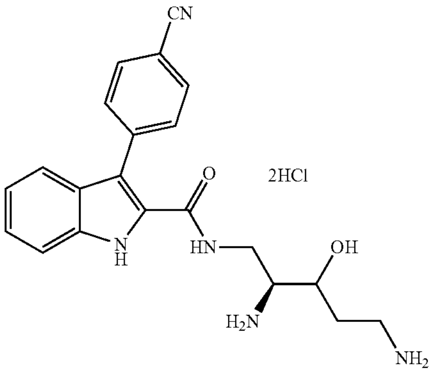 [SMILES: N#Cc1ccc(-c2c(C(=O)NC[C@H](N)C(O)CCN)[nH]c3ccccc23)cc1] 2HCl | >100 | 0.125 (8) | 2 (1) | 2 (16) |
| 4 | 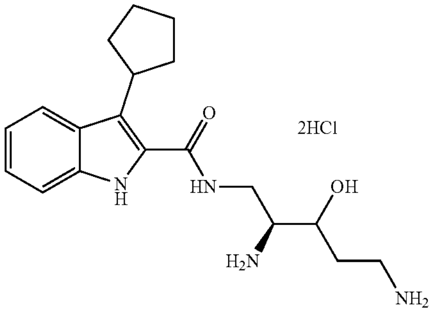 [SMILES: NCCC(O)[C@@H](N)CNC(=O)c1[nH]c2ccccc2c1C1CCCC1] 2HCl | >100 | 0.063 (32) | 0.5 (4) | 1 (32) |
| 5 | 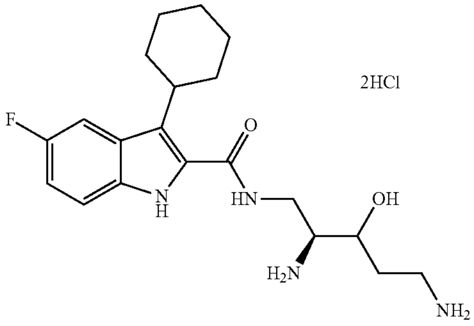 [SMILES: NCCC(O)[C@@H](N)CNC(=O)c1[nH]c2ccc(F)cc2c1C1CCCCC1] 2HCl | 50 | 0.063 (32) | 0.125 (16) | 1 (32) |
| 6 | 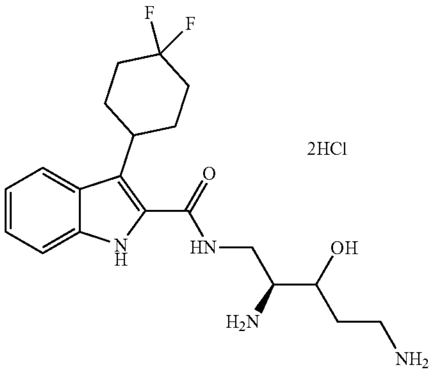 [SMILES: NCCC(O)[C@@H](N)CNC(=O)c1[nH]c2ccccc2c1C1CCC(F)(F)CC1] 2HCl | 100 | 0.016 (64) | 0.5 (4) | 2 (16) |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 7 | 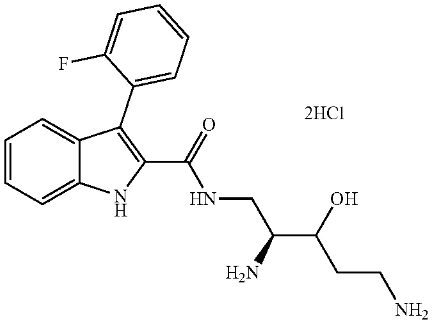 [SMILES: NCCC(O)[C@@H](N)CNC(=O)c1[nH]c2ccccc2c1-c1ccccc1F] 2HCl | >100 | 0.5 (2) | 2 (1) | 8 (4) |
| 8 | 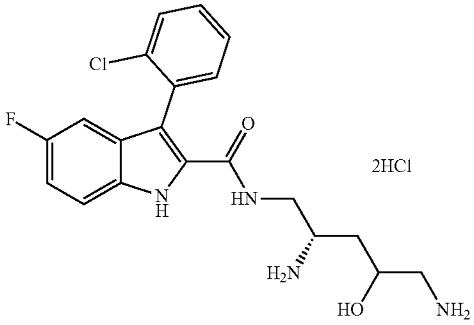 [SMILES: NCC(O)C[C@H](N)CNC(=O)c1[nH]c2ccc(F)cc2c1-c1ccccc1Cl] 2HCl | >100 | 0.063 (16) | 1 (2) | 2 (16) |
| 9 | 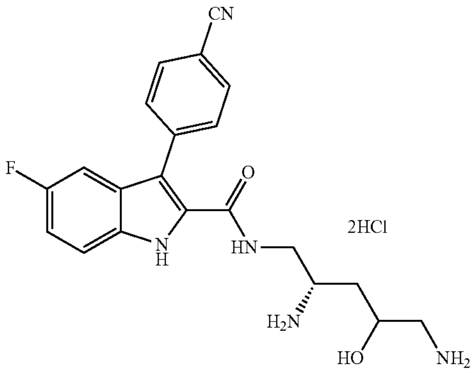 [SMILES: N#Cc1ccc(-c2c(C(=O)NC[C@@H](N)CC(O)CN)[nH]c3ccc(F)cc23)cc1] 2HCl | >100 | 0.031 (32) | 1 (2) | 1 (32) |
| 10 | 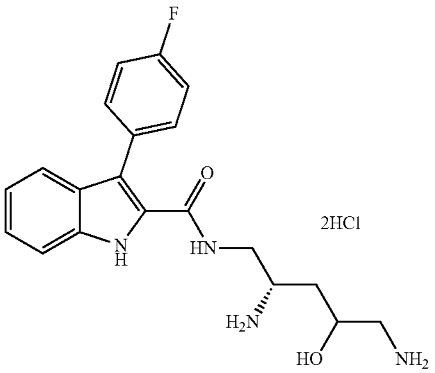 [SMILES: NCC(O)C[C@H](N)CNC(=O)c1[nH]c2ccccc2c1-c1ccc(F)cc1] 2HCl | 100 | 0.063 (16) | 0.5 (4) | 1 (32) |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 11 | 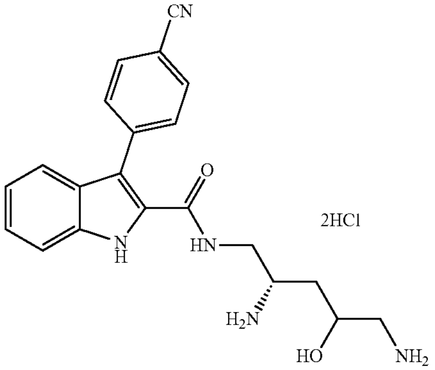 [SMILES: N#Cc1ccc(-c2c(C(=O)NC[C@@H](N)CC(O)CN)[nH]c3ccccc23)cc1] 2HCl | >100 | 0.063 (16) | 2 (1) | 2 (16) |
| 12 | 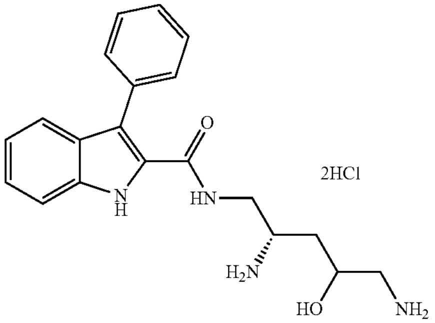 [SMILES: NCC(O)C[C@H](N)CNC(=O)c1[nH]c2ccccc2c1-c1ccccc1] 2HCl | >100 | 0.063 (16) | 1 (2) | 1 (32) |
| 13 | 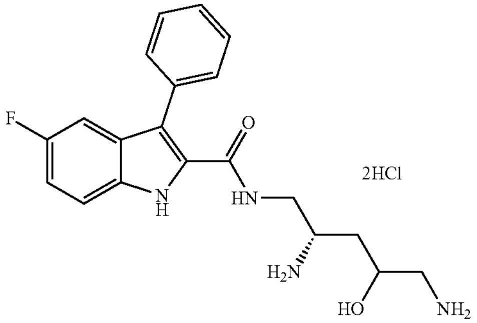 [SMILES: NCC(O)C[C@H](N)CNC(=O)c1[nH]c2ccc(F)cc2c1-c1ccccc1] 2HCl | >100 | 0.031 (32) | 1 (2) | 1 (32) |
| 14 | 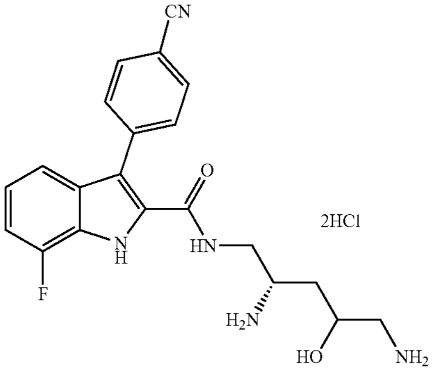 [SMILES: N#Cc1ccc(-c2c(C(=O)NC[C@@H](N)CC(O)CN)[nH]c3c(F)cccc23)cc1] 2HCl | >100 | 0.031 (32) | 2 (1) | 2 (16) |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 15 | 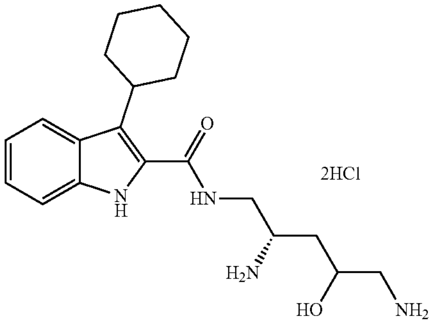 [SMILES: NCC(O)C[C@H](N)CNC(=O)c1[nH]c2ccccc2c1C1CCCCC1] | 50 | 0.031 (32) | 0.5 (4) | 1 (32) |
| 16 | 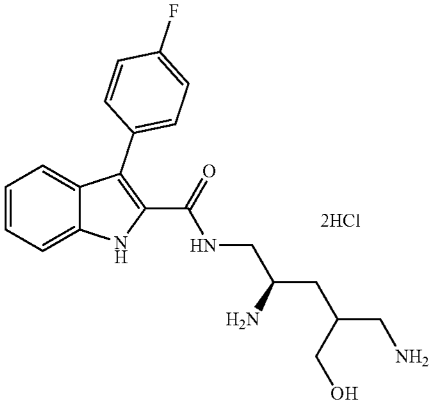 [SMILES: NCC(CO)C[C@@H](N)CNC(=O)c1[nH]c2ccccc2c1-c1ccc(F)cc1] | >100 | 0.063 (16) | 1 (2) | 1 (32) |
| 17 | 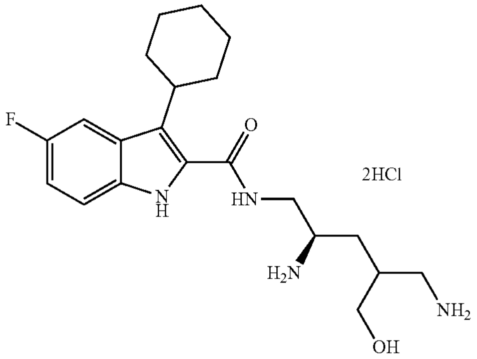 [SMILES: NCC(CO)C[C@@H](N)CNC(=O)c1[nH]c2ccc(F)cc2c1C1CCCCC1] | 25 | 0.063 (32) | 0.25 (8) | 1 (32) |
| 18 | 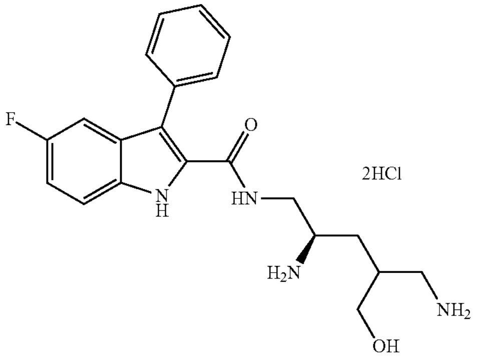 [SMILES: NCC(CO)C[C@@H](N)CNC(=O)c1[nH]c2ccc(F)cc2c1-c1ccccc1] | >100 | 0.063 (32) | ND | ND |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 19 | 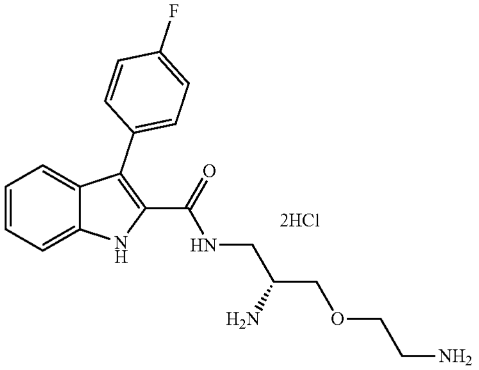 [SMILES: NCCOC[C@H](N)CNC(=O)c1[nH]c2ccccc2c1-c1ccc(F)cc1] 2HCl | >100 | 0.063 (16) | 1 (2) | 2 (16) |
| 20 | 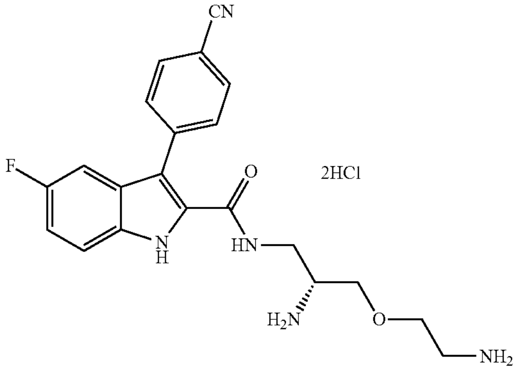 [SMILES: N#Cc1ccc(-c2c(C(=O)NC[C@@H](N)COCCN)[nH]c3ccc(F)cc23)cc1] 2HCl | >100 | 0.063 (16) | 1 (2) | 2 (16) |
| 21 | 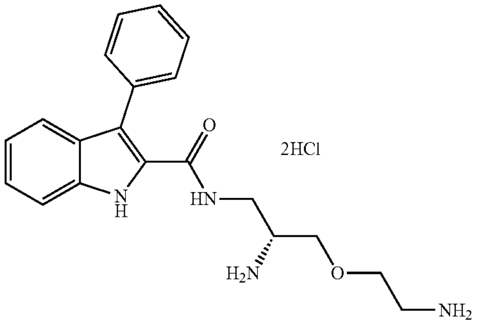 [SMILES: NCCOC[C@H](N)CNC(=O)c1[nH]c2ccccc2c1-c1ccccc1] 2HCl | >100 | 0.25 (4) | 2 (1) | 2 (16) |
| 22 | 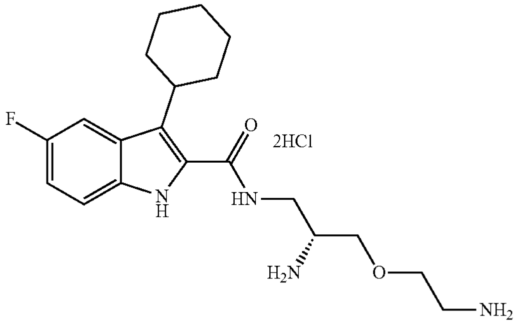 [SMILES: NCCOC[C@H](N)CNC(=O)c1[nH]c2ccc(F)cc2c1C1CCCCC1] 2HCl | 25 | 0.031 (32) | ND | ND |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 23 | 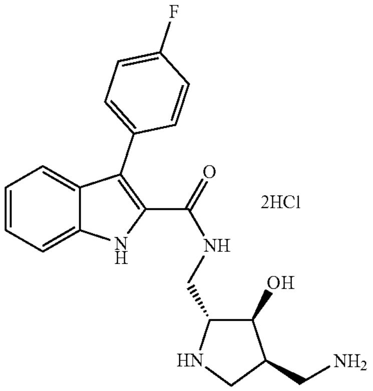 [SMILES: NC[C@H]1CN[C@H](CNC(=O)c2[nH]c3ccccc3c2-c2ccc(F)cc2)[C@H]1O] | >100 | 0.125 (8) | 1 (2) | 2 (16) |
| 24 | 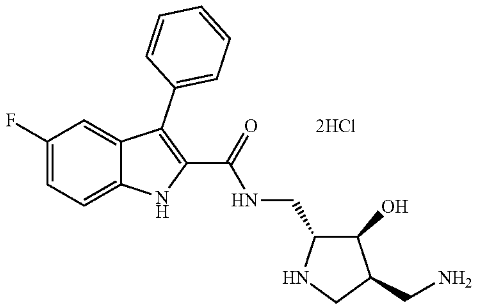 [SMILES: NC[C@H]1CN[C@H](CNC(=O)c2[nH]c3ccc(F)cc3c2-c2ccccc2)[C@H]1O] | >100 | 0.063 (16) | ND | ND |
| 25 | 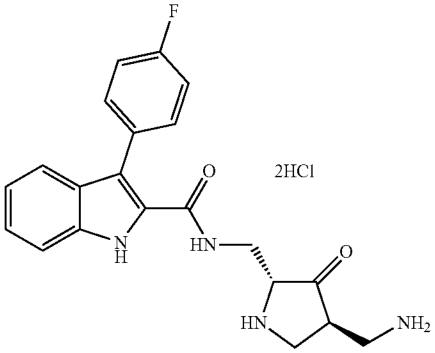 [SMILES: NC[C@H]1CN[C@H](CNC(=O)c2[nH]c3ccccc3c2-c2ccc(F)cc2)C1=O] | >100 | 1 (1) | 2 (1) | 32 (1) |
| 26 | 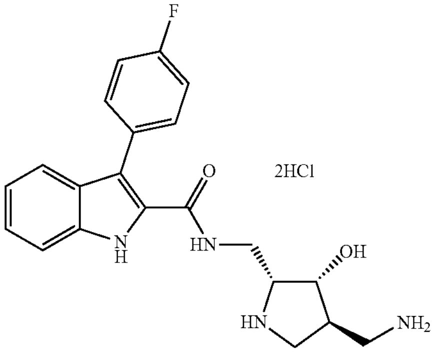 [SMILES: NC[C@H]1CN[C@H](CNC(=O)c2[nH]c3ccccc3c2-c2ccc(F)cc2)[C@@H]1O] | >100 | 0.063 (16) | 1 (2) | 1 (32) |

TABLE 1-continued
| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 27 | 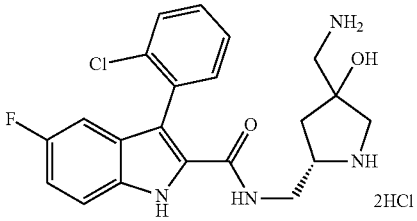 [SMILES: NCC1(O)CN[C@H](CNC(=O)c2[nH]c3ccc(F)cc3c2-c2ccccc2Cl)C1] 2HCl | >100 | 1 (1) | ND | ND |
| 28 | 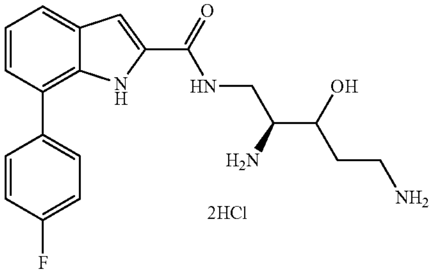 [SMILES: NCCC(O)[C@@H](N)CNC(=O)c1cc2cccc(-c3ccc(F)cc3)c2[nH]1] 2HCl | 50 | 0.063 (16) | NA | NA |
| 29 | 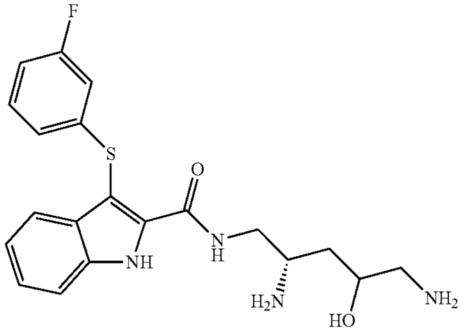 [SMILES: NCC(O)C[C@H](N)CNC(=O)c1[nH]c2ccccc2c1Sc1cccc(F)c1] | 200 | 0.031 (32) | 1 (2) | 0.5 (64) |
| 30 | 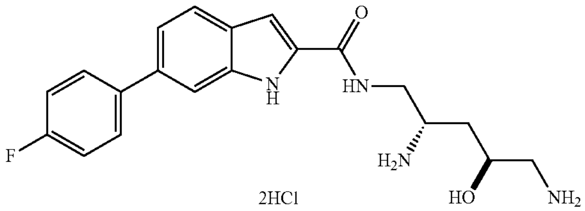 [SMILES: NC[C@@H](O)C[C@H](N)CNC(=O)c1cc2ccc(-c3ccc(F)cc3)cc2[nH]1] 2HCl | 50 | 0.063 (16) | NA | NA |
| 31 | 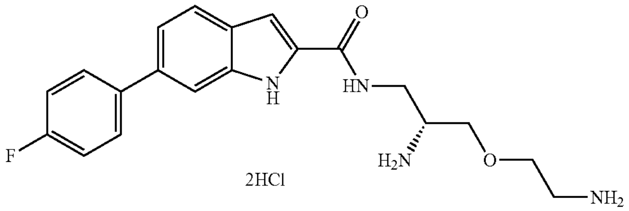 [SMILES: NCCOC[C@H](N)CNC(=O)c1cc2ccc(-c3ccc(F)cc3)cc2[nH]1] 2HCl | >200 | 0.125 (8) | 0.5 (4) | 1 (32) |
| 32 | 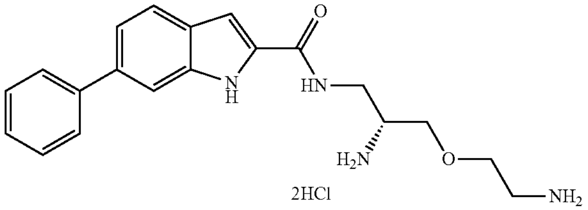 [SMILES: NCCOC[C@H](N)CNC(=O)c1cc2ccc(-c3ccccc3)cc2[nH]1] 2HCl | >200 | 0.25 (4) | NA | NA |

TABLE 1-continued

| Example | Structure | Intrinsic MIC of Compound (μg/mL) | Enhanced Antibiotic's Activity MIC (μg/mL) (fold increase) with compound at 6.25 μg/mL Levofloxacin[1] | Ceftazidime[2] | Doxycycline[3] |
|---|---|---|---|---|---|
| 33 | 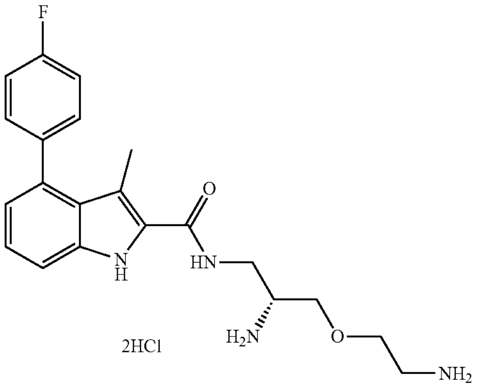 [SMILES: Cc1c(C(=O)NC[C@@H](N)COCCN)[nH]c2cccc(-c3ccc(F)cc3)c12] 2HCl | 100 | 0.032 (32) | NA | 0.25 (128) |
| 34 | 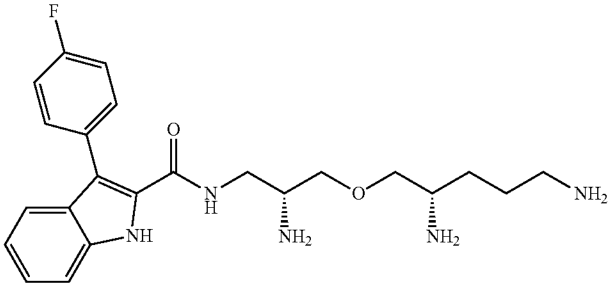 3HCl | >200 | 0.125 (8) | NA | 1 (32) |
| 35 | 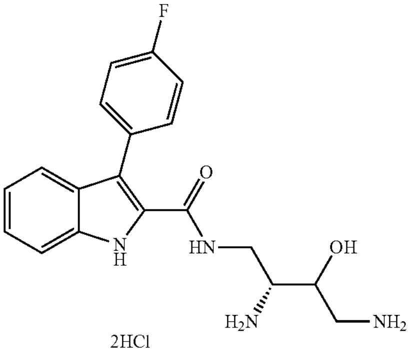 [SMILES: NCC(O)[C@H](N)CNC(=O)c1[nH]c2ccccc2c1-c1ccc(F)cc1] 2HCl | 200 | 0.25 (4) | NA | NA |
| 36 | 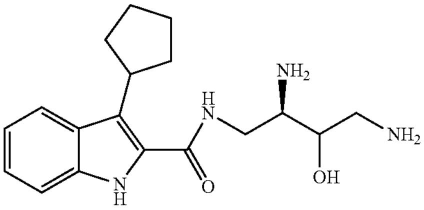 2HCl | 100 | 0.125 (8) | 1 (2) | 1 (32) |

[1]These data were generated using Levofloxacin as the antibiotic and the various EPIs against Pseudomonas aeruginosa ATCC 27853.

[2]These data were generated using Ceftazidime as the antibiotic and the various EPIs against Pseudomonas aeruginosa ATCC 27853.

[3]These data were generated using Doxycycline as the antibiotic and the various EPIs against Pseudomonas aeruginosa ATCC 27853.

The invention will now be illustrated by the following non-limiting examples.

Preparation of Amine Intermediates A to I

Table 2 shows amine intermediates that were used to prepare compounds described herein.

TABLE 2

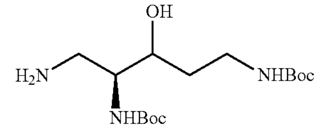 [SMILES: CC(C)(C)OC(=O)NCCC(O)[C@H](CN)NC(=O)OC(C)(C)C]

Intermediate A

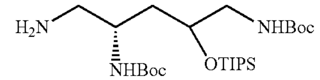

Intermediate B

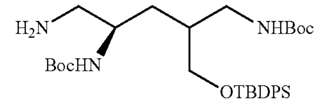

Intermediate C

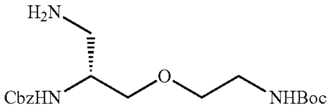 [SMILES: CC(C)(C)OC(=O)NCCOC[C@@H](CN)NC(=O)OCc1ccccc1]

Intermediate D

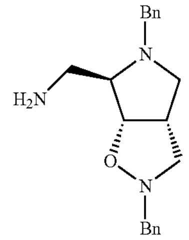 [SMILES: NC[C@@H]1[C@H]2ON(Cc3ccccc3)C[C@H]2CN1Cc1ccccc1]

Intermediate E

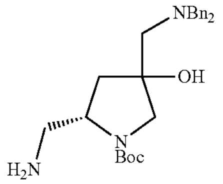

Intermediate F

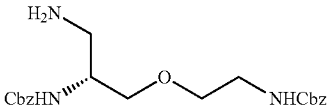 [SMILES: NC[C@H](COCCNC(=O)OCc1ccccc1)NC(=O)OCc1ccccc1]

Intermediate G

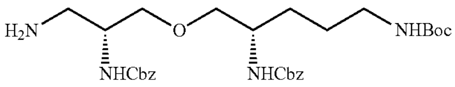 [SMILES: CC(C)(C)OC(=O)NCCC[C@@H](COC[C@@H](CN)NC(=O)OCc1ccccc1)NC(=O)OCc1ccccc1]

Intermediate H

TABLE 2-continued

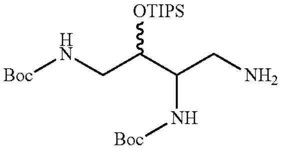

Intermediate I

Preparation of amine Intermediate A (di-tert-butyl ((4S)-5-amino-3-hydroxypentane-1,4-diyl)dicarbamate)

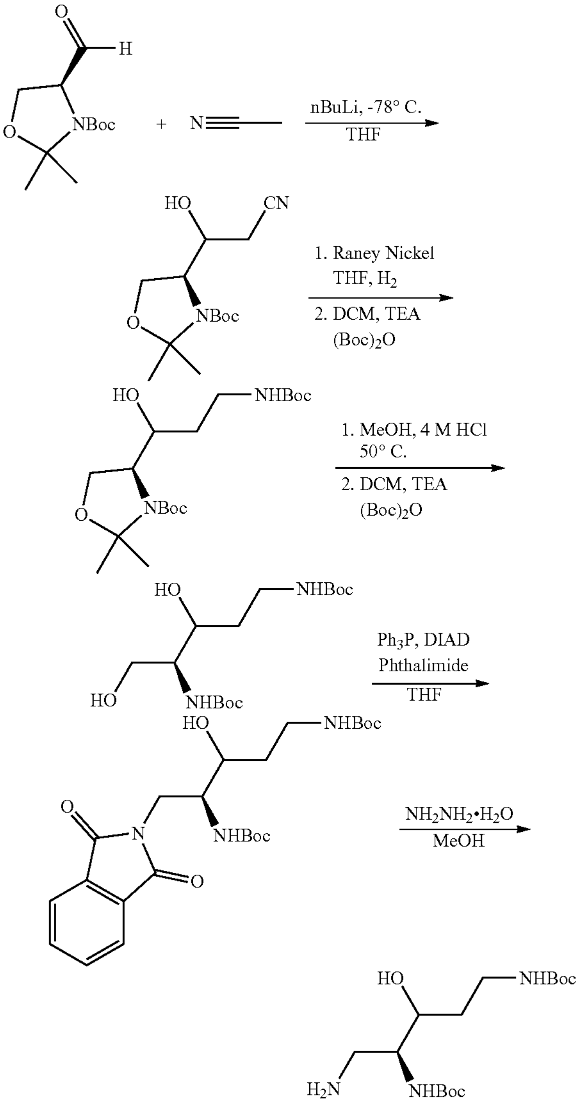

Amine intermediate A

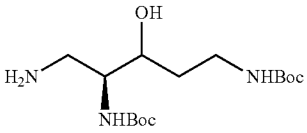

di-tert-butyl ((4S)-5-amino-3-hydroxypentane-1,4-diyl)dicarbamate

To a solution of di-tert-butyl ((4S)-5-(1,3-dioxoisoindolin-2-yl)-3-hydroxypentane-1,4-diyl)dicarbamate (0.7 g, 1.51 mmol) in MeOH (10 mL) was added hydrazine monohydrate (0.35 mL, 4.53 mmol). The mixture was stirred at 50° C. for 1 h, then cooled to room temperature with stirring for additional 2 h. The reaction mixture was concentrated, and the residue was triturated with $CH_2Cl_2$. The solid was removed by filtration. The filtrate was diluted with $CH_2Cl_2$ and washed with brine. The organic layer was dried over $Na_2SO_4$, filtered and concentrated to afford the desired product (0.46 g, 91% yield) as a white solid. The crude product was used in next step without further purification. $^1H$ NMR (300 MHz, $CDCl_3$) δ 5.24 (br s, 1H), 5.03 (br s, 1H), 3.70 (m, 1H), 3.44 (m, 2H), 3.20 (m, 1H), 2.98 (m, 2H), 1.64 (m, 2H), 1.43 (m, 18H).

The requisite intermediates were prepared as shown in the following steps.

Step 1)

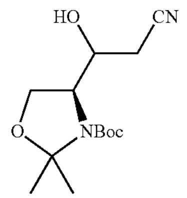

tert-butyl (4S)-4-(−2-cyano-1-hydroxyethyl)-2,2-dimethyloxazolidine-3-carboxylate To a solution of acetonitrile (2.08 mL, 40 mmol) in dry THF (50 mL) at −78° C. under $N_2$ was added n-BuLi (2.5 M in hexanes, 12 mL, 30 mmol) dropwise over 15 min. The reaction mixture was stirred at −78° C. for 1 h. A solution of tert-butyl (S')-4-formyl-2,2-dimethyloxazolidine-3-carboxylate (5 g, 21.8 mmol) in THF (10 mL) was added dropwise over 10 min. The reaction mixture was stirred at −78° C. for 2 h, then quenched by addition of saturated $NH_4Cl$. The resulting mixture was stirred at room temperature for 30 min, diluted with EtOAc. The organic solution was washed with brine, dried over $Na_2SO_4$, filtered, and concentrated to give a crude product (5.5 g, 93% yield) as a light brown liquid. The crude product was used in next step without further purification. $^1H$ NMR (300 MHz, $CDCl_3$) δ 5.08 (d, J=4.5 Hz, 1H), 3.79-4.36 (m, 4H), 2.43-2.68 (m, 2H), 1.48-1.61 (m, 15H).

Step 2)

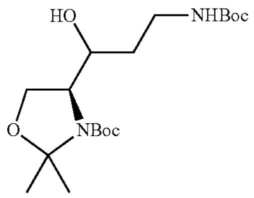

tert-butyl (4S)-4-(3-((tert-butoxycarbonyl)amino)-1-hydroxypropyl)-2,2-dimethyloxazolidine-3-carboxylate To a solution tert-butyl (S)-4-((R)-2-cyano-1-hydroxyethyl)-2,2-dimethyloxazolidine-3-carboxylate (3.0 g, 11.1 mmol) in THF (50 mL) was added Raney-Ni (3 g, $H_2O$ was removed by washing with dry THF). The reaction mixture was hydrogenated under hydrogen (55 psi) at room temperature overnight. The solid was removed by passing through a Celite plug. The Celite was washed with $CH_2Cl_2$. To the filtrate was added TEA (3.1 mL, 22.2 mmol), $(Boc)_2O$ (2.9 g, 13.3 mmol), stirred at room temperature for 3 h, then concentrated to afford a residue. The residue was diluted with EtOAc and washed with $H_2O$, saturated $NaHCO_3$, and brine. The organic solution was dried over $Na_2SO_4$, filtered, and concentrated to give a crude product. The crude product was purified by column chromatography on silica gel using 10-30% EtOAc/Hexanes to afford the desired product (2.9 g, 72% yield) as a white solid. $^1H$ NMR (300 MHz, $CDCl_3$) δ 5.12 (br s, 1H), 4.41 (br s, 1H), 4.05 (m, 1H), 3.77 (m, 2H), 3.46 (m, 1H), 3.21 (m, 1H), 1.43-1.58 (m, 26H).

Step 3)

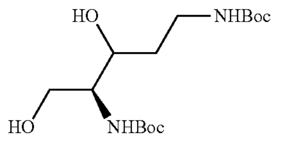 [SMILES: CC(C)(C)OC(=O)NCCC(O)[C@H](CO)NC(=O)OC(C)(C)C]

di-tert-butyl ((4S)-3,5-dihydroxypentane-1,4-diyl)dicarbamate

To a solution of tert-butyl (4S)-4-(3-((tert-butoxycarbonyl)amino)-1-hydroxypropyl)-2,2-dimethyloxazolidine-3-carboxylate (2.27 g, 6.1 mmol) in MeOH (30 mL) was added HCl (4 M in dioxane, 7.6 mL, 30.4 mmol). The reaction mixture was stirred at 50° C. for 1 h, then concentrated to give a residue. The residue was dissolved in $MeOH/CH_2Cl_2$ (5 mL/50 mL) to which TEA (3.4 mL, 24.4 mmol) and $(Boc)_2O$ (3.97 g, 18.2 mmol) were added. The reaction mixture was stirred at room temperature for 3 h, then concentrated to afford a residue. The residue was diluted with EtOAc and washed with $H_2O$, saturated $NaHCO_3$, and brine. The organic solution was dried over $Na_2SO_4$, filtered, and concentrated to give a crude product. The crude product was purified by column chromatography on silica gel using EtOAc to afford the desired product (1.88 g, 93% yield) as a white solid. $^1H$ NMR (300 MHz, $CDCl_3$) δ 5.49 (d, J=7.8 Hz, 1H), 4.98 (br s, 1H), 4.53 (br s, 1H), 3.09-3.40 (m, 6H), 1.63 (m, 2H), 1.43 (s, 9H), 1.42 (s, 9H).

Step 4)

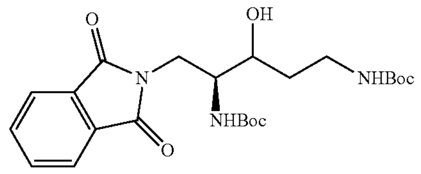 [SMILES: CC(C)(C)OC(=O)NCCC(O)[C@H](CN1C(=O)c2ccccc2C1=O)NC(=O)OC(C)(C)C]

di-tert-butyl ((4S)-5-(1,3-dioxoisoindolin-2-yl)-3-hydroxypentane-1,4-diyl)dicarbamate To a solution of di-tert-butyl ((4S)-3,5-dihydroxypentane-1,4-diyl)dicarbamate (1.88 g, 5.30 mmol), triphenylphosphine (1.47 g, 5.63 mmol) and phthalimide (0.83 g, 5.63 mmol) in THE (200 mL) was added DIAD (1.14 mL, 5.63 mmol) at 0° C. The reaction mixture was stirred at 0° C., then warmed to the room temperature overnight. The reaction mixture was concentrated and purified by column chromatography on silica gel using 20-50% EtOAc/hexanes to give the product (0.7 g, 27% yield) as a white solid. $^1H$ NMR (300 MHz, $CDCl_3$) δ 7.83 (m, 2H), 7.69 (m, 2H), 5.31 (br s, 1H), 4.92 (br s, 1H), 4.23 (br s, 1H), 3.89 (m, 3H), 3.68 (m, 1H), 3.52 (m, 1H), 3.14 (m, 1H), 1.72 (m, 2H), 1.42 (s, 9H), 1.23 (s, 9H).

Preparation of amine Intermediate B (di-tert-butyl ((4S)-5-amino-2-Pic ((triisopropylsilyl)oxy)pentane-1,4-diyl)dicarbamate)

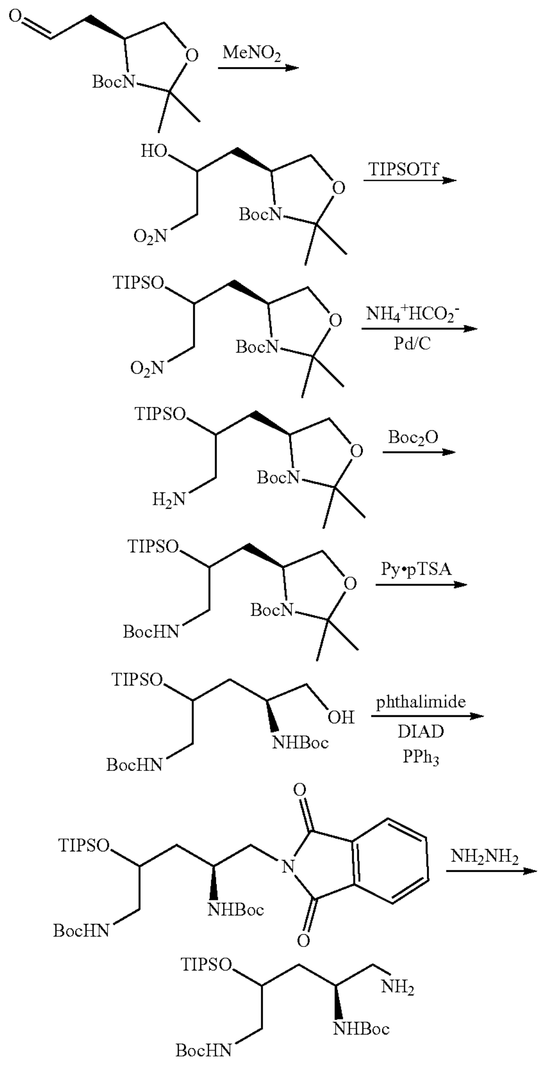

Amine intermediate B

-continued

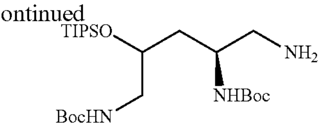

di-tert-butyl ((4S)-5-amino-2-((triisopropylsilyl)oxy)pentane-1,4-diyl)dicarbamate To a solution of di-tert-butyl ((4S)-5-hydroxy-2-((triisopropylsilyl)oxy)pentane-1,4-diyl)dicarbamate (3.72 g, 6 mmol) in EtOH (15 mL) was added $NH_2NH_2 \cdot H_2O$ (3.0 mL, 62 mmol). It was stirred at 50° C. for 3 hrs and then the white ppt was filtered off and was washed with EtOH. The combined filtrate was concentrated and dissolved in DCM, then washed with water, sat. $NaHCO_3$ solution and brine. After dried over anhydrous $Na_2SO_4$, filtered, concentrated it was purified with column chromatography on silica gel to provide the amine as a colorless oil (1.52 g, 52% yield). $^1H$ NMR (300 MHz, $CDCl_3$): δ 5.45 (br s, 1H), 5.05 (br s, 1H), 4.79 (br s, 1H), 4.00 (m, 1H), 3.60 (m, 2H), 3.15 (m, 1H), 2.73 (m, 2H), 1.56-1.78 (m, 2H), 1.45 (br, 21H), 1.06 (br, 18H). MS (ESI): Calcd for $C_{24}H_{52}N_3O_5Si^+[M+H]^+$: 490.37, found: 490.25 $[M+H]^+$.

The requisite intermediates were prepared as shown in the following steps.

Step 1)

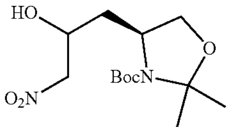 [SMILES: CC(C)(C)OC(=O)N1[C@@H](CC(O)C[N+](=O)[O-])COC1(C)C]

tert-butyl (4S)-4-(2-hydroxy-3-nitropropyl)-2,2-dimethyloxazolidine-3-carboxylate To a solution of tert-butyl (S)-2,2-dimethyl-4-(2-oxoethyl)oxazolidine-3-carboxylate (5.0 g, 20.6 mmol) in nitromethane (10 mL, 178.0 mmol) was added TBAF solution (1.0 M in THF, 3 mL, 3 mmol) at 0° C. and the resulting solution was stirred at room temperature overnight. The reaction mixture was diluted with EtOAc, quenched with aq. sat. $NH_4Cl$ solution, washed with water, brine, and then dried over anhydrous $Na_2SO_4$. The solids were filtered off and solvent was removed in vacuo, the residue was dissolved in DCM and loaded on column chromatography on silica gel. The desired alcohol was collected (6.0 g, 96% yield) as a colorless oil with the eluent of 0-40% of EtOAc in hexane. MS (ESI): Calcd for $C_{13}H_{25}N_2O_6^+$305.17 $[M+H]^+$, found 305.00 $[M+H]^+$.

Step 2)

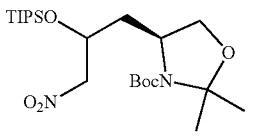

tert-butyl (4S)-2,2-dim ethyl-4-(3-nitro-2-((triisopropylsilyl)oxy)propyl)oxazolidine-3-carboxylate To a solution of tert-butyl (4S)-4-(2-hydroxy-3-nitropropyl)-2,2-dimethyloxazolidine-3-carboxylate (6.0 g, 19.7 mmol) in DCM (200 mL) was added 2,6-lutidine (3.26 mL, 28 mmol) and TIPSOTf (7 mL, 26 mmol) dropwise at 0° C. The reaction mixture was stirred at 0° C. to room temperature overnight then quenched with water, extracted with EtOAc, washed with $NaHCO_3$ solution and $NH_4C_1$ solution. The combined organic layers were washed with brine, dried over anhydrous $Na_2SO_4$, filtered off and concentrated in vacuo. The crude product was purified with flash chromatography on silica gel with 0-15% EtOAc in hexane to afford the silyl ether as a colorless oil (7.9 g, 87% yield). $^1$H NMR (300 MHz, $CDCl_3$): δ 4.64-4.87 (m, 1H), 4.42-4.58 (m, 2H), 3.92-4.02 (m, 2H), 3.70-3.88 (m, 1H), 1.96-2.13 (m, 1H), 1.81-1.95 (m, 1H), 1.55 (s, 3H), 1.47 (s, 3H), 1.46 (s, 12H), 1.05 (br, 18H). MS (ESI): Calcd for $C_{22}H_{45}N_2O_6Si^+$[M+H]$^+$: 461.30, found: 483.20 [M+Na]$^+$.

Step 3)

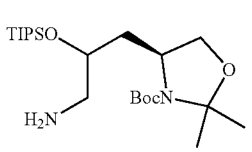

tert-butyl (4S)-4-(3-amino-2-((triisopropylsilyl)oxy)propyl)-2,2-dimethyloxazolidine-3-carboxylate To a solution of tert-butyl (4S)-2,2-dimethyl-4-(3-nitro-2-(triisopropylsilyl)oxy)-propyl)oxazolidine-3-carboxylate (7.9 g, 17.16 mmol) in MeOH (90 mL) was added ammonium formate (10.85 g, 171.6 mmol) and palladium on carbon (10%, 2.1 g, 1.97 mmol) under $N_2$. After stirring the reaction mixture for 1 day at room temperature, the catalyst was removed by filtrating through a pad of Celite and the filtrate was concentrated in vacuo. The residue was purified by silica gel column chromatography using EtOAc as eluent to provide the desired amine as a colorless oil (6.5 g, 88% yield). $^1$H NMR (300 MHz, $CDCl_3$): δ 6.18 (br, 2H), 3.85-4.11 (m, 1H), 3.78-3.83 (m, 2H), 3.42 (dd, J=4.1, 13.0 Hz, 1H), 2.99-3.22 (m, 2H), 1.88-2.10 (m, 2H), 1.53 (s, 3H), 1.46 (br, 15H), 1.05 (br, 18H). MS (ESI): Calcd for $C_{22}H_{47}N_2O_4Si^+$[M+H]$^+$: 431.33, found: 431.20 [M+H]$^+$.

Step 4)

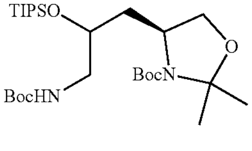

tert-butyl (4S)-4-(3-((tert-butoxycarbonyl)amino)-2-((triisopropylsilyl)oxy)propyl)-2,2-dimethyloxazolidine-3-carboxylate To a solution of tert-butyl (4S)-4-(3-amino-2-((triisopropylsilyl)oxy)propyl)-2,2-dimethyloxazolidine-3-carboxylate (6.5 g, 15.1 mmol) in DCM (80 mL) was added $Boc_2O$ (4.94 g, 22.5 mmol) and TEA (4.18 mL, 30 mmol). The reaction mixture was stirred overnight at room temperature Then it was diluted with DCM, washed with water, brine and dried over anhydrous $Na_2SO_4$. After removing solvent in vacuo, it was purified by silica gel column chromatography with 0-30% EtOAc in hexane as eluents to give a colorless oil as the protected product (7.45 g, 93% yield). $^1$H NMR (300 MHz, $CDCl_3$): δ 5.92 (br s, 1H), 4.06 (m, 1H), 3.94 (m, 2H), 3.83 (m, 2H), 3.03 (m, 1H), 1.78-1.93 (m, 2H), 1.48 (br, 12H), 1.43 (br, 15H), 1.05 (br, 18H).

Step 5)

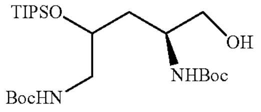

di-tert-butyl ((4S)-5-hydroxy-2-((triisopropylsilyl)oxy)pentane-1,4-diyl)dicarbamate Pic To a solution of tert-butyl (4S)-4-(3-((tert-butoxycarbonyl)amino)-2-((triisopropylsilyl)oxy)propyl)-2,2-dimethyloxazolidine-3-carboxylate (7.45 g, 14.1 mmol) in MeOH (50 mL) was added pyridinium p-toluenesulfonate (2.11 g, 8.4 mmol). It was refluxed for 4 hr. MeOH was removed in vacuo and the residue was dissolved in EtOAc, washed with water, brine and dried over anhydrous $Na_2SO_4$. After concentration, it was purified by column chromatography on silica gel with 0-70% EtOAc in hexane as eluents to give a colorless oil (2.95 g, 43% yield) and 1.15 g starting material was recovered. $^1$H NMR (300 MHz, $CDCl_3$): δ 5.45 (br s, 1H), 5.02 (bs, 1H), 4.09 (m, 1H), 3.75 (m, 1H), 3.59 (m, 2H), 3.31 (m, 1H), 3.15 (m, 1H), 2.80 (br, 1H), 1.62-1.83 (m, 2H), 1.43 (br, 21H), 1.05 (br, 18H). MS (ESI): Calcd for $C_{24}H_{51}N_2O_6Si^+$[M+H]$^+$: 491.35, found: 491.30 [M+H]$^+$.

Step 6)

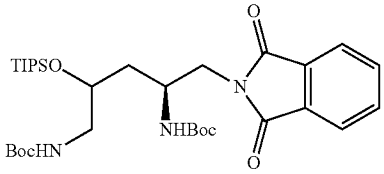

di-tert-butyl ((4S)-5-(1,3-dioxoisoindolin-2-yl)-2-((triisopropylsilyl)oxy)pentane-1,4-diyl)dicarbamate To a solution of di-tert-butyl ((4S)-5-hydroxy-2-((triisopropylsilyl)oxy)pentane-1,4-diyl)dicarbamate (2.95 g, 6 mmol) in THF (40 mL) was added triphenylphosphine (2.36 g, 9 mmol), phthalimide (1.33 g, 9 mmol), followed by DIAD (1.65 mL, 8.4 mmol) at 0° C. Then it was stirred at 0° C. to room temperature overnight. The mixture was diluted with EtOAc, washed with water, brine and concentrated under reduced pressure and the residue was purified using column chromatography on silica gel with 0-40% EtOAc in hexane as eluents to give phthalimide product (3.72 g, 99%) as a colorless oil which solidified after standing. $^1$H NMR (300 MHz, $CDCl_3$): δ 7.86 (m, 2H), 7.78 (m, 2H), 6.35 (br, 2H), 4.05 (m, 2H), 3.70 (m, 1H), 3.60 (m, 1H), 3.29 (m, 1H), 3.18 (m, 1H), 1.63-1.82 (m, 2H), 1.43 (s, 3H), 1.27 (br, 9H), 1.24 (br, 9H), 1.06 (br, 18H). MS (ESI): Calcd for $C_{32}H_{54}N_3O_7Si^+[M+H]^+$: 620.37, found: 642.45 $[M+Na]^+$.

Preparation of amine Intermediate C (di-tert-butyl ((4R)-5-amino-2-(((tert-butyldiphenyl silyl)oxy) methyl)pentane-1,4-diyl)dicarbamate)

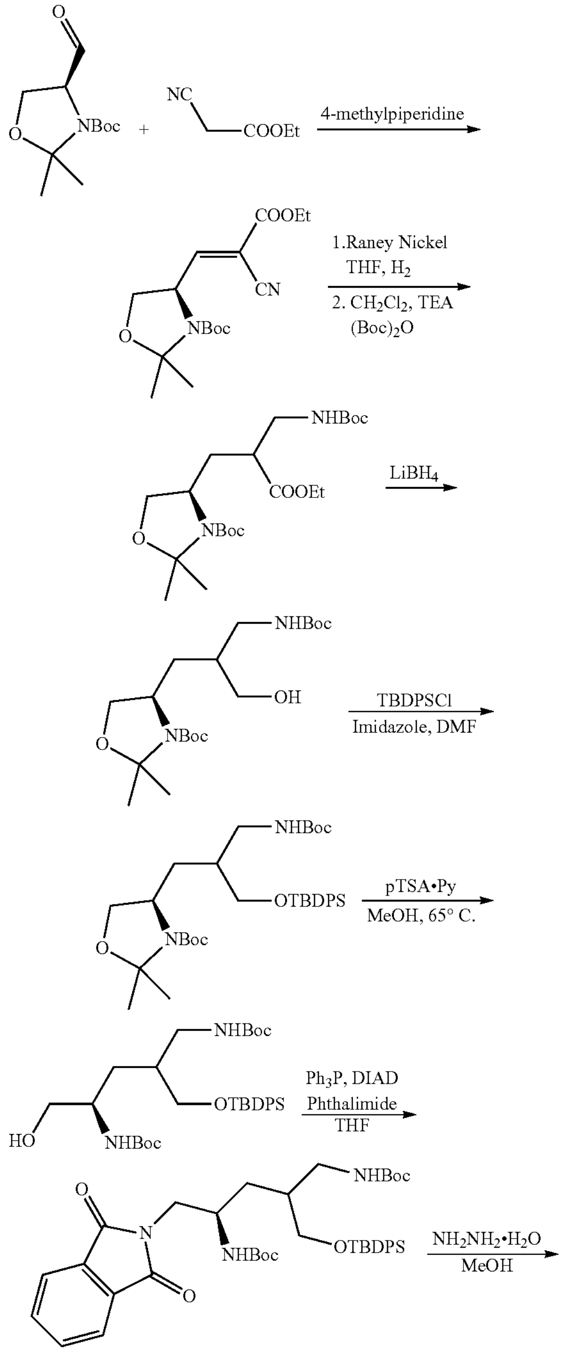

-continued

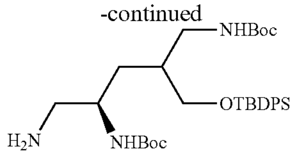

Amine intermediate C

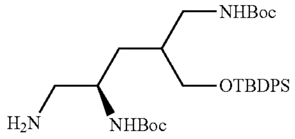

di-tert-butyl ((4R)-5-amino-2-(((tert-butyldiphenyl-silyl)oxy)methyl)pentane-1,4-diyl)dicarbamate To a solution of di-tert-butyl ((4R)-2-(((tert-butyldiphenylsilyl)oxy)methyl)-5-(1,3-dioxo-2,3-dihydro-1H-inden-2-yl)pentane-1,4-diyl)dicarbamate (2.52 g, 3.52 mmol) in MeOH (50 mL) was added hydrazine monohydrate (0.83 mL, 10.6 mmol). The mixture was stirred at room temperature and the precipitate formed was filtered off and washed with $CH_2Cl_2$. The filtrate was concentrated and diluted with $CH_2Cl_2$, washed with saturated $NaHCO_3$, brine and dried over $Na_2SO_4$. The organic solution was filtered and concentrated to give a crude product. The crude product was purified on silica gel column chromatography. Elution with EtOAc, then 10% MeOH/$CH_2Cl_2$ with 1% $NH_3$·$H_2O$ afforded the product (1.32 g, 54% yield) as a colorless gum. $^1$H NMR (300 MHz, $CDCl_3$) δ 7.64 (m, 4H), 7.41 (m, 6H), 4.65-4.90 (br, 2H), 3.40-3.68 (m, 3H), 3.17 (m, 2H), 2.51-2.70 (m, 2H), 1.75 (br s, 1H), 1.41 (s, 18H), 1.22-1.42 (m, 2H), 1.06 (s, 9H).

The requisite intermediates were prepared as shown in the following steps.

Step 1)

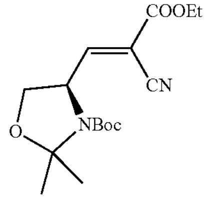

tert-butyl (4R)-4-(2-cyano-3-ethoxy-3-oxoprop-1-en-1-yl)-2,2-dimethyloxazolidine-3-carboxylate To a solution of tert-butyl (S)-4-formyl-2,2-dimethyloxazolidine-3-carboxylate (5.0 g, 21.8 mmol), ethyl 2-cyanoacetate (2.47 g, 21.8 mmol) in $CH_2Cl_2$ (60 mL) at room temperature was added 4-methylpiperidine (216 mg, 2.18 mmol). The reaction mixture was stirred for 2 h then concentrated and purified by column chromatography on silica gel by using 10% EtOAc/hexanes. The mixture of cis- and trans-products (4.95 g, 70% yield) was collected as colorless oil.

Step 2)

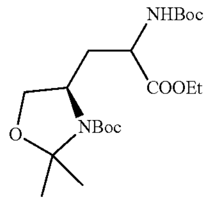

tert-butyl (4R)-4-(2-(((tert-butoxycarbonyl)amino) methyl)-3-ethoxy-3-oxopropyl)-2,2-dimethyloxazolidine-3-carboxylate To a solution tert-butyl (4R)-4-(2-cyano-3-ethoxy-3-oxoprop-1-en-1-yl)-2,2-dimethyloxazolidine-3-carboxylate (2.5 g, 7.72 mmol) in THF (40 mL) was added Raney-Ni (2.5 g, $H_2O$ was removed by washing with dry THF). The reaction mixture was hydrogenated under hydrogen (55 psi) at room temperature overnight. The solid was removed by passing through a Celite plug. The Celite was washed with $CH_2Cl_2$. TEA (1.30 mL, 9.26 mmol), $(Boc)_2O$ (2.02 g, 9.26 mmol) was added to the filtrate and stirred at room temperature for 3 h and then concentrated to afford a residue. The residue was diluted with EtOAc and washed with $H_2O$, saturated $NaHCO_3$, and brine. The organic solution was dried over $Na_2SO_4$, filtered and concentrated to give a crude product. The crude product was purified by column chromatography on silica gel using 10-30% EtOAc/Hexanes to afford the desired product (2.4 g, 72% yield) as a white solid. $^1H$ NMR (300 MHz, $CDCl_3$) δ 5.21 (br s, 1H), 4.86 (br s, 1H), 4.08-4.19 (m, 2H), 3.23-4.02 (m, 5H), 2.60 (m, 1H), 1.67 (m, 2H), 1.58 (s, 3H), 1.40-1.55 (m, 21H), 1.21-1.32 (m, 3H).

Step 3)

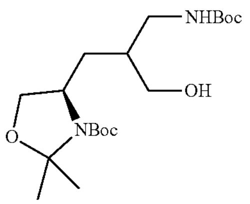

tert-butyl (4R)-4-(3-((tert-butoxycarbonyl)amino)-2-(hydroxymethyl)propyl)-2,2-dimethyloxazolidine-3-carboxylate To a solution of tert-butyl (4R)-4-(2-(((tert-butoxycarbonyl)amino)methyl)-3-ethoxy-3-oxopropyl)-2,2-dim ethyloxazolidine-3-carboxylate (4.8 g, 11.2 mmol) in THF (100 mL) at room temperature was added $LiBH_4$ (730 mg, 33.5 mmol). The reaction mixture was stirred at room temperature overnight then quenched by the addition of acetone in portions and the resulting mixture was concentrated to give a residue. The residue was diluted with EtOAc and washed with $H_2O$, saturated $NaHSO_4$, and brine. The organic solution was dried over $Na_2SO_4$, filtered, and concentrated to give the crude product (4.3 g, 99% yield). It was used directly for next step without further purification. $^1H$ NMR (300 MHz, $CDCl_3$) δ 5.65 (br s, 1H), 4.97 (br s, 1H), 3.05-4.22 (m, 7H), 2.06 (m, 1H), 1.33-1.72 (m, 26H).

Step 4)

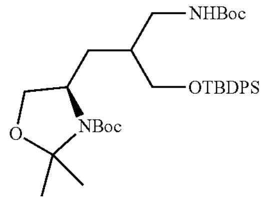

tert-butyl (4R)-4-(3-((tert-butoxycarbonyl)amino)-2-(((tert-butyldiphenylsilyl)oxy)methyl)propyl)-2,2-dimethyloxazolidine-3-carboxylate To a solution of tert-butyl (4R)-4-(3-((tert-butoxycarbonyl)amino)-2-(hydroxymethyl)-propyl)-2,2-dim ethyloxazolidine-3-carboxylate (4.3 g, 11.2 mmol) in DMF (50 mL) was added imidazole (1.65 g, 24.2 mmol), and TBDPSCl (3.98 g, 14.5 mmol). The above reaction mixture was stirred at room temperature overnight, then diluted with EtOAc and washed with 15% LiCl solution, saturated $NaHCO_3$, and brine. The organic layer was dried over $Na_2SO_4$ and filtered. The filtrate was concentrated and purified using column chromatography on silica gel to give the desired product (6.57 g, 94% yield) as a colorless oil. $^1H$ NMR (300 MHz, $CDCl_3$) δ 7.64 (m, 4H), 7.42 (m, 6H), 5.12-5.39 (m, 2H), 2.92-3.90 (m, 7H), 1.29-1.80 (m, 27H), 1.06 (s, 9H).

Step 5)

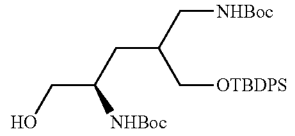

di-tert-butyl ((4R)-2-(((tert-butyldiphenylsilyl)oxy) methyl)-5-hydroxypentane-1,4-diyl)dicarbamate To a solution of tert-butyl (4R)-4-(3-((tert-butoxycarbonyl)amino)-2-(((tert-butyldiphenylsilyl)oxy)methyl)propyl)-2,2-dimethyloxazolidine-3-carboxylate (6.57 g, 10.5 mmol) in MeOH (100 mL) was added pyridinium p-toluenesulfonate (1.93 g, 7.68 mmol). The reaction mixture was stirred at 65° C. for 3 h then cooled to room temperature, concentrated, and diluted with EtOAc. The organic solution was washed with water, brine and dried over $Na_2SO_4$. The crude product was purified by column chromatography on silica gel using 10-50% EtOAc in hexane. A colorless oil was collected (3.10 g, 50% yield). $^1H$ NMR (300 MHz, $CDCl_3$) δ 7.64 (m, 4H), 7.43 (m, 6H), 4.64-5.01 (br m, 2H), 3.44-3.70 (m, 5H), 2.97-3.26 (m, 3H), 1.75 (br s, 1H), 1.39-1.42 (m, 20H), 1.07 (s, 9H).

Step 6)

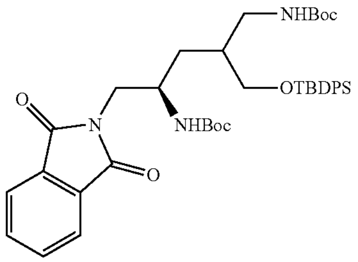

di-tert-butyl ((4R)-2-(((tert-butyldiphenylsilyl)oxy) methyl)-5-(1,3-dioxoisoindolin-2-yl)pentane-1,4-diyl)dicarbamate To a solution of di-tert-butyl ((4R)-2-(((tert-butyldiphenylsilyl)oxy)methyl)-5-hydroxypentane-1,4-diyl)dicarbamate (2.52 g, 4.30 mmol), triphenylphosphine (1.24 g, 4.73 mmol) and phthalimide (695 mg, 4.73 mmol) in THE (50 mL) was added DIAD (0.96 mL, 4.73 mmol) at 0° C. The reaction mixture was stirred at 0° C., then room temperature overnight. The reaction mixture was concentrated and purified by column chromatography on silica gel using 5-20% EtOAc/hexanes to give the desired product (2.51 g, 82% yield) as a white solid. $^1$H NMR (300 MHz, $CDCl_3$) δ 7.82 (m, 2H), 7.60-7.71 (m, 6H), 7.35-7.44 (m, 6H), 6.43 (br s, 1H), 4.68-4.84 (m, 1H), 4.00 (m, 1H), 3.65 (m, 3H), 3.13 (m, 2H), 1.59-1.83 (m, 2H), 1.30-1.48 (m, 1H), 1.26 (m, 18H), 1.06 (s, 9H).

Preparation of amine Intermediate D (benzyl (R)-(1-amino-3-(2-((tert-butoxycarbonyl)amino)ethoxy) propan-2-yl)carbamate)

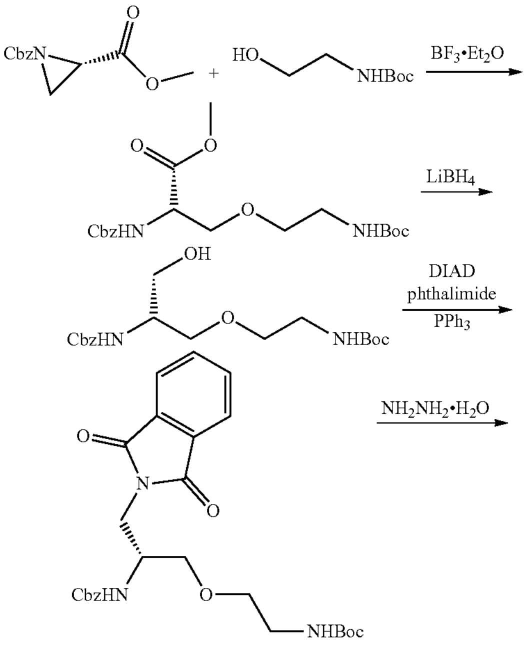

-continued

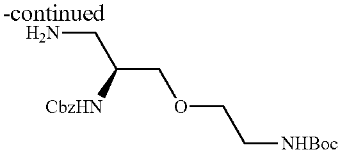

Amine intermediate D

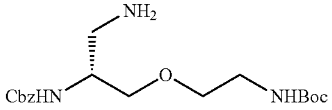

benzyl (R)-(1-amino-3-(2-((tert-butoxycarbonyl) amino)ethoxy)propan-2-yl)carbamate To a solution of benzyl (R)-(1-(2-((tert-butoxycarbonyl) amino)ethoxy)-3-(1,3-dioxoisoindolin-2-yl)propan-2-yl) carbamate (525 mg, 1.06 mmol) in EtOH (8 mL) was added $NH_2NH_2 \cdot H_2O$ (0.2 mL, 4 mmol). It was stirred at 50° C. for 4 hr, then the white ppt was filtered off and washed with EtOH. The filtrate was concentrated and dissolved in EtOAc, then washed with water, sat. $NaHCO_3$ solution and brine. After dried over anhydrous $Na_2SO_4$, it was concentrated and purified by column chromatography on silica gel to provide a colorless oil (330 mg, 85% yield). (300 MHz, $CDCl_3$) δ 7.27-7.40 (m, 5H), 5.36 (br s, 1H), 5.11 (m, 2H), 4.90 (br, 1H), 3.77 (m, 1H), 3.58 (m, 1H), 3.49 (m, 4H), 3.29 (m, 2H), 2.86 (m, 1H), 1.44 (s, 9H). MS (ESI): Calcd for $C_{18}H_{30}N_3O_5^+$ 368.21 [M+H]$^+$, found 368.25 [M+H]$^+$.

The requisite intermediates were prepared as shown in the following steps.

Step 1)

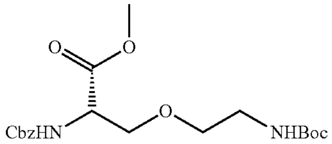

methyl N-((benzyloxy)carbonyl)-O-(2-((tert-butoxy-carbonyl)amino)ethyl)-L-serinate To a solution of tert-butyl (2-hydroxyethyl)carbamate (3.23 g, 20 mmol) and (S)-1-benzyl 2-methyl aziridine-1,2-dicarboxylate (0.94 g, 4 mmol) in $CH_2Cl_2$ (20 mL) was added $BF_3 \cdot Et_2O$ (0.286 mL, 2.33 mmol) at 0° C. slowly under $N_2$. The reaction mixture was allowed to warm slowly to room temperature and was stirred overnight. The reaction mixture was partitioned between EtOAc and saturated $NaHCO_3$. The combined organic phase was washed with brine and dried over $Na_2SO_4$, filtered, and concentrated. The crude product was purified by column chromatography on silica gel (0-50% EtOAc in hexane) to give methyl N-((benzyloxy)carbonyl)-O-(2-((tert-butoxycarbonyl)amino)ethyl)-L-serinate (0.87 g, 55% yield). $^1$H NMR (300 MHz, $CDCl_3$) δ 7.35 (m, 5H), 5.66 (br s, 1H), 5.13 (s, 2H), 4.79 (br, 1H), 4.51 (m, 1H), 3.77 (s, 3H), 3.74 (m, 2H), 3.48 (m, 2H), 3.27 (m, 2H), 1.45 (s, 3H), 1.43 (s, 6H). MS (ESI): Calcd for $C_{19}H_{29}N_2O_7^+$ 397.20 [M+H]$^+$, found 397.25 [M+H]$^+$.

Step 2)

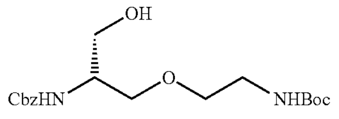

benzyl (R)-(1-(2-((tert-butoxycarbonyl)amino)ethoxy)-3-hydroxypropan-2-yl)carbamate To a solution of methyl N-((benzyloxy)carbonyl)-O-(2-((tert-butoxycarbonyl)amino)ethyl)-L-serinate (0.86 g, 2.17 mmol) in THE (10 mL) was added $LiBH_4$ (95 mg, 4.3 mmol) at room temperature. It was stirred at room temperature overnight and quenched with water, extracted with EtOAc, washed with water, brine and dried over $Na_2SO_4$. The concentrated crude product was purified by silica gel column chromatography using 0-70% EtOAc in hexane to provide the alcohol (0.54 g, 67% yield) as a colorless oil. MS (ESI): Calcd for $C_{18}H_{29}N_2O_6^+$369.20 $[M+H]^+$, found 369.20 $[M+H]^+$.

Step 3)

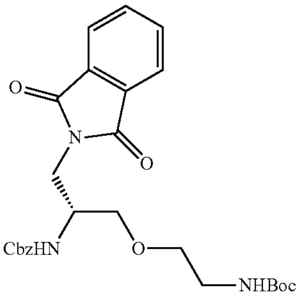

benzyl (R)-(1-(2-((tert-butoxycarbonyl)amino)ethoxy)-3-(1,3-dioxoisoindolin-2-yl)propan-2-yl)carbamate To a solution of benzyl (R)-(1-(2-((tert-butoxycarbonyl)amino)ethoxy)-3-hydroxypropan-2-yl)carbamate (0.535 g, 1.45 mmol) in THE (15 mL) was added phthalimide (0.255 g, 1.74 mmol) and $PPh_3$ (0.455 g, 1.74 mmol). Then DIAD (0.34 mL, 1.74 mmol) was added slowly at 0° C. under $N_2$. It was stirred at 0° C. to room temperature for 5 hrs, then quenched with water, extracted with EtOAc, washed with water and brine, dried and concentrated. The crude product was loaded on a silica gel column and purified with 0-70% EtOAc in hexane to provide the product (0.525 g, 73% yield) as a colorless oil. $^1H$ NMR (300 MHz, $CDCl_3$) δ 7.84 (m, 2H), 7.72 (m, 2H), 7.29 (m, 5H), 5.41 (br s, 1H), 4.99 (m, 2H), 4.79 (br, 1H), 4.71 (m, 1H), 3.90 (m, 2H), 3.57 (m, 1H), 3.49 (m, 3H), 3.28 (m, 2H), 1.44 (s, 9H). MS (ESI): Calcd for $C_{26}H_{32}N_3O_7$ 498.23 $[M+H]^+$, found 498.25 $[M+H]^+$.

Preparation of amine Intermediate E (((3aR,6R,6aS)-2,5-dibenzylhexahydro-2H-pyrrolo[3,4-d]isoxazol-6-yl)methanamine)

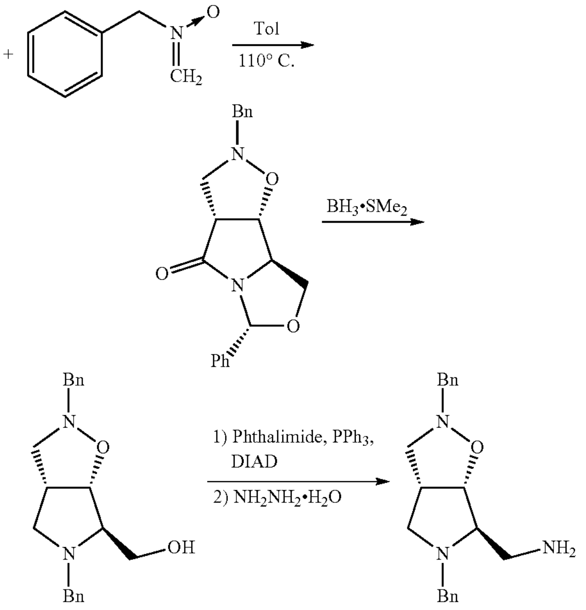

Amine intermediate E

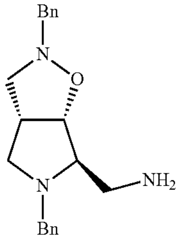

((3aR,6R,6aS)-2,5-dibenzylhexahydro-2H-pyrrolo[3,4-d]isoxazol-6-yl)methanamine

To a mixture of ((3aR,6R,6aS)-2,5-dibenzylhexahydro-2H-pyrrolo[3,4-d]isoxazol-6-yl)methanol (1.39 g, 4.3 mmol) in 30 mL of THE was added phthalimide (0.69 g, 4.73 mmol), triphenylphosphine (1.23 g, 4.73 mmol). Then diisopropyl azodicarboxylate (0.96 g, 4.73 mmol) was added at 0° C. Reaction mixture was stirred at room temperature overnight. Solvent was removed and residue was directly purified on column chromatography on silica gel to give 1.37 g of intermediate. To this intermediate (1.37 g, 3 mmol) in methanol (30 mL) was added 1.5 mL of hydrazine monohydrate. Reaction mixture was stirred at 50° C. for 1 hour after which the solvent was removed, residue was diluted with 30 mL of DCM. White solid was formed and filtered off, washed with DCM. The solution was collected and washed with brine and dried over $Na_2SO_4$. Solvent was removed and residue was purified on column chromatography on silica gel to give the product (0.45 g, 32% yield) as a colorless oil. $^1H$ NMR (300 MHz, $CDCl_3$) δ 7.22-7.38 (m, 10H), 4.58 (m, 1H), 4.08 (m, 1H), 3.90 (m, 3H), 3.25 (br, 1H), 3.12 (t, J=8.1 Hz, 1H), 2.78-3.00 (m, 5H), 2.40-2.62 (m, 2H), 2.25 (t, J=8.1 Hz, 1H).

The requisite intermediates were prepared as shown in the following steps.

Step 1)

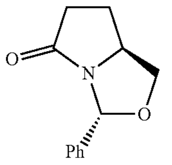 [SMILES: O=C1CC[C@H]2CO[C@H](c3ccccc3)N12]

(5R,7aR)-5-phenylhexahydro-3H-pyrrolizin-3-one

To a stirred solution of (S)-5-(hydroxymethyl)pyrrolidin-2-one (10.0 g, 87 mmol) in toluene (80 mL) was added benzaldehyde (10.6 g, 100 mmol) and 4-methylbenzene-sulfonic acid hydrate (1.0 g, 5 mmol). It was stirred at reflux overnight and water was removed using a Dean-Stark trap. Then solvent was removed in vacuo and the residue was dissolved in DCM and purified by column chromatography on silica gel. Product was collected as a colorless oil (16.6 g, 94%). $^1$H NMR (300 MHz, $CDCl_3$) δ 7.26-7.51 (m, 5H), 6.36 (s, 1H), 4.25 (m, 1H), 4.16 (m, 1H), 3.48 (t, J=7.8 Hz, 1H), 2.82 (m, 1H), 2.58 (m, 1H), 2.39 (m, 1H), 1.98 (m, 1H).

Step 2)

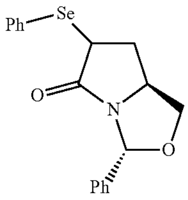 [SMILES: O=C1C([Se]c2ccccc2)C[C@H]2CO[C@H](c3ccccc3)N12]

(3R,7aS)-3-phenyl-6-(phenyl selanyl)tetrahydro-3H, 5H-pyrrolo[1,2-c]oxazol-5-one To a stirred solution of LDA (67 mmol, prepared by treatment of diisopropylamine (6.8 g, 67 mmol) in 60 mL of THF with n-Butyllithium (2.5 M in hexanes, 26.8 mL, 67 mmol) at −78° C. under $N_2$) was added a solution of the (3R,7aS)-3-phenyltetrahydro-3H,5H-pyrrolo[1,2-c]oxazol-5-one (9.7 g, 33 mmol) in 30 mL of THF and it was stirred for 30 min. The resulting enolate was rapidly added to a solution of phenylselenyl bromide (prepared by treatment of diphenyldiselenide (9.85 g, 31.6 mmol) in 30 mL of THF with bromine (4.96 g, 31 mmol) at 0° C. under $N_2$. After stirring for 15 minutes, reaction mixture was poured into a mixture of HCl (0.5 N, 150 mL, 75 mmol) and extracted with EtOAc. The Combined organic layer was washed with water, Saturated aqueous $NaHCO_3$ and brine, and dried over $Na_2SO_4$. After filtration, solvent was removed in vacuo and the residue was purified by column chromatography on silica gel to give the product (4.0 g, 24% yield). $^1$H NMR (300 MHz, $CDCl_3$) δ 7.64 (m, 2H), 7.33 (m, 4H), 7.26 (m, 2H), 7.18 (m, 2H), 6.27 (s, 1H), 3.97 (dd, $J_1$=4.7, 6.9 Hz, 1H), 3.60 (quint, J=6.5 Hz, 1H), 3.40 (t, J=8.0 Hz, 1H), 2.51 (m, 2H).

Step 3)

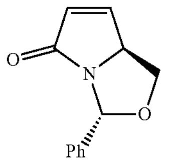 [SMILES: O=C1C=C[C@H]2CO[C@H](c3ccccc3)N12]

(3R,7aS)-3-phenyl-1,7a-dihydro-3H, 5H-pyrrolo[1, 2-c]oxazol-5-one

To a solution of (3R,7aS)-3-phenyl-6-(phenylselanyl)tetrahydro-3H,5H-pyrrolo[1,2-c]oxazol-5-one (4.0 g, 11.1 mmol) in DCM (50 mL) was added pyridine (1.72 mL) and hydrogen peroxide (3.4 mL, 30% in water) at 0° C. Reaction mixture was stirred at room temperature for 2 hours. The mixture was diluted with 50 mL of DCM and 100 mL of 0.5 N HCl, the organic layer was washed with water, saturated aqueous $NaHCO_3$ and brine, and dried over $Na_2SO_4$. After filtration, solvent was removed in vacuo and the residue was purified by column chromatography on silica gel to give the product (1.94 g, 86% yield). $^1$H NMR (300 MHz, $CDCl_3$) δ 7.53 (m, 2H), 7.34-7.43 (m, 3H), 7.27 (dd, J=2.0, 5.8 Hz, 1H), 6.19 (m, 1H), 6.17 (dd, J=1.5, 5.8 Hz, 1H), 4.63 (m, 1H), 4.27 (m, 1H), 3.43 (t, J=8.4 Hz, 1H).

Step 4)

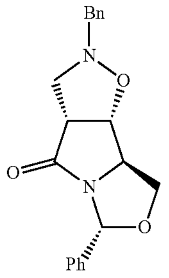 [SMILES: O=C1[C@@H]2CN(Cc3ccccc3)O[C@@H]2[C@H]2CO[C@H](c3ccccc3)N12]

(3aR,6R,8aR,8bS)-2-benzyl-6-phenylhexahydro-4H, 6H-oxazolo[3',4':1,5]pyrrolo[3,4-d]isoxazol-4-one A mixture of (3R,7aS)-3-phenyl-1,7a-dihydro-3H, 5H-pyrrolo[1,2-c]oxazol-5-one (1.6 g, 8 mmol) and N-benzylmethanimine oxide (1.6 g, 12 mmol) (prepared by treating N-benzylhydroxylamine HCl salt with formalin in EtOH in the presence of NaOH) in toluene (10 mL) was stirred at 110° C. overnight. After concentration, the residue was dissolved in small amount of DCM and insoluble solid was filtered off. Solvent was removed and residue was purified by column chromatography on silica gel to give the product as a pale-yellow thick oil (2.4 g, 89% yield). $^1$H NMR (300 MHz, $CDCl_3$) δ 7.20-7.50 (m, 10H), 6.35 (s, 1H), 4.67 (d, J=8 Hz, 1H), 4.24-4.36 (t, J=8 Hz, 1H), 4.02-4.16 (m, 1H), 3.99 (s, 2H), 3.40-3.70 (m, 3H), 2.78-2.96 (m, 1H).

Step 5)

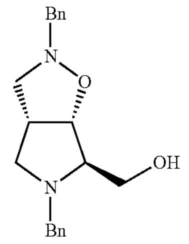 [SMILES: OC[C@@H]1[C@H]2ON(Cc3ccccc3)C[C@H]2CN1Cc1ccccc1]

((3aR,6R,6aS)-2,5-dibenzylhexahydro-2H-pyrrolo[3,4-d]isoxazol-6-yl)methanol

To a solution of (3aR,6R,8aR,8bS)-2-benzyl-6-phenyl-hexahydro-4H,6H-oxazolo[3',4':1,5]pyrrolo[3,4-d]isoxazol-4-one (2.4 g, 7.1 mmol) in THF (30 mL) was added borane dimethylsulfide solution (2M in THF, 12 mL, 24 mmol). Reaction mixture was stirred at reflux for 2 hours then cooled to 0° C., to this mixture was slowly added aq. HCl solution (6 M, 12 mL, 72 mmol). Resulting reaction mixture was stirred at 70° C. for 30 minutes then cooled to 0° C. again, 30% aq. NaOH solution was added to adjust the pH to over 10. The mixture was extracted with 3×50 mL of EtOAc. The combined organic layer was washed with brine and dried. Solvent was removed and the residue was purified by column chromatography on silica gel to give the product (1.39 g, 60% yield) as a colorless oil. $^1$H NMR (300 MHz, $CDCl_3$) δ 7.25-7.39 (m, 10H), 4.67 (dd, J=4.8, 8.0 Hz, 1H), 4.09 (d, J=12.9 Hz, H), 3.98 (d, J=12.9 Hz, H), 3.92 (br, 1), 3.84 (dd, J=2.3, 11.3 Hz, 1H), 3.73 (d, J=11.0 Hz, 1H), 3.30 (d, J=12.9 Hz, 1H), 3.18 (t, J=8.7 Hz, 1H), 2.95 (m, 1H), 2.89 (m, 1H), 2.74 (m, 1H), 2.51 (m, 1H), 2.34 (t, J=8.7 Hz, 1H).

Preparation of amine Intermediate F (tert-butyl (2S)-2-(aminomethyl)-4-((dibenzylamino)methyl)-4-hydroxypyrrolidine-1-carboxylate)

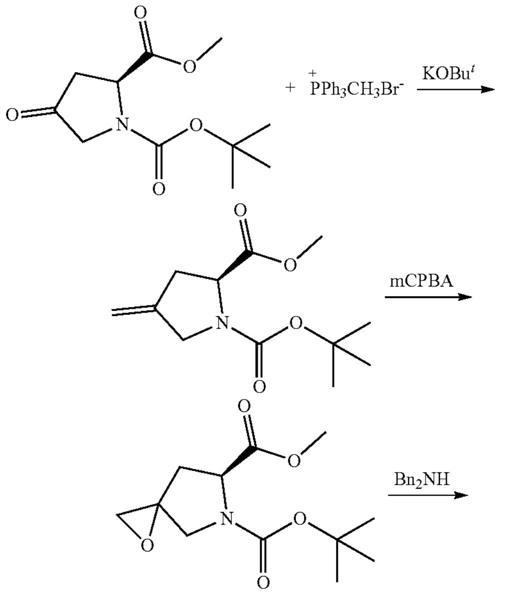

-continued

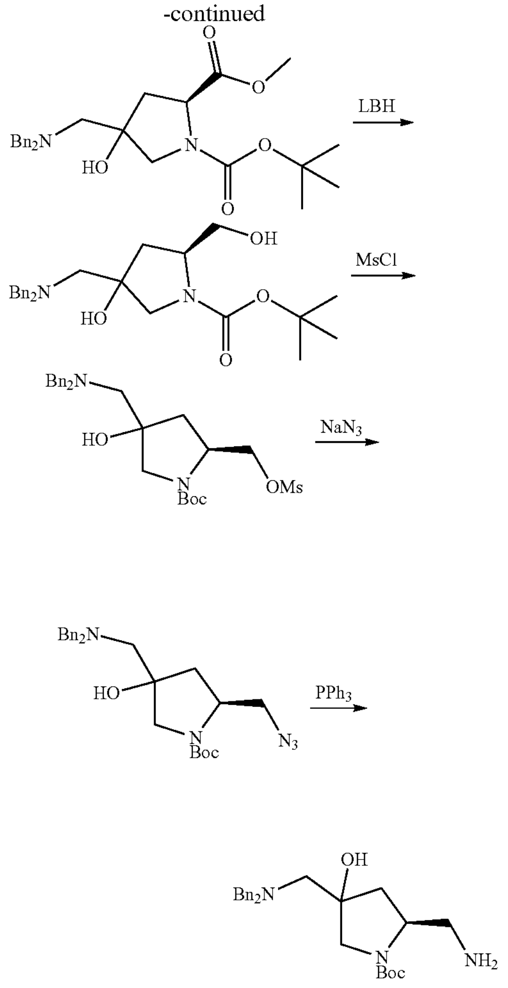

Amine intermediate F

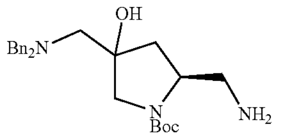

tert-butyl (2S)-2-(aminomethyl)-4-((dibenzylamino)methyl)-4-hydroxypyrrolidine-1-carboxylate To a solution of tert-butyl (2S)-2-(azidomethyl)-4-((dibenzylamino)methyl)-4-hydroxypyrrolidine-1-carboxylate (42 mg, 0.1 mmol) in THF (2 mL) was added $PPh_3$ (50 mg, 0.2 mmol). It was heated at 50° C. for 1 hr. To the reaction mixture was added EtOAc then washed with water, brine and concentrated. It was purified by column chromatography on silica gel (0-100% ethyl acetate in hexane) to give the product as a colorless oil (22 mg, 52% yield). $^1$H NMR (300 MHz, $CDCl_3$) δ 7.36 (m, 4H), 7.31 (m, 4H), 7.25 (m, 2H), 3.92 (d, J=9.4 Hz, 1H), 3.72 (m, 4H), 3.51 (m, 1H), 3.27 (m, 1H), 3.05 (d, J=11.4 Hz, 1H), 2.61 (m, 2H), 2.48 (d, J=13.3 Hz, 1H), 2.42 (br s, 2H), 2.08 (m, 1H), 1.75 (t, J=14.3 Hz, 1H), 1.44 (s, 9H). MS (ESI): Calcd for $C_{26}H_{33}N_3O_3^+$ 426.27 [M+H]$^+$, found 426.15 [M+H]$^+$.

The requisite intermediates were prepared as shown in the following steps.

Step 1)

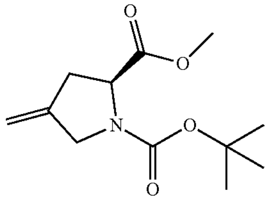 [SMILES: C=C1C[C@@H](C(=O)OC)N(C(=O)OC(C)(C)C)C1]

1-(tert-butyl) 2-methyl (S)-4-methylenepyrrolidine-1,2-dicarboxylate

To a suspension of methyltriphenylphosphonium bromide (12 g, 22.6 mmol) in THE (90 mL) was added $KOBu^t$ solution in 50 mL THF (3.77 g, 33.6 mmol) at 0° C. under $N_2$. The reaction mixture was stirred for 2 h at the same temperature and added to a solution of 1-(tert-butyl) 2-methyl (S)-4-oxopyrrolidine-1,2-dicarboxylate (6.05 g, 25.0 mmol) in THE (30 mL) slowly. The reaction was stirred at 0° C. for 1 h and then at room temperature for 3 h. The reaction was quenched with sat. aq. solution of $NH_4C_1$ and extracted with EtOAc. The combined organics were dried over $Na_2SO_4$, filtered, concentrated, and purified by column chromatography on silica gel (0-20% EtOAc in hexanes) to provide the product (3.98 g, 66% yield) as a colorless oil. $^1$H NMR (300 MHz, $CDCl_3$) δ 4.97-5.04 (m, 2H), 4.36-4.53 (m, 1H), 4.09 (s, 1H), 4.05 (s, 1H), 3.72 (s, 3H), 2.86-3.05 (m, 1H), 2.56-2.67 (m, 1H), 1.47 (s, 3H), 1.42 (s, 6H). MS (ESI): Calcd for $C_{12}H_{20}NO_4^+$242.14 [M+H]$^+$, found 242.15 [M+H]$^+$.

Step 2)

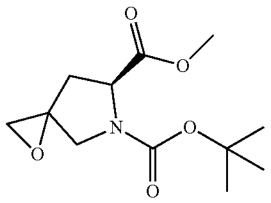 [SMILES: COC(=O)[C@@H]1CC2(CO2)CN1C(=O)OC(C)(C)C]

5-(tert-butyl) 6-methyl (6S)-1-oxa-5-azaspiro[2.4]heptane-5,6-dicarboxylate

To a solution of 1-(tert-butyl) 2-methyl (S)-4-methylenepyrrolidine-1,2-dicarboxylate (1.85 g, 7.7 mmol) in DCM (50 mL) was added mCPBA (4.29 g, 77%, 19.1 mmol) at 0° C. The reaction was stirred at 0° C. to room temperature for 8 h. TLC showed starting material was remaining. Another batch of mCPBA (2.00 g, 8.9 mmol) was added. It was stirred at room temperature overnight. The reaction was quenched with 10% aq. $Na_2SO_3$ solution, extracted with EtOAc. The organic phase was washed with sat. aq. $NaHCO_3$, water, brine, and dried over $Na_2SO_4$. After concentration, the residue was purified by column chromatography on silica gel (20-35% EtOAc in hexane) to provide two diastereomers (0.52 g, 26% and 1.39 g, 71% yield) as colorless powder. The relatively polar diastereomer's $^1$H NMR was provided. $^1$H NMR (300 MHz, $CDCl_3$) δ 4.42-4.60 (m, 1H), 3.78 (m, 1H), 3.77 (s, 3H), 3.48 (dd, J=12.4, 15.6 Hz, 1H), 2.19 (m, 1H), 2.89 (m, 1H), 2.58-2.73 (m, 1H), 1.91-2.04 (m, 1H), 1.47 (s, 3H), 1.43 (s, 6H). MS (ESI): Calcd for $C_{12}H_{20}NO_5^+$258.13 [M+H]$^+$, found 257.95[M+H]$^+$.

Step 3)

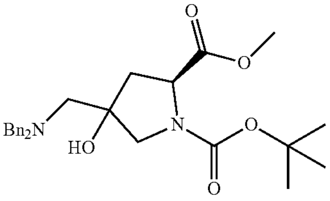

1-(tert-butyl) 2-methyl (2S)-4-((dibenzylamino)methyl)-4-hydroxypyrrolidine-1,2-dicarboxylate To a solution of the epoxide (1.2 g, 4.66 mmol) in ACN (10 mL) was added dibenzylamine (4 mL, 20 mmol) at 0° C. It was stirred at 0° C. to room temperature overnight. Then it was concentrated and loaded on silica gel column chromatography and purified with MeOH in EtOAc to provide the product (0.35 g, 21% yield). $^1$H NMR (300 MHz, $CDCl_3$) δ 7.35 (m, 10H), 4.16 (m, 1H), 3.75 (s, 3H), 3.58 (s, 4H), 3.53 (m, 1H), 3.17 (m, 1H), 2.66 (s, 2H), 2.02 (m, 2H), 1.43 (s, 3H), 1.39 (s, 6H). MS (ESI): Calcd for $C_{26}H_{35}N_2O_5^+$455.26 [M+H]$^+$, found 455.10 [M+H]$^+$.

Step 4)

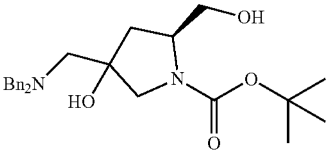

tert-butyl (2S)-4-((dibenzylamino)methyl)-4-hydroxy-2-(hydroxymethyl)pyrrolidine-1-carboxylate To a solution of 1-(tert-butyl) 2-methyl (2S)-4-((dibenzylamino)methyl)-4-hydroxypyrrolidine-1,2-dicarboxylate (165 mg, 0.36 mmol) in THE (5 mL) was added $LiBH_4$ (22 mg, 1 mmol) at room temperature. It was stirred at room temperature overnight and quenched with water, extracted with EtOAc, washed with water, brine and dried over anhydrous $Na_2SO_4$. The concentrated crude colorless oil was used for next step reaction without further purification (0.15 g, 98% yield). MS (ESI): Calcd for $C_{26}H_{35}N_2O_4^+$ 427.26 [M+H]$^+$, found 427.15 [M+H]$^+$.

Step 5)

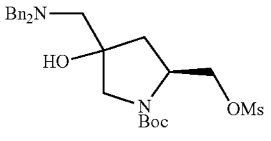

tert-butyl (2S)-4-((dibenzylamino)methyl)-4-hydroxy-2-(((methyl sulfonyl)oxy)methyl)pyrrolidine-1-carboxylate To a solution of tert-butyl (2S)-4-((dibenzylamino) methyl)-4-hydroxy-2-(hydroxymethyl)pyrrolidine-1-carboxylate (0.15 g, 0.36 mmol) in DCM (5 mL) was added DIEA (0.12 mL, 0.7 mmol). Then MsCl (0.035 mL, 0.44 mmol) was added at 0° C. It was stirred at 0° C. to room temperature overnight and extracted with EtOAc, washed with water, $NaHCO_3$, brine and dried over $Na_2SO_4$. After filtering off, the filtrate was concentrated and loaded on silica gel column with 0-30% EtOAc in hexane as eluents to provide the mesylate (0.15 g, 83% yield). MS (ESI): Calcd for $C_{26}H_{37}N_2O_6^+$505.23 $[M+H]^+$, found 505.20 $[M+H]^+$.

Step 6)

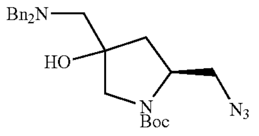

tert-butyl (2S)-2-(azidomethyl)-4-((dibenzylamino) methyl)-4-hydroxypyrrolidine-1-carboxylate To a solution of tert-butyl (2S)-4-((dibenzylamino) methyl)-4-hydroxy-2-(((methylsulfonyl)oxy)methyl)pyrrolidine-1-carboxylate (0.15 g, 0.3 mmol) in DMF (2 mL) was added NaN3 under $N_2$. It was heated at 90° C. overnight. Then the reaction mixture was diluted with EtOAc, washed with water, brine and dried over $Na_2SO_4$. After concentration it was purified by column chromatography on silica gel to provide the above intermediate (0.045 g, 33% yield). MS (ESI): Calcd for $C_{25}H_{34}N_5O_3^+$452.26 $[M+H]^+$, found 452.20 $[M+H]^+$.

Preparation of Amine Intermediate G: benzyl (R)-(1-amino-3-(2-(((benzyloxy)carbonyl)amino)ethoxy) propan-2-yl)carbamate

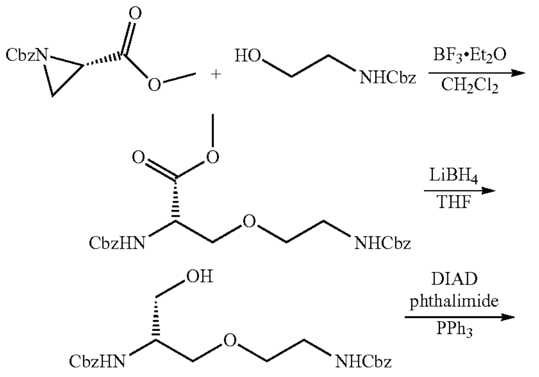

-continued

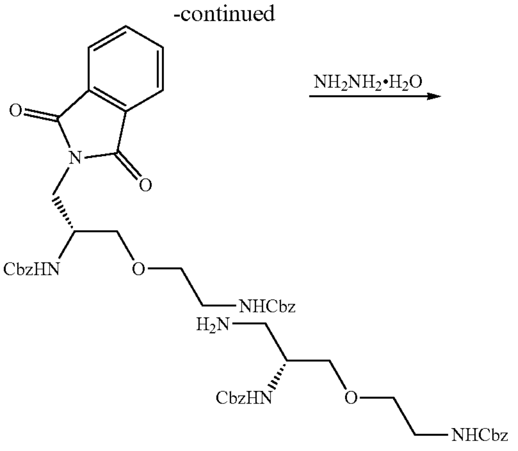

Amine intermediate G

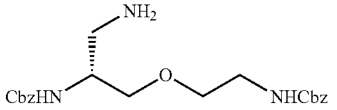

benzyl (R)-(1-amino-3-(2-(((benzyloxy)carbonyl) amino)ethoxy)propan-2-yl)carbamate To a solution of benzyl (R)-(1-(2-(((benzyloxy)carbonyl) amino)ethoxy)-3-(1,3-dioxoisoindolin-2-yl)propan-2-yl) carbamate (9.0 g, 16.9 mmol) in EtOH (80 mL) was added $NH_2NH_2 \cdot H_2O$ (5 mL, 103 mmol). It was stirred at room temperature overnight, then the white ppt was filtered off and washed with EtOH. The filtrate was concentrated and dissolved in EtOAc, then washed with water, sat. $NaHCO_3$ solution and brine. After dried over anhydrous $Na_2SO_4$, it was concentrated and purified by column chromatography on silica gel to provide a colorless oil (5.8 g, 86% yield). (300 MHz, $CDCl_3$) δ 7.27-7.38 (m, 10H), 5.28 (br s, 1H), 5.20 (br s, 1H), 5.09 (s, 4H), 3.75 (m, 1H), 3.57 (m, 1H), 3.49 (m, 5H), 3.36 (m, 2H). MS (ESI): Calcd for $C_{21}H_{28}N_3O_5$ 402.21 $[M+H]^+$, found 401.95 $[M+H]^+$.

The requisite intermediates were prepared as follows:

Step 1)

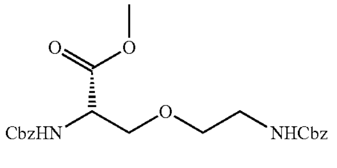

methyl N-((benzyloxy)carbonyl)-O-(2-(((benzyloxy) carbonyl)amino)ethyl)-L-serinate To a solution of benzyl (2-hydroxyethyl)carbamate (17.9 g, 92 mmol) and (S)-1-benzyl 2-methyl aziridine-1,2-dicarboxylate (7.2 g, 30.5 mmol) in $CH_2Cl_2$ (130 mL) was added $BF_3 \cdot Et_2O$ (1.92 mL, 15.3 mmol) at 0° C. slowly under $N_2$. The reaction mixture was allowed to warm slowly to r.t. and was stirred overnight. The reaction mixture was partitioned between DCM and saturated $Na_2CO_3$. The combined organic phase was washed with brine and dried over anhydrous $Na_2SO_4$, filtered, and concentrated. The crude product was purified by column chromatography on silica gel (0-50% EtOAc in hexane) to give methyl N-((benzyloxy)carbonyl)-O-(2-(((benzyloxy)carbonyl)amino)ethyl)-L-serinate (10.15 g, 77% yield). $^1H$ NMR (300 MHz, $CDCl_3$) δ 7.29-7.43 (m, 10H), 5.63 (br d, 1H), 5.11 (s, 2H), 5.08 (s, 2H), 5.04 (br s, 1H), 4.50 (m, 1H), 3.84 (m, 1H), 3.73 (s, 3H), 3.68 (m, 1H), 3.50 (m, 2H), 3.35 (m, 2H). MS (ESI): Calcd for $C_{22}H_{27}N_2O_7$ 431.18 $[M+H]^+$, found 431.05 $[M+H]^+$.

Step 2)

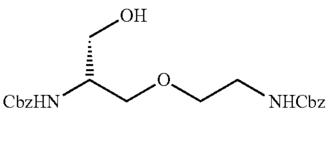

benzyl (R)-(1-(2-(((benzyloxy)carbonyl)amino)ethoxy)-3-hydroxypropan-2-yl)carbamate To a solution of methyl N-((benzyloxy)carbonyl)-O-(2-(((benzyloxy)carbonyl)amino)ethyl)-L-serinate (10.15 g, 23.6 mmol) in THE (250 mL) was added $LiBH_4$ (1.03 g, 47.2 mmol) at r.t. It was stirred at r.t. overnight and quenched with water, extracted with EtOAc, washed with water, brine and dried over anhydrous $Na_2SO_4$. The concentrated crude product was purified on silica gel column chromatography using 50-80% EtOAc in hexane to provide benzyl (R)-(1-(2-(((benzyloxy)carbonyl)amino)ethoxy)-3-hydroxypropan-2-yl)carbamate (8.25 g, 87% yield) as a colorless oil. MS (ESI): Calcd for $C_{21}H_{27}N_2O_6^+$ 403.19 $[M+H]^+$, found 403.05 $[M+H]^+$.

Step 3)

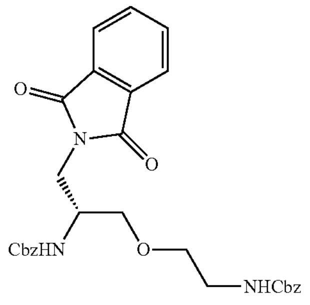 [SMILES: O=C(NCCOC[C@@H](CN1C(=O)c2ccccc2C1=O)NC(=O)OCc1ccccc1)OCc1ccccc1]

benzyl (R)-(1-(2-(((benzyloxy)carbonyl)amino)ethoxy)-3-(1,3-dioxoisoindolin-2-yl)propan-2-yl)carbamate To a solution of benzyl (R)-(1-(2-(((benzyloxy)carbonyl)amino)ethoxy)-3-hydroxypropan-2-yl)carbamate (8.23 g, 20.5 mmol) in THE (150 mL) was added phthalimide (4.44 g, 30.2 mmol) and $PPh_3$ (7.92 g, 30.2 mmol). Then DIAD (5.93 mL, 30.2 mmol) was added slowly at 0° C. under $N_2$. It was stirred at 0° C. to r.t. overnight, then quenched with water, extracted with EtOAc, washed with water and brine, dried and concentrated. The crude product was loaded on silica gel column chromatography and purified with 0-70% EtOAc in hexane to provide the product (8.0 g, 73% yield) as a colorless oil. MS (ESI): Calcd for $C_{29}H_{30}N_3O_7^+$ 532.20 $[M+H]^+$, found 532.10 $[M+H]^+$.

Preparation of Amine Intermediate H: benzyl tert-butyl ((S')-5-((R)-3-amino-2-(((benzyloxy)carbonyl)amino-propoxy)pentane-1,4-diyl)dicarbamate

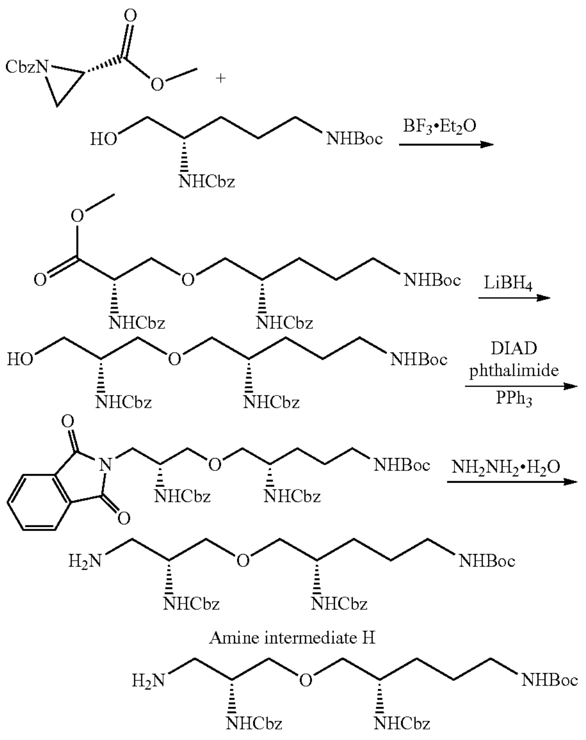

benzyl tert-butyl ((S)-5-((R)-3-amino-2-(((benzyloxy)carbonyl)amino)propoxy)pentane-1,4-diyl)dicarbamate To a solution of benzyl tert-butyl ((S)-5-((R)-2-(((benzyloxy)carbonyl)amino)-3-(1,3-dioxoisoindolin-2-yl)propoxy)pentane-1,4-diyl)dicarbamate (140 mg, 0.2 mmol) in EtOH (5 mL) was added $NH_2NH_2 \cdot H_2O$ (0.1 mL, 2 mmol). It was stirred at r.t., then the white ppt was filtered off and washed with EtOH. The filtrate was concentrated and dissolved in EtOAc, then washed with water, sat. $NaHCO_3$ solution and brine. After dried over anhydrous $Na_2SO_4$, it was concentrated and purified by column chromatography on silica gel to provide a colorless oil (87 mg, 78% yield). MS (ESI): Calcd for $C_{29}H_{43}N_4O_7$ 559.31 $[M+H]^+$, found 559.20 $[M+H]^+$ The requisite intermediates were prepared as follows:

Step 1)

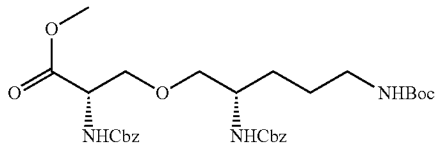 [SMILES: COC(=O)[C@H](COC[C@H](CCCNC(=O)OC(C)(C)C)NC(=O)OCc1ccccc1)NC(=O)OCc1ccccc1]

methyl N-((benzyloxy)carbonyl)-O—((S)-2-(((benzyloxy)carbonyl)amino)-5-((tert-butoxycarbonyl)amino)pentyl)-L-serinate To a solution of tert-butyl (2-hydroxyethyl)carbamate (1.4 g, 4 mmol) and (S)-1-benzyl 2-methyl aziridine-1,2-dicarboxylate (0.94 g, 4 mmol) in $CH_2Cl_2$ (20 mL) was added $BF_3 \cdot Et_2O$ (0.13 mL, 1 mmol) at 0° C. slowly under $N_2$. The reaction mixture was allowed to warm to r.t. and was stirred overnight. The reaction mixture was partitioned between DCM and saturated $NaHCO_3$. The combined organic phase was washed with brine and dried over anhydrous $Na_2SO_4$, filtered, and concentrated. The crude product was purified by column chromatography on silica gel (0-50% EtOAc in hexane) to give the product (0.50 g, 21% yield) as a colorless oil. MS (ESI): Calcd for $C_{30}H_{42}N_3O_9^+$588.29 $[M+H]^+$, found 588.20 $[M+H]^+$ Step 2)

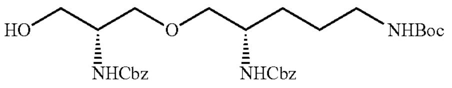 [SMILES: CC(C)(C)OC(=O)NCCC[C@@H](COC[C@@H](CO)NC(=O)OCc1ccccc1)NC(=O)OCc1ccccc1]

benzyl tert-butyl ((5)-5-((R)-2-(((benzyloxy)carbonyl)amino)-3-hydroxypropoxy)pentane-1,4-diyl) dicarbamate To a solution of methyl N-((benzyloxy)carbonyl)-O—((S)-2-(((benzyloxy)carbonyl)amino)-5-((tert-butoxycarbonyl)amino)pentyl)-L-serinate (0.46 g, 0.78 mmol) in THF (5 mL) was added $LiBH_4$ (55 mg, 2.5 mmol) at r.t. It was stirred at r.t. overnight and then quenched with water, extracted with EtOAc, washed with water, brine and dried over $Na_2SO_4$. The concentrated crude product was purified on a silica gel column chromatography using 0-100% EtOAc in hexane to provide the alcohol (0.155 g, 36% yield) as a colorless oil. $^1H$ NMR (300 MHz, $CDCl_3$) δ 7.30-7.40 (m, 10H), 5.64 (br s, 1H), 5.10 (m, 4H), 3.94 (m, 2H), 3.82 (m, 1H), 3.70 (m, 1H), 3.58 (m, 3H), 3.47 (m, 2H), 3.35 (m, 1H), 1.54 (m, 4H), 1.44 (s, 9H). MS (ESI): Calcd for $C_{29}H_{42}N_3O_8$ 560.30 $[M+H]^+$, found 560.20 $[M+H]^+$.

Step 3)

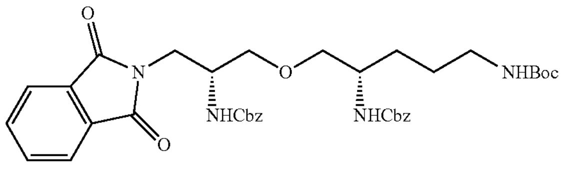 [SMILES: CC(C)(C)OC(=O)NCCC[C@@H](COC[C@@H](CN1C(=O)c2ccccc2C1=O)NC(=O)OCc1ccccc1)NC(=O)OCc1ccccc1]

benzyl tert-butyl ((S)-5-((R)-2-(((benzyloxy)carbonyl)amino)-3-(1,3-dioxoisoindolin-2-yl)propoxy) pentane-1,4-diyl)dicarbamate To a solution of benzyl tert-butyl ((S)-5-((R)-2-(((benzyloxy)carbonyl)amino)-3-hydroxypropoxy)pentane-1,4-diyl) dicarbamate (0.155 g, 0.27 mmol) in THF (5 mL) was added phthalimide (0.061 g, 0.4 mmol) and $PPh_3$ (0.11 g, 0.4 mmol). Then DIAD (0.08 mL, 0.4 mmol) was added slowly at 0° C. under $N_2$. It was stirred at 0° C. to r.t. for 5 hrs, then quenched with water, extracted with EtOAc, washed with water and brine, dried and concentrated. The crude product was loaded on a silica gel column chromatography and purified with 0-70% EtOAc in hexane to provide the product (0.14 g, 75% yield) as a colorless oil. $^1H$ NMR (300 MHz, $CDCl_3$) δ 7.80 (m, 2H), 7.70 (m, 2H), 7.34 (m, 5H), 7.27 (m, 5H), 5.51 (br s, 1H), 5.08 (m, 2H), 4.99 (m, 2H), 4.15 (m, 1H), 3.90 (m, 3H), 3.84 (m, 1H), 3.48 (m, 1H), 3.45 (m, 1H), 3.35 (m, 1H), 3.17 (m, 1H), 3.11 (m, 1H), 1.58 (m, 4H), 1.43 (s, 9H). MS (ESI): Calcd for $C_{37}H_{44}N_4NaO_9^+$711.30 $[M+Na]^+$, found 711.25 $[M+Na]^+$.

Preparation of amine I: (S)-di-tert-butyl (4-amino-2-((triisopropylsilyl)oxy)butane-1,3-diyl)dicarbamate

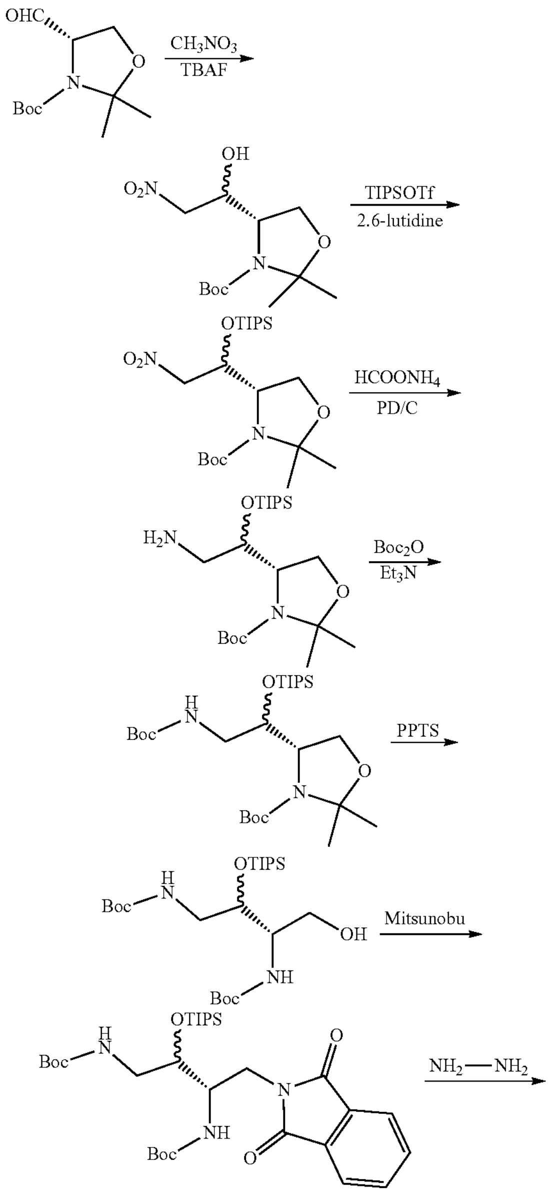

-continued

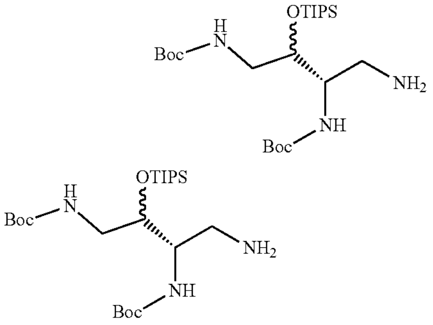

di-tert-butyl (4-amino-2-((triisopropylsilyl)oxy)butane-1,3-diyl)(S)-dicarbamate To a solution of 110 mg of (S)-di-tert-butyl (4-(1,3-dioxoisoindolin-2-yl)-2-((triisopropylsilyl) oxy)butane-1,3-diyl)dicarbamate (0.18 mmol) in 2 mL of methanol was added 0.1 mL of hydrazine hydrate. Reaction mixture was stirred at 50° C. for 1 hour then cooled to room temperature. Solvent removed by rotovapor, white solid was filter of and washed with dichloromethane. Combined organic layer washed with water, brine and dried over $Na_2SO_4$. Solvent removed and residue was purified on column to give 72 mg amine, 83.7%. 1H NMR (300 MHz, CDCl3) δ 5.01-5.18 (br s, 1H), 3.98-4.02 (br s, 1H), 3.52-3.16 (br s, 1H), 3.18-3.26 (m, 1H), 2.73-2.96 (br s, 1H), 1.55-1.93 (br s, 1H), 1.41 (s, 18H), 1.00-1.11 (m, 3H), 1.05 (s, 18H);

The requisite intermediates were prepared as follows:

Step 1)

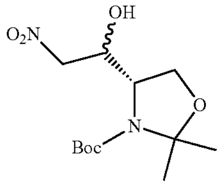 [SMILES: CC(C)(C)OC(=O)N1[C@H](C(O)C[N+](=O)[O-])COC1(C)C]

tert-butyl (S)-4-(1-hydroxy-2-nitroethyl)-2,2-dimethyloxazolidine-3-carboxylate

To a solution of (S)-tert-butyl 4-formyl-2,2-dimethyloxazolidine-3-carboxylate (5.0 g, 20.6 mmol) in 10 mL of nitromethane (178 mmol) was added 3 mL of TBAF solution (1.0 M/THF, 3 mmol) at 0° C. with stirring. Resulting reaction mixture was stirred at room temperature overnight then diluted with 100 mL of EtOAc. The mixture was continuously washed with 0.5 N HCl, water, aq. Sat. $NaHCO_3$, brine then dried over $Na_2SO_4$. Solvent removed and residue was purified on column to give 5.2 g nitro compound as white solid, 82%. 1H NMR (300 MHz, CDCl3) δ 4.78 (br s, 1H), 4.38-4.51 (m, 3H), 3.39-4.19 (m, 3H), 1.58 (s, 3H), 1.56 (s, 3H), 1.49 (s, 9H);

Step 2)

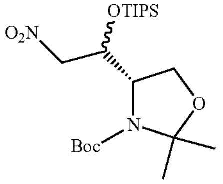

tert-butyl (S)-2,2-dimethyl-4-(2-nitro-1-((triisopropylsilyl)oxy)ethyl)oxazolidine-3-carboxylate To solution of (S)-tert-butyl 4-(1-hydroxy-2-nitroethyl)-2,2-dimethyloxazolidine-3-carboxylate (1.2 g, 41.4 mmol) in 30 mL of dichloromethane was added 2,6-lutidine (0.65 mL, 5.6 mmol) and TIPSOTf (1.4 mL, 5.2 mmol) dropwise at 0° C. Reaction mixture was stirred at room temperature overnight then diluted with 30 mL of dichloromethane. The mixture was washed with 0.5 N HCl, water, aq. Sat. $NaHCO_3$, brine and dried over $Na_2SO_4$. Solvent removed and residue was purified on column to give 1.6 g product as oil, 86.7%. 1H NMR (300 MHz, CDCl3) δ 4.64 (br s, 1H), 4.39-4.52 (m, 2H), 4.00-4.11 (m, 2H), 3.94 (br s, 1H), 1.48-1.59 (m, 3H), 1.48 (s, 9H), 1.06 (s, 18H).

Step 3)

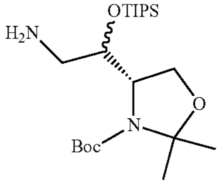

tert-butyl (S)-4-(2-amino-1-((triisopropylsilyl)oxy) ethyl)-2,2-dimethyloxazolidine-3-carboxylate To solution of (S)-tert-butyl 2,2-dimethyl-4-(2-nitro-1-((triisopropylsilyl)oxy)ethyl) oxazolidine-3-carboxylate (1.4 g, mmol) in 20 mL of methanol was added 0.5 g of Pd/C (10%) and 2.2 g of $HCOONH_4$. Reaction mixture was stirred at room temperature overnight then filtered through a peddle of celite, washed with methanol and then concentrated. Residue was purified on column to give 0.66 g product of free amine as oil, 59%. 1H NMR (300 MHz, CDCl3) δ 4.00-4.13 (m, 2H), 3.55-3.90 (m, 2H), 2.60-2.80 (m, 2H), 1.50-1.65 (m, 3H), 1.57 (s, 3H), 1.51 (s, 3H), 1.48 (s, 9H), 1.06 (s, 18H).

Step 4)

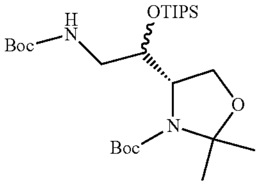

tert-butyl (S)-4-(3,3-diisopropyl-2,10,10-trimethyl-8-oxo-4,9-dioxa-7-aza-3-silaundecan-5-yl)-2,2-dimethyloxazolidine-3-carboxylate To a solution of 0.6 g of (S)-tert-butyl 4-(2-amino-1-((triisopropylsilyl)oxy)ethyl)-2,2-dimethyloxazolidine-3-carboxylate (4, 0.6 g, mmol) in 10 mL of dichloromethane was added 0.6 g of triethylamine and 0.35 g of $Boc_2O$. Reaction mixture was stirred at room temperature overnight then diluted with 20 mL of dichloromethane. The mixture was washed with 0.5 N HCl, water, aq. Sat. $NaHCO_3$, brine and dried over $Na_2SO_4$. Solvent removed and residue was purified on column to give 0.42 g protected diamine as colorless oil, 56.4%. 1H NMR (300 MHz, CDCl3) δ 5.22-5.30 (br s, 1H), 4.07-4.32 (m, 1H), 3.89-3.92 (m, 2H), 3.35-3.67 (m, 1H), 3.00-3.18 (m, 1H), 1.51-1.64 (m, 3H), 1.61 (s, 3H), 1.52 (s, 3H), 1.48 (s, 9H), 1.47 (s, 9H), 1.08 (s, 18H).

Step 5)

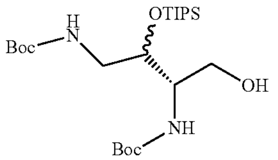

di-tert-butyl (4-hydroxy-2-((triisopropylsilyl)oxy) butane-1,3-diyl)(S)-dicarbamate To a solution of 0.42 g of (S)-tert-butyl 4-(3,3-diisopropyl-2,10,10-trimethyl-8-oxo-4,9-dioxa-7-aza-3-silaundecan-5-yl)-2,2-dimethyloxazolidine-3-carboxylate (0.81 mmol) in 10 mL of methanol was added PPTS (121 mg, 0.48 mmol). Reaction mixture was stirred at reflux for 4 hour then cooled to room temperature. The mixture was washed with 0.5 N HCl, water, aq. Sat. $NaHCO_3$, brine and dried over $Na_2SO_4$. Solvent removed and residue was purified on column to give 100 mg alcohol as colorless oil, 26.0%. 1H NMR (300 MHz, CDCl3) δ 5.24 (br s, 1H), 4.93 (br s, 1H), 4.03-4.09 (m, 1H), 3.93 (d, J=9 Hz, 1H), 3.60-3.73 (m, 2H), 3.20-3.38 (m, 2H), 3.05 (br s, 1H), 1.41 (s, 9H), 1.39 (s, 9H), 0.99-1.05 (m, 3H), 1.06 (d, J=3 Hz, 18H).

Step 6)

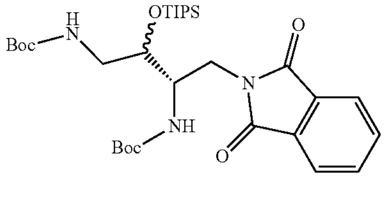

di-tert-butyl (4-(1,3-dioxoisoindolin-2-yl)-2-((triisopropylsilyl)oxy)butane-1,3-diyl)(S)-dicarbamate To a solution of 100 mg of (S)-di-tert-butyl (4-hydroxy-2-((triisopropylsilyl)oxy)butane-1,3-diyl)dicarbamate (0.21 mmol) in 10 mL of THE was added isoindoline-1,3-dione (34 mg, 0.23 mmol), triphenylphosphine (30 mg, 0.27 mmol) and (E)-diisopropyl diazene-1,2-dicarboxylate (46 mg, 0.23) at 0° C. Reaction mixture was stirred at room temperature overnight. The mixture was poured into 10 mL of water and extracted with 3×10 mL of EtOAc followed by washing with 0.5 N HCl, water, aq. Sat. $NaHCO_3$, brine and dried over $Na_2SO_4$. Solvent removed and residue was purified on column to give 110 mg product as white solid, 86.8%. 1H NMR (300 MHz, CDCl3) δ 7.79-7.85 (m, 2H), 7.65-7.68 (m, 2H), 5.07 (br s, 1H), 4.95 (d, J=9.3 Hz, 1H), 4.05-4.13 (m, 2H), 3.80-3.91 (m, 2H), 3.49 (br s, 1H), 3.22-3.31 (m, 1H), 1.44 (s, 9H, 1.18-1.30 (m, 3H), 1.21 (s, 9H), 1.09 (s, 18H).

Example 1. Preparation of N-((2S,3R)-2,5-diamino-3-hydroxypentyl)-3-(4-fluorophenyl)-1H-indole-2-carboxamide hydrogen chloride salt

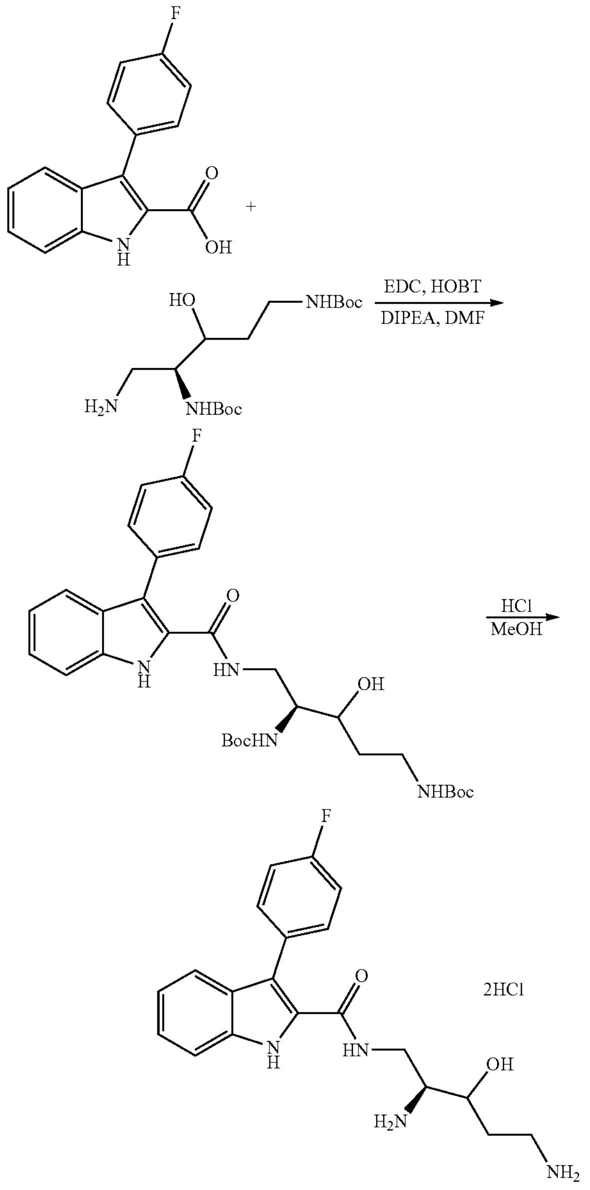

-continued

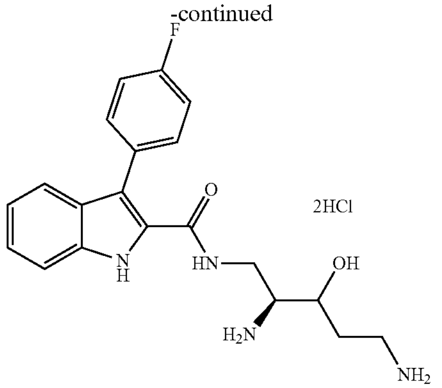

N-((2S)-2,5-diamino-3-hydroxypentyl)-3-(4-fluorophenyl)-1H-indole-2-carboxamide hydrogen chloride salt To a solution of di-tert-butyl ((4S)-5-(3-(4-fluorophenyl)-1H-indole-2-carboxamido)-3-hydroxypentane-1,4-diyl)dicarbamate (80 mg, 0.14 mmol) in MeOH (5 mL) was added HCl (4 M in dioxane, 0.5 mL, 2 mmol). The reaction mixture was stirred at 50° C. for 1 h then concentrated to give a residue. The residue was triturated with EtOAc to give the desired product (52 mg, 84% yield) as a yellow solid. $^{1}H$ NMR (300 MHz, $D_2O$) δ 7.51 (m, 4H), 7.33 (m 1H), 7.23 (m, 2H), 7.15 (m, 1H), 3.92 (m, 1H), 3.66 (m, 1H), 3.48 (m, 2H), 3.07 (m, 2H), 1.81 (m, 2H). MS (ESI): Calcd for $C_{20}H_{24}FN_4O_2^+$ 371.19 $[M+H]^+$, found 371.05 $[M+H]^+$.

The requisite intermediate was prepared as shown in the following step.

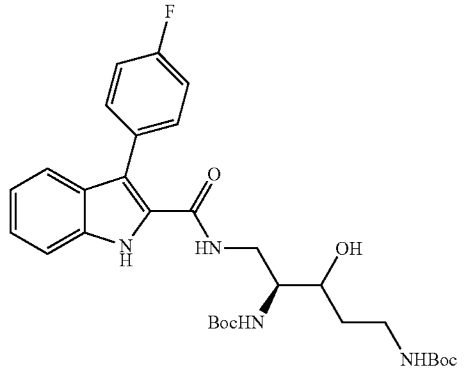 [SMILES: CC(C)(C)OC(=O)NCCC(O)[C@H](CNC(=O)c1[nH]c2ccccc2c1-c1ccc(F)cc1)NC(=O)OC(C)(C)C]

di-tert-butyl ((4S)-5-(3-(4-fluorophenyl)-1H-indole-2-carboxamido)-3-hydroxypentane-1,4-diyl)dicarbamate To a solution of 3-(4-fluorophenyl)-1H-indole-2-carboxylic acid (46 mg, 018 mmol) in dry DMF (1 mL) was added DIPEA (0.07 mL, 0.36 mmol), HOBt (15 mg, 0.11 mmol) and EDC (38 mg, 0.21 mmol). The reaction mixture was stirred at room temperature for 10 min then di-tert-butyl ((3R,4S)-5-amino-3-hydroxypentane-1,4-diyl) dicarbamate (AA) (60 mg, 0.18 mmol) was added. The reaction mixture was stirred at room temperature overnight then added $H_2O$ with stirring. A solid was formed and collected by filtration. After air drying the solid was purified by chromatography on silica gel. Elution with 50% EtOAc/hexanes afforded the desired compound (80 mg, 78% yield) as greenish yellow solid. $^{1}H$ NMR (300 MHz, $CDCl_3$) δ 9.70 (br s, 1H), 7.10-7.51 (m, 8H), 6.53 (br s, 1H), 4.94 (br, 2H), 4.50 (br s, 1H), 3.90 (m, 1H), 3.50 (m, 4H), 3.09 (m, 1H), 1.30-1.70 (m, 20H).

Example 2. Preparation of N-((2S)-2,5-diamino-3-hydroxypentyl)-3-phenyl-1H-indole-2-carboxamide hydrogen chloride salt

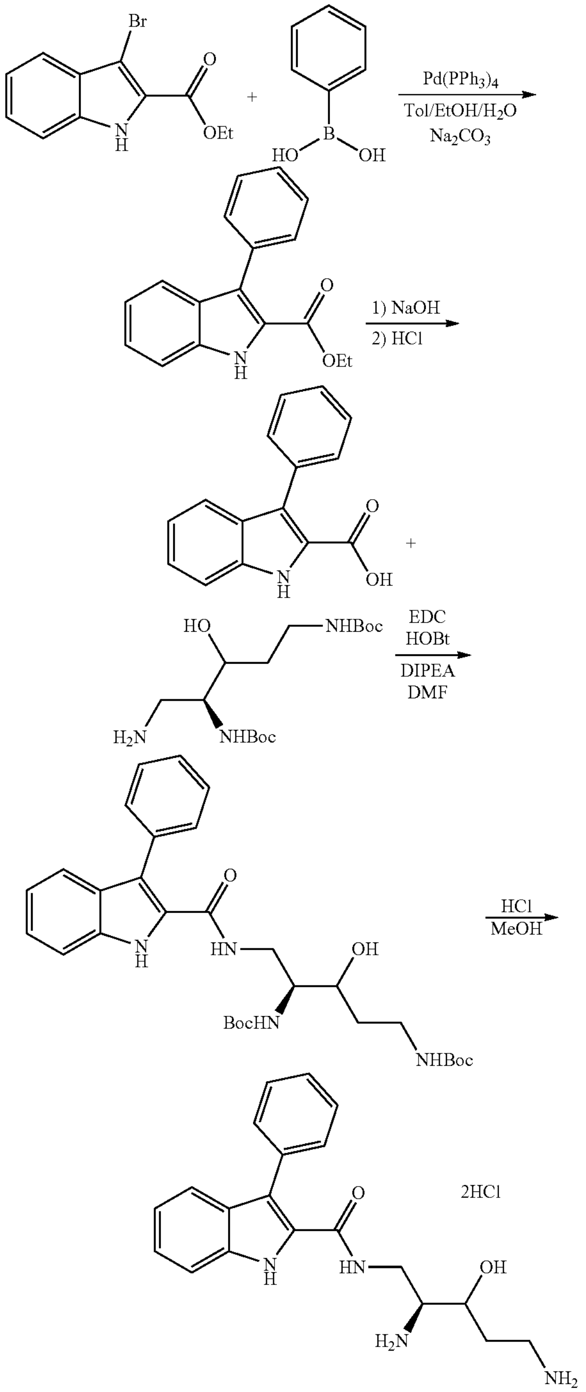

-continued

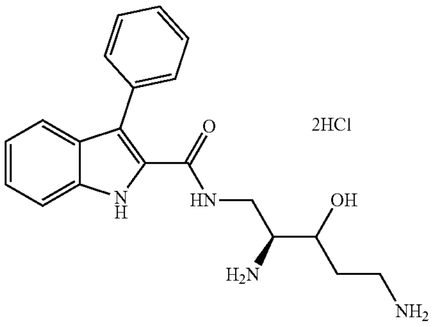 [SMILES: NCCC(O)[C@@H](N)CNC(=O)c1[nH]c2ccccc2c1-c1ccccc1]

N-((2S)-2,5-diamino-3-hydroxypentyl)-3-phenyl-1H-indole-2-carboxamide hydrogen chloride salt To a solution of di-tert-butyl ((4S)-3-hydroxy-5-(3-phenyl-1H-indole-2-carboxamido)pentane-1,4-diyl)dicarbamate (73 mg, 0.13 mmol) in MeOH (5 mL) was added HCl (4 M in dioxane, 0.5 mL, 2 mmol). The reaction mixture was stirred at 50° C. for 1 h then concentrated to give a residue. The residue was triturated with EtOAc to give the desired product (38 mg, 68% yield) as off white solid. $^1$H NMR (300 MHz, $D_2O$) δ 7.83 (m, 1H), 7.56 (m, 7H), 7.36 (m, 1H), 7.16 (m, 1H), 3.90 (d, J=9.9 Hz, 1H), 3.63 (m, 1H), 3.50 (m, 2H), 3.05 (m, 2H), 1.82 (m, 2H). MS (ESI): Calcd for $C_{20}H_{25}N_4O_2$ 353.20 $[M+H]^+$, found 353.00 $[M+H]^+$.

The requisite intermediates were prepared as shown in the following steps.

Step 1)

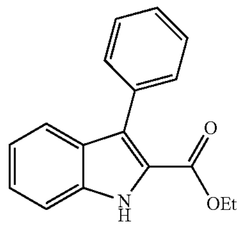 [SMILES: CCOC(=O)c1[nH]c2ccccc2c1-c1ccccc1]

ethyl 3-phenyl-1H-indole-2-carboxylate

The mixture of ethyl 3-bromo-1H-indole-2-carboxylate (1.35 g, 5 mmol), phenylboronic acid (1.0 g, 8.2 mmol), toluene, ethanol and saturated $Na_2CO_3$ solution (40/10/10 mL) was degassed and Pd(dppf)$Cl_2$ (50 mg, 0.068 mmol) was added. The reaction mixture was heated at 100° C. for 1 h, it was extracted with EtOAc and washed with brine and dried over $Na_2SO_4$, then concentrated. It was purified by column chromatography on silica gel with 0-20% EtOAc in hexane as eluents to give the product (0.63 g, 48% yield) as a white powder.

Step 2)

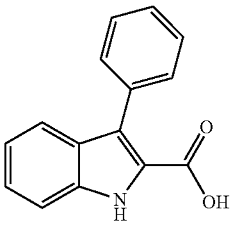 [SMILES: O=C(O)c1[nH]c2ccccc2c1-c1ccccc1]

3-phenyl-1H-indole-2-carboxylic acid

To a solution of ethyl 3-phenyl-1H-indole-2-carboxylate (630 mg, 2.37 mmol) in THE (10 mL) was added NaOH solution (2 M, 6 mL). It was heated at 50° C. overnight. THE was removed in vacuo and the residue was acidified with HCl solution. The precipitate was filtered and washed with water. It was dried to provide the product as a pale brown powder (480 mg, 85% yield) which was used for next step reaction without further purification. $^1$H NMR (300 MHz, DMSO-$d_6$) δ 11.55 (br s, 1H), 7.50 (m, 2H), 7.43 (m, 2H), 7.36 (m, 2H), 7.27 (m, 1H), 7.20 (m, 1H), 7.01 (m, 1H). MS (ESI): Calcd for $C_{15}H_{12}NO_2^+$ 238.09 $[M+H]^+$, found 237.85 $[M+H]^+$.

Step 3)

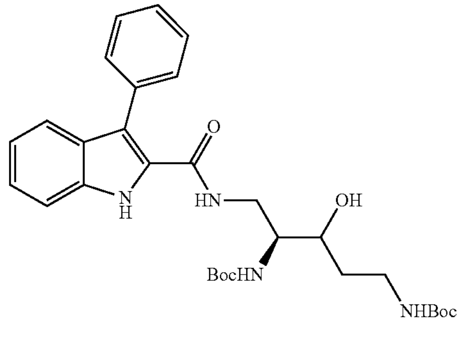 [SMILES: CC(C)(C)OC(=O)NCCC(O)[C@H](CNC(=O)c1[nH]c2ccccc2c1-c1ccccc1)NC(=O)OC(C)(C)C]

di-tert-butyl ((4S)-3-hydroxy-5-(3-phenyl-1H-indole-2-carboxamido)pentane-1,4-diyl)dicarbamate To a solution of 3-phenyl-1H-indole-2-carboxylic acid (43 mg, 018 mmol) in dry DMF (1 mL) was added DIPEA (0.07 mL, 0.36 mmol), HOBt (15 mg, 0.11 mmol) and EDC (38 mg, 0.21 mmol). The reaction mixture was stirred at room temperature for 10 min then di-tert-butyl ((3R,4S)-5-amino-3-hydroxypentane-1,4-diyl) dicarbamate (Amine Intermediate A) (60 mg, 0.18 mmol) was added. The reaction mixture was stirred at room temperature overnight then added $H_2O$ with stirring. A solid was formed and was collected by filtration. After air drying the solid was purified by chromatography on silica gel. Elution with 50% EtOAc/hexanes afforded the desired compound (73 mg, 73% yield) as greenish yellow solid. $^1$H NMR (300 MHz, $CDCl_3$) δ 9.73 (br s, 1H), 7.45-7.59 (m, 7H), 7.32 (m, 1H), 7.12 (m, 1H), 6.47 (br s, 1H), 4.99 (br s, 1H), 4.89 (d, J=8.7 Hz, 1H), 4.40 (d, J=4.2 Hz, 1H), 3.31-3.95 (m, 4H), 3.10 (m, 1H), 1.30-1.75 (m, 20H).

Example 3. Preparation of 3-(4-cyanophenyl)-N-((2S)-2,5-diamino-3-hydroxypentyl)-1H-indole-2-carboxamide hydrogen chloride salt

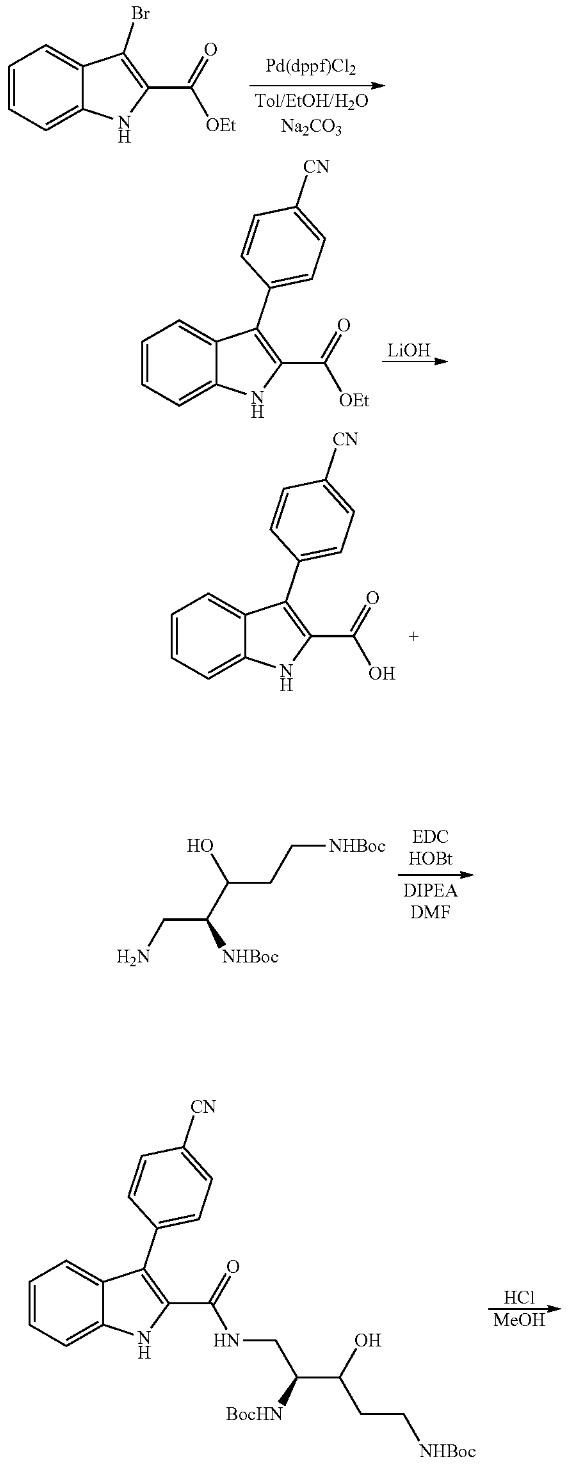

-continued

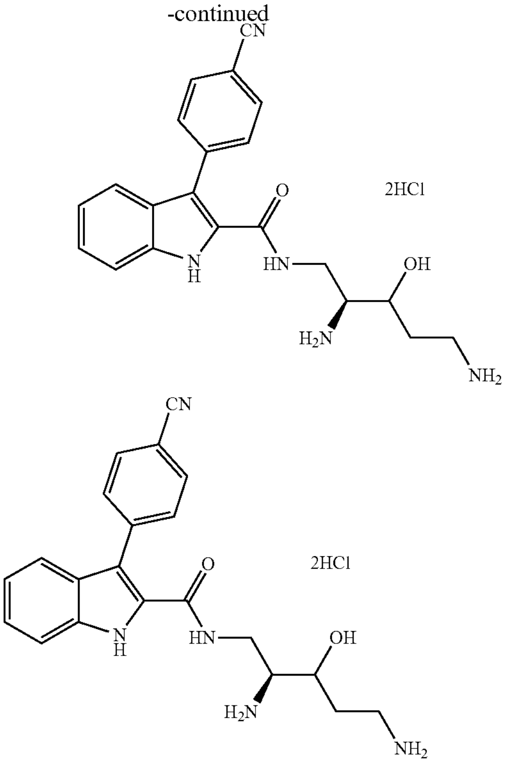

3-(4-cyanophenyl)-N-((2S)-2,5-diamino-3-hydroxypentyl)-1H-indole-2-carboxamide hydrogen chloride salt To a solution of di-tert-butyl ((4S)-5-(3-(4-cyanophenyl)-1H-indole-2-carboxamido)-3-hydroxypentane-1,4-diyl)dicarbamate (72 mg, 0.12 mmol) in MeOH (5 mL) was added HCl (4 M in dioxane, 0.5 mL, 2 mmol). The reaction mixture was stirred at 50° C. for 1 h then concentrated to give a residue. The residue was triturated with EtOAc to give the desired product (35 mg, 63% yield) as yellow solid. $^1$H NMR (300 MHz, $D_2O$) δ 7.80 (d, J 7.5 Hz, 2H), 7.57 (m, 4H), 7.37 (m, 1H), 7.16 (m, 1H), 3.95 (m, 1H), 3.67 (m, 1H), 3.50 (m, 2H), 3.08 (m, 2H), 1.83 (m, 2H). MS (ESI): Calcd for $C_{21}H_{24}N_5O_2$ 378.19 $[M+H]^+$, found 378.05 $[M+H]^+$.

The requisite intermediates were prepared as shown in the following steps.

Step 1)

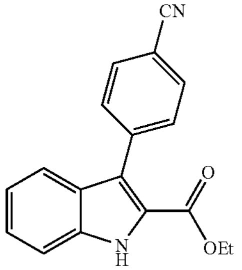 [SMILES: CCOC(=O)c1[nH]c2ccccc2c1-c1ccc(C#N)cc1]

ethyl 3-(4-cyanophenyl)-1H-indole-2-carboxylate

The mixture of ethyl 3-bromo-5-1H-indole-2-carboxylate (268 mg, 1.0 mmol), (4-cyanophenyl)boronic acid (220 mg, 1.5 mmol), toluene, ethanol and saturated $Na_2CO_3$ solution (15/4/4 mL) was degassed and Pd(dppf)$Cl_2$ (50 mg, 0.07 mmol) was added. The reaction mixture was heated at 105° C. overnight, it was extracted with EtOAc and washed with brine and dried over $Na_2SO_4$, then concentrated. It was purified by column chromatography on silica gel with 0-15% EtOAc in hexane as eluents to give the product (126 mg, 43% yield) as an off-white powder. $^1$H NMR (300 MHz, $CDCl_3$) δ 9.08 (br s, 1H), 7.75 (d, J=6.3 Hz, 2H), 7.68 (d, J=6.3 Hz, 2H), 7.57 (m, 1H), 7.48 (m, 1H), 7.40 (m, 1H), 7.19 (m, 1H), 4.31 (q, J=7.1 Hz, 2H), 1.26 (t, J=7.1 Hz, 3H). MS (ESI): Calcd for $C_{18}H_{19}N_2O_2^+$291.11 [M+H]$^+$, found 291.20 [M+H]$^+$.

Step 2)

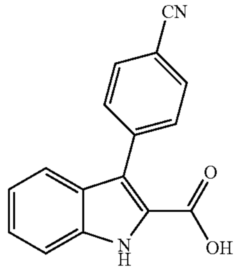 [SMILES: N#Cc1ccc(-c2c(C(=O)O)[nH]c3ccccc23)cc1]

3-(4-cyanophenyl)-1H-indole-2-carboxylic acid

To a solution of ethyl 3-(4-cyanophenyl)-1H-indole-2-carboxylate (122 mg, 0.4 mmol) in THE (10 mL) was added LiOH solution (2 M, 2 mL). It was heated at 50° C. until no starting material left. THE was removed in vacuo and the residue was acidified with HCl solution. The precipitate was collected and washed with water. It was dried to provide the acid as a pale brown powder (95 mg, 86% yield) which was used for next step reaction without further purification. Calcd for $C_{16}H_{11}N_2O_2^+$ 263.08 [M+H]$^+$, found 263.10 [M+H]$^+$.

Step 3)

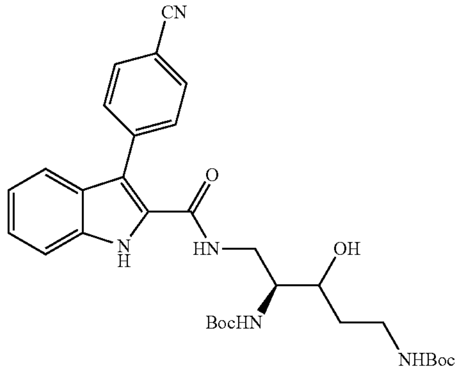 [SMILES: CC(C)(C)OC(=O)NCCC(O)[C@H](CNC(=O)c1[nH]c2ccccc2c1-c1ccc(C#N)cc1)NC(=O)OC(C)(C)C]

di-tert-butyl ((4S)-5-(3-(4-cyanophenyl)-1H-indole-2-carboxamido)-3-hydroxypentane-1,4-diyl)dicarbamate To a solution of 3-(4-cyanophenyl)-1H-indole-2-carboxylic acid (47 mg, 018 mmol) in dry DMF (1 mL) was added DIPEA (0.07 mL, 0.36 mmol), HOBt (15 mg, 0.11 mmol) and EDC (38 mg, 0.21 mmol). The reaction mixture was stirred at room temperature for 10 min then di-tert-butyl ((3R,4S)-5-amino-3-hydroxypentane-1,4-diyl) dicarbamate (Amine Intermediate A) (60 mg, 0.18 mmol) was added. The reaction mixture was stirred at room temperature overnight then added $H_2O$ with stirring. A solid was formed and collected by filtration. After air drying the solid was purified by chromatography on silica gel. Elution with 50% EtOAc/hexanes afforded the desired compound (72 mg, 69% yield) as green solid. $^1$H NMR (300 MHz, $CDCl_3$) δ 9.93 (br s, 1H), 7.82 (d, J=7.5 Hz, 2H), 7.65 (d, J=7.5 Hz, 2H), 7.48 (m, 2H), 7.34 (m, 1H), 7.16 (m, 1H), 6.76 (br s, 1H), 5.06 (d, J=8.7 Hz, 1H), 4.86 (br s, 1H), 4.47 (br s, 1H), 3.30-3.73 (m, 4H), 3.03 (m, 1H), 1.30-1.60 (m, 20H).

Example 4. Preparation of 3-cyclopentyl-N-((2S)-2,5-diamino-3-hydroxypentyl)-1H-indole-2-carboxamide hydrogen chloride salt

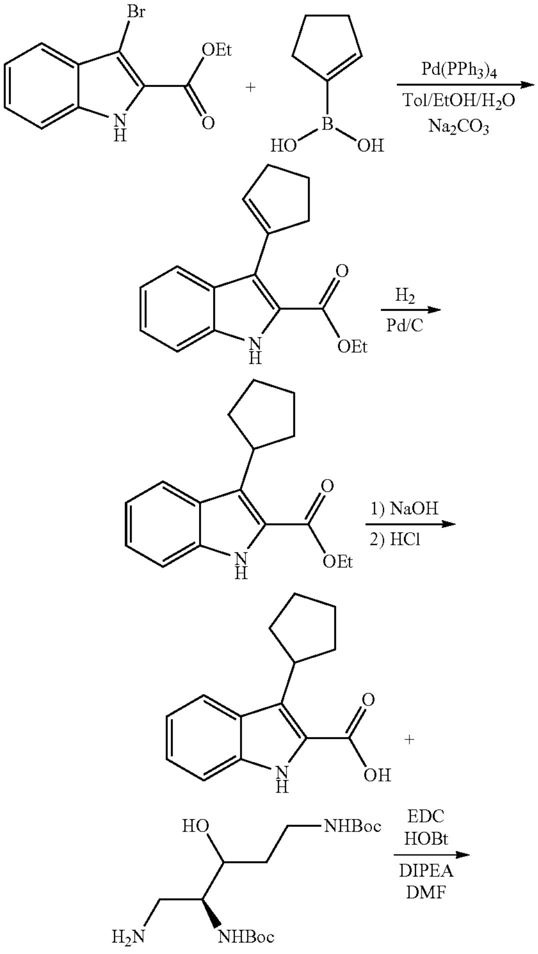

-continued

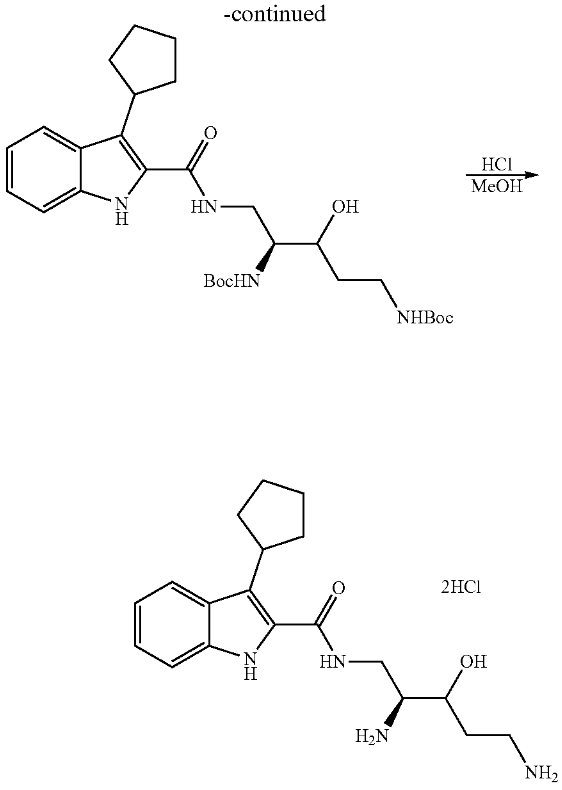

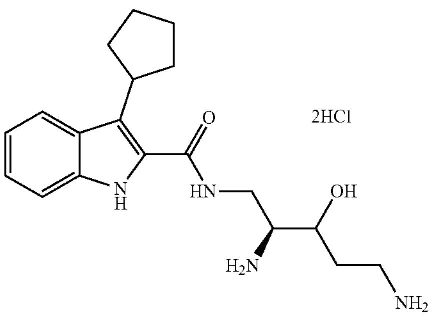 [SMILES: NCCC(O)[C@@H](N)CNC(=O)c1[nH]c2ccccc2c1C1CCCC1]

3-cyclopentyl-N-((2S)-2,5-diamino-3-hydroxypentyl)-1H-indole-2-carboxamide hydrogen chloride salt To a solution of di-tert-butyl ((4S)-5-(3-cyclopentyl-1H-indole-2-carboxamido)-3-hydroxypentane-1,4-diyl)dicarbamate (53 mg, 0.1 mmol) in MeOH (2 mL) was added HCl (4 M in dioxane, 0.5 mL, 2 mmol). The reaction mixture was stirred at 50° C. for 1 h then concentrated to give a residue. The residue was triturated with EtOAc to give the desired product (20 mg, 49% yield) as off white solid. $^1H$ NMR (300 MHz, $D_2O$) δ 7.83 (d, J=8.4 Hz, 1H), 7.47 (d, J=8.7 Hz, 1H), 7.30 (m, 1H), 7.11 (m, 1H), 4.06 (m, 2H), 3.78 (m, 1H), 3.59-3.69 (m, 3H), 3.14 (m, 2H), 1.81-2.03 (m, 6H), 1.70 (m, 2H), 1.17 (m, 2H). MS (ESI): Calcd for $C_{19}H_{29}N_4O_2$ 345.23 $[M+H]^+$, found 345.00 $[M+H]^+$.

The requisite intermediates were prepared as shown in the following steps.

Step 1)

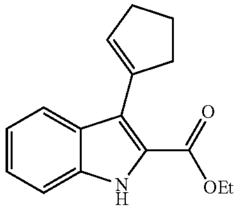 [SMILES: CCOC(=O)c1[nH]c2ccccc2c1C1=CCCC1]

ethyl 3-(cyclopent-1-en-1-yl)-1H-indole-2-carboxylate

Ethyl 3-bromo-1H-indole-2-carboxylate (1.6 g, 6 mmol) and cyclopent-1-en-1-ylboronic acid (1 g, 8.9 mmol) in a mixture of toluene, ethanol and saturated $Na_2CO_3$ solution (40/8/8 mL) was degassed and Pd(dppf)$Cl_2$ (150 mg, 0.2 mmol) was added. The reaction mixture was heated at 100° C. for 4 hours, it was extracted with EtOAc and washed with brine and dried over $Na_2SO_4$, then concentrated. It was purified by column chromatography on silica gel with 0-20% EtOAc in hexane as eluents to give the product (1.48 g, 97% yield) as a white powder. $^1H$ NMR (300 MHz, $CDCl_3$) δ 8.82 (br s, 1H), 7.73 (m, 1H), 7.37 (m, 1H), 7.33 (m, 2H), 7.16 (m, 1H), 5.98 (m, 1H), 4.39 (q, J=7.1 Hz, 2H), 2.81 (m, 2H), 2.62 (m, 2H), 2.08 (m, 2H), 1.41 (t, J=7.1 Hz, 3H).

Step 2)

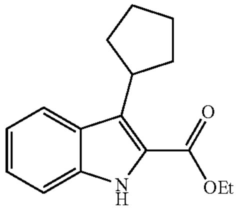 [SMILES: CCOC(=O)c1[nH]c2ccccc2c1C1CCCC1]

ethyl 3-cyclopentyl-1H-indole-2-carboxylate

To a solution of ethyl 3-(cyclopent-1-en-1-yl)-1H-indole-2-carboxylate (1.48 g, 5.8 mmol) in MeOH (50 mL) was added Pd/C (10 w/w %, 150 mg, 0.14 mmol). It was stirred under $H_2$ (50 psi) overnight. The catalyst was filter off through a Celite pad and washed with MeOH. The combined filtrate was concentrated and used without further purification (1.40 g, 94%).

Step 3)

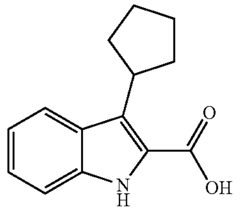 [SMILES: O=C(O)c1[nH]c2ccccc2c1C1CCCC1]

3-cyclopentyl-1H-indole-2-carboxylic acid

To a solution of ethyl 3-cyclopentyl-1H-indole-2-carboxylate (1.4 g, 5.4 mmol) in THE (10 mL) was added NaOH solution (2 M, 20 mL). It was heated at 50° C. overnight. THE was removed in vacuo and the residue was acidified with HCl solution. The precipitate was filtered and washed with water. It was dried to provide the acid as a pale brown powder (0.56 g, 45% yield) which was used for next step reaction without further purification. MS (ESI): Calcd for $C_{14}H_{16}NO_2^+$ 230.12 $[M+H]^+$, found 229.85 $[M+H]^+$.

Step 4)

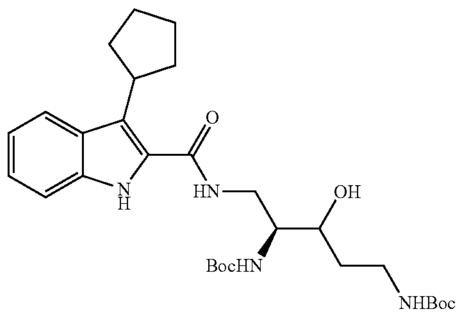 [SMILES: CC(C)(C)OC(=O)NCCC(O)[C@H](CNC(=O)c1[nH]c2ccccc2c1C1CCCC1)NC(=O)OC(C)(C)C]

di-tert-butyl ((4S)-5-(3-cyclopentyl-1H-indole-2-carboxamido)-3-hydroxypentane-1,4-diyl)dicarbamate To a solution of 3-cyclopentyl-1H-indole-2-carboxylic acid (39 mg, 018 mmol) in dry DMF (1 mL) was added DIPEA (0.07 mL, 0.36 mmol), HOBt (15 mg, 0.11 mmol) and EDC (38 mg, 0.21 mmol). The reaction mixture was stirred at room temperature for 10 min then di-tert-butyl ((3R,4S)-5-amino-3-hydroxypentane-1,4-diyl) dicarbamate (Amine Intermediate A) (60 mg, 0.18 mmol) was added. The reaction mixture was stirred at room temperature overnight then added $H_2O$ with stirring. A solid was formed and collected by filtration. After air drying the solid was purified by chromatography on silica gel. Elution with 50% EtOAc/hexanes afforded the desired compound (53 mg, 54% yield) as yellow solid. $^1H$ NMR (300 MHz, $CDCl_3$) δ 9.15 (br s, 1H), 7.73 (d, J=8.1 Hz, 2H), 7.34 (d, J=8.4 Hz, 1H), 7.23 (m, 1H), 7.06 (m, 1H), 5.39 (d, J=6.3 Hz, 1H), 5.16-5.18 (br, 1H), 4.93 (br, 1H), 4.83 (br s, 1H), 3.40-3.95 (m, 6H), 3.10 (m, 1H), 1.30-2.15 (m, 28H).

Example 5. Preparation of 3-cyclohexyl-N-((2S)-2,5-diamino-3-hydroxypentyl)-1H-indole-2-carboxamide hydrogen chloride salt

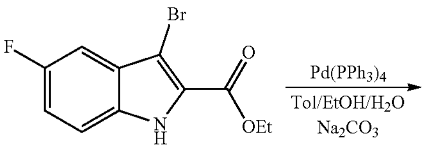

-continued

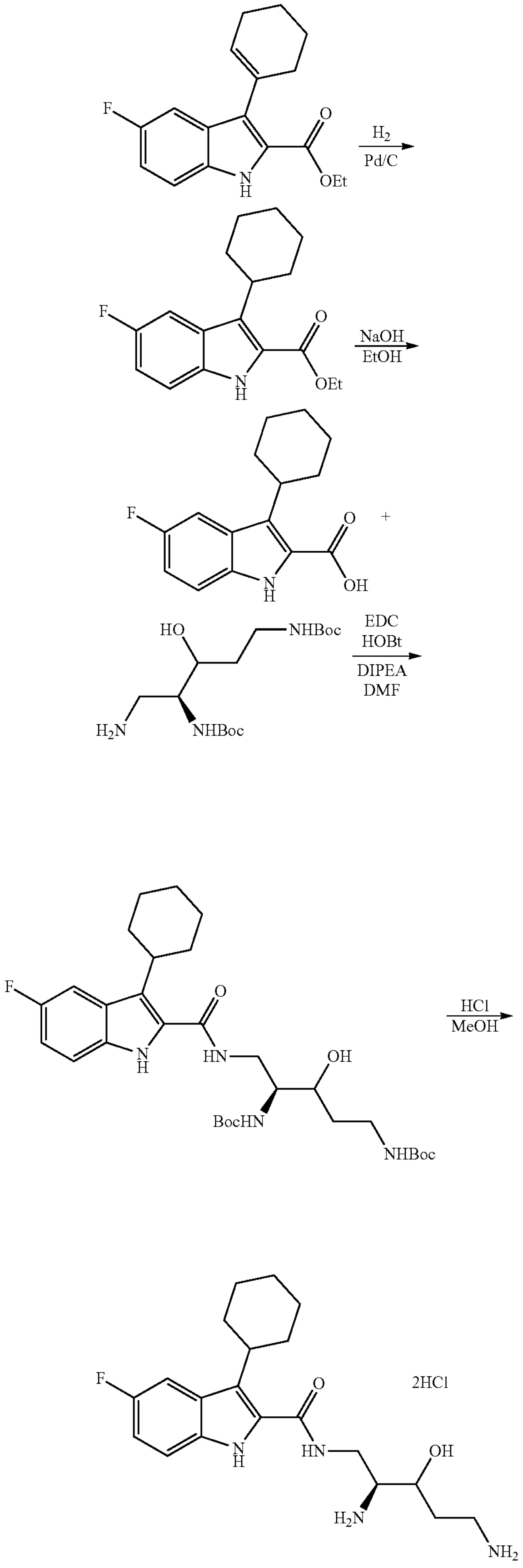

-continued

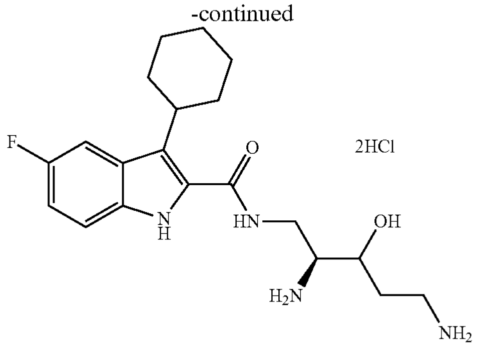

3-cyclohexyl-N-((2S)-2,5-diamino-3-hydroxypentyl)-5-fluoro-1H-indole-2-carboxamide hydrogen chloride salt To a solution of di-tert-butyl ((4S)-5-(3-cyclohexyl-5-fluoro-1H-indole-2-carboxamido)-3-hydroxypentane-1,4-diyl)dicarbamate (30 mg, 0.05 mmol) in MeOH (2 mL) was added HCl (4 M in dioxane, 0.3 mL, 1.2 mmol). The reaction mixture was stirred at 50° C. for 1 h then concentrated to give a residue. The residue was triturated with EtOAc to give the desired product (17 mg, 74% yield) as a brown solid. $^1$H NMR (300 MHz, $D_2O$) δ 7.68 (d, J 10.8 Hz, 1H), 7.43 (dd, J=4.5, 8.7 Hz, 1H), 7.10 (m, 1H), 4.08 (m, 1H), 3.80 (m, 1H), 3.61 (m, 2H), 3.10-3.32 (m, 3H), 1.68-2.06 (m, 8H), 1.35 (m, 4H). MS (ESI): Calcd for $C_{20}H_{30}FN_4O_2^+$ 377.23 $[M+H]^+$, found 377.05 $[M+H]^+$.

The requisite intermediates were prepared as shown in the following steps.

Step 1)

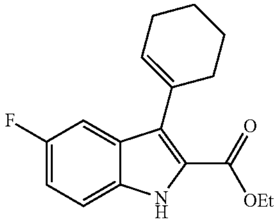 [SMILES: CCOC(=O)c1[nH]c2ccc(F)cc2c1C1=CCCCC1]

ethyl 3-(cyclohex-1-en-1-yl)-5-fluoro-1H-indole-2-carboxylate

Ethyl 3-bromo-5-fluoro-1H-indole-2-carboxylate (650 mg, 2.3 mmol) and cyclohex-1-en-1-ylboronic acid (350 mg, 2.4 mmol) in a mixture of toluene, ethanol and saturated $Na_2CO_3$ solution (20/6/6 mL) was degassed and Pd(dppf)$Cl_2$ (100 mg, 0.14 mmol) was added to the reaction mixture. It was heated at 100° C. overnight and extracted with EtOAc, washed with brine and concentrated. Then it was purified by column chromatography on silica gel to give the product (400 mg, 61% yield) as an off-white powder. $^1$H NMR (300 MHz, $CDCl_3$) δ 8.79 (br s, 1H), 7.30 (m, 1H), 7.27 (m, 1H), 7.09 (dt, J=2.5, 8.9 Hz, 1H), 5.78 (m, 1H), 4.38 (q, J=7.1 Hz, 2H), 2.35 (m, 2H), 2.26 (m, 2H), 1.78 (m, 4H), 1.41 (t, J=7.1 Hz, 3H).

Step 2)

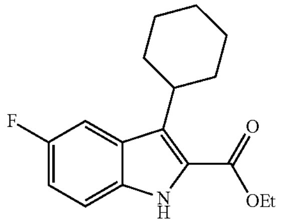 [SMILES: CCOC(=O)c1[nH]c2ccc(F)cc2c1C1CCCCC1]

ethyl 3-cyclohexyl-1H-indole-2-carboxylate

To a solution of ethyl 3-(cyclohex-1-en-1-yl)-1H-indole-2-carboxylate (0.2 g, 0.7 mmol) in MeOH was added Pd/C (10 w/w %, 50 mg, 0.05 mmol). It was stirred under $H_2$ (55 psi) overnight. The catalyst was filter off through a Celite pad and washed with MeOH. The combined filtrate was concentrated and used without further purification (0.19 g, 95%). MS (ESI): Calcd for $C_{17}H_{19}FNO_2$·288.14 $[M-H]^-$, found 287.95 $[M-H]^-$.

Step 3)

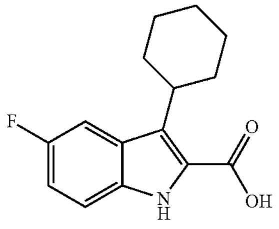 [SMILES: O=C(O)c1[nH]c2ccc(F)cc2c1C1CCCCC1]

3-(cyclohex-1-en-1-yl)-5-fluoro-1H-indole-2-carboxylic acid

To a solution of ethyl 3-cyclohexyl-1H-indole-2-carboxylate (200 mg, 0.7 mmol) in THE (10 mL) was added NaOH solution (2 M, 10 mL). It was heated at 50° C. overnight. THE was removed in vacuo and the residue was acidified with HCl solution. The precipitate was filtered and washed with water. It was dried to provide the product as a pale brown powder (116 mg, 63% yield) which was used for next step reaction without further purification. MS (ESI): Calcd for $C_{15}H_{13}FNO_2^+$ 260.11 $[M+H]^+$, found 260.05 $[M+H]^+$.

Step 4)

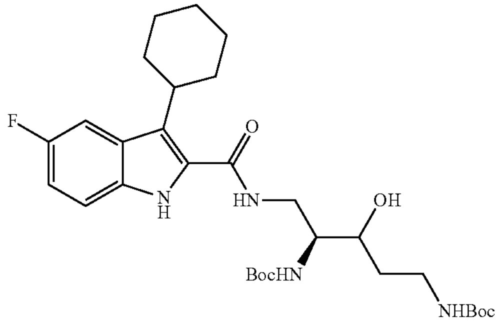 [SMILES: CC(C)(C)OC(=O)NCCC(O)[C@H](CNC(=O)c1[nH]c2ccc(F)cc2c1C1CCCCC1)NC(=O)OC(C)(C)C]

di-tert-butyl ((4S)-5-(3-cyclohexyl-5-fluoro-1H-indole-2-carboxamido)-3-hydroxypentane-1,4-diyl) dicarbamate To a solution of 3-cyclohexyl-5-fluoro-1H-indole-2-carboxylic acid (20 mg, 0.08 mmol) in dry DMF (1 mL) was added DIPEA (0.03 mL, 0.15 mmol), HOBt (6.2 mg, 0.05 mmol) and EDC (16 mg, 0.08 mmol). The reaction mixture was stirred at room temperature for 10 min then di-tert-butyl ((3R,4S)-5-amino-3-hydroxypentane-1,4-diyl) dicarbamate (Amine Intermediate A) (26 mg, 0.08 mmol) was added. The reaction mixture was stirred at room temperature overnight then added $H_2O$ with stirring. A solid was formed and collected by filtration. After air drying the solid was purified by chromatography on silica gel. Elution with 50% EtOAc/hexanes afforded the desired compound (30 mg, 54% yield) as yellow solid. $^1H$ NMR (300 MHz, $CDCl_3$) δ 9.42 (br s, 1H), 7.49 (m, 1H), 7.23 (m, 1H), 6.96 (m, 1H), 5.43 (d, J=7.5 Hz, 1H), 4.93 (br s, 1H), 3.77 (m, 2H), 3.63 (m, 1H), 3.52 (m, 1H), 3.24 (m, 1H), 3.12 (m, 1H), 1.78-2.00 (m, 8H), 1.61 (m, 2H), 1.36-1.40 (m, 20H).

Example 6. Preparation of N-((2S)-2,5-diamino-3-hydroxypentyl)-3-(4,4-difluorocyclohexyl)-1H-indole-2-carboxamide hydrogen chloride salt

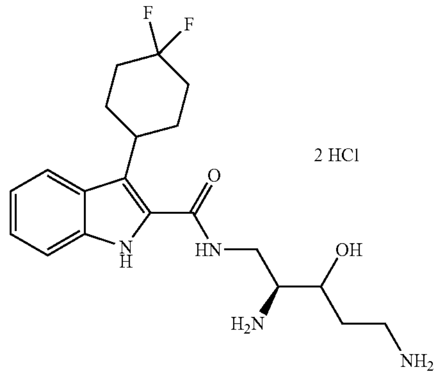 [SMILES: NCCC(O)[C@@H](N)CNC(=O)c1[nH]c2ccccc2c1C1CCC(F)(F)CC1]

N-((2S)-2,5-diamino-3-hydroxypentyl)-3-(4,4-difluorocyclohexyl)-1H-indole-2-carboxamide hydrogen chloride salt To a solution of di-tert-butyl ((4S)-5-(3-(4,4-difluorocyclohexyl)-1H-indole-2-carboxamido)-3-hydroxypentane-1,4-diyl)dicarbamate (23 mg, 0.04 mmol) in MeOH (2 mL) was added HCl (4 M in dioxane, 0.3 mL, 1.2 mmol). The reaction mixture was stirred at 50° C. for 1 h then concentrated to give a residue. The residue was triturated with EtOAc to give the product (12 mg, 67% yield) as a brown solid. $^1H$ NMR (300 MHz, $D_2O$) δ 7.91 (d, J 8.1 Hz, 1H), 7.50 (d, J=8.1 Hz, 1H), 7.33 (m, 1H), 7.15 (m, 1H), 4.08 (m, 1H), 3.81 (m, 1H), 3.62 (m, 2H), 3.50 (m, 1H), 3.16 (m, 2H), 2.10-2.36 (m, 4H), 1.80-2.08 (m, 6H). MS (ESI): Calcd for $C_{20}H_{29}F_2N_4O_2^+$ 395.23 $[M+H]^+$, found 395.05 $[M+H]^+$.

The requisite intermediates were prepared as shown in the following steps.

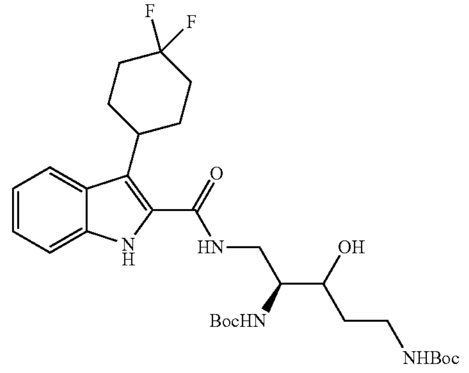 [SMILES: CC(C)(C)OC(=O)NCCC(O)[C@H](CNC(=O)c1[nH]c2ccccc2c1C1CCC(F)(F)CC1)NC(=O)OC(C)(C)C]

di-tert-butyl ((4S)-5-(3-(4,4-difluorocyclohexyl)-1H-indole-2-carboxamido)-3-hydroxypentane-1,4-diyl) dicarbamate To a solution of 3-(4,4-difluorocyclohexyl)-1H-indole-2-carboxylic acid (22 mg, 0.08 mmol) (prepared in a similar manner of Example 4) in dry DMF (1 mL) was added DIPEA (0.03 mL, 0.15 mmol), HOBt (6.2 mg, 0.05 mmol) and EDC (16 mg, 0.08 mmol). The reaction mixture was stirred at room temperature for 10 min then di-tert-butyl ((3R,4S)-5-amino-3-hydroxypentane-1,4-diyl) dicarbamate (Amine Intermediate A) (26 mg, 0.08 mmol) was added. The reaction mixture was stirred at room temperature overnight then added $H_2O$ with stirring. A solid was formed and collected by filtration. After air drying the solid was purified by column chromatography on silica gel. Elution with 50% EtOAc/hexanes afforded the desired compound (23 mg, 49% yield) as off-white solid. $^1H$ NMR (300 MHz, $CDCl_3$) δ 9.28 (br s, 1H), 7.80 (d, J=8.4 Hz, 1H), 7.34 (m, 2H), 7.23 (m, 1H), 7.09 (m, 1H), 5.44 (d, J=7.5 Hz, 1H), 4.99 (br s, 1H), 4.90 (br, 1H), 3.78 (m, 2H), 3.60 (m, 2H), 3.51 (m, 2H), 3.12 (m, 1H), 2.37 (m, 2H), 2.21 (m, 2H), 1.93 (m, 4H), 161 (m, 2H), 1.36-1.40 (m, 18H).

Example 7. Preparation of N-((2S)-2,5-diamino-3-hydroxypentyl)-3-(2-fluorophenyl)-1H-indole-2-carboxamide hydrogen chloride salt

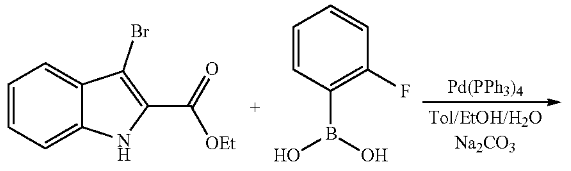

-continued

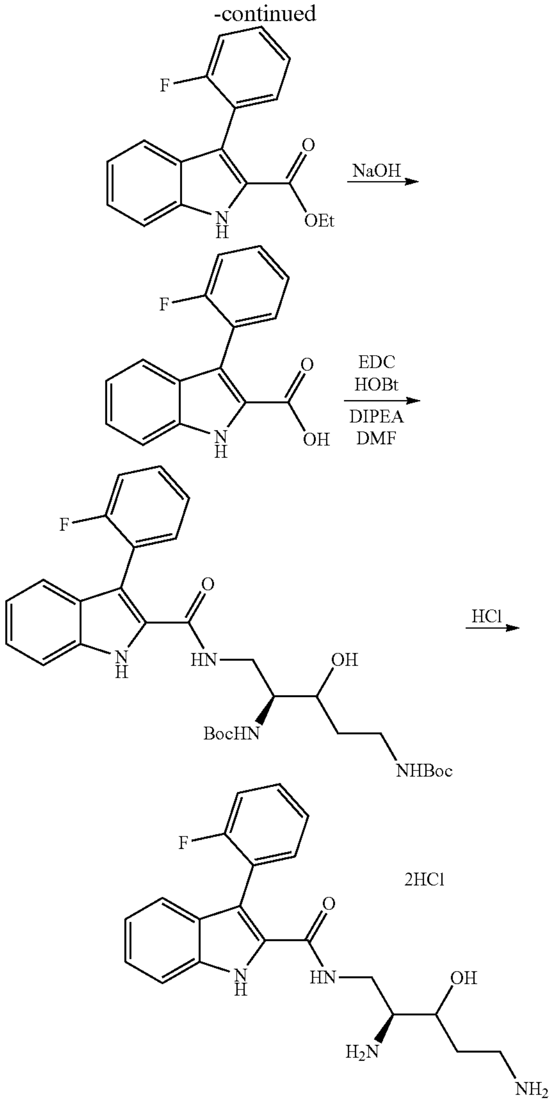

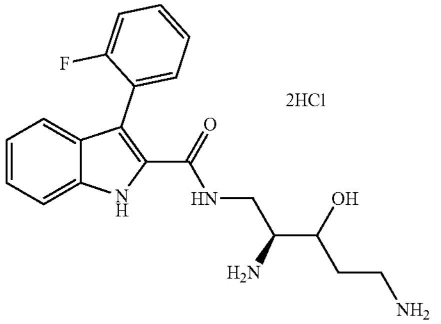

N-((2S)-2,5-diamino-3-hydroxypentyl)-3-(2-fluorophenyl)-1H-indole-2-carboxamide hydrogen chloride salt To a solution of di-tert-butyl ((4S)-5-(3-(2-fluorophenyl)-1H-indole-2-carboxamido)-3-hydroxypentane-1,4-diyl)dicarbamate (18 mg, 0.032 mmol) in methanol (1 mL) was added HCl (4 M in dioxane, 0.2 mL, 0.8 mmol). Reaction mixture was stirred at 50° C. for 30 minutes then solvents were removed in vacuo. Residue was washed with small amount of ethyl ether and dried. Product was collected as a gray solid (7.4 mg, 53% yield). $^{1}H$ NMR (300 MHz, $D_2O$) δ 7.15-7.62 (m, 8H), 3.93 (d, J=9.0 Hz, 1H), 3.22-3.79 (m, 4H), 3.11 (t, J=4.5 Hz, 1H), 1.66 (m, 2H). MS (ESI): Calcd for $C_{20}H_{24}FN_4O_2^+$ 371.19 $[M+H]^+$, found 371.00 $[M+H]^+$.

The requisite intermediates were prepared as shown in the following steps.

Step 1)

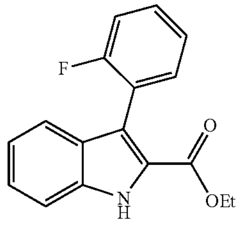 [SMILES: CCOC(=O)c1[nH]c2ccccc2c1-c1ccccc1F]

ethyl 3-(2-fluorophenyl)-1H-indole-2-carboxylate

Ethyl 3-bromo-1H-indole-2-carboxylate (268 mg, 1 mmol) and (2-fluorophenyl)boronic acid (280 mg, 2 mmol) in a mixture of toluene, ethanol and 2 M $Na_2CO_3$ solution (10/3/3 mL) was degassed and $Pd(dppf)Cl_2$ (30 mg, 0.04 mmol) was added. The reaction mixture was heated at 100° C. for 3 hours and it was extracted with EtOAc and washed with water, brine and dried over anhydrous sodium sulfate. Then it was concentrated, and the residue was purified by column chromatography on silica gel to give the product (220 mg, 78% yield) as an off-white powder.

Step 2)

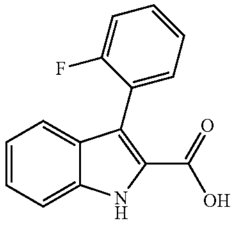 [SMILES: O=C(O)c1[nH]c2ccccc2c1-c1ccccc1F]

3-(2-fluorophenyl)-1H-indole-2-carboxylic acid

To a solution of ethyl 3-(2-fluorophenyl)-5-1H-indole-2-carboxylate (220 mg, 1.4 mmol) in THF (10 mL) was added NaOH solution (2 M, 5 mL). It was heated at 50° C. overnight. THF was removed in vacuo and the residue was acidified with HCl solution. The precipitate was filtered and washed with water. It was dried to provide the product as a pale brown powder (230 mg, 56% yield) which was used for next step reaction without further purification. $^{1}H$ NMR (300 MHz, DMSO-$d_6$) δ 11.98 (br s, 1H), 7.38-7.53 (m, 3H), 7.22-7.36 (m, 4H), 7.07 (t, J=7.5 Hz, 1H). MS (ESI): Calcd for $C_{15}H_{11}FNO_2^+$ 256.08 $[M+H]^+$, found 255.85 $[M+H]^+$.

Step 3)

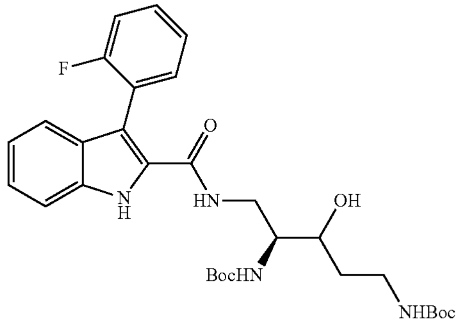 [SMILES: CC(C)(C)OC(=O)NCCC(O)[C@H](CNC(=O)c1[nH]c2ccccc2c1-c1ccccc1F)NC(=O)OC(C)(C)C]

di-tert-butyl ((4S)-5-(3-(2-fluorophenyl)-1H-indole-2-carboxamido)-3-hydroxypentane-1,4-diyl)dicarbamate To a solution of di-tert-butyl ((4S)-5-amino-3-hydroxypentane-1,4-diyl)dicarbamate acetate (28 mg, 0.07 mmol) (Amine Intermediate A) in DMF (1 mL) was added 3-(2-fluorophenyl)-1H-indole-2-carboxylic acid (22 mg, 0.085 mmol), EDC (17 mg, 0.11 mmol), HOBt (5 mg, 0.03 mmol) and DIPEA (14 mg, 0.13 mmol). Resulting reaction mixture was stirred at room temperature overnight then diluted with water and stirred for 30 minutes. The precipitate was filtered and washed with small amount of water then dissolved in DCM, washed with brine, and dried. After concentration, the residue was purified on column chromatography on silica gel to give the product as a light yellow solid (23 mg, 74% yield). $^1H$ NMR (300 MHz, $CDCl_3$) δ 9.65 (br s, 1H), 7.41-7.56 (m, 4H), 7.26-7.38 (m, 3H), 7.14 (t, J=8.1 Hz, 1H), 6.52 (br s, 1H), 4.80-4.99 (m, 2H), 4.38-4.46 (m, 1H), 3.61-3.78 (m, 2H), 3.32-3.58 (m, 3H), 3.01-3.23 (m, 1H), 1.63 (m, 2H), 1.40 (br, 18H); MS (ESI): Calcd for $C_{30}H_{40}FN_4O_6^+$ 571.29 $[M+H]^+$, found 571.25 $[M+H]^+$.

Example 8. Preparation of 3-(2-chlorophenyl)-N-((2S)-2,5-diamino-4-hydroxypentyl)-5-fluoro-1H-indole-2-carboxamide hydrogen chloride salt

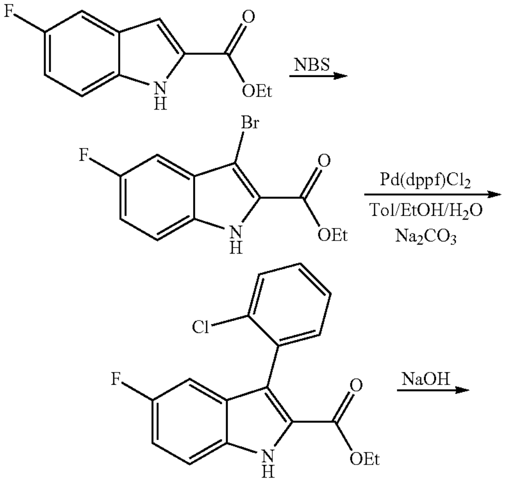

-continued

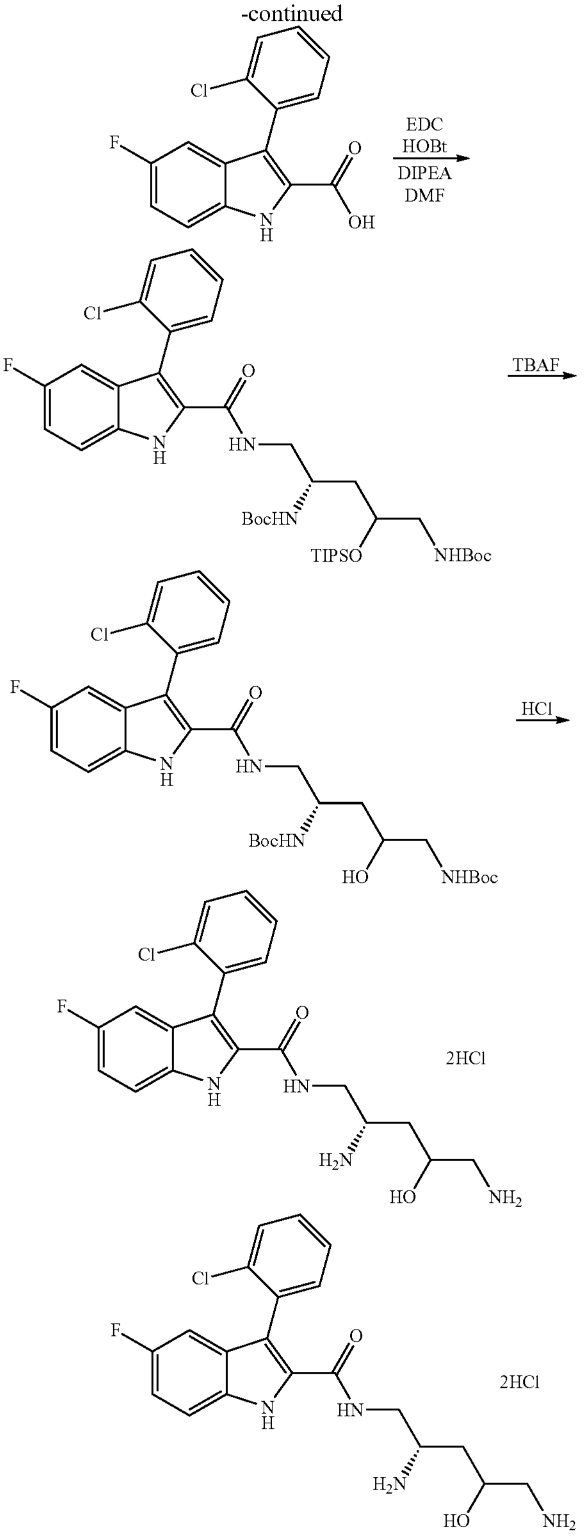

3-(2-chlorophenyl)-N-((2S)-2,5-diamino-4-hydroxypentyl)-5-fluoro-1H-indole-2-carboxamide hydrogen chloride salt To a solution of (S)-di-tert-butyl (5-(6-benzyl-1H-indole-2-carboxamido)pentane-1,4-diyl)dicarbamate (6 mg, 0.01 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as an off-white powder (4 mg, 84% yield). $^1$H NMR (300 MHz, $D_2O$) δ 7.64 (m, 1H), 7.53 (m, 2H), 7.48 (m, 2H), 7.17 (m, 1H), 7.11 (m, 1H), 4.06 (m, 1H), 3.70 (m, 1H), 3.62 (m, 2H), 3.57 (m, 1H), 3.09 (m, 1H), 2.91 (m, 1H), 1.76 (m, 1H), 1.68 (m, 1H). MS (ESI): Calcd for $C_{20}H_{23}ClFN_4O_2^+$ 405.15 [M+H]$^+$, found 404.95 [M+H]$^+$.

The requisite intermediates were prepared as shown in the following steps.

Step 1)

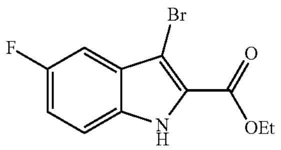 [SMILES: CCOC(=O)c1[nH]c2ccc(F)cc2c1Br]

ethyl 3-bromo-5-fluoro-1H-indole-2-carboxylate

To a solution of ethyl 5-fluoro-1H-indole-2-carboxylate (5 g, 24.2 mmol) in dry THE (10 mL) was added NBS (4.73 g, 26.6 mmol) at −78° C. Once the temperature reached to room temperature, it was washed with water, sat. $NaHCO_3$ and brine. After removing solvent in vacuo, the residue was used for next step reaction without purification (6.58 g, 95% yield) as a white powder. $^1$H NMR (300 MHz, $CDCl_3$) δ 9.28 (br s, 1H), 7.37 (m, 1H), 7.32 (m, 1H), 7.14 (m, 1H), 4.46 (q, J=7.2 Hz, 2H), 1.47 (t, J=7.2 Hz, 3H). MS (ESI): Calcd for $C_{11}H_{10}BrFNO_2^-$ 285.98 and 287.98 [M−H]$^-$, found 285.85 and 287.85 [M−H]$^-$.

Step 2)

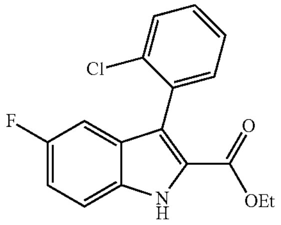 [SMILES: CCOC(=O)c1[nH]c2ccc(F)cc2c1-c1ccccc1Cl]

ethyl 3-(2-chlorophenyl)-5-fluoro-1H-indole-2-carboxylate

Ethyl 3-bromo-5-fluoro-1H-indole-2-carboxylate (620 mg, 2.1 mmol) and (2-chlorophenyl)boronic acid (495 mg, 3.2 mmol) in a mixture of toluene, ethanol and 2 M $Na_2CO_3$ solution (20/4/8 mL) was degassed and Pd(dppf)$Cl_2$ (100 mg, 0.11 mmol) was added. The reaction mixture was heated at 110° C. overnight and it was extracted with EtOAc and washed with brine and dried over anhydrous sodium sulfate. Then it was concentrated, and the residue was purified by column chromatography on silica gel to give the product (450 mg, 68% yield) as an off-white powder. $^1$H NMR (300 MHz, $CDCl_3$) δ 8.97 (br s, 1H), 7.48 (m, 1H), 7.37 (m, 1H), 7.34 (m, 3H), 7.29 (m, 1H), 7.09 (m, 1H), 4.23 (q, J=7.2 Hz, 2H), 1.13 (t, J=7.2 Hz, 3H). MS (ESI): Calcd for $C_{17}H_{14}ClFNO_2^+$ 318.07 [M+H]$^+$, found 317.90 [M+H]$^+$.

Step 3)

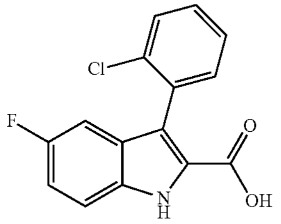 [SMILES: O=C(O)c1[nH]c2ccc(F)cc2c1-c1ccccc1Cl]

3-(2-chlorophenyl)-5-fluoro-1H-indole-2-carboxylic acid

To a solution of ethyl 3-(2-chlorophenyl)-5-fluoro-1H-indole-2-carboxylate (450 mg, 1.4 mmol) in THE (10 mL) was added NaOH solution (2 M, 5 mL). It was heated at 50° C. overnight. THE was removed in vacuo and the residue was acidified with HCl solution. The precipitate was filtered and washed with water. It was dried to provide the product as a pale brown powder (230 mg, 56% yield) which was used for next step reaction without further purification. MS (ESI): Calcd for $C_{15}H_{10}ClFNO_2^+$ 290.04 [M+H]$^+$, found 289.85 [M+H]$^+$.

Step 4)

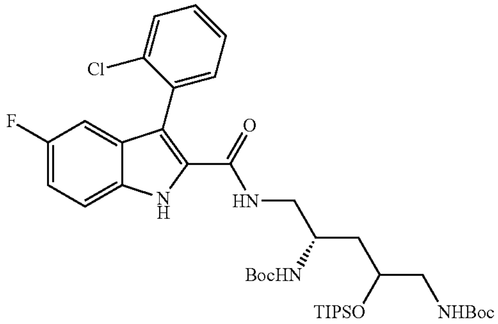

di-tert-butyl ((4S)-5-(3-(2-chlorophenyl)-5-fluoro-1H-indole-2-carboxamido)-2-((triisopropylsilyl)oxy)pentane-1,4-diyl)dicarbamate To a solution of 3-(2-chlorophenyl)-5-fluoro-1H-indole-2-carboxylic acid (15 mg, 0.05 mmol) in dry DMF (0.5 mL) was added DIPEA (0.034 mL, 0.2 mmol), HOBt (10 mg, 0.06 mmol) and EDC (12 mg, 0.06 mmol). The reaction mixture was stirred at room temperature and di-tert-butyl ((4S)-5-amino-2-((triisopropylsilyl)oxy)pentane-1,4-diyl) dicarbamate (Amine Intermediate B) (25 mg, 0.05 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel using 50-70% EtOAc in hexane to give the product (18 mg, 47% yield) as a pale brown powder. $^1$H NMR (300 MHz, $CDCl_3$) δ 9.75 (br s, 1H), 7.63 (m, 1H), 7.51 (m, 1H), 7.46 (m, 2H), 7.37 (m, 2H), 7.09 (m, 1H), 6.94 (br s, 1H), 5.27 (br s, 1H), 4.82 (br, 1H), 4.00 (m, 1H), 3.68 (m, 1H), 3.42 (m, 2H), 3.26 (m, 1H), 3.13 (m, 1H), 1.66 (m, 2H), 1.43 (s, 9H), 1.39 (s, 12H), 1.04 (s, 18H). MS (ESI): Calcd for $C_{39}H_{59}ClFN_4O_6Si^+$761.39 [M+H]$^+$, found 761.35 [M+H]$^+$.

Step 5)

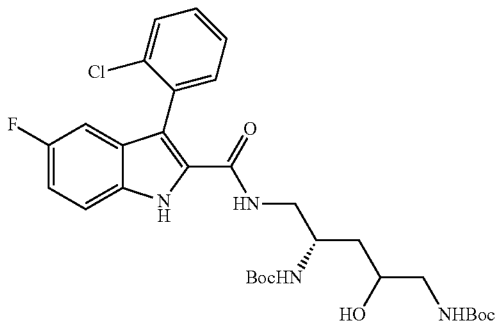 [SMILES: CC(C)(C)OC(=O)NCC(O)C[C@@H](CNC(=O)c1[nH]c2ccc(F)cc2c1-c1ccccc1Cl)NC(=O)OC(C)(C)C]

di-tert-butyl ((4S)-5-(3-(2-chlorophenyl)-5-fluoro-1H-indole-2-carboxamido)-2-hydroxypentane-1,4-diyl)dicarbamate To a solution of di-tert-butyl ((4S)-5-(3-(2-chlorophenyl)-5-fluoro-1H-indole-2-carboxamido)-2-((triisopropylsilyl)oxy)pentane-1,4-diyl)dicarbamate (17 mg, 0.022 mmol) in THE (2 mL) was added TBAF solution (1.0 M in THF, 0.4 mL, 0.4 mmol) at room temperature It was stirred for 0.5 hr, then concentrated and loaded on silica gel column chromatography and purified with 50-70% EtOAc in hexane to provide the alcohol as a white powder (7 mg, 53% yield). MS (ESI): Calcd for $C_{30}H_{39}ClFN_4O_6^+$ 605.25 [M+H]$^+$, found 605.20 [M+H]$^+$.

Example 9. Preparation of 3-(4-cyanophenyl)-N-((2S)-2,5-diamino-4-hydroxypentyl)-5-fluoro-1H-indole-2-carboxamide hydrogen chloride salt

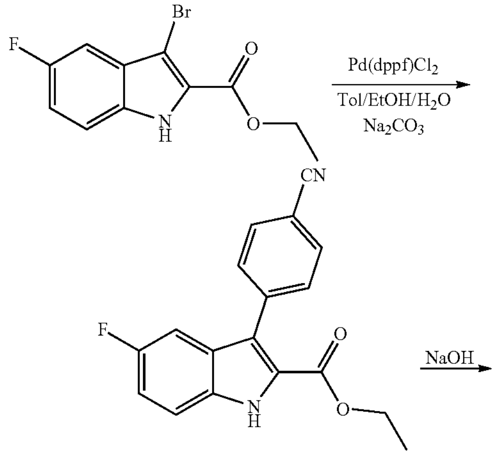

-continued

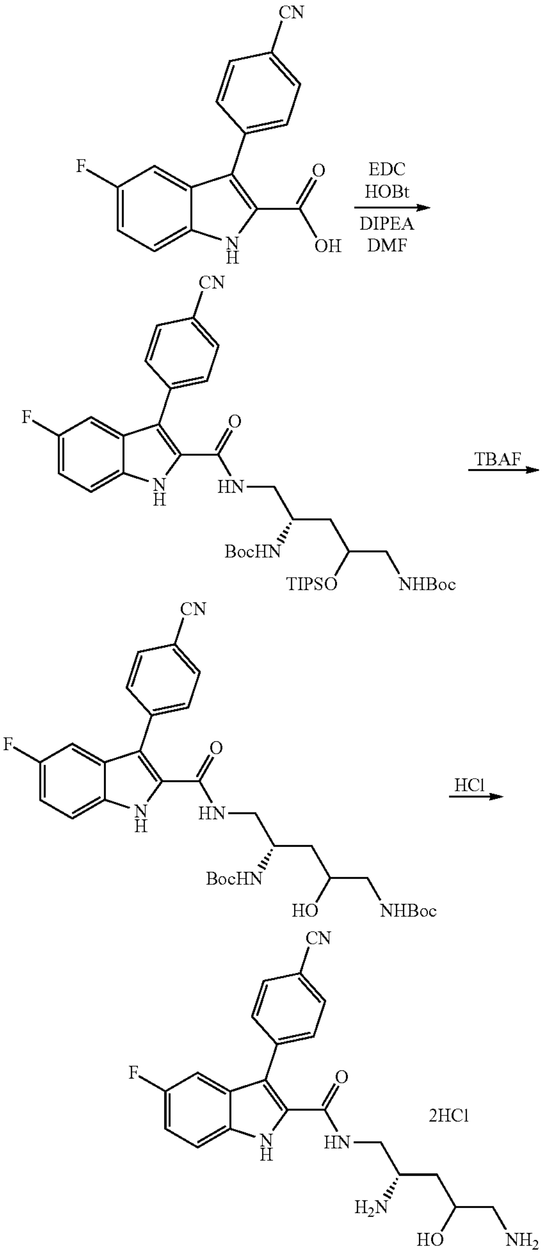

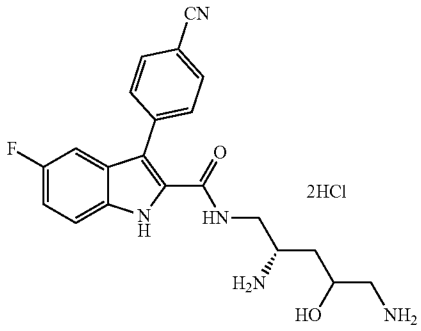

3-(4-cyanophenyl)-N-((2S)-2,5-diamino-4-hydroxypentyl)-5-fluoro-1H-indole-2-carboxamide hydrogen chloride salt To a solution of di-tert-butyl ((4S)-5-(3-(4-cyanophenyl)-5-fluoro-1H-indole-2-carboxamido)-2-hydroxypentane-1,4-diyl)dicarbamate (16 mg, 0.027 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as an off-white powder (11 mg, 87% yield). $^1$H NMR (300 MHz, $D_2O$) δ 7.84 (d, J 8.3 Hz, 2H), 7.64 (d, J 8.3 Hz, 2H), 7.50 (dd, J=4.4, 12.0 Hz, 1H), 7.29 (d, J=9.8 Hz, 1H), 7.64 (m, 1H), 4.03 (m, 1H), 3.61 (m, 2H), 3.48 (m, 1H), 3.06 (m, 1H), 2.89 (m, 1H), 1.77 (m, 2H). MS (ESI): Calcd for $C_{21}H_{23}FN_5O_2^+$ 396.18 $[M+H]^+$, found 396.00 $[M+H]^+$.

The requisite intermediates were prepared as shown in the following steps.

Step 1)

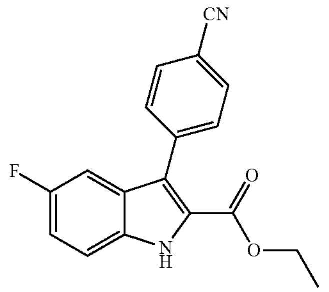 [SMILES: CCOC(=O)c1[nH]c2ccc(F)cc2c1-c1ccc(C#N)cc1]

ethyl 3-(4-cyanophenyl)-5-fluoro-1H-indole-2-carboxylate

Ethyl 3-bromo-5-fluoro-1H-indole-2-carboxylate (570 mg, 2.0 mmol) and (4-cyanophenyl)boronic acid (350 mg, 2.4 mmol) in a mixture of toluene, ethanol and saturated $Na_2CO_3$ solution (20/6/6 mL) was degassed and Pd(dppf) $Cl_2$ (100 mg, 0.14 mmol) was added. The reaction mixture was heated at 110° C. overnight, it was extracted with EtOAc and washed with brine and dried over $Na_2SO_4$, then concentrated. It was purified by column chromatography on silica gel to give the product (325 mg, 53% yield) as an off-white powder. $^1$H NMR (300 MHz, $CDCl_3$) δ 9.11 (br s, 1H), 7.75 (d, J=6.3 Hz, 2H), 7.69 (d, J=6.3 Hz, 2H), 7.42 (m, 1H), 7.19 (m, 2H), 4.31 (q, J=7.1 Hz, 2H), 1.26 (t, J=7.1 Hz, 3H).

Step 2)

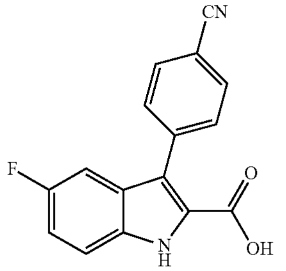 [SMILES: N#Cc1ccc(-c2c(C(=O)O)[nH]c3ccc(F)cc23)cc1]

3-(4-cyanophenyl)-5-fluoro-1H-indole-2-carboxylic acid

To a solution of ethyl 3-(4-cyanophenyl)-5-fluoro-1H-indole-2-carboxylate (320 mg, 1.04 mmol) in THF (10 mL) was added NaOH solution (2 M, 10 mL). It was heated at 65° C. for 1 hr. THF was removed in vacuo and the residue was acidified with HCl solution. The precipitate was filtered and washed with water. It was dried to provide the acid as a pale brown powder (235 mg, 81% yield) which was used for next step without further purification.

Step 3)

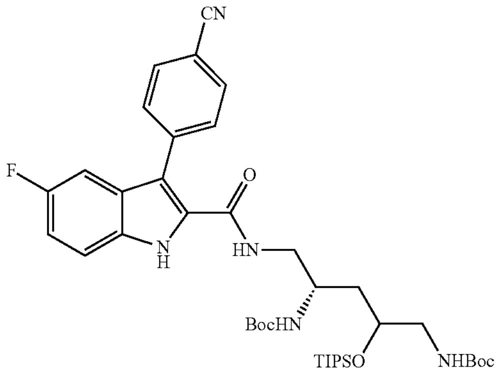

di-tert-butyl ((4S)-5-(3-(4-cyanophenyl)-5-fluoro-1H-indole-2-carboxamido)-2-((triisopropylsilyl)oxy)pentane-1,4-diyl)dicarbamate To a solution of 3-(4-cyanophenyl)-5-fluoro-1H-indole-2-carboxylic acid (28 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl) dicarbamate (Amine Intermediate B) (37 mg, 0.075 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel using 50-70% EtOAc in hexane as eluents to give the amide (33 mg, 59% yield) as a white powder. $^1$H NMR (300 MHz, $CDCl_3$) δ 9.44 (br s, 1H), 7.82 (d, J=8.1 Hz, 2H), 7.69 (d, J=8.1 Hz, 2H), 7.39 (m, 1H), 7.10 (m, 2H), 6.71 (br s, 1H), 5.27 (br s, 1H), 4.77 (br, 1H), 4.01 (m, 1H), 3.71 (m, 1H), 3.41 (m, 2H), 3.25 (m, 1H), 3.16 (m, 1H), 1.63 (m, 2H), 1.41 (s, 9H), 1.25 (s, 12H), 1.06 (s, 18H). MS (ESI): Calcd for $C_{40}H_{59}FN_5O_6Si^+$752.42 $[M+H]^+$, found 752.60 $[M+H]^+$.

Step 4)

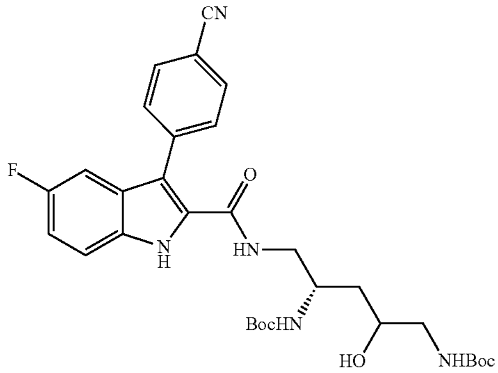 [SMILES: CC(C)(C)OC(=O)NCC(O)C[C@@H](CNC(=O)c1[nH]c2ccc(F)cc2c1-c1ccc(C#N)cc1)NC(=O)OC(C)(C)C]

di-tert-butyl ((4S)-5-(3-(4-cyanophenyl)-5-fluoro-1H-indole-2-carboxamido)-2-hydroxypentane-1,4-diyl)dicarbamate To a solution of tert-butyl ((4S)-5-(3-(4-cyanophenyl)-5-fluoro-1H-indole-2-carboxamido)-2-((triisopropylsilyl)oxy) pentane-1,4-diyl)dicarbamate (32 mg, 0.056 mmol) in THE (2 mL) was added TBAF solution (1.0 M in THF, 0.4 mL, 0.4 mmol) at room temperature It was stirred for 0.5 hr, concentrated and loaded on column chromatography on silica gel and purified with 40-65% EtOAc in hexane to provide the alcohol as a white powder (17 mg, 51% yield).

Example 10. Preparation of 3-(4-fluorophenyl)-N-((2S)-2,5-diamino-4-hydroxypentyl)-1H-indole-2-carboxamide hydrogen chloride salt

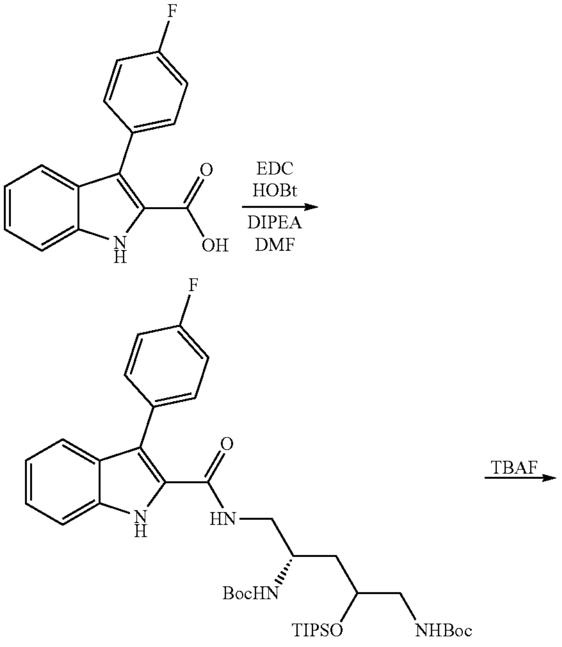

-continued

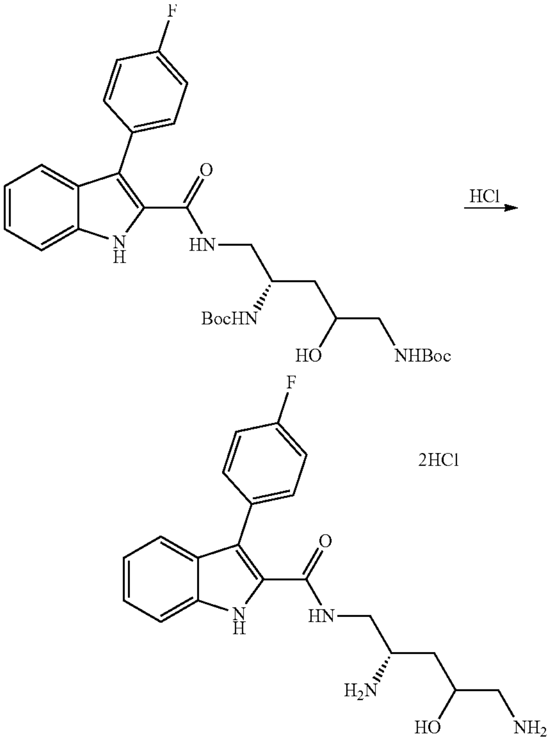

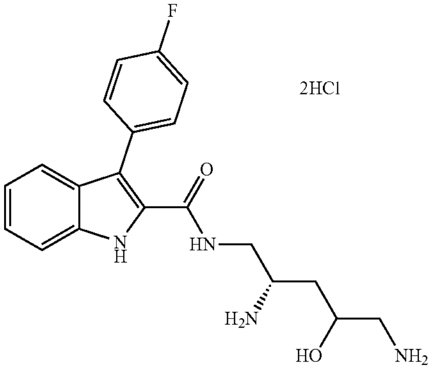 [SMILES: NCC(O)C[C@H](N)CNC(=O)c1[nH]c2ccccc2c1-c1ccc(F)cc1]

3-(4-fluorophenyl)-N-((2S)-2,5-diamino-4-hydroxy-pentyl)-1H-indole-2-carboxamide hydrogen chloride salt To a solution of di-tert-butyl ((4S)-5-(3-(4-fluorophenyl)-1H-indole-2-carboxamido)-2-hydroxypentane-1,4-diyl)di-carbamate (16 mg, 0.027 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as a white powder (11 mg, 87% yield). $^1$H NMR (300 MHz, $D_2O$) δ 7.50-7.63 (m, 5H), 7.38 (m, 1H), 7.21 (m, 2H), 7.18 (m, 1H), 4.03 (m, 1H), 3.48-3.75 (m, 3H), 3.05 (m, 1H), 2.90 (m, 1H), 1.72 (m, 2H). MS (ESI): Calcd for $C_{20}H_{24}FN_4O_2^+$ 371.18 [M+H]$^+$, found 371.00 [M+H]$^+$.

The requisite intermediates were prepared as shown in the following steps.

Step 1)

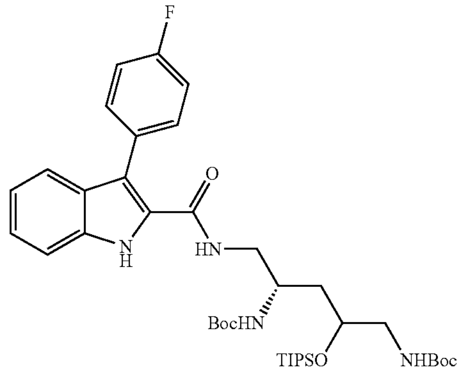

di-tert-butyl ((4S)-5-(3-(4-fluorophenyl)-1H-indole-2-carboxamido)-2-((triisopropylsilyl)oxy)pentane-1,4-diyl)dicarbamate To a solution of 3-(4-fluorophenyl)-1H-indole-2-carboxylic acid (26 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl)dicarbamate (Amine Intermediate B) (49 mg, 0.1 mmol) was added. The reaction was continued at room temperature overnight. It was extracted with EtOAc and washed with water and brine. The organic layer was dried over anhydrous sodium sulfate and filtered. The filtrate was concentrated and purified by column chromatography on silica gel using 50-70% EtOAc in hexane as eluents to give the amide (52 mg, 72% yield) as a white powder. MS (ESI): Calcd for $C_{39}H_{60}FN_4O_6Si^+$ 727.43 $[M+H]^+$, found 727.55 $[M+H]^+$.

Step 2)

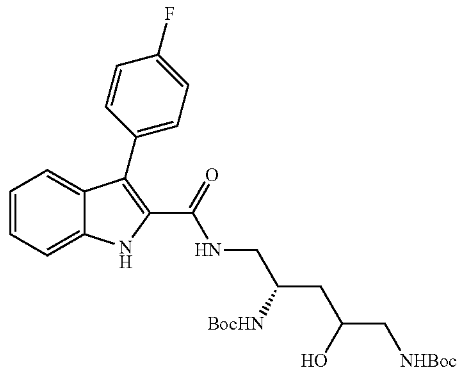 [SMILES: CC(C)(C)OC(=O)NCC(O)C[C@@H](CNC(=O)c1[nH]c2ccccc2c1-c1ccc(F)cc1)NC(=O)OC(C)(C)C]

di-tert-butyl ((4S)-5-(3-(4-fluorophenyl)-1H-indole-2-carboxamido)-2-hydroxypentane-1,4-diyl)dicarbamate To a solution of di-tert-butyl ((4S)-5-(3-(4-fluorophenyl)-1H-indole-2-carboxamido)-2-((triisopropylsilyl)oxy)pentane-1,4-diyl)dicarbamate (30 mg, 0.041 mmol) in THE (5 mL) was added TBAF solution (1.0 M in THF, 0.4 mL, 0.4 mmol) at room temperature. It was stirred for 1 hr and concentrated, then loaded on silica gel column chromatography and purified with 50-80% EtOAc in hexane to provide the alcohol as a white powder (15 mg, 64% yield). $^1H$ NMR (300 MHz, $CDCl_3$) δ 9.34 (br s, 1H), 7.41-7.53 (m, 4H), 7.34 (m, 1H), 7.25 (m, 2H), 7.15 (m, 2H), 6.10 (m, 1H) 5.21 (br s, 1H), 5.03 (br s, 1H), 4.37 (br, 1H), 4.01 (m, 1H), 3.77 (m, 1H), 3.65 (m, 1H), 3.24-3.53 (m, 3H), 2.95 (m, 1H), 1.62 (m, 2H), 1.41 (br, 18H). MS (ESI): Calcd for $C_{30}H_{40}FN_4O_6^+$ 571.29 $[M+H]^+$, found 571.25 $[M+H]^+$.

Example 11. Preparation of 3-(4-cyanophenyl)-N-((2S)-2,5-diamino-4-hydroxypentyl)-1H-indole-2-carboxamide hydrogen chloride salt

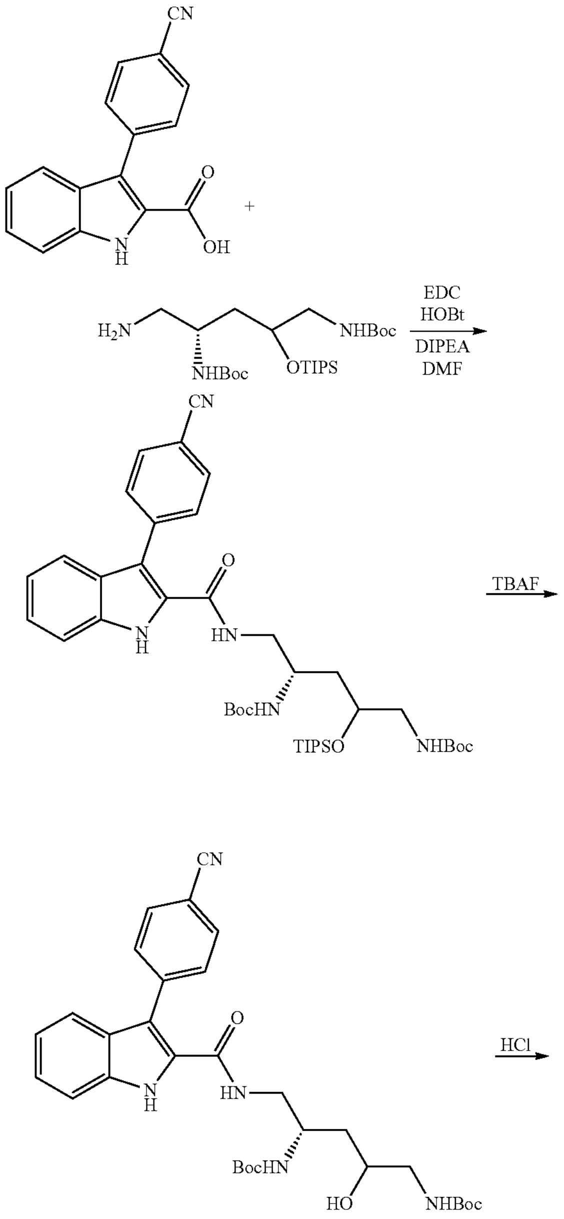

-continued

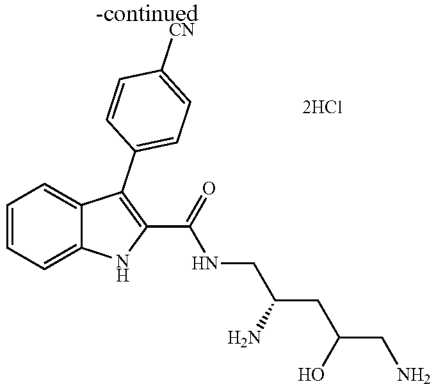

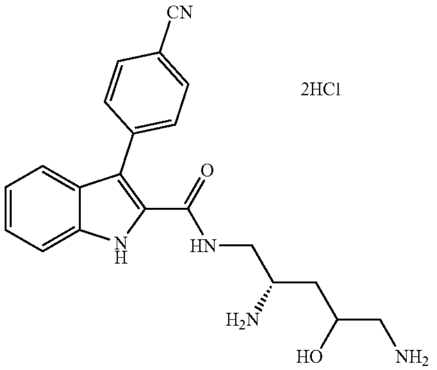 [SMILES: N#Cc1ccc(-c2c(C(=O)NC[C@@H](N)CC(O)CN)[nH]c3ccccc23)cc1]

3-(4-cyanophenyl)-N-((2S)-2,5-diamino-4-hydroxy-pentyl)-1H-indole-2-carboxamide hydrogen chloride salt To a solution of di-tert-butyl ((4S)-5-(3-(4-cyanophenyl)-1H-indole-2-carboxamido)-2-hydroxypentane-1,4-diyl)dicarbamate (18 mg, 0.03 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as an off-white powder (10 mg, 72% yield). $^{1}H$ NMR (300 MHz, $D_2O$) δ 7.77 (m, 2H), 7.71 (m, 2H), 7.50 (m, 2H), 7.27 (m, 1H), 7.10 (m, 1H), 4.04 (m, 1H), 3.48-3.72 (m, 3H), 3.31 (m, 2H), 3.01 (m, 1H), 2.83 (m, 1H), 1.85 (m, 1H), 1.67 (m, 1H). MS (ESI): Calcd for $C_{21}H_{24}FN_5O_2^+$ 378.19 $[M+H]^+$, found 378.95 $[M+H]^+$.

The requisite intermediates were prepared as shown in the following steps.

Step 1)

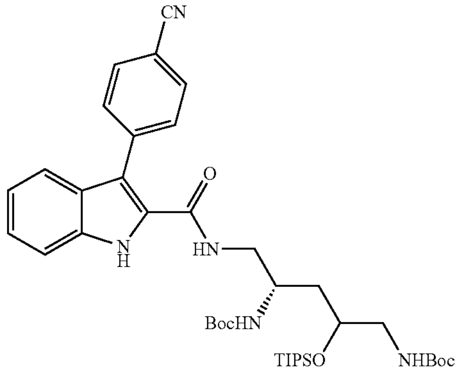

di-tert-butyl ((4S)-5-(3-(4-cyanophenyl)-1H-indole-2-carboxamido)-2-((triisopropylsilyl)oxy)pentane-1,4-diyl)dicarbamate To a solution of 3-(4-cyanophenyl)-1H-indole-2-carboxylic acid (26 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl)dicarbamate (Amine Intermediate B) (49 mg, 0.1 mmol) was added. The reaction was continued at room temperature overnight. It was extracted with EtOAc and washed with water and brine. The organic layer was dried over anhydrous sodium sulfate and filtered. The filtrate was concentrated and purified by column chromatography on silica gel using 30-60% EtOAc in hexane as eluents to give two diastereomers (55 mg, 73% yield) as a white powder. MS (ESI): Calcd for $C_{40}H_{60}N_5O_6Si^+$734.43 $[M+H]^+$, found 756.55 $[M+Na]^+$.

Step 2)

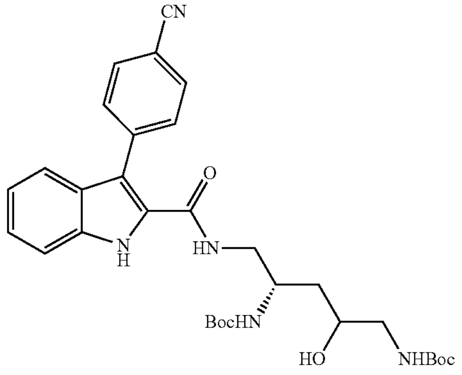 [SMILES: CC(C)(C)OC(=O)NCC(O)C[C@@H](CNC(=O)c1[nH]c2ccccc2c1-c1ccc(C#N)cc1)NC(=O)OC(C)(C)C]

di-tert-butyl ((4S)-5-(3-(4-cyanophenyl)-1H-indole-2-carboxamido)-2-hydroxypentane-1,4-diyl)dicarbamate To a solution of the less polar one of the two diastereomers of di-tert-butyl ((4S)-5-(3-(4 cyanophenyl)-1H-indole-2- carboxamido)-2-((triisopropylsilyl)oxy)pentane-1,4-diyl)dicarbamate (35 mg, 0.046 mmol) in THF (5 mL) was added TBAF solution (1.0 M in THF, 0.4 mL, 0.4 mmol) at room temperature It was stirred for 1 hr and concentrated, then loaded on column chromatography on silica gel and purified with 40-80% EtOAc in hexane to provide the alcohol as a white powder (18 mg, 67% yield). MS (ESI): Calcd for $C_{31}H_{40}N_5O_6^+$ 578.29 $[M+H]^+$, found 578.25 $[M+H]^+$.

Example 12. Preparation of N-((2S)-2,5-diamino-4-hydroxypentyl)-3-phenyl-1H-indole-2-carboxamide hydrogen chloride salt

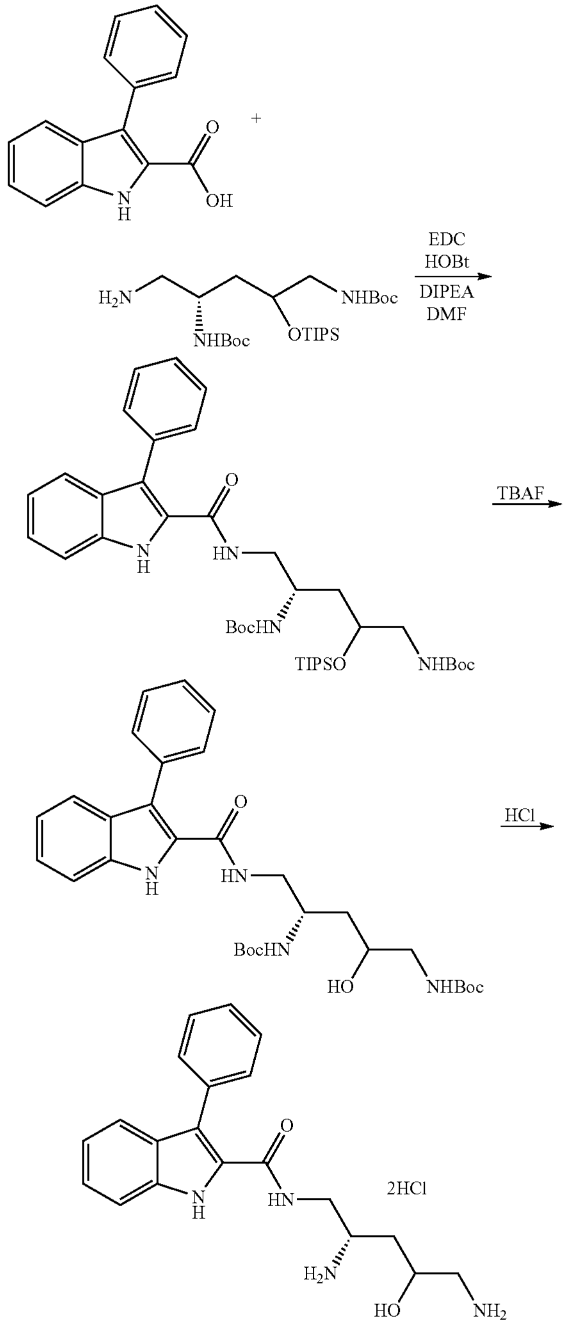

-continued

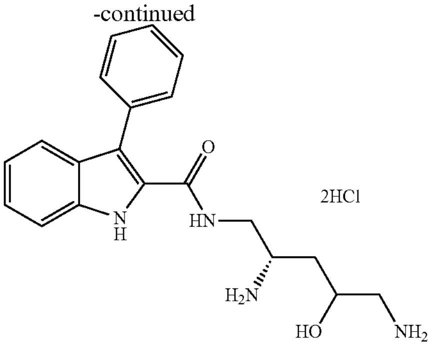

N-((2S)-2,5-diamino-4-hydroxypentyl)-3-phenyl-1H-indole-2-carboxamide hydrogen chloride salt To a solution of di-tert-butyl ((4S)-5-(3-phenyl)-1H-indole-2-carboxamido)-2-hydroxypentane-1,4-diyl)dicarbamate (18 mg, 0.032 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as an off-white powder (10 mg, 74% yield). $^1H$ NMR (300 MHz, $D_2O$) δ 7.73 (m, 1H), 7.64-7.72 (m, 5H), 7.61 (m, 1H), 7.50 (m, 1H), 7.31 (m, 1H), 4.11 (m, 1H), 3.56-3.76 (m, 3H), 3.17 (m, 1H), 3.00 (m, 1H), 1.81 (m, 2H). MS (ESI): Calcd for $C_{20}H_{25}N_4O_2^+$ 353.18 $[M+H]^+$, found 353.00 $[M+H]^+$.

The requisite intermediates were prepared as shown in the following steps.

Step 1)

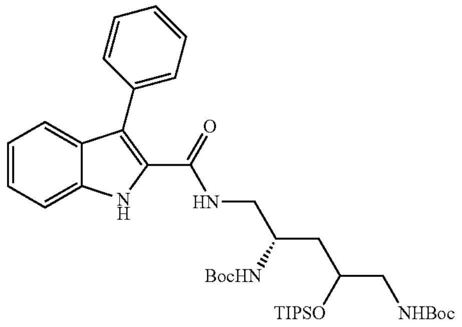

di-tert-butyl ((4S)-5-(3-phenyl-1H-indole-2-carboxamido)-2-((triisopropylsilyl)oxy)pentane-1,4-diyl) dicarbamate To a solution of 3-phenyl-1H-indole-2-carboxylic acid (24 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl)dicarbamate (Amine Intermediate B) (49 mg, 0.1 mmol) was added. The reaction was continued at room temperature overnight. It was extracted with EtOAc and washed with water and brine. The organic layer was dried over anhydrous sodium sulfate and filtered. The filtrate was concentrated and purified by column chromatography on silica gel using 20-60% EtOAc in hexane as eluents to give two diastereomers (60 mg, 85% yield) as a white powder. $^1$H NMR (300 MHz, $CDCl_3$) δ 9.26 (br s, 1H), 7.57 (m, 1H), 7.54 (m, 4H), 7.27 (t, J=8.1 Hz, 2H), 7.69 (d, J=8.1 Hz, 2H), 7.33 (m, 1H), 7.13 (m, 1H), 6.16 (br s, 1H), 5.13 (br s, 1H), 4.87 (br, 1H), 3.99 (m, 1H), 3.61 (m, 2H), 3.54 (m, 1H), 3.26 (m, 1H), 3.10 (m, 1H), 1.60 (m, 2H), 1.39 (s, 9H), 1.38 (s, 12H), 1.04 (s, 18H). MS (ESI): Calcd for $C_{39}H_{61}N_4O_6Si^+$709.43 $[M+H]^+$, found 709.45 $[M+H]^+$.

Step 2)

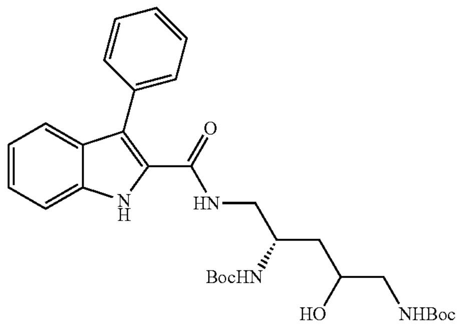 [SMILES: CC(C)(C)OC(=O)NCC(O)C[C@@H](CNC(=O)c1[nH]c2ccccc2c1-c1ccccc1)NC(=O)OC(C)(C)C]

di-tert-butyl ((4S)-2-hydroxy-5-(3-phenyl-1H-indole-2-carboxamido)pentane-1,4-diyl)dicarbamate To a solution of the less polar one of the two diastereomers of di-tert-butyl ((4S)-5-(3-phenyl)-1H-indole-2-carboxamido)-2-((triisopropylsilyl)oxy)pentane-1,4-diyl)dicarbamate (40 mg, 0.055 mmol) in THE (5 mL) was added TBAF solution (1.0 M in THF, 0.4 mL, 0.4 mmol) at room temperature It was stirred for 1 hr and concentrated, then loaded on column chromatography on silica gel and purified with 50-80% EtOAc in hexane to provide the alcohol as a white powder (18 mg, 58% yield). MS (ESI): Calcd for $C_{30}H_{41}N_4O_6^+$ 553.30 $[M+H]^+$, found 553.15 $[M+H]^+$.

Example 13. Preparation of N-((2S)-2,5-diamino-4-hydroxypentyl)-5-fluoro-3-phenyl-1H-indole-2-carboxamide hydrogen chloride salt

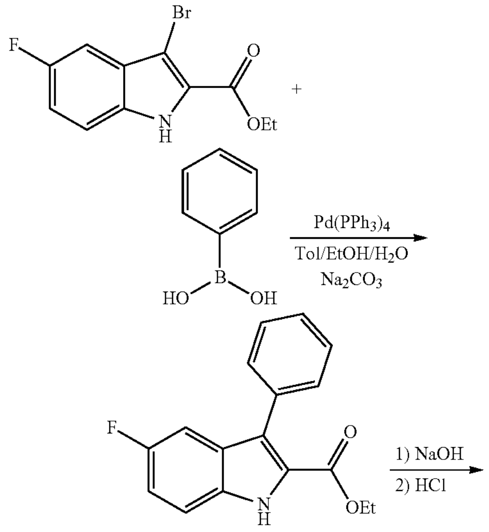

-continued

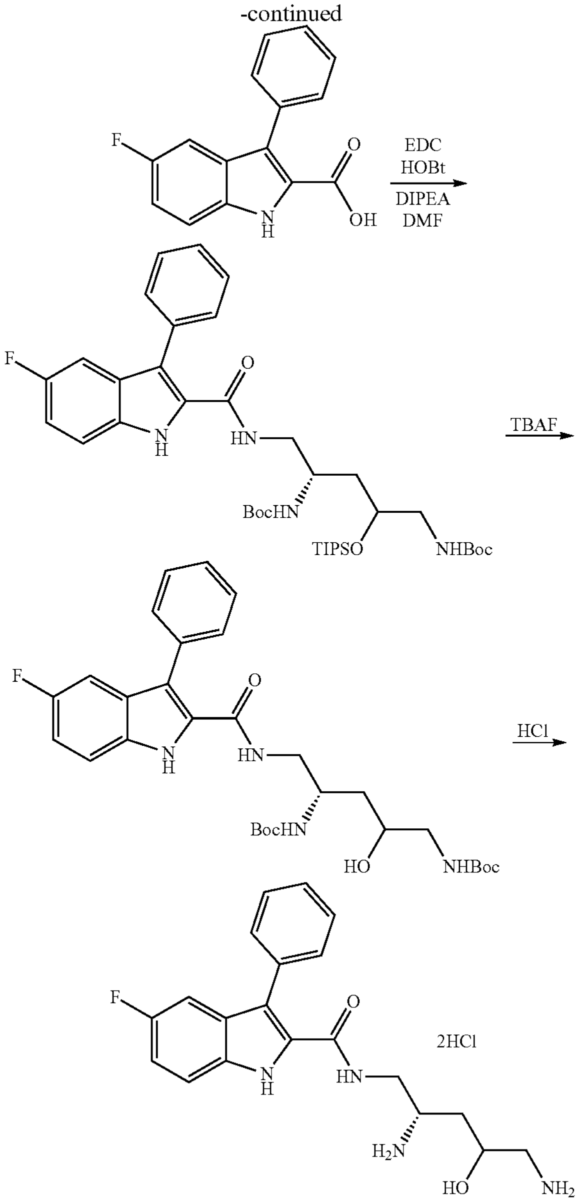

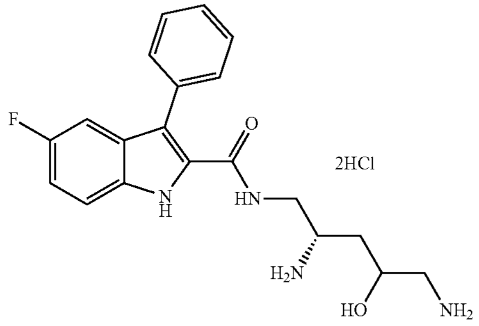

N-((2S)-2,5-diamino-4-hydroxypentyl)-5-fluoro-3-phenyl-1H-indole-2-carboxamide hydrogen chloride salt To a solution of di-tert-butyl ((4S)-5-(5-fluoro-3-phenyl-1H-indole-2-carboxamido)-2-hydroxypentane-1,4-diyl)dicarbamate (17 mg, 0.03 mmol) in MeOH (2 mL) HCl solution (4 M in dioxane, 0.1 mL, 0.4 mmol) was added. It was stirred at room temperature for 2 hrs, then solvent was removed in vacuo. The residue was triturated with EtOAc and the precipitate was collected as an off-white powder (10 mg, 76% yield). $^1$H NMR (300 MHz, $CD_3OD$) δ 7.73 (m, 4H), 7.0 (m, 2H), 7.36 (m, 1H), 7.26 (m, 1H), 4.08 (m, 1H), 3.50-3.74 (m, 6H), 3.13 (m, 1H), 2.98 (m, 1H), 1.78 (m, 2H). MS (ESI): Calcd for $C_{20}H_{25}FN_4O_2^+$ 370.19 [M+H]$^+$, found 371.00 [M+H]$^+$.

The requisite intermediates were prepared as shown in the following steps.

Step 1)

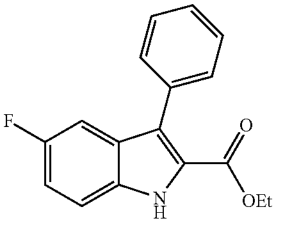 [SMILES: CCOC(=O)c1[nH]c2ccc(F)cc2c1-c1ccccc1]

ethyl 5-fluoro-3-phenyl-1H-indole-2-carboxylate

Ethyl 5-fluoro-3-bromo-1H-indole-2-carboxylate (0.86 g, 3 mmol) and phenylboronic acid (0.5 g, 4.1 mmol) in a mixture of toluene, ethanol and saturated $Na_2CO_3$ solution (20/4/4 mL) was degassed and Pd(dppf)$Cl_2$ (50 mg, 0.07 mmol) was added. The reaction mixture was heated at 100° C. for 2 h, it was extracted with EtOAc and washed with brine and dried over $Na_2SO_4$, then concentrated. It was purified by column chromatography on silica gel with 0-20% EtOAc in hexane as eluents to give the product (0.51 g, 61% yield) as a white powder.

Step 2)

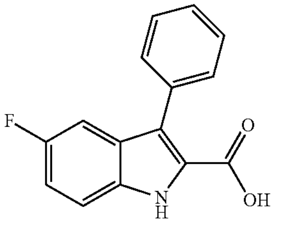 [SMILES: O=C(O)c1[nH]c2ccc(F)cc2c1-c1ccccc1]

5-fluoro-3-phenyl-1H-indole-2-carboxylic acid

To a solution of ethyl 5-fluoro-3-phenyl-1H-indole-2-carboxylate (500 mg, 1.78 mmol) in THF (10 mL) was added NaOH solution (2 M, 5 mL). It was heated at 50° C. overnight. THF was removed in vacuo and the residue was acidified with HCl solution. The precipitate was filtered and washed with water. It was dried to provide the product as a pale brown powder (390 mg, 86% yield) which was used for next step reaction without further purification. $^1$H NMR (300 MHz, DMSO-$d_6$) δ 13.0 (br s, 1H), 11.95 (br s, 1H), 7.50 (m, 2H), 7.45 (m, 2H), 7.38-7.43 (m, 2H), 7.33 (m, 1H), 7.09-7.18 (m, 2H). MS (ESI): Calcd for $C_{15}H_{11}FNO_2^+$ 256.08 [M+H]$^+$, found 255.80 [M+H]$^+$.

Step 3)

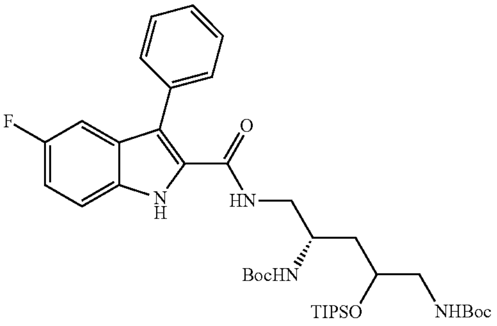

di-tert-butyl ((4S)-5-(5-fluoro-3-phenyl-1H-indole-2-carboxamido)-2-((triisopropylsilyl)oxy)pentane-1,4-diyl)dicarbamate To a solution of 5-fluoro-3-phenyl-1H-indole-2-carboxylic acid (26 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl)dicarbamate (Amine Intermediate B) (49 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel using 20-60% EtOAc in hexane as eluents to give two diastereomers (54 mg, 74% yield) as a white powder. $^1$H NMR (300 MHz, $CDCl_3$) δ 9.22 (br s, 1H), 7.57 (m, 1H), 7.51 (m, 4H), 7.37 (m, 1H), 7.09 (m, 2H), 6.17 (br s, 1H), 5.07 (br s, 1H), 4.82 (br, 1H), 3.99 (m, 1H), 3.62 (m, 2H), 3.54 (m, 1H), 3.29 (m, 1H), 3.09 (m, 1H), 1.60 (m, 2H), 1.39 (s, 9H), 1.38 (s, 12H), 1.04 (s, 18H). MS (ESI): Calcd for $C_{39}H_{60}FN_4O_6Si^+$727.43 [M+H]$^+$, found 727.40 [M+H]$^+$.

Step 4)

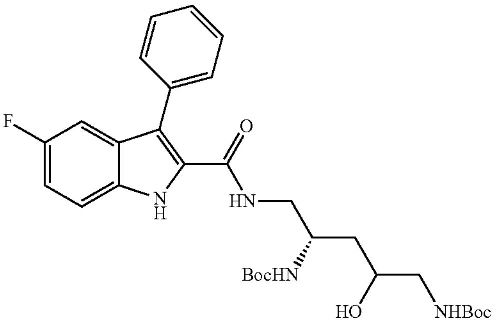 [SMILES: CC(C)(C)OC(=O)NCC(O)C[C@@H](CNC(=O)c1[nH]c2ccc(F)cc2c1-c1ccccc1)NC(=O)OC(C)(C)C]

di-tert-butyl ((4S)-5-(5-fluoro-3-phenyl-1H-indole-2-carboxamido)-2-hydroxypentane-1,4-diyl)dicarbamate To a solution of the less polar one of the two diastereomers of di-tert-butyl ((4S)-5-(5-fluoro-3-phenyl-1H-indole-2-carboxamido)-2-((triisopropylsilyl)oxy)pentane-1,4-diyl)dicarbamate (33 mg, 0.045 mmol) in THE (5 mL) was added TBAF solution (1.0 M in THF, 0.4 mL, 0.4 mmol) at room temperature It was stirred for 1 hr and concentrated, then loaded on silica gel column chromatography and purified with 50-80% EtOAc in hexane to provide the alcohol as a white powder (17 mg, 65% yield). MS (ESI): Calcd for $C_{30}H_{40}FN_4O_6^+$571.29 $[M+H]^+$, found 571.15 $[M+H]^+$.

Example 14. Preparation of 3-(4-cyanophenyl)-N-((2S)-2,5-diamino-4-hydroxypentyl)-7-fluoro-1H-indole-2-carboxamide hydrogen chloride salt

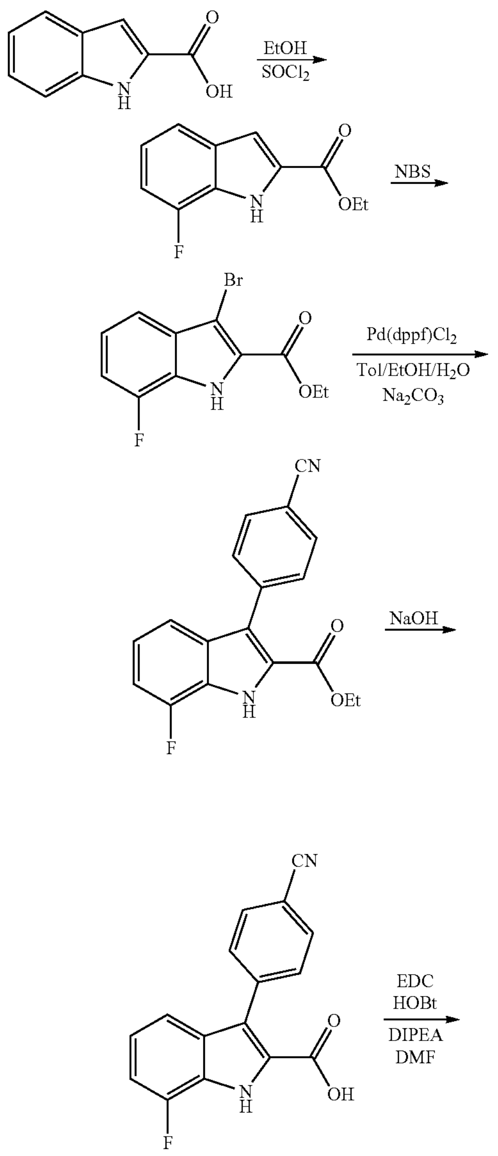

-continued

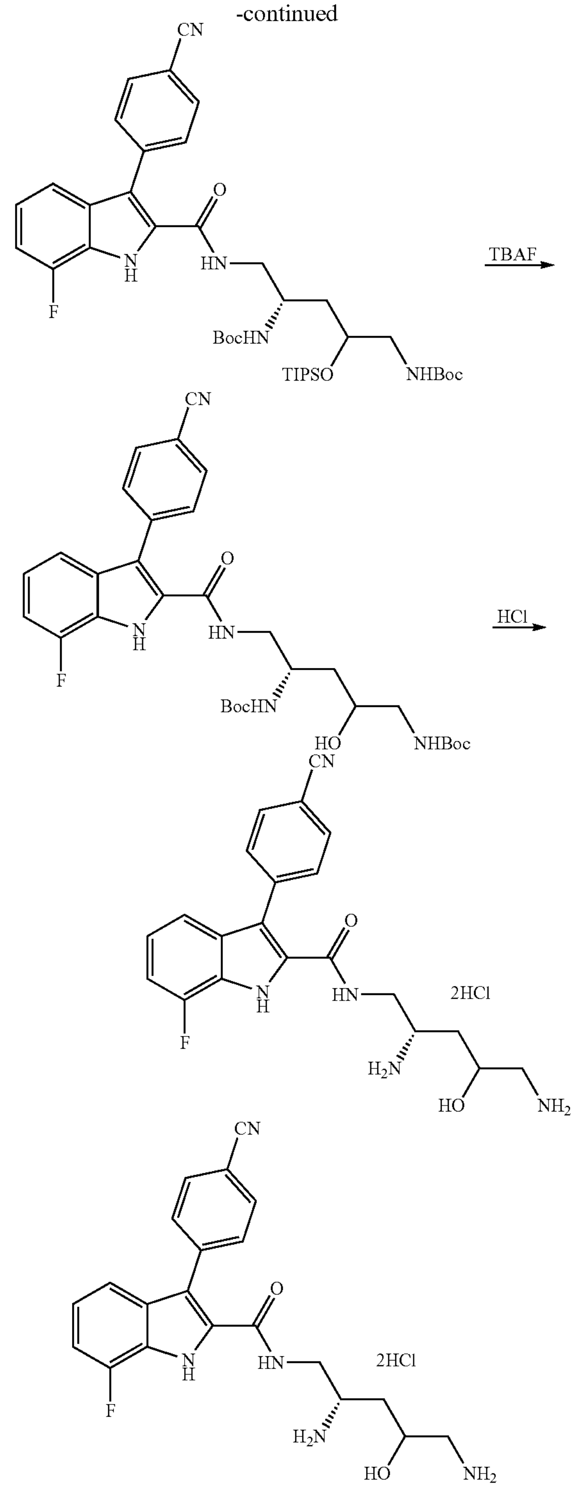

3-(4-cyanophenyl)-N-((2S)-2,5-diamino-4-hydroxypentyl)-7-fluoro-1H-indole-2-carboxamide hydrogen chloride salt To a solution of di-tert-butyl ((4S)-5-(3-(4-cyanophenyl)-7-fluoro-1H-indole-2-carboxamido)-2-hydroxypentane-1,4-diyl)dicarbamate (11 mg, 0.018 mmol) in MeOH (2 mL) HCl solution (4 M in dioxane, 0.1 mL, 0.4 mmol) was added.

It was stirred at room temperature for 2 hrs, then solvent was removed in vacuo. The residue was triturated with EtOAc and the precipitate was collected as an off-white powder (7 mg, 81% yield). $^1H$ NMR (300 MHz, $D_2O$) δ 7.99 (d, J=8.3 Hz, 2H), 7.80 (d, J=8.3 Hz, 2H), 7.54 (m, 1H), 7.26 (m, 1H), 7.64 (m, 1H), 4.17 (m, 1H), 3.80 (m, 1H), 3.76 (m, 2H), 3.66 (m, 1H), 3.22 (m, 1H), 3.03 (m, 1H), 1.91 (m, 2H). MS (ESI): Calcd for $C_{21}H_{23}FN_5O_2^+$ 396.18 [M+H]$^+$, found 396.00 [M+H]$^+$.

The requisite intermediates were prepared as shown in the following steps.

Step 1)

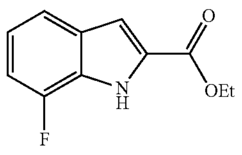 [SMILES: CCOC(=O)c1cc2cccc(F)c2[nH]1]

ethyl 7-fluoro-1H-indole-2-carboxylate

To a suspension of 7-fluoro-1H-indole-2-carboxylic acid (0.8 g, 4.4 mmol) in EtOH (50 mL) was added $SOCl_2$ (0.66 mL, 9 mmol) very slowly. The mixture was heated under reflux until TLC showed no starting material left. Solvent was removed in vacuo and the crude product was dissolved in EtOAc, washed with sat. $NaHCO_3$ solution, brine and dried over $Na_2SO_4$. After filtering off, the organic phase was removed in vacuo to provide the ester as a brown powder (0.88 g, 95% yield) after drying. It was used for next step reaction without purification.

Step 2)

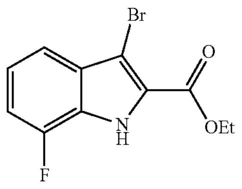 [SMILES: CCOC(=O)c1[nH]c2c(F)cccc2c1Br]

ethyl 3-bromo-7-fluoro-1H-indole-2-carboxylate

To a solution of ethyl 7-fluoro-1H-indole-2-carboxylate (0.45 g, 2.2 mmol) in dry THE (10 mL) was added NBS (0.39 g, 2.2 mmol) at −78° C. Once the temperature reached to room temperature it was washed with water, sat. $NaHCO_3$ and brine. After removing solvent in vacuo, the residue was used for next step reaction without purification (0.60 g, 96% yield) as a white powder. $^1H$ NMR (300 MHz, $CDCl_3$) δ 9.25 (br s, 1H), 7.45 (m, 1H), 7.16 (m, 1H), 7.10 (m, 1H), 4.48 (q, J=7.2 Hz, 2H), 1.47 (t, J=7.2 Hz, 3H).

Step 3)

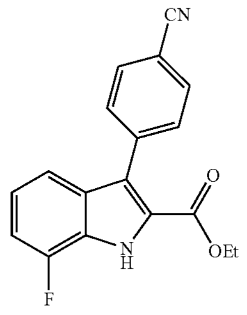 [SMILES: CCOC(=O)c1[nH]c2c(F)cccc2c1-c1ccc(C#N)cc1]

ethyl 3-(4-cyanophenyl)-7-fluoro-1H-indole-2-carboxylate

Ethyl 3-bromo-7-fluoro-1H-indole-2-carboxylate (200 mg, 0.7 mmol) and (4-cyanophenyl)boronic acid (147 mg, 1 mmol) in a mixture of toluene, ethanol and saturated $Na_2CO_3$ solution (10/3/3 mL) was degassed and Pd(dppf)$Cl_2$ (30 mg, 0.04 mmol) was added. The reaction mixture was heated at 100° C. overnight, it was extracted with EtOAc and washed with brine and dried over $Na_2SO_4$, then concentrated. It was purified by column chromatography on silica gel with 0-25% EtOAc in hexane as eluents to give the product (93 mg, 43% yield) as an off-white powder. $^1H$ NMR (300 MHz, $CDCl_3$) δ 9.22 (br s, 1H), 7.75 (d, J=8.4 Hz, 2H), 7.67 (d, J=8.4 Hz, 2H), 7.33 (m, 1H), 7.10 (m, 2H), 4.33 (q, J=7.1 Hz, 2H), 1.23 (t, J=7.1 Hz, 3H).

Step 4)

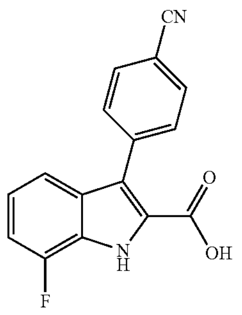 [SMILES: N#Cc1ccc(-c2c(C(=O)O)[nH]c3c(F)cccc23)cc1]

3-(4-cyanophenyl)-7-fluoro-1H-indole-2-carboxylic acid

To a solution of ethyl 3-(4-cyanophenyl)-7-fluoro-1H-indole-2-carboxylate (93 mg, 0.3 mmol) in THF (4 mL) was added LiOH solution (2 M, 2 mL). It was heated at 45° C. for 2 hrs. THF was removed in vacuo and the residue was acidified with HCl solution. The precipitate was filtered and washed with water. It was dried to provide the acid as a pale brown powder (60 mg, 71% yield) which was used for next step reaction without further purification. MS (ESI): Calcd for $C_{16}H_8FN_2O_2^-$ 279.06 [M−H]$^-$, found 279.00 [M−H]$^-$.

Step 5)

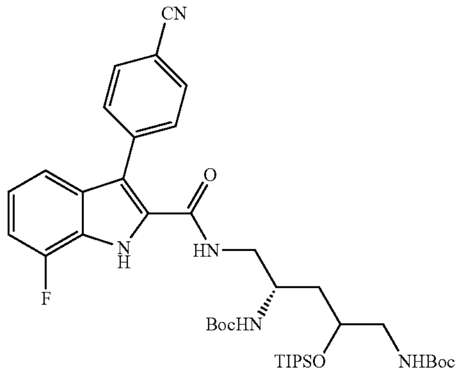

di-tert-butyl ((4S)-5-(3-(4-cyanophenyl)-7-fluoro-1H-indole-2-carboxamido)-2-((triisopropylsilyl)oxy) pentane-1,4-diyl)dicarbamate To a solution of 3-(4-cyanophenyl)-7-fluoro-1H-indole-2-carboxylic acid (28 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl) dicarbamate (Amine Intermediate B) (49 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel using 40-70% EtOAc in hexane as eluents to give two diastereomers (51 mg, 68% yield) as a white powder. $^1$H NMR (300 MHz, $CDCl_3$) δ 9.44 (br s, 1H), 7.82 (d, J=8.1 Hz, 2H), 7.69 (d, J=8.1 Hz, 2H), 7.39 (m, 1H), 7.10 (m, 2H), 6.71 (br s, 1H), 5.27 (br s, 1H), 4.77 (br, 1H), 4.01 (m, 1H), 3.71 (m, 1H), 3.41 (m, 2H), 3.25 (m, 1H), 3.16 (m, 1H), 1.63 (m, 2H), 1.41 (s, 9H), 1.25 (s, 12H), 1.06 (s, 18H). MS (ESI): Calcd for $C_{40}H_{59}FN_5O_6Si^+$752.42 $[M+H]^+$, found 752.40 $[M+H]^+$.

Step 6)

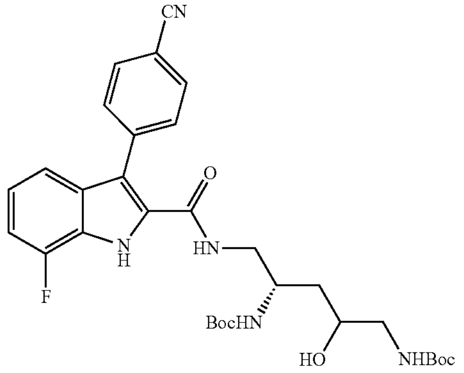 [SMILES: CC(C)(C)OC(=O)NCC(O)C[C@@H](CNC(=O)c1[nH]c2c(F)cccc2c1-c1ccc(C#N)cc1)NC(=O)OC(C)(C)C]

di-tert-butyl ((4S)-5-(3-(4-cyanophenyl)-7-fluoro-1H-indole-2-carboxamido)-2-hydroxypentane-1,4-diyl)dicarbamate To a solution of the relatively polar one of the two diastereomers of tert-butyl ((4S)-5-(3-(4-cyanophenyl)-7-fluoro-1H-indole-2-carboxamido)-2-((triisopropylsilyl)oxy) pentane-1,4-diyl)dicarbamate (20 mg, 0.026 mmol) in THE (2 mL) was added TBAF solution (1.0 M in THF, 0.4 mL, 0.4 mmol) at room temperature It was stirred for 0.5 hr, concentrated and loaded on silica gel column chromatography and purified with 40-65% EtOAc in hexane to provide the alcohol as a white powder (11 mg, 69% yield). MS (ESI): Calcd for $C_{31}H_{39}FN_5O_6^+$ 596.29 $[M+H]^+$, found 596.25 $[M+H]^+$.

Example 15. Preparation of 3-cyclohexyl-N-((2S)-2,5-diamino-4-hydroxypentyl)-1H-indole-2-carboxamide hydrogen chloride salt

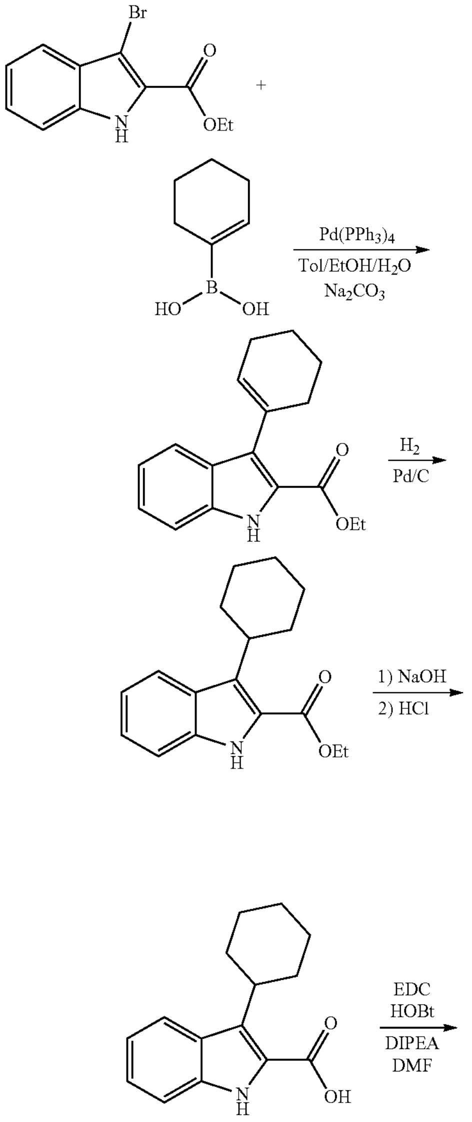

-continued

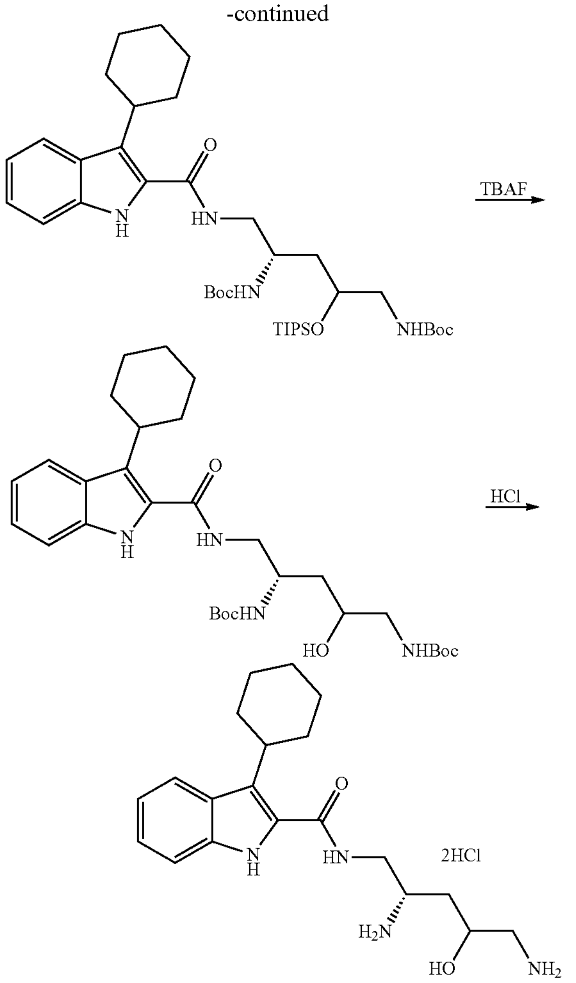

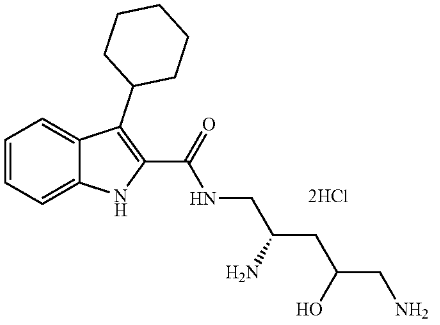

3-cyclohexyl-N-((2S)-2,5-diamino-4-hydroxypentyl)-1H-indole-2-carboxamide hydrogen chloride salt To a solution of di-tert-butyl ((4S)-5-(3-cyclohexyl-1H-indole-2-carboxamido)-2-hydroxypentane-1,4-diyl)dicarbamate (20 mg, 0.036 mmol) in MeOH (2 mL) HCl solution (4 M in dioxane, 0.1 mL, 0.4 mmol) was added. It was stirred at room temperature for 2 hrs, then solvent was removed in vacuo. The residue was loaded on a C18 column and purified with EtOH in water to provide the product as a colorless powder (7 mg, 45% yield). $^1$H NMR (300 MHz, $CD_3OD$) δ 7.81 (d, J=8.2 Hz, 1H), 7.37 (d, J=8.2 Hz, 1H), 7.18 (m, 1H), 7.00 (m, 1H), 3.92 (m, 1H), 3.54 (m, 1H), 3.48 (m, 1H), 3.23 (m, 1H), 2.85 (m, 1H), 2.73 (m, 1H), 2.05 (m, 1H), 1.73-1.95 (m, 6H), 1.26-1.54 (m, 4H). MS (ESI): Calcd for $C_{20}H_{31}N_4O_2^+$ 359.24 [M+H]$^+$, found 359.05 [M+H]$^+$.

The requisite intermediates were prepared as shown in the following steps.

Step 1)

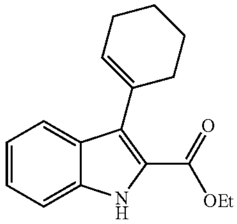 [SMILES: CCOC(=O)c1[nH]c2ccccc2c1C1=CCCCC1]

ethyl 3-(cyclohex-1-en-1-yl)-1H-indole-2-carboxylate

Ethyl 3-bromo-1H-indole-2-carboxylate (1.0 g, 3.73 mmol) and cyclohex-1-en-1-ylboronic acid (0.7 g, 5.56 mmol) in a mixture of toluene, ethanol and saturated $Na_2CO_3$ solution (30/6/6 mL) was degassed and Pd(dppf)$Cl_2$ (70 mg, 0.1 mmol) was added. The reaction mixture was heated at 100° C. for 4 hours, it was extracted with EtOAc and washed with brine and dried over $Na_2SO_4$, then concentrated. It was purified by column chromatography on silica gel with 0-20% EtOAc in hexane as eluents to give the product (0.98 g, 99% yield) as an off-white powder. $^1$H NMR (300 MHz, $CDCl_3$) δ 8.74 (br s, 1H), 7.37 (d, J=7.6 Hz, 1H), 7.34 (m, 1H), 7.32 (m, 1H), 7.13 (m, 1H), 5.80 (m, 1H), 4.38 (q, J=7.1 Hz, 2H), 2.37 (m, 2H), 2.27 (m, 2H), 1.78 (m, 4H), 1.41 (t, J=7.1 Hz, 3H).

Step 2)

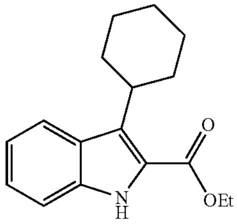 [SMILES: CCOC(=O)c1[nH]c2ccccc2c1C1CCCCC1]

ethyl 3-cyclohexyl-1H-indole-2-carboxylate

To a solution of ethyl 3-(cyclohex-1-en-1-yl)-1H-indole-2-carboxylate (0.98 g, 3.6 mmol) in MeOH (50 mL) was added Pd/C (10 w/w %, 100 mg, 0.09 mmol). It was stirred under $H_2$ (50 psi) overnight. The catalyst was filter off through a Celite pad and washed with MeOH. The combined filtrate was concentrated and used without further purification (0.77 g, 78%). $^1$H NMR (300 MHz, $CDCl_3$) δ 8.67 (br s, 1H), 7.93 (d, J=8.2 Hz, 1H), 7.36 (m, 1H), 7.29 (m, 1H), 7.10 (m, 1H), 4.40 (q, J=7.1 Hz, 2H), 3.74 (m, 1H), 1.99 (m, 2H), 1.87 (m, 6H), 1.78 (m, 4H), 1.46 (m, 2H), 1.43 (t, J=7.1 Hz, 3H).

Step 3)

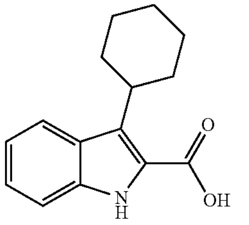 [SMILES: O=C(O)c1[nH]c2ccccc2c1C1CCCCC1]

3-cyclohexyl-1H-indole-2-carboxylic acid

To a solution of ethyl 3-cyclohexyl-1H-indole-2-carboxylate (770 mg, 2.8 mmol) in THE (4 mL) was added NaOH solution (2 M, 10 mL). It was heated at 50° C. overnight. THE was removed in vacuo and the residue was acidified with HCl solution. The precipitate was filtered and washed with water. It was dried to provide the acid as a pale brown powder (250 mg, 36% yield) which was used for next step reaction without further purification. MS (ESI): Calcd for $C_{15}H_{18}NO_2^+$ 244.14 $[M+H]^+$, found 243.90 $[M+H]^+$.

Step 4)

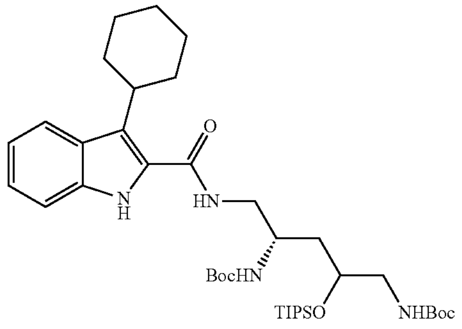

di-tert-butyl ((4S)-5-(3-cyclohexyl-1H-indole-2-carboxamido)-2-((triisopropylsilyl)oxy)pentane-1,4-diyl)dicarbamate To a solution of 3-cyclohexyl-1H-indole-2-carboxylic acid (24 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and di-tert-butyl ((4S)-5-amino-2-((triisopropylsilyl)oxy)pentane-1,4-diyl)dicarbamate (Amine Intermediate B) (49 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel using 50-70% EtOAc in hexane as eluents to give the amide (42 mg, 59% yield) as a white powder. $^1H$ NMR (300 MHz, $CDCl_3$) δ 8.66 (br s, 1H), 7.93 (m, 1H), 7.36 (m, 1H), 7.29 (m, 1H), 7.09 (m, 1H), 6.84 (br s, 1H), 5.11 (br s, 1H), 4.95 (br, 1H), 4.03 (m, 1H), 3.73 (m, 2H), 3.47 (m, 1H), 3.35 (m, 1H), 3.18 (m, 1H), 2.00 (m, 1H), 1.71-1.98 (m, 4H), 1.60 (m, 2H), 1.33-1.50 (m, 27H), 1.07 (s, 18H). MS (ESI): Calcd for $C_{39}H_{67}N_4O_6Si^+$ 715.48 $[M+H]^+$, found 715.40 $[M+H]^+$.

Step 5)

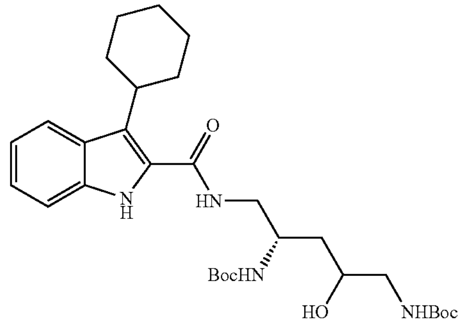 [SMILES: CC(C)(C)OC(=O)NCC(O)C[C@@H](CNC(=O)c1[nH]c2ccccc2c1C1CCCCC1)NC(=O)OC(C)(C)C]

di-tert-butyl ((4S)-5-(3-cyclohexyl-1H-indole-2-carboxamido)-2-hydroxypentane-1,4-diyl)dicarbamate To a solution of di-tert-butyl ((4S)-5-(3-cyclohexyl-1H-indole-2-carboxamido)-2-((triisopropylsilyl)oxy)pentane-1,4-diyl)dicarbamate (42 mg, 0.059 mmol) in THE (5 mL) was added TBAF solution (1.0 M in THF, 0.4 mL, 0.4 mmol) at room temperature It was stirred for 1 hr and concentrated, then loaded on silica gel column chromatography and purified with 50-80% EtOAc in hexane to provide the alcohol as a white powder (20 mg, 61% yield). MS (ESI): Calcd for $C_{30}H_{47}N_4O_6$ 559.35 $[M+H]^+$, found 559.05 $[M+H]^+$.

Example 16. Preparation of N-((2R)-2,5-diamino-4-(hydroxymethyl)pentyl)-3-(4-fluorophenyl)-1H-indole-2-carboxamide hydrogen chloride salt

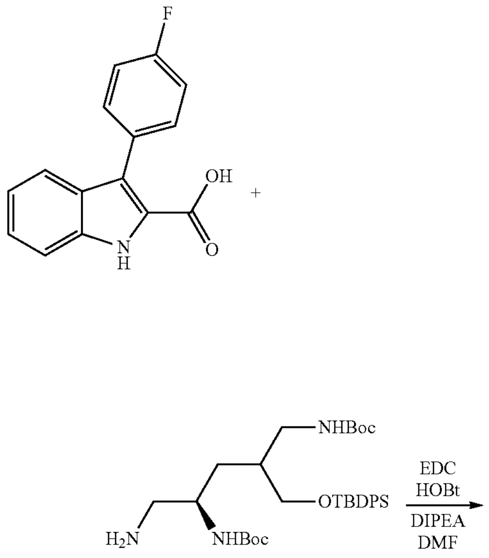

-continued

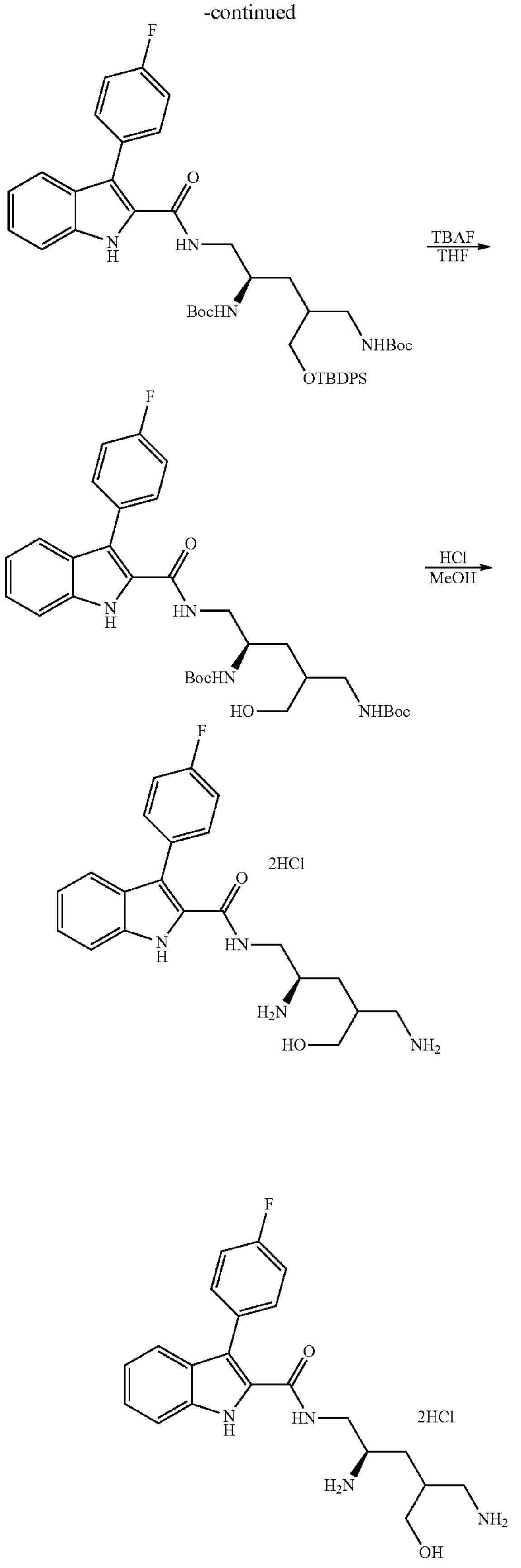

N-((2R)-2,5-diamino-4-(hydroxymethyl)pentyl)-3-(4-fluorophenyl)-1H-indole-2-carboxamide hydrogen chloride salt To a solution of di-tert-butyl ((4R)-5-(3-(4-fluorophenyl)-1H-indole-2-carboxamido)-2-(hydroxymethyl)pentane-1,4-diyl)dicarbamate (136 mg, 0.23 mmol) in MeOH (5 mL) was added HCl (0.5 mL, 4 N in dioxane). The reaction mixture was stirred at 50° C. for 1 h and then concentrated to give a residue. The residue was triturated with EtOAc to give the desired product (75 mg, 71% yield) as a white solid. $^1$H NMR (300 MHz, $D_2O$) δ 7.55 (m, 4H), 7.15-7.39 (m, 4H), 3.54-3.68 (m, 3H), 3.44-3.52 (m 2H), 3.00 (m, 2H), 2.00 (m, 1H), 1.57 (m, 2H). MS (EPI): Calcd for $C_{21}H_{26}FN_4O_2^+$ 385.20 [M+H]$^+$, found 385.00 [M+H]$^+$.

The requisite intermediates were prepared as shown in the following steps.

Step 1)

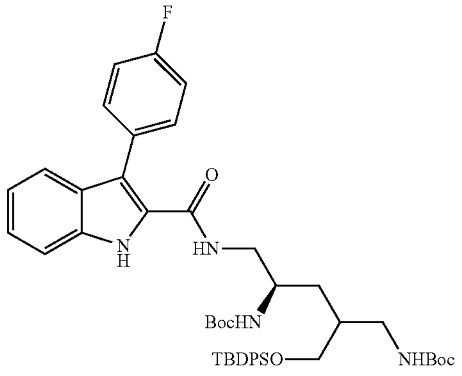

di-tert-butyl ((4R)-2-(((tert-butyldiphenylsilyl)oxy)methyl)-5-(3-(4-fluorophenyl)-1H-indole-2-carboxamido)pentane-1,4-diyl)dicarbamate To a solution of 3-(4-fluorophenyl)-1H-indole-2-carboxylic acid (106 mg, 041 mmol) in dry DMF (3 mL) was added DIPEA (0.14 mL, 0.75 mmol), HOBt (30 mg, 0.23 mmol) and EDC (80 mg, 0.41 mmol). The reaction mixture was stirred at room temperature for 10 min and then di-tert-butyl ((3R,4S)-5-amino-3-hydroxypentane-1,4-diyl) dicarbamate (Amine Intermediate C) (223 mg, 0.38 mmol) was added. The reaction mixture was stirred at room temperature overnight then added $H_2O$ with stirring. A solid was formed and collected by filtration. After air drying the solid was purified by chromatography on silica gel. Elution with 10-20% EtOAc/hexanes afforded the desired compound (270 mg, 86% yield) as a white solid. $^1$H NMR (300 MHz, $CDCl_3$) δ 9.22 (br s, 1H), 7.63 (m, 4H), 7.31-7.52 (m, 11H), 7.23 (m, 2H), 7.13 (m, 1H), 6.14 (br s, 1H), 4.80 (br s, 1H), 4.57 (d, J=9.0 Hz), 1H), 3.42-3.65 (m, 4H), 3.05-3.25 (m, 3H), 1.73 (m, 1H), 1.22-1.44 (m, 20H), 1.04 (s, 9H).

Step 2)

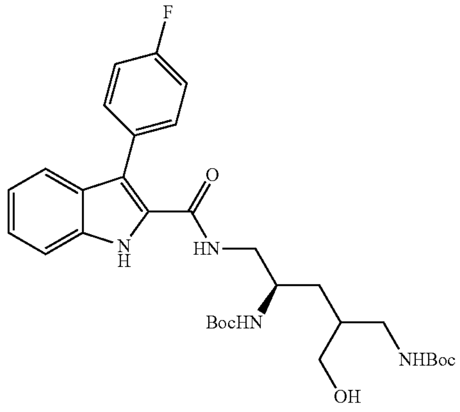 [SMILES: CC(C)(C)OC(=O)NCC(CO)C[C@H](CNC(=O)c1[nH]c2ccccc2c1-c1ccc(F)cc1)NC(=O)OC(C)(C)C]

di-tert-butyl ((4R)-5-(3-(4-fluorophenyl)-1H-indole-2-carboxamido)-2-(hydroxymethyl)pentane-1,4-diyl) dicarbamate To a solution of di-tert-butyl ((4R)-2-(((tert-butyldiphenylsilyl)oxy)methyl)-5-(3-(4-fluorophenyl)-1H-indole-2-carboxamido)pentane-1,4-diyl)dicarbamate (0.27 g, 0.33 mmol) in THF (15 mL) was added TBAF solution in THF (1.0 M, 1.0 mL, 1.0 mmol). It was stirred at room temperature until no starting material remained in the reaction mixtures. The crude product was purified by column chromatography on silica gel using 50% EtOAc in hexane as eluents. A white solid was collected (0.136 g, 71% yield). $^1$H NMR (300 MHz, $CDCl_3$) δ 9.86 (br s, 1H), 7.40-7.51 (m, 4H), 7.22-7.34 (m, 3H), 7.12 (m, 1H), 6.16 (br, 1H), 5.07-5.19 (m, 1H), 4.69-4.86 (m, 1H), 3.06-3.86 (m, 7H), 1.63 (m, 1H), 1.20-1.44 (m, 20H).

Example 17. Preparation of N-((2R)-2,5-diamino-4-(hydroxymethyl)pentyl)-5-fluoro-3-phenyl-1H-indole-2-carboxamide hydrogen chloride salt

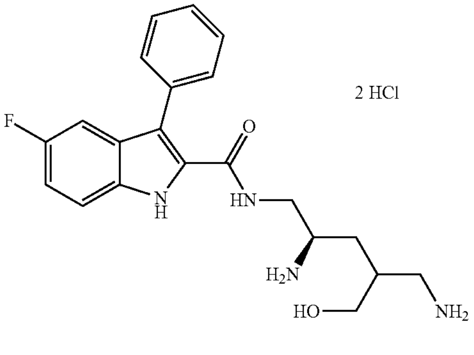 [SMILES: NCC(CO)C[C@@H](N)CNC(=O)c1[nH]c2ccc(F)cc2c1-c1ccccc1]

N-((2R)-2,5-diamino-4-(hydroxymethyl)pentyl)-5-fluoro-3-phenyl-1H-indole-2-carboxamide hydrogen chloride salt To a solution of di-tert-butyl ((4R)-5-(5-fluoro-3-phenyl-1H-indole-2-carboxamido)-2-(hydroxymethyl)pentane-1,4-diyl)dicarbamate (52 mg, 0.09 mmol) in MeOH (3 mL) was added HCl (0.5 mL, 4 N in dioxane, 2 mmol). The reaction mixture was stirred at 50° C. for 1 h and then concentrated to give a residue. The residue was triturated with EtOAc to give the desired product (27 mg, 66% yield) as white solid. $^1$H NMR (300 MHz, $D_2O$) δ 7.44-7.58 (m, 5H), 7.27 (m, 1H), 7.16 (m, 1H), 3.54-3.67 (m, 3H), 3.44-3.50 (m 2H), 2.99 (m, 2H), 2.00 (m, 1H), 1.56 (m, 2H). MS (EPI): Calcd for $C_{21}H_{26}FN_4O_2^+$ 385.20 [M+H]$^+$, found 385.00 [M+H]$^+$.

The requisite intermediates were prepared as shown in the following steps.

Step 1)

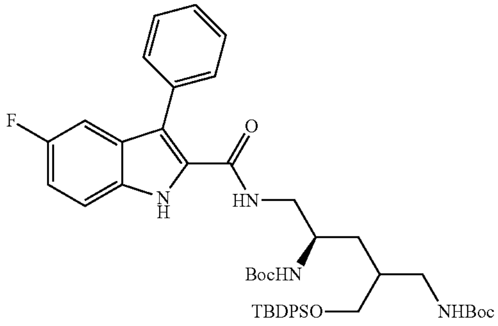

di-tert-butyl ((4R)-2-(((tert-butyldiphenylsilyl)oxy)methyl)-5-(5-fluoro-3-phenyl-1H-indole-2-carboxamido)pentane-1,4-diyl)dicarbamate To a solution of 5-fluoro-3-phenyl-1H-indole-2-carboxylic acid (45 mg, 018 mmol) in dry DMF (2 mL) was added DIPEA (0.06 mL, 0.32 mmol), HOBt (13 mg, 0.10 mmol) and EDC (34 mg, 0.18 mmol). The reaction mixture was stirred at room temperature for 10 min and then di-tert-butyl ((3R,4S)-5-amino-3-hydroxypentane-1,4-diyl) dicarbamate (Amine Intermediate C) (96 mg, 0.16 mmol) was added. The reaction mixture was stirred at room temperature overnight then added $H_2O$ with stirring. A solid was formed and collected by filtration. After air drying the solid was purified by chromatography on silica gel. Elution with 10-20% EtOAc/hexanes afforded the desired compound (130 mg, 98% yield) as a white solid. $^1$H NMR (300 MHz, $CDCl_3$) δ 9.45 (br s, 1H), 7.63 (m, 4H), 7.31-7.52 (m, 12H), 6.09 (br s, 1H), 4.82 (br s, 1H), 4.48-4.64 (m, 1H), 3.32-3.65 (m, 4H), 3.05-3.28 (m, 3H), 1.71 (m, 1H), 1.22-1.41 (m, 20H), 1.04 (s, 9H).

Step 2)

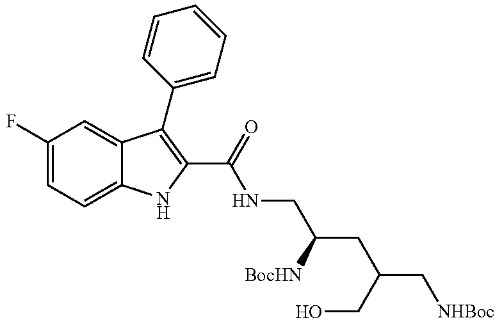 [SMILES: CC(C)(C)OC(=O)NCC(CO)C[C@H](CNC(=O)c1[nH]c2ccc(F)cc2c1-c1ccccc1)NC(=O)OC(C)(C)C]

di-tert-butyl ((4R)-5-(5-fluoro-3-phenyl-1H-indole-2-carboxamido)-2-(hydroxymethyl)pentane-1,4-diyl) dicarbamate To a solution of di-tert-butyl ((4R)-2-(((tert-butyldiphenylsilyl)oxy)methyl)-5-(5-fluoro-3-phenyl-1H-indole-2-carboxamido)pentane-1,4-diyl)dicarbamate (130 mg, 0.16 mmol) in THE (10 mL) was added TBAF solution in THE (1.0 M, 0.5 mL, 0.5 mmol). It was stirred at room temperature until no starting material remained in the reaction mixtures. The crude product was purified by column chromatography on silica gel using 50% EtOAc in hexane to afford the desired product as a white solid (53 mg, 57% yield). $^1H$ NMR (300 MHz, $CDCl_3$) δ 9.76 (br s, 1H), 7.45-7.60 (m, 5H), 7.40 (m, 1H), 7.07 (m, 2H), 6.18 (br s, 1H), 4.98-5.19 (m, 1H), 4.56-4.80 (m, 1H), 3.02-3.81 (m, 7H), 1.62 (m, 1H), 1.20-1.44 (m, 20H).

Example 18. Preparation of 3-cyclohexyl-N-((2R)-2,5-diamino-4-(hydroxymethyl)pentyl)-5-fluoro-1H-indole-2-carboxamide hydrogen chloride salt

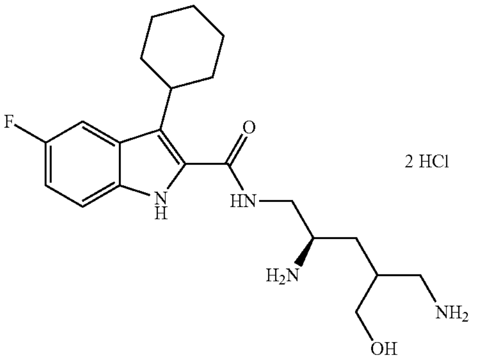 [SMILES: NCC(CO)C[C@@H](N)CNC(=O)c1[nH]c2ccc(F)cc2c1C1CCCCC1]

3-cyclohexyl-N-((2R)-2,5-diamino-4-(hydroxymethyl)pentyl)-5-fluoro-1H-indole-2-carboxamide hydrogen chloride salt To a solution of di-tert-butyl ((4R)-5-(3-cyclohexyl-5-fluoro-1H-indole-2-carboxamido)-2-(hydroxymethyl)pentane-1,4-diyl)dicarbamate (16 mg, 0.03 mmol) in MeOH (1 mL) was added HCl (0.2 mL, 4 M in dioxane, 0.8 mmol). The reaction mixture was stirred at 50° C. for 1 h then concentrated to give a residue. The residue was triturated with EtOAc to afford the desired product (7 mg, 54% yield) as white solid. $^1H$ NMR (300 MHz, $D_2O$) δ 7.68 (dd, J=2.4, 10.5 Hz, 1H), 7.44 (dd, J=4.5, 8.7 Hz, 1H), 7.10 (m, 1H), 3.59-3.80 (m, 5H), 3.27 (m, 1H), 3.08 (m, 1H), 2.20 (m, 1H), 1.66-1.98 (m, 10H), 1.35 (m, 3H). MS (EPI): Calcd for $C_{21}H_{32}FN_4O_2^+$ 391.25 $[M+H]^+$, found 391.05 $[M+H]^+$.

The requisite intermediates were prepared as shown in the following steps.

Step 1)

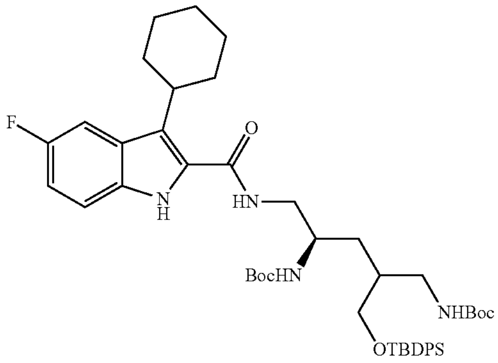

di-tert-butyl ((4R)-2-(((tert-butyldiphenylsilyl)oxy)methyl)-5-(3-cyclohexyl-5-fluoro-1H-indole-2-carboxamido)pentane-1,4-diyl)dicarbamate To a solution of 3-cyclohexyl-5-fluoro-1H-indole-2-carboxylic acid (24 mg, 0.09 mmol) in dry DMF (1 mL) was added DIPEA (0.03 mL, 0.16 mmol), HOBt (7 mg, 0.05 mmol) and EDC (17 mg, 0.09 mmol). The reaction mixture was stirred at room temperature for 10 min then di-tert-butyl ((3R,4S)-5-amino-3-hydroxypentane-1,4-diyl) dicarbamate (Amine Intermediate C) (48 mg, 0.08 mmol) was added. The reaction mixture was stirred at room temperature overnight then added $H_2O$ with stirring. A solid was formed and collected by filtration. After air drying the solid was purified by chromatography on silica gel. Elution with 10-20% EtOAc/hexanes afforded the desired compound (26 mg, 34% yield) as a white solid. $^1H$ NMR (300 MHz, $CDCl_3$) δ 9.22 (br s, 1H), 7.65 (m, 4H), 7.50 (m, 1H), 7.36-7.45 (m, 5H), 7.23 (m, 1H), 7.04 (br, 1H), 6.90-7.01 (m, 1H), 4.99 (d, J=8.4 Hz, 1H), 4.48-4.64 (m, 1H), 4.69 (br s, 1H), 3.80 (m, 1H), 3.61 (m, 2H), 3.47 (m, 2H), 3.15 (m, 2H), 1.85 (m, 9H), 1.22-1.54 (m, 23H), 1.07 (m, 9H).

Step 2)

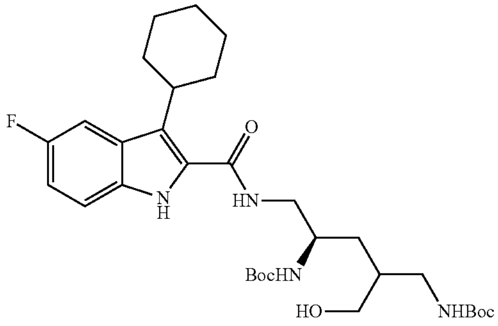 [SMILES: CC(C)(C)OC(=O)NCC(CO)C[C@H](CNC(=O)c1[nH]c2ccc(F)cc2c1C1CCCCC1)NC(=O)OC(C)(C)C]

di-tert-butyl ((4R)-5-(3-cyclohexyl-5-fluoro-1H-indole-2-carboxamido)-2-(hydroxymethyl)pentane-1,4-diyl)dicarbamate To a solution of di-tert-butyl ((4R)-2-(((tert-butyldiphenylsilyl)oxy)methyl)-5-(3-cyclohexyl-5-fluoro-1H-indole- 2-carboxamido)pentane-1,4-diyl)dicarbamate (25 mg, 0.03 mmol) in THE (1 mL) was added TBAF solution in THE (1.0 M, 0.2 mL, 0.2 mmol). It was stirred at room temperature until no starting material remained in the reaction mixtures. The crude product was purified by column chromatography on silica gel using 50% EtOAc in hexane to afford the desired product as white solid (16 mg, 88% yield). $^{1}$H NMR (300 MHz, $CDCl_3$) δ 9.24 (br s, 1H), 7.50 (dd, J=2.1, 10.5 Hz, 1H), 7.22 (m, 1H), 6.98 (m, 1H), 6.89 (br s, 1H), 4.95 (m, 2H), 3.85 (m, 1H), 3.54 (m, 4H), 3.20 (m, 3H), 1.85 (m, 9H), 1.22-1.54 (m, 23H).

-continued

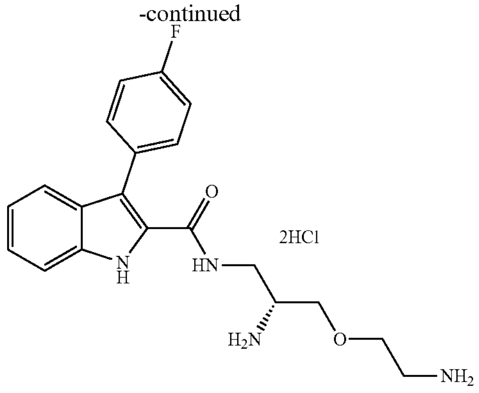

Example 19. Preparation of (R)—N-(2-amino-3-(2-aminoethoxy)propyl)-3-(4-fluorophenyl)-1H-indole-2-carboxamide hydrogen chloride salt

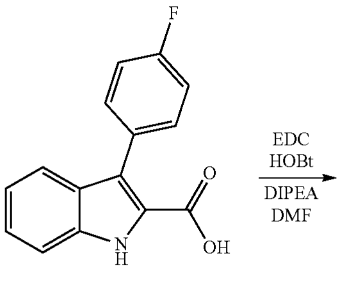

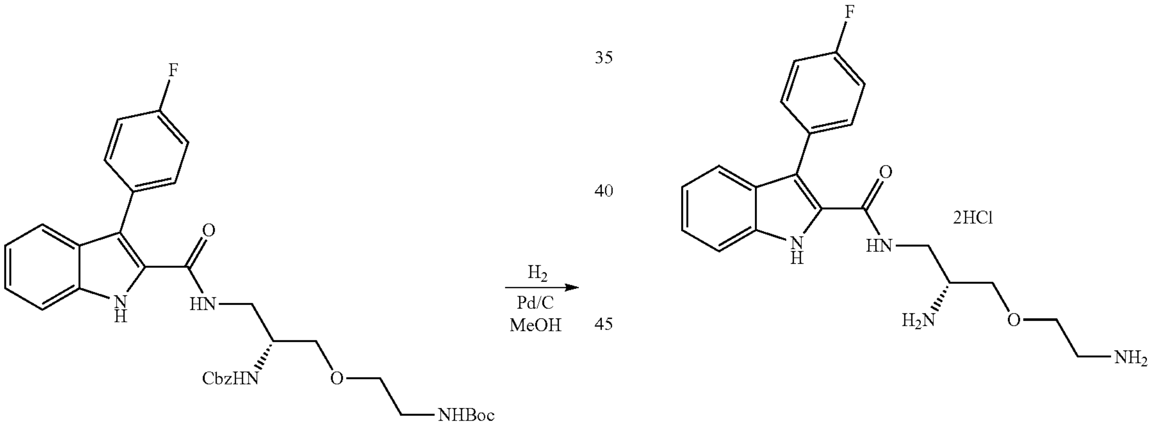

(R)—N-(2-amino-3-(2-aminoethoxy)propyl)-3-(4-fluorophenyl)-1H-indole-2-carboxamide hydrogen chloride salt

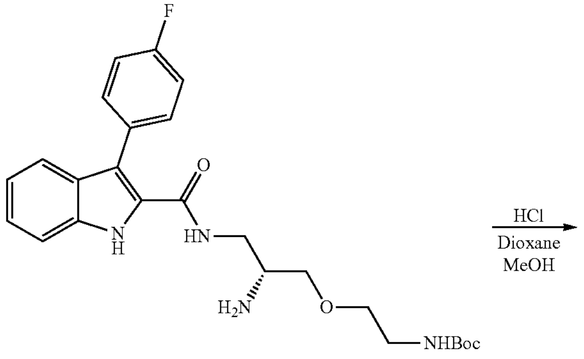

To a solution of tert-butyl (R)-(2-(2-amino-3-(3-(4-fluorophenyl)-1H-indole-2-carboxamido)propoxy)ethyl)carbamate (25 mg, 0.05 mmol) in MeOH (5 mL) HCl solution (4 M in dioxane, 0.15 mL, 0.6 mmol) was added. It was stirred at room temperature for 2 hrs, then solvent was removed in vacuo. The residue was triturated with EtOAc and the precipitate was collected as a pale brown powder (16 mg, 65% yield). $^{1}$H NMR (300 MHz, $D_2O$) δ 7.59 (m, 2H), 7.55 (m, 2H), 7.38 (m, 1H), 7.28 (d, J=9.0 Hz, 2H), 7.20 (t, J=7.5 Hz, 1H), 3.72 (m, 2H), 3.69 (m, 2H), 3.56 (m, 3H), 3.18 (m, 2H). MS (ESI): Calcd for $C_{20}H_{24}FN_4O_2^+$ 371.19 $[M+H]^+$, found 371.00 $[M+H]^+$.

The requisite intermediates were prepared as shown in the following steps.

Step 1)

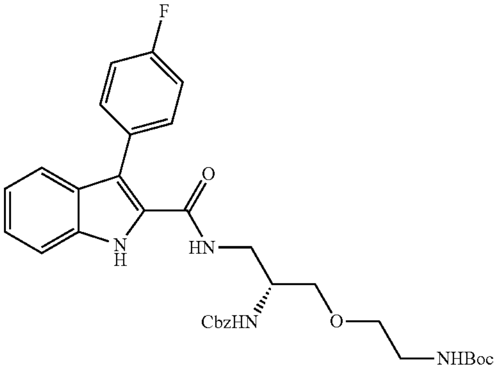 [SMILES: CC(C)(C)OC(=O)NCCOC[C@@H](CNC(=O)c1[nH]c2ccccc2c1-c1ccc(F)cc1)NC(=O)OCc1ccccc1]

tert-butyl (R)-(2-(2-(((benzyloxy)carbonyl)amino)-3-(3-(4-fluorophenyl)-1H-indole-2-carboxamido)propoxy)ethyl)carbamate To a solution of 3-(4-fluorophenyl)-1H-indole-2-carboxylic acid (26 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and benzyl (R)-(1-amino-3-(2-((tert-butoxycarbonyl)amino)ethoxy)propan-2-yl)carbamate (Amine Intermediate D) (37 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel to give the product (50 mg, 83% yield) as a white powder. $^1H$ NMR (300 MHz, $CDCl_3$) δ 9.31 (br s, 1H), 7.44 (m, 4H), 7.31 (m, 5H), 7.21 (m, 3H), 7.14 (m, 1H), 6.17 (br s, 1H), 5.29 (br s, 1H), 5.06 (m, 2H), 3.80 (m, 1H), 3.57 (m, 2H), 3.48 (m, 2H), 3.39 (m, 2H), 3.26 (m, 2H), 1.44 (s, 9H). MS (ESI): Calcd for $C_{33}H_{38}FN_4O_6^+$ 605.28 $[M+H]^+$, found 605.20 $[M+H]^+$.

Step 2)

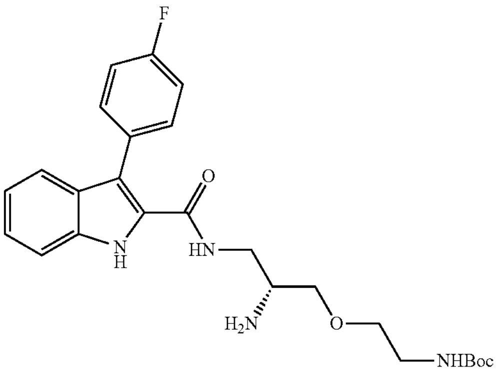 [SMILES: CC(C)(C)OC(=O)NCCOC[C@H](N)CNC(=O)c1[nH]c2ccccc2c1-c1ccc(F)cc1]

tert-butyl (R)-(2-(2-amino-3-(3-(4-fluorophenyl)-1H-indole-2-carboxamido)propoxy)ethyl)carbamate To a solution of tert-butyl (R)-(2-(2-(((benzyloxy)carbonyl)amino)-3-(3-(4-fluorophenyl)-1H-indole-2-carboxamido)propoxy)ethyl)carbamate (50 mg, 0.08 mmol) in MeOH (5 mL) was added Pd/C (10%, 20 mg, 0.02 mmol). Then it was stirred under $H_2$ (50 psi) overnight. It was filtered through a Celite pad and washed with methanol, then concentrated to provide the crude product which was purified by column chromatography on silica gel to give the amine as an off-white powder (25 mg, 64% yield). MS (ESI): Calcd for $C_{25}H_{32}FN_4O_4^+$ 471.24 $[M+H]^+$, found 471.15 $[M+H]^+$.

Example 20. Preparation of (R)—N-(2-amino-3-(2-aminoethoxy)propyl)-3-(4-cyanophenyl)-5-fluoro-1H-indole-2-carboxamide hydrogen chloride salt

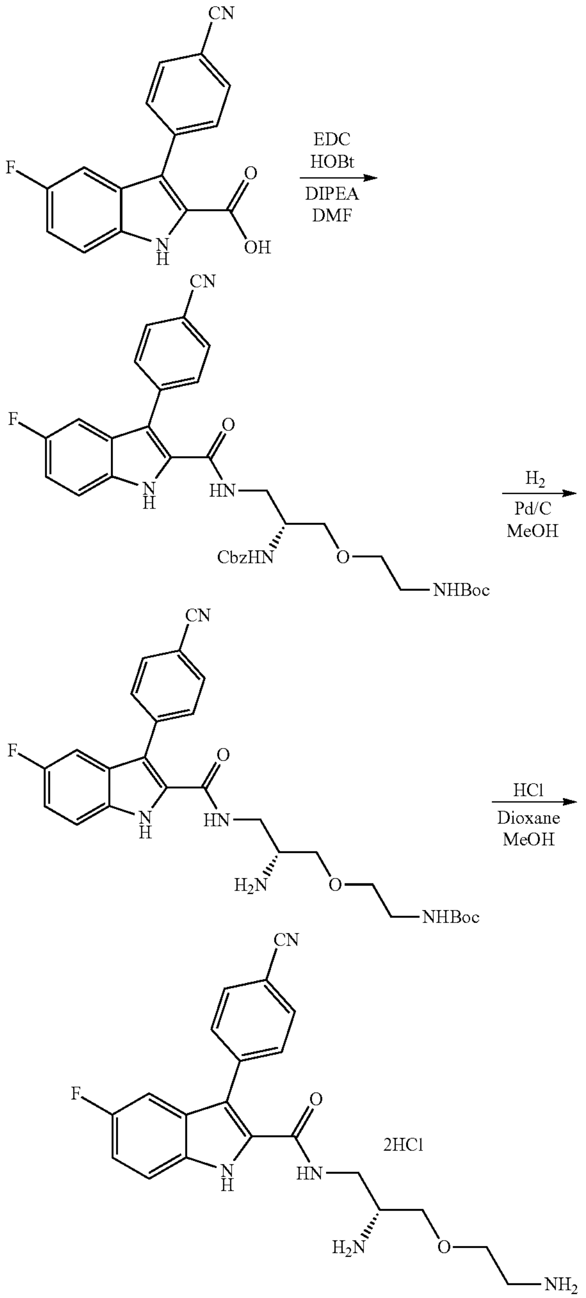

-continued

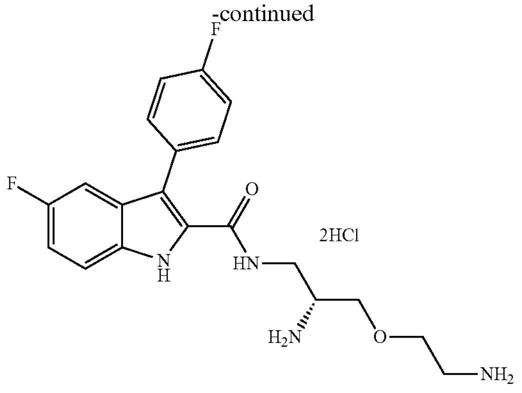

(R)—N-(2-amino-3-(2-aminoethoxy)propyl)-3-(4-cyanophenyl)-5-fluoro-1H-indole-2-carboxamide hydrogen chloride salt To a solution tert-butyl (R)-(2-(2-amino-3-(3-(4-cyano-phenyl)-5-fluoro-1H-indole-2-carboxamido)propoxy)ethyl) carbamate (16 mg, 0.03 mmol) in MeOH (5 mL) HCl solution (4 M in dioxane, 0.15 mL, 0.6 mmol) was added. It was stirred at room temperature for 1 hour then solvent was removed in vacuo at 50° C. The residue was dissolved in water and loaded on $C_{18}$ column chromatography and purified with 0-15% EtOH in water to give the desired product as a white powder (8 mg, 52% yield). $^1$H NMR (300 MHz, $D_2O$) δ 7.86 (d, J=8.2 Hz, 2H), 7.65 (d, J=8.2 Hz, 2H), 7.52 (t, J=4.4 Hz, 1H), 7.31 (d, J=9.4 Hz, 1H), 6.87 (t, J=9.4 Hz, 1H), 3.72 (m, 2H), 3.68 (m, 2H), 3.58 (m, 3H), 3.19 (m, 2H). MS (ESI): Calcd for $C_{21}H_{23}FN_5O_2^+$ 396.18 $[M+H]^+$, found 396.05 $[M+H]^+$.

The requisite intermediates were prepared as shown in the following steps.

Step 1)

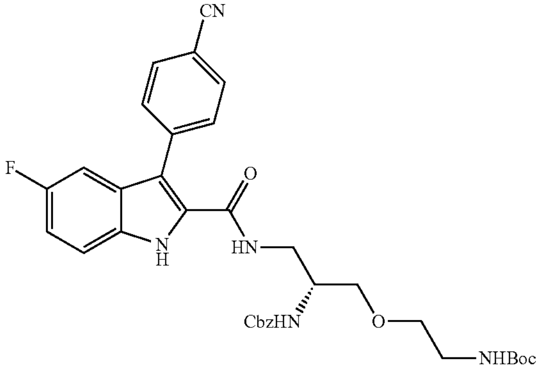 [SMILES: CC(C)(C)OC(=O)NCCOC[C@@H](CNC(=O)c1[nH]c2ccc(F)cc2c1-c1ccc(C#N)cc1)NC(=O)OCc1ccccc1]

tert-butyl (R)-(2-(2-(((benzyloxy)carbonyl)amino)-3-(3-(4-cyanophenyl)-5-fluoro-1H-indole-2-carboxamido)propoxy)ethyl)carbamate To a solution of 3-(4-cyanophenyl)-5-fluoro-1H-indole-2-carboxylic acid (28 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and benzyl (R)-(1-amino-3-(2-((tert-butoxycarbonyl)amino)ethoxy)propan-2-yl)carbamate (Amine Intermediate D) (37 mg, 0.1 mmol) was added. The reaction mixture was stirred at room temperature overnight. It was extracted with EtOAc and washed with water and brine. The organic layer was dried over $Na_2SO_4$ and filtered. The filtrate was concentrated and purified by column chromatography on silica gel to give the product (43 mg, 68% yield) as a white powder. $^1$H NMR (300 MHz, $CDCl_3$) δ 9.66 (br s, 1H), 7.77 (m, 2H), 7.61 (m, 2H), 7.42 (m, 2H), 7.28 (m, 4H), 7.11 (m, 2H), 6.45 (br s, 1H), 5.39 (br s, 1H), 5.06 (m, 2H), 3.85 (m, 1H), 3.56 (m, 3H), 3.47 (m, 3H), 3.28 (m, 2H), 1.44 (s, 9H). MS (ESI): Calcd for $C_{34}H_{37}FN_5O_6^+$ 630.27 $[M+H]^+$, found 630.25 $[M+H]^+$.

Step 2)

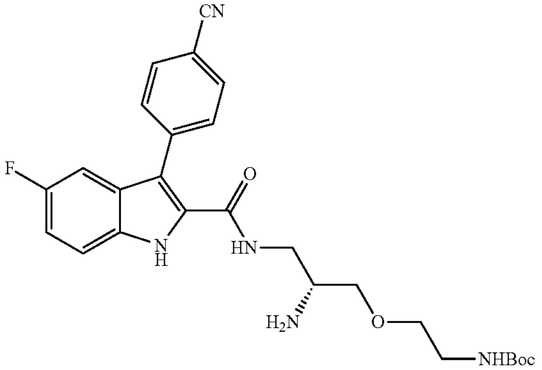 [SMILES: CC(C)(C)OC(=O)NCCOC[C@H](N)CNC(=O)c1[nH]c2ccc(F)cc2c1-c1ccc(C#N)cc1]

tert-butyl (R)-(2-(2-amino-3-(3-(4-cyanophenyl)-5-fluoro-1H-indole-2-carboxamido)propoxy)ethyl) carbamate To a solution of tert-butyl (R)-(2-(2-(((benzyloxy)carbonyl)amino)-3-(3-(4-cyanophenyl)-5-fluoro-1H-indole-2-carboxamido)propoxy)ethyl)carbamate (43 mg, 0.068 mmol) in MeOH (5 mL) was added Pd/C (10%, 35 mg, 0.03 mmol). Then it was stirred under $H_2$ (50 psi) overnight. It was filtered through a Celite pad and washed with methanol, then concentrated to provide the crude product which was purified on column chromatography on silica gel with MeOH in EtOAc as eluents to give the amine as an off-white powder (16 mg, 47% yield). MS (ESI): Calcd for $C_{26}H_{31}N_5O_4^+$496.23 $[M+H]^+$, found 496.15 $[M+H]^+$.

Example 21. Preparation of (R)—N-(2-amino-3-(2-aminoethoxy)propyl)-3-phenyl-1H-indole-2-carboxamide hydrogen chloride salt

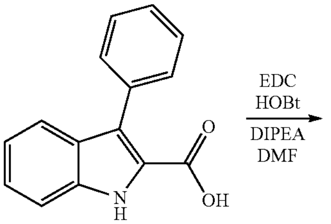

-continued

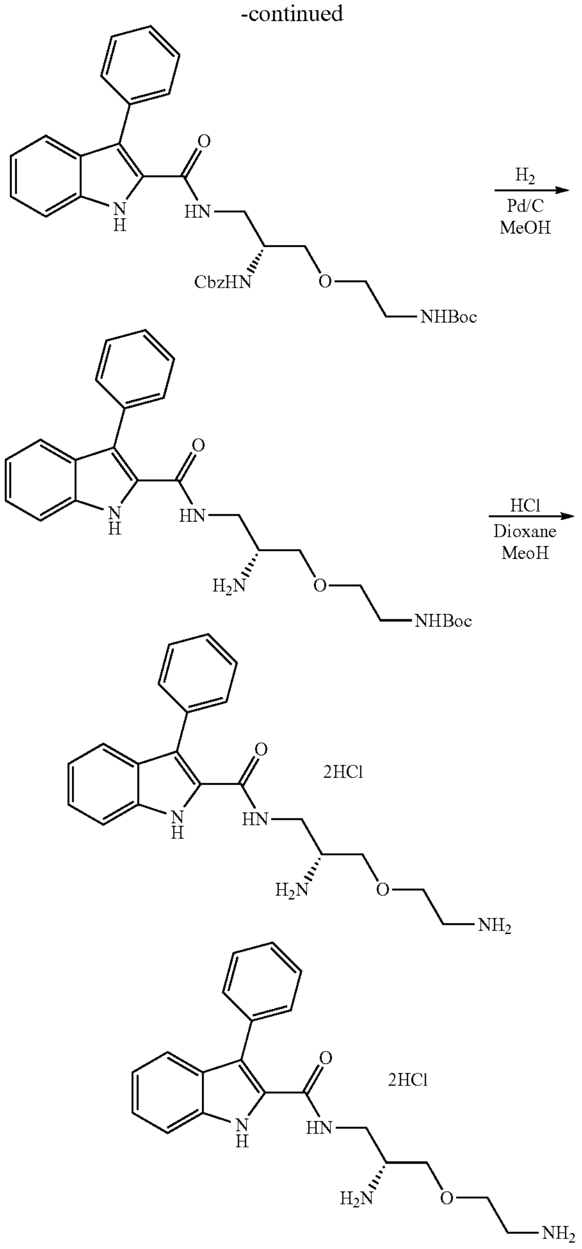

(R)—N-(2-amino-3-(2-aminoethoxy)propyl)-3-phenyl-1H-indole-2-carboxamide hydrogen chloride salt To a solution of tert-butyl (R)-(2-(2-amino-3-(3-phenyl-1H-indole-2-carboxamido)propoxy)ethyl)carbamate (20 mg, 0.044 mmol) in MeOH (5 mL) HCl solution (4 M in dioxane, 0.15 mL, 0.6 mmol) was added. It was stirred at room temperature until no starting material left, then solvent was removed in vacuo. The residue was dissolved in water and loaded on C18 column chromatography and purified with 0-15% EtOH in water to give the desired product as a white powder (11 mg, 59% yield). $^1$H NMR (300 MHz, $CD_3OD$) δ 7.56 (m, 2H), 7.54 (m, 2H), 7.51 (m, 1H), 7.48 (m, 1H), 7.45 (m, 1H), 7.30 (t, J=7.5 Hz, 1H), 7.10 (t, J=7.5 Hz, 1H), 3.72 (m, 2H), 3.67 (m, 2H), 3.60 (m, 1H), 3.52 (m, 2H), 3.18 (m, 2H). MS (ESI): Calcd for $C_{20}H_{25}N_4O_2^+$ 353.20 $[M+H]^+$, found 353.00 $[M+H]^+$.

The requisite intermediates were prepared as shown in the following steps.

Step 1)

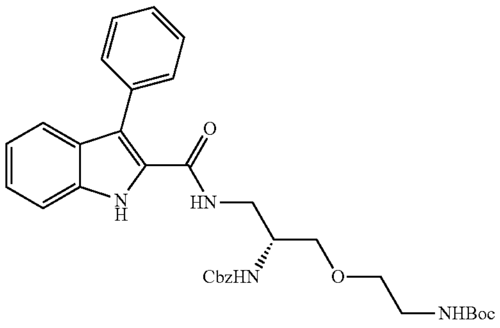 [SMILES: CC(C)(C)OC(=O)NCCOC[C@@H](CNC(=O)c1[nH]c2ccccc2c1-c1ccccc1)NC(=O)OCc1ccccc1]

tert-butyl (R)-(2-(2-(((benzyloxy)carbonyl)amino)-3-(3-phenyl-1H-indole-2-carboxamido)propoxy)ethyl)carbamate To a solution of 3-phenyl-1H-indole-2-carboxylic acid (24 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and benzyl (R)-(1-amino-3-(2-((tert-butoxycarbonyl)amino)ethoxy)propan-2-yl)carbamate (Amine Intermediate D) (37 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel to give the product (30 mg, 51% yield) as a white powder. $^1$H NMR (300 MHz, $CDCl_3$) δ 9.25 (br s, 1H), 7.51 (m, 1H), 7.45 (m, 3H), 7.44 (m, 2H), 7.32 (m, 5H), 7.27 (m, 2H), 7.13 (m, 1H), 6.19 (br s, 1H), 5.28 (br s, 1H), 5.13 (br, 1H), 5.06 (s, 2H), 3.77 (m, 1H), 3.56 (m, 2H), 3.44 (m, 3H), 3.32 (m, 1H), 3.23 (m, 2H), 1.44 (s, 9H). MS (ESI): Calcd for $C_{33}H_{39}N_4O_6^+$587.29 $[M+H]^+$, found 587.15 $[M+H]^+$.

Step 2)

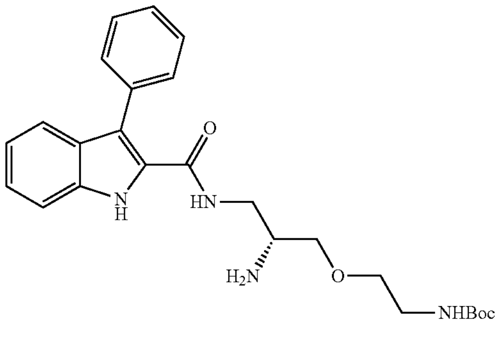 [SMILES: CC(C)(C)OC(=O)NCCOC[C@H](N)CNC(=O)c1[nH]c2ccccc2c1-c1ccccc1]

tert-butyl (R)-(2-(2-amino-3-(3-phenyl-1H-indole-2-carboxamido)propoxy)ethyl)carbamate To a solution tert-butyl (R)-(2-(2-(((benzyloxy)carbonyl) amino)-3-(3-phenyl-1H-indole-2-carboxamido)propoxy)

ethyl)carbamate (30 mg, 0.05 mmol) in MeOH (5 mL) was added Pd/C (10%, 20 mg, 0.02 mmol). Then it was stirred under $H_2$ (55 psi) overnight. It was filtered through a Celite pad and washed with methanol, then concentrated to provide the crude product as an off-white powder (20 mg, 87% yield). MS (ESI): Calcd for $C_{25}H_{33}N_4O_4^+$453.25 $[M+H]^+$, found 453.10 $[M+H]^+$.

Example 22. Preparation of (R)—N-(2-amino-3-(2-aminoethoxy)propyl)-3-cyclohexyl-5-fluoro-1H-indole-2-carboxamide hydrogen chloride salt

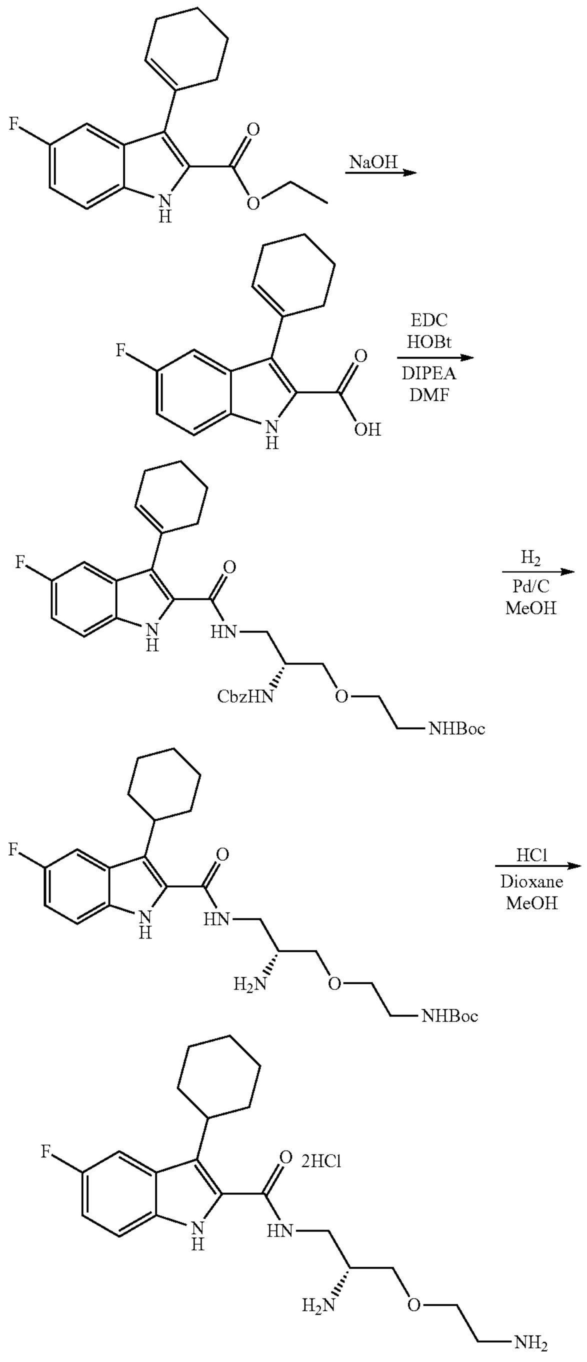

-continued

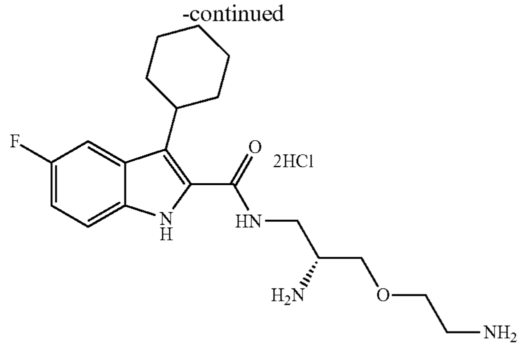

(R)—N-(2-amino-3-(2-aminoethoxy)propyl)-3-cyclohexyl-5-fluoro-1H-indole-2-carboxamide hydrogen chloride salt To a solution tert-butyl (R)-(2-(2-amino-3-(3-cyclohexyl-5-fluoro-1H-indole-2-carboxamido)propoxy)ethyl)carbamate (20 mg, 0.035 mmol) in MeOH (5 mL) HCl solution (4 M in dioxane, 0.15 mL, 0.6 mmol) was added. It was stirred at room temperature until no starting material left, then solvent was removed in vacuo. The residue was triturated with EtOAc and the precipitate was collected as a pale brown powder (9 mg, 57% yield). $^1H$ NMR (300 MHz, $CD_3OD$) δ 7.86 (dd, J=2.3, 10.2 Hz, 1H), 7.38 (dd, J=4.6, 9.1 Hz, 1H), 7.01 (m, 1H), 3.76 (m, 4H), 3.64 (m, 2H), 3.58 (m, 1H), 3.21 (m, 2H), 1.91 (m, 1H), 1.87 (m, 4H), 1.82 (m, 4H), 1.44 (m, 2H). MS (ESI): Calcd for $C_{20}H_{30}FN_4O_2^+$ 377.23 $[M+H]^+$, found 377.00 $[M+H]^+$.

The requisite intermediates were prepared as shown in the following steps.

Step 1)

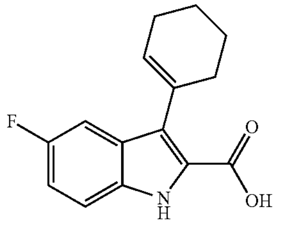 [SMILES: O=C(O)c1[nH]c2ccc(F)cc2c1C1=CCCCC1]

3-(cyclohex-1-en-1-yl)-5-fluoro-1H-indole-2-carboxylic acid

To a solution of ethyl 3-(cyclohex-1-en-1-yl)-5-fluoro-1H-indole-2-carboxylate (200 mg, 0.7 mmol) in THF (10 mL) was added NaOH solution (2 M, 10 mL). It was heated at 50° C. overnight. THF was removed in vacuo and the residue was acidified with HCl solution. The precipitate was filtered and washed with water. It was dried to provide the product as a pale brown powder (110 mg, 61% yield) which was used for next step reaction without further purification. MS (ESI): Calcd for $C_{15}H_{13}FNO_2^-$ 258.10 $[M-H]^-$, found 258.05 $[M-H]^-$.

Step 2)

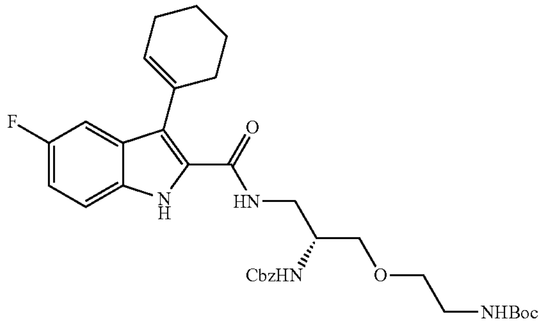 [SMILES: CC(C)(C)OC(=O)NCCOC[C@@H](CNC(=O)c1[nH]c2ccc(F)cc2c1C1=CCCCC1)NC(=O)OCc1ccccc1]

tert-butyl (R)-(2-(2-(((benzyloxy)carbonyl)amino)-3-(3-cyclohexyl-1H-indole-2-carboxamido)propoxy)ethyl)carbamate To a solution of 3-(cyclohex-1-en-1-yl)-5-fluoro-1H-indole-2-carboxylic acid (29 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at room temperature and benzyl (R)-(1-amino-3-(2-((tert-butoxycarbonyl)amino)ethoxy)propan-2-yl)carbamate (Amine Intermediate D) (37 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated and purified by column chromatography on silica gel to give the product (43 mg, 75% yield) as a white powder. MS (ESI): Calcd for $C_{33}H_{42}FN_4O_6^+$609.31 $[M+H]^+$, found 609.20 $[M+H]^+$.

Step 3)

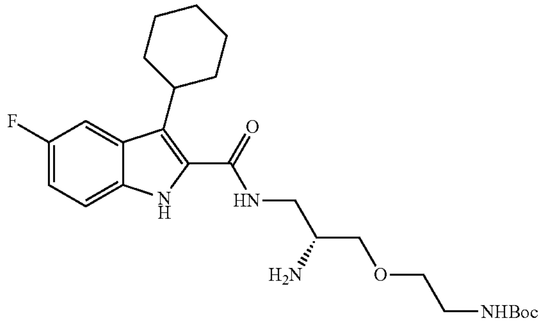 [SMILES: CC(C)(C)OC(=O)NCCOC[C@H](N)CNC(=O)c1[nH]c2ccc(F)cc2c1C1CCCCC1]

tert-butyl (R)-(2-(2-amino-3-(3-cyclohexyl-5-fluoro-1H-indole-2-carboxamido)propoxy)ethyl)carbamate To a solution of tert-butyl (R)-(2-(2-(((benzyloxy)carbonyl)amino)-3-(3-cyclohexyl-5-fluoro-1H-indole-2-carboxamido)propoxy)ethyl)carbamate (40 mg, 0.7 mmol) in MeOH (5 mL) was added Pd/C (10%, 20 mg, 0.02 mmol). Then it was stirred under $H_2$ (50 psi) overnight. It was filtered through a Celite pad and washed with methanol, then concentrated to provide the crude product which was purified on column chromatography on silica gel to give the amine as an off-white powder (20 mg, 50% yield). MS (ESI): Calcd for $C_{25}H_{38}N_4O_4^+$477.29 $[M+H]^+$, found 477.15 $[M+H]^+$.

Example 23. Preparation of N-(((2R,3S,4S)-4-(aminomethyl)-3-hydroxypyrrolidin-2-yl)methyl)-3-(4-fluorophenyl)-1H-indole-2-carboxamide hydrogen chloride salt

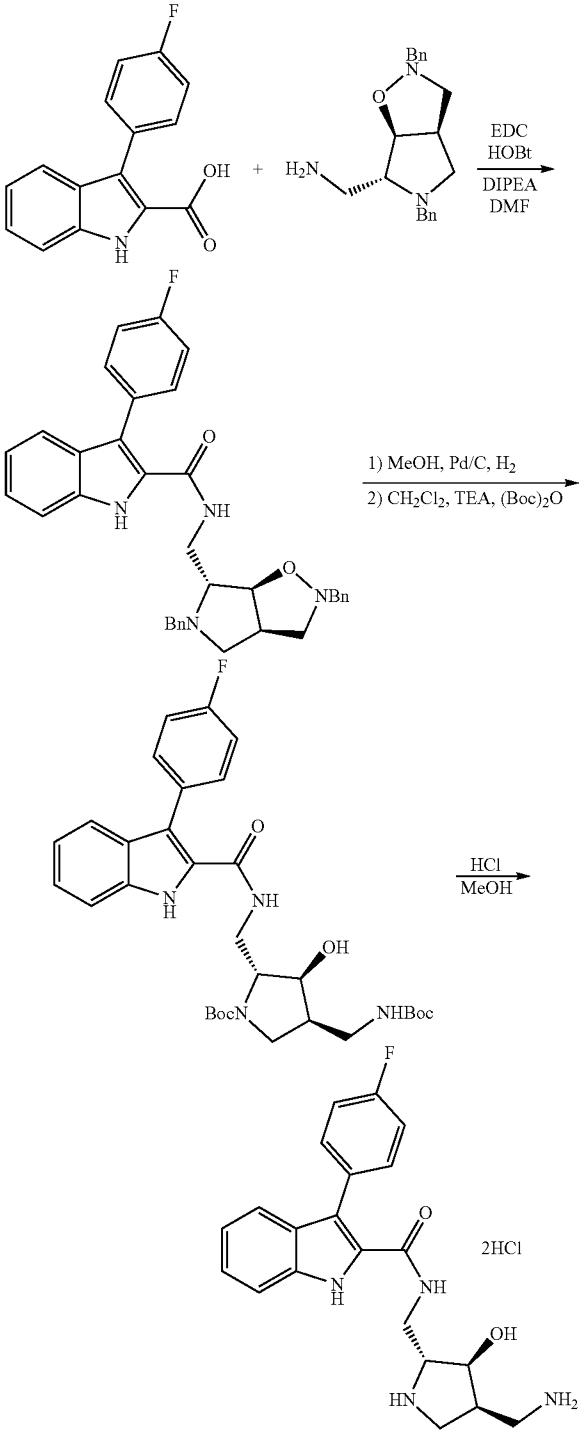

-continued

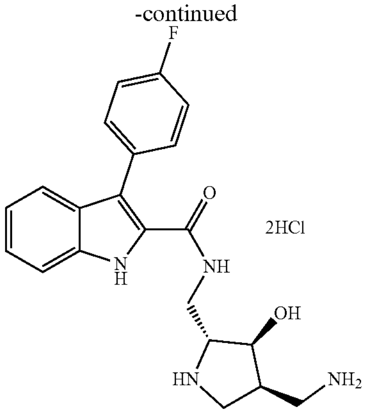

N-(((2R,3S,4S)-4-(aminomethyl)-3-hydroxypyrrolidin-2-yl)methyl)-3-(4-fluorophenyl)-1H-indole-2-carboxamide hydrogen chloride salt To a solution of tert-butyl (2R,3S,4S)-4-(((tert-butoxycarbonyl)amino)methyl)-2-((3-(4-fluorophenyl)-1H-indole-2-carboxamido)methyl)-3-hydroxypyrrolidine-1-carboxylate (30 mg, 0.05 mmol) in MeOH (2 mL) was added HCl (4 M in dioxane, 0.5 mL, 2 mmol). The reaction mixture was stirred at 50° C. for 1 h and then concentrated to give a residue. The residue was triturated with EtOAc to give the desired product (17 mg, 73% yield) as yellow solid. $^1H$ NMR (300 MHz, $D_2O$) δ 7.52-7.63 (m, 4H), 7.39 (m, 1H), 7.29 (m, 2H), 7.20 (m, 1H), 4.38 (m, 1H), 3.49-3.77 (m, 4H), 3.11-3.34 (m, 3H), 2.76 (m, 1H). MS (ESI): Calcd for $C_{21}H_{24}FN_4O_2$ 383.19 [M+H$^+$], found 382.95 [M+H]$^+$.

The requisite intermediates were prepared as shown in the following steps.

Step 1)

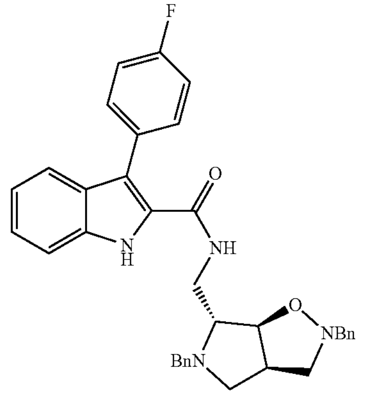 [SMILES: O=C(NC[C@@H]1[C@H]2ON(Cc3ccccc3)C[C@H]2CN1Cc1ccccc1)c1[nH]c2ccccc2c1-c1ccc(F)cc1]

N-(((3aR,6R,6aS)-2,5-dibenzylhexahydro-2H-pyrrolo[3,4-d]isoxazol-6-yl)methyl)-3-(4-fluorophenyl)-1H-indole-2-carboxamide To a solution of 3-(4-fluorophenyl)-1H-indole-2-carboxylic acid (356 mg, 1.40 mmol) in dry DMF (5 mL) was added DIPEA (0.41 mL, 2.33 mmol), HOBt (95 mg, 0.70 mmol) and EDC (267 mg, 1.40 mmol). The reaction mixture was stirred at room temperature for 10 min and then a solution of ((3aR,6R,6aS)-2,5-dibenzylhexahydro-2H-pyrrolo[3,4-d]isoxazol-6-yl)methanamine (Amine Intermediate E) (377 mg, 1.17 mmol) in DMF (5 mL) was added. The reaction mixture was stirred at room temperature overnight then added $H_2O$ with stirring. A solid was formed and collected by filtration. After air drying the solid was purified by chromatography on silica gel. Elution with 50-100% EtOAc/hexanes afforded the desired compound (625 mg, 95% yield) as white solid. $^1H$ NMR (300 MHz, $CDCl_3$) δ 9.34 (br s, 1H), 7.00-7.50 (m, 14H), 6.41 (d, J=4.8 Hz, 1H), 4.13 (m, 1H), 4.04 (m, 1H), 3.86 (m, 2H), 3.73 (d, J=12.9 Hz, 1H), 3.36 (d, J=12.9 Hz, 1H), 3.10 (d, J=12.3 Hz, 1H), 2.90 (m, 1H), 2.83 (m, 1H), 2.68 (m, 1H), 2.61 (m, 1H), 2.44 (m, 1H), 2.11 (m, 1H).

Step 2)

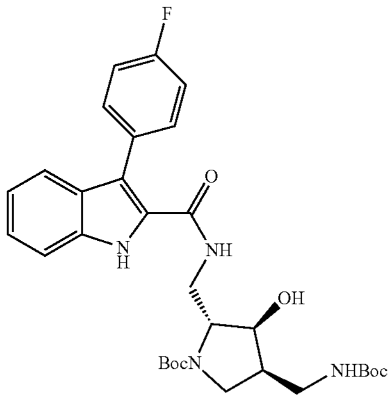 [SMILES: CC(C)(C)OC(=O)NC[C@H]1CN(C(=O)OC(C)(C)C)[C@H](CNC(=O)c2[nH]c3ccccc3c2-c2ccc(F)cc2)[C@H]1O]

tert-butyl (2R,3S,4S)-4-(((tert-butoxycarbonyl)amino)methyl)-2-((3-(4-fluorophenyl)-1H-indole-2-carboxamido)methyl)-3-hydroxypyrrolidine-1-carboxylate To a solution of N-(((3aR,6R,6aS)-2,5-dibenzylhexahydro-2H-pyrrolo[3,4-d]isoxazol-6-yl)methyl)-3-(4-fluorophenyl)-1H-indole-2-carboxamide (625 mg, 1.11 mmol) in MeOH (50 mL) was added Pd/C (10%, 200 mg, 0.2 mmol). The reaction mixture was stirred under $H_2$ at 55 psi at room temperature overnight. The completion of the reaction was monitored by checking the disappearance of the staring material by LC-MS. The solid was removed by passing through Celite pad, and was washed with MeOH. The filtrate was concentrated, then dissolved in $CH_2Cl_2$. To this solution was added TEA (0.39 mL, 2.79 mmol) and $(Boc)_2O$ (535 mg, 2.45 mmol). The resulting reaction mixture was stirred at room temperature for 2 h, then diluted with $CH_2Cl_2$, washed with saturated $NaHCO_3$ solution, brine, and dried over $Na_2SO_4$. After removal of solid, the organic solution was concentrated and purified by chromatography on silica gel. Elution with 50-100% EtOAc/hexanes afforded the desired compound (365 mg, 56% yield) as white solid. $^1H$ NMR (300 MHz, $CDCl_3$) δ 9.30 (br s, 1H), 7.46 (m, 4H), 7.10-7.36 (m, 4H), 6.64 (br s, 1H), 5.95 (br s, 1H), 4.89 (br s, 1H), 4.60 (br, 1H), 3.94 (br s, 1H), 3.75 (m, 1H), 3.34-3.60 (m, 3H), 3.24 (m, 1H), 3.08 (m, 1H), 2.93 (m, 1H), 2.19 (m, 1H), 1.36-1.44 (m, 18H).

Example 24. Preparation of N-(((2R,3S,4S)-4-(aminomethyl)-3 hydroxypyrrolidin-2-yl)methyl)-5-fluoro-3-phenyl-1H-indole-2-carboxamide hydrogen chloride salt

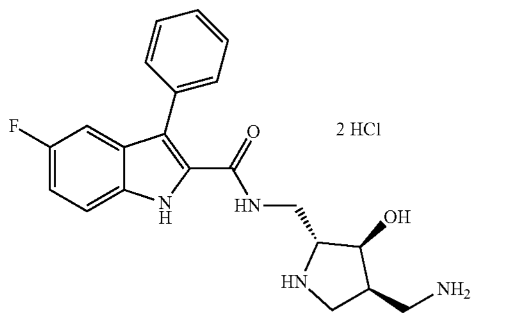 [SMILES: NC[C@H]1CN[C@H](CNC(=O)c2[nH]c3ccc(F)cc3c2-c2ccccc2)[C@H]1O]

N-(((2R,3S,4S)-4-(aminomethyl)-3-hydroxypyrrolidin-2-yl)methyl)-5-fluoro-3-phenyl-1H-indole-2-carboxamide hydrogen chloride salt To a solution of tert-butyl (2R,3S,4S)-4-(((tert-butoxycarbonyl)amino)methyl)-2-((5-fluoro-3-phenyl-1H-indole-2-carboxamido)methyl)-3-hydroxypyrrolidine-1-carboxylate (18 mg, 0.03 mmol) in MeOH (1 mL) was added HCl (4 M in dioxane, 0.2 mL, 0.4 mmol). The reaction mixture was stirred at 50° C. for 1 h and then concentrated to give a residue. The residue was triturated with EtOAc to give the desired product (10 mg, 71% yield) as a white solid. $^{1}H$ NMR (300 MHz, $D_2O$) δ 7.48-7.66 (m, 6H), 7.30 (dd, J=2.1, 9.9 Hz, 1H), 7.20 (m, 1H), 4.40 (m, 1H), 3.52-3.81 (m, 4H), 3.34 (m, 2H), 3.19 (m, 1H), 2.81 (m, 1H). MS (ESI): Calcd for $C_{21}H_{24}FN_4O_2$ 383.19 [M+H$^+$], found 382.95 [M+H]$^+$.

The requisite intermediates were prepared as shown in the following steps.

Step 1)

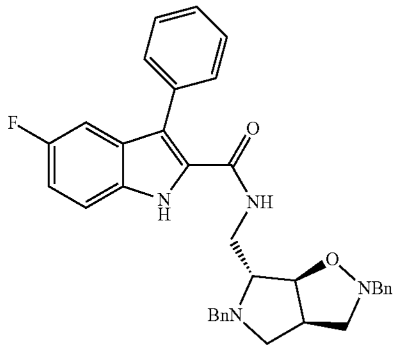 [SMILES: O=C(NC[C@@H]1[C@H]2ON(Cc3ccccc3)C[C@H]2CN1Cc1ccccc1)c1[nH]c2ccc(F)cc2c1-c1ccccc1]

N-(((3aR,6R,6aS)-2,5-dibenzylhexahydro-2H-pyrrolo[3,4-d]isoxazol-6-yl)methyl)-5-fluoro-3-phenyl-1H-indole-2-carboxamide To a solution of 5-fluoro-3-phenyl-1H-indole-2-carboxylic acid (36 mg, 0.14 mmol) in dry DMF (1 mL) was added DIPEA (0.04 mL, 0.23 mmol), HOBt (9.5 mg, 0.07 mmol) and EDC (27 mg, 0.14 mmol). The reaction mixture was stirred at room temperature for 10 min and then a solution of ((3aR,6R,6aS)-2,5-dibenzylhexahydro-2H-pyrrolo[3,4-d]isoxazol-6-yl)methanamine (Amine Intermediate E) (38 mg, 0.12 mmol) in DMF (5 mL) was added. The reaction mixture was stirred at room temperature overnight after which $H_2O$ was added with stirring. A solid was formed which was collected by filtration. After air drying, the solid was purified by chromatography on silica gel. Elution with 50-100% EtOAc/hexanes afforded the desired compound (35 mg, 53% yield) as white solid. $^{1}H$ NMR (300 MHz, $CDCl_3$) δ 9.73 (br s, 1H), 7.22-7.52 (m, 10H), 7.07 (m, 2H), 6.99 (m, 2H), 6.53 (d, J=4.5 Hz, 1H), 4.16 (m, 1H), 4.05 (m, 1H), 3.87 (m, 2H), 3.72 (d, J=12.9 Hz, 1H), 3.36 (d, J=15 Hz, 1H), 3.08 (d, J=12.3 Hz, 1H), 2.74-2.88 (m, 2H), 2.69 (m, 1H), 2.60 (m, 1H), 2.42 (m, 1H), 2.08 (m, 1H).

Step 2)

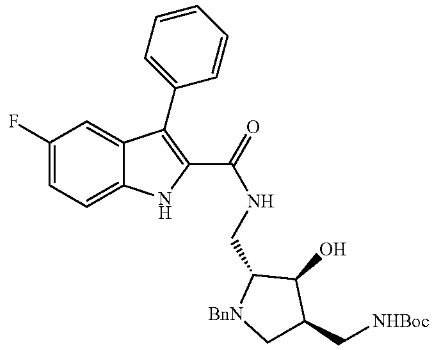 [SMILES: CC(C)(C)OC(=O)NC[C@H]1CN(Cc2ccccc2)[C@H](CNC(=O)c2[nH]c3ccc(F)cc3c2-c2ccccc2)[C@H]1O]

tert-butyl (2R,3S,4S)-4-(((tert-butoxycarbonyl)amino)methyl)-2-((5-fluoro-3-phenyl-1H-indole-2-carboxamido)methyl)-3-hydroxypyrrolidine-1-carboxylate To a solution of N-(((3aR,6R,6aS)-2,5-dibenzylhexahydro-2H-pyrrolo[3,4-d]isoxazol-6-yl)methyl)-5-fluoro-3-phenyl-1H-indole-2-carboxamide (22 mg, 0.04 mmol) in MeOH (10 mL) was added Pd/C (10%, 30 mg, 0.03 mmol). The reaction mixture was stirred under $H_2$ at 55 psi at room temperature overnight. The completion of the reaction was monitored by checking the disappearance of the staring material by LC-MS. The solid was removed by passing through a celite pad, and was washed with MeOH. The filtrate was concentrated and then dissolved in $CH_2Cl_2$. To this solution was added TEA (0.014 mL, 0.1 mmol), $(Boc)_2O$ (19 mg, 0.09 mmol). The resulting reaction mixture was stirred at room temperature for 2 h, then diluted with $CH_2Cl_2$, washed with saturated $NaHCO_3$ solution, brine, and dried over $Na_2SO_4$. After removal of solid the organic solution was concentrated and purified by chromatography on silica gel. Elution with 50-100% EtOAc/hexanes afforded the desired compound (18 mg, 78% yield) as white solid. $^{1}H$ NMR (300 MHz, $CDCl_3$) δ 9.65 (br s, 1H), 7.35-7.60 (m, 6H), 7.09 (m, 2H), 6.49 (br s, 1H), 6.08 (br s, 1H), 4.93 (br s, 1H), 4.58 (br, 1H), 3.93 (s, 1H), 3.73 (m, 1H), 3.36-3.62 (m, 3H), 3.22 (m, 1H), 3.07 (m, 1H), 2.92 (m, 1H), 2.19 (m, 1H), 1.36-1.44 (m, 18H).

Example 25. Preparation of N-(((2R,4S)-4-(aminomethyl)-3-oxopyrrolidin-2-yl)methyl)-3-(4-fluorophenyl)-1H-indole-2-carboxamide hydrogen chloride salt

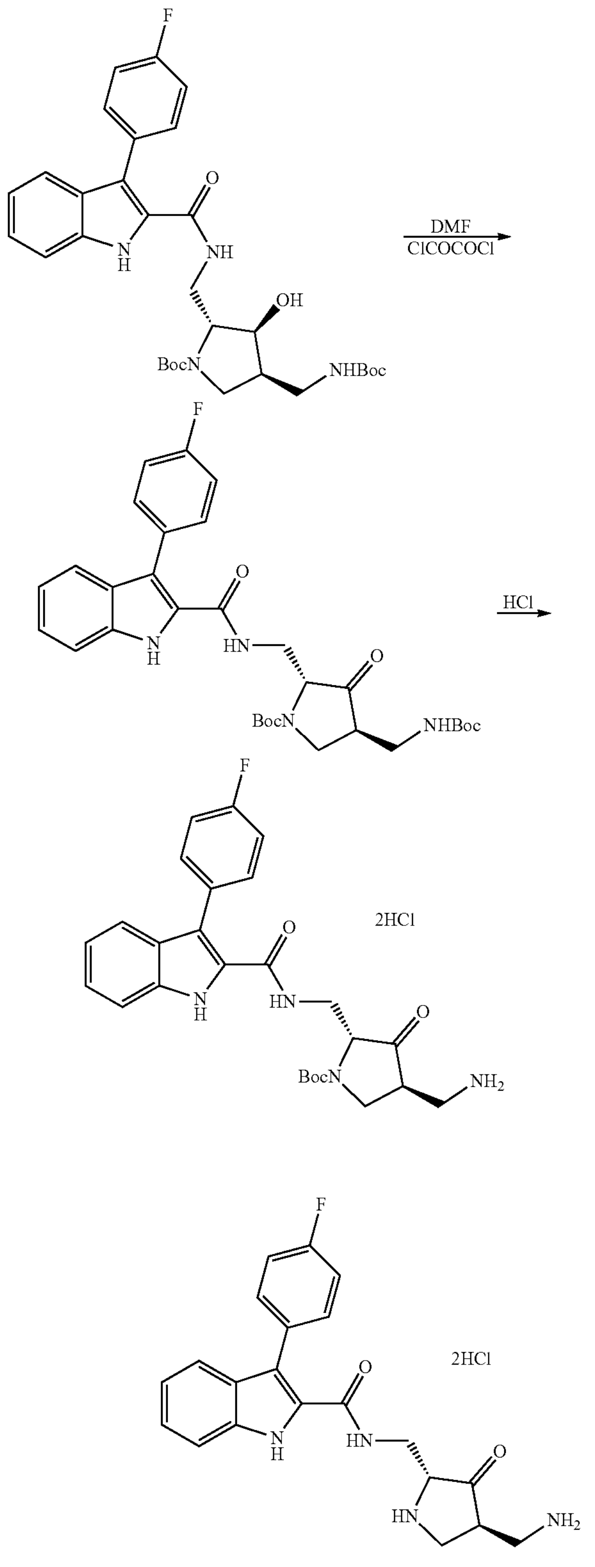

N-(((2R,4S)-4-(aminomethyl)-3-oxopyrrolidin-2-yl)methyl)-3-(4-fluorophenyl)-1H-indole-2-carboxamide hydrogen chloride salt To a solution of tert-butyl (2R,4S)-4-(((tert-butoxycarbonyl)amino)methyl)-2-((3-(4-fluorophenyl)-1H-indole-2-carboxamido)methyl)-3-oxopyrrolidine-1-carboxylate (25 mg, 0.043 mmol) in 0.5 mL of methanol was added 0.2 mL of HCl (4N in dioxane, 0.8 mmol). Reaction mixture was stirred at 50° C. for 30 minutes and then solvents were removed in vacuo. Residue was washed with ethyl ether and dried. The product was collected as a beige solid (11 mg, 56% yield). $^1H$ NMR (300 MHz, $D_2O$) δ 7.49 (m, 2H), 7.38 (m 2H), 7.31 (m, 1H), 7.91 (m, 2H), 7.11 (m, 1H), 4.17 (m, 1H), 3.58-3.69 (m, 2H), 3.37-3.49 (m, 2H), 3.04-3.33 (m, 2H), 2.62 (m, 1H). MS (ESI): Calcd for $C_{21}H_{22}FN_4O_2^+$ 381.17 $[M+H]^+$, found 380.95 $[M+H]^+$.

The requisite intermediate was prepared as shown in the following step.

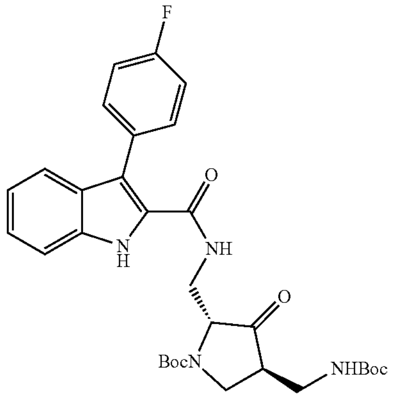 [SMILES: CC(C)(C)OC(=O)NC[C@H]1CN(C(=O)OC(C)(C)C)[C@H](CNC(=O)c2[nH]c3ccccc3c2-c2ccc(F)cc2)C1=O]

tert-butyl (2R,4S)-4-(((tert-butoxycarbonyl)amino)methyl)-2-((3-(4-fluorophenyl)-1H-indole-2-carboxamido)methyl)-3-oxopyrrolidine-1-carboxylate To a stirred solution of DMSO (11.6 mg, 0.15 mmol) in DCM (2 mL) was added oxalyl chloride (9.45 mg, 0.08 mmol) at −78° C. under nitrogen. After 15 minutes a solution of (2R,3S,4S)-tert-butyl 4-(((tert-butoxycarbonyl)amino)methyl)-2-((3-(4-fluorophenyl)-1H-indole-2-carboxamido)methyl)-3-hydroxypyrrolidine-1-carboxylate (29 mg, 0.05 mmol) (prepared as in Example 23, step 2) in DCM (1 mL) was added. After 10 minutes, triethylamine (15 mg, 0.15 mmol) was added and it was stirred for additional 15 minutes, then warmed to room temperature slowly and stirred for 1 hour. Solvent was removed and the residue was purified on column chromatography on silica gel to give the product (25 mg, 86% yield). MS (ESI): Calcd for $C_{31}H_{38}FN_4O_6^+$ 581.28 $[M+H]^+$, found 581.15 $[M+H]^+$.

Example 26. Preparation of N-(((2R,3R,4S)-4-(aminomethyl)-3-hydroxypyrrolidin-2-yl)methyl)-3-(4-fluorophenyl)-1H-indole-2-carboxamide hydrogen chloride salt

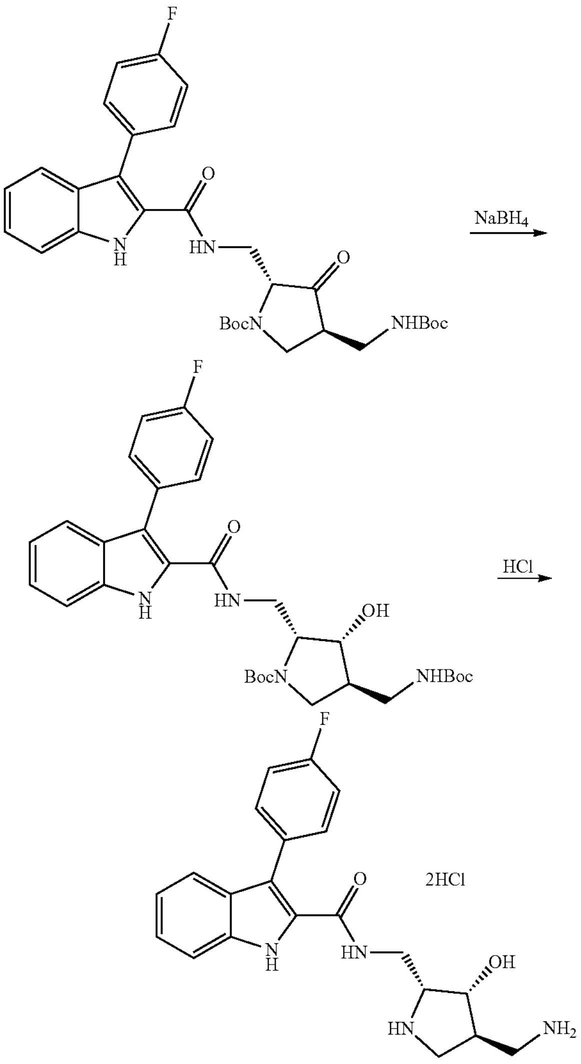

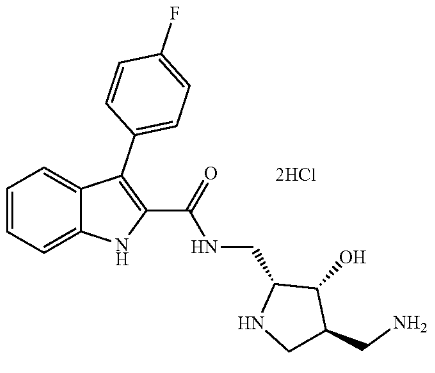

N-(((2R,3R,4S)-4-(aminomethyl)-3-hydroxypyrrolidin-2-yl)methyl)-3-(4-fluorophenyl)-1H-indole-2-carboxamide hydrogen chloride salt To a solution of tert-butyl (2R,3R,4S)-4-(((tert-butoxycarbonyl)amino)methyl)-2-((3-(4-fluorophenyl)-1H-indole-2-carboxamido)methyl)-3-hydroxypyrrolidine-1-carboxylate (6 mg, 0.01 mmol) in 0.5 mL of methanol was added 0.1 mL of HCl (4N in dioxane, 0.4 mmol). Reaction mixture was stirred at 50° C. for 30 minutes then solvents were removed in vacuo. The residue was washed with small amount of ethyl ether and dried to provide the product as a beige solid (2.3 mg, 49% yield). MS (ESI): Calcd for $C_{21}H_{24}FN_4O_2^+$ 383.19 $[M+H]^+$, found 383.10 $[M+H]^+$.

The requisite intermediate was prepared as shown in the following step.

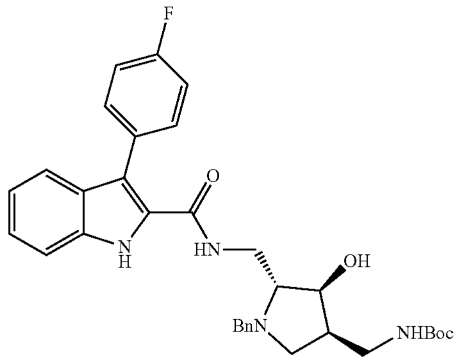 [SMILES: CC(C)(C)OC(=O)NC[C@H]1CN(Cc2ccccc2)[C@H](CNC(=O)c2[nH]c3ccccc3c2-c2ccc(F)cc2)[C@H]1O]

tert-butyl (2R,3R,4S)-4-(((tert-butoxycarbonyl) amino)methyl)-2-((3-(4-fluorophenyl)-1H-indole-2-carboxamido)methyl)-3-hydroxypyrrolidine-1-carboxylate To a stirred solution of tert-butyl (2R,4S)-4-(((tert-butoxycarbonyl)amino)methyl)-2-((3-(4-fluorophenyl)-1H-indole-2-carboxamido)methyl)-3-oxopyrrolidine-1-carboxylate (obtained as described in Example 25) (20 mg, 0.034 mmol) in 1 mL of methanol was added $NaBH_4$ (30 mg, 0.8 mmol) by portions at 0° C. Reaction mixture was stirred at room temperature for 20 minutes, TLC indicated two products were formed. The first product's $R_f$=0.52 and the second product's $R_f$=0.48 (EtOAc/Hexanes=1/1), ratio was around ½. Reaction was quenched by adding sat. aq. $NH_4C_1$ and extracted by ethyl acetate, washed with brine, and dried over $Na_2SO_4$. After filtration, solvent was removed in vacuo, residue was purified on column chromatography on silica gel to give the major product (6 mg, 30% yield). NMR (300 MHz, $CDCl_3$) δ 9.40 (br s, 1H), 7.08-7.55 (m, 8H), 6.68 (br s, 1H), 5.02 (br, 1H), 3.80-4.06 (m, 2H), 3.44-3.78 (m, 3H), 3.20-3.40 (m, 1H), 2.73-3.18 (m, 3H), 1.39 (br, 18H). MS (ESI): Calcd for $C_{31}H_{40}FN_4O_6^+$ 583.29 $[M+H]^+$, found 583.20 $[M+H]^+$

Example 27. Preparation of N-(((2S)-4-(aminomethyl)-4-hydroxypyrrolidin-2-yl)methyl)-3-(2-chlorophenyl)-5-fluoro-1H-indole-2-carboxamide hydrogen chloride salt

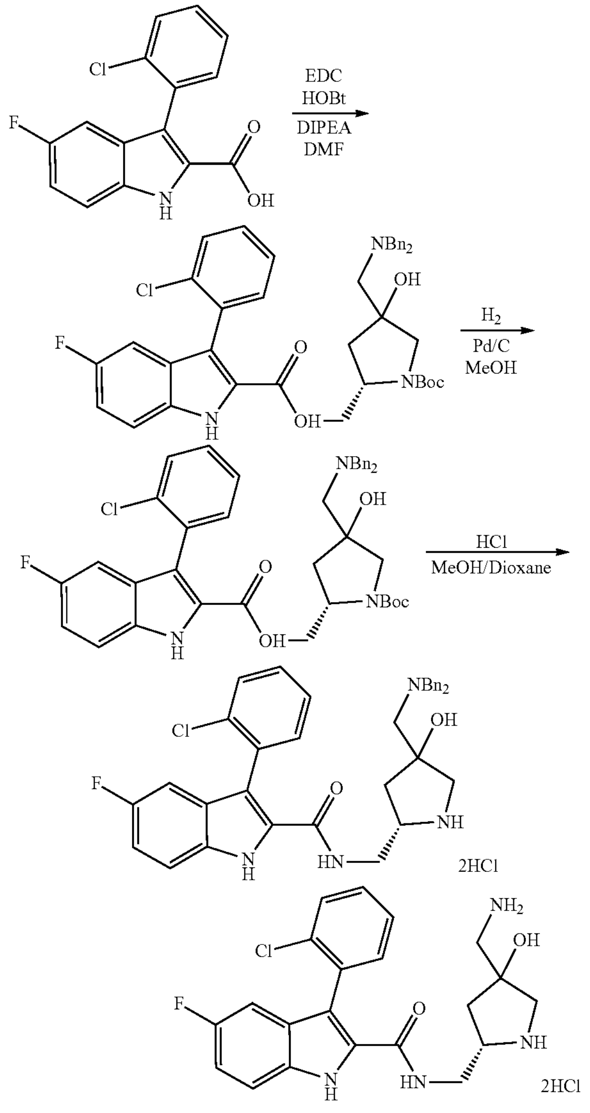

N-(((2S)-4-(aminomethyl)-4-hydroxypyrrolidin-2-yl)methyl)-3-(2-chlorophenyl)-5-fluoro-1H-indole-2-carboxamide hydrogen chloride salt To a solution of tert-butyl (2S)-4-(aminomethyl)-2-((3-(2-chlorophenyl)-5-fluoro-1H-indole-2-carboxamido)methyl)-4-hydroxypyrrolidine-1-carboxylate (17 mg, 0.032 mmol) in MeOH (5 mL) HCl solution (4 M in dioxane, 0.2 mL, 0.8 mmol) was added. It was stirred at room temperature for 1 hour, then solvent was removed in vacuo at 55° C. The residue was loaded on a C18 column chromatography and purified with EtOH in water to give the product as a white powder (6 mg, 34% yield). $^1$H NMR (300 MHz, $D_2O$) δ 7.49 (m, 2H), 7.43 (m, 3H), 7.12 (m, 2H), 4.04 (m, 1H), 3.66 (m, 2H), 3.50 (m, 2H), 3.32 (m, 2H), 3.09 (m, 1H), 2.35 (m, 1H), 1.98 (m, 1H).

The requisite intermediates were prepared as shown in the following steps.

Step 1)

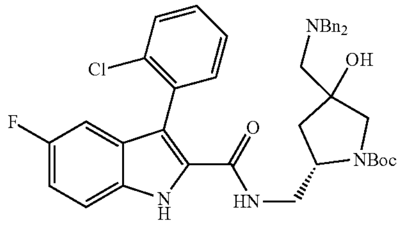

tert-butyl (2S)-2-((3-(2-chlorophenyl)-5-fluoro-1H-indole-2-carboxamido)methyl)-4-((dibenzylamino)methyl)-4-hydroxypyrrolidine-1-carboxylate To a solution of 3-(2-chlorophenyl)-5-fluoro-1H-indole-2-carboxylic acid (29 mg, 0.1 mmol) in dry DMF (0.5 mL) was added DIPEA (0.035 mL, 0.2 mmol), HOBt (10 mg, 0.06 mmol) and EDC (23 mg, 0.12 mmol). The reaction mixture was stirred at room temperature and tert-butyl (2S)-2-(aminomethyl)-4-((dibenzylamino)methyl)-4-hydroxypyrrolidine-1-carboxylate (Amine Intermediate F) (33 mg, 0.077 mmol) was added. The reaction mixture was stirred at room temperature overnight. It was extracted with EtOAc and washed with water and brine. The organic layer was dried over anhydrous $Na_2SO_4$ and filtered. The filtrate was concentrated and purified by column chromatography on silica gel to give the product (22 mg, 42% yield) as a colorless powder. MS (ESI): Calcd for $C_{40}H_{43}ClFN_4O_4^+$ 697.29 $[M+H]^+$, found 697.25 $[M+H]^+$.

Step 2)

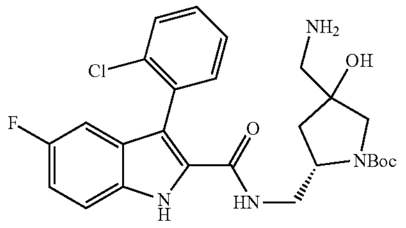 [SMILES: CC(C)(C)OC(=O)N1CC(O)(CN)C[C@H]1CNC(=O)c1[nH]c2ccc(F)cc2c1-c1ccccc1Cl]

tert-butyl (2S)-4-(aminomethyl)-2-((3-(2-chlorophenyl)-5-fluoro-1H-indole-2-carboxamido)methyl)-4-hydroxypyrrolidine-1-carboxylate To a solution of tert-butyl (2S)-2-((3-(2-chlorophenyl)-5-fluoro-1H-indole-2-carboxamido)methyl)-4-((dibenzylamino)methyl)-4-hydroxypyrrolidine-1-carboxylate (22 mg, 0.032 mmol) in MeOH (5 mL) was added Pd/C (10%, 20 mg, 0.02 mmol). The reaction mixture was stirred under $H_2$ (55 psi) overnight. It was filtered through a Celite pad and washed with methanol, then concentrated to provide the crude product which was used for next step reaction without further purification.

Example 28. Preparation of N-((2S)-2,5-diamino-3-hydroxypentyl)-7-(4-fluorophenyl)-1H-indole-2-carboxamide hydrogen chloride salt

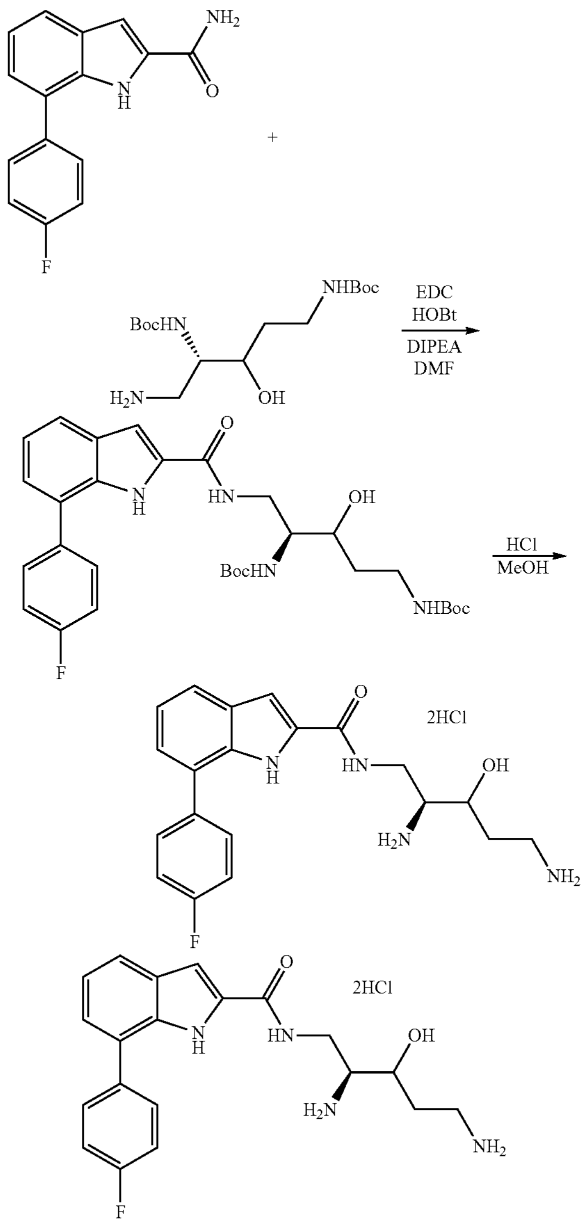

N-((2S)-2,5-diamino-3-hydroxypentyl)-7-(4-fluorophenyl)-1H-indole-2-carboxamide hydrogen chloride salt To a solution of di-tert-butyl ((4S)-5-(7-(4-fluorophenyl)-1H-indole-2-carboxamido)-3-hydroxypentane-1,4-diyl)dicarbamate (35 mg, 0.063 mmol) in methanol (1 mL) was added HCl (4 M in dioxane, 0.2 mL, 0.8 mmol). Reaction mixture was stirred at 50° C. for 30 minutes then solvents were removed in vacuo. Residue was triturated with small amount of ethyl acetate and dried. Product was collected as an off white solid (16 mg, 59% yield). MS (ESI): Calcd for $C_{20}H_{24}FN_4O_2^+$371.19 $[M+H]^+$, found 371.05 $[M+H]^+$.

The requisite intermediate was prepared as follows:

Step 1)

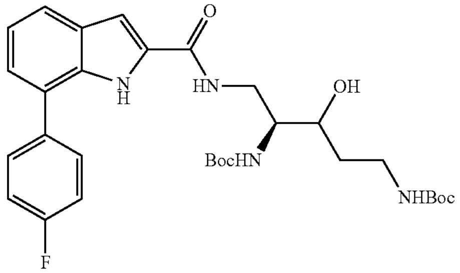 [SMILES: CC(C)(C)OC(=O)NCCC(O)[C@H](CNC(=O)c1cc2cccc(-c3ccc(F)cc3)c2[nH]1)NC(=O)OC(C)(C)C]

di-tert-butyl ((4S)-5-(7-(4-fluorophenyl)-1H-indole-2-carboxamido)-3-hydroxypentane-1,4-diyl)dicarbamate To a solution of di-tert-butyl ((4S)-5-amino-3-hydroxypentane-1,4-diyl)dicarbamate acetate (Amine Intermediate A) (56 mg, 0.17 mmol) in DMF (2.0 mL) was added 7-(4-fluorophenyl)-1H-indole-2-carboxylic acid (44 mg, 0.17 mmol), EDC (39 mg, 0.21 mmol), HOBt (14 mg, 0.10 mmol) and DIPEA (44 mg, 0.34 mmol). The resulting reaction mixture was stirred at room temperature overnight then diluted with water and stirred for 30 minutes. The precipitate was filtered and washed with small amount of water then dissolved in DCM, washed with brine, and dried. After concentration, the residue was purified by column chromatography on silica gel to give the product as a light-yellow solid (45 mg, 45% yield). $^{1}$H NMR (300 MHz, $CDCl_3$) δ 9.15 (br s, 1H), 7.63 (m, 1H), 7.58 (m, 2H), 7.25 (m, 2H), 7.22 (m, 2H), 6.95 (d, J=2.1 Hz, 1H), 5.31 (br s, 1H), 4.86 (br s, 1H), 4.81 (br s, 1H), 3.61-3.78 (m, 2H), 3.32-3.58 (m, 3H), 3.01-3.23 (m, 1H), 1.65 (m, 2H), 1.42 (br, 18H).

Example 29. Preparation of N-((2S)-2,5-diamino-4-hydroxypentyl)-3-((3-fluorophenyl)thio)-1H-indole-2-carboxamide hydrogen chloride salt

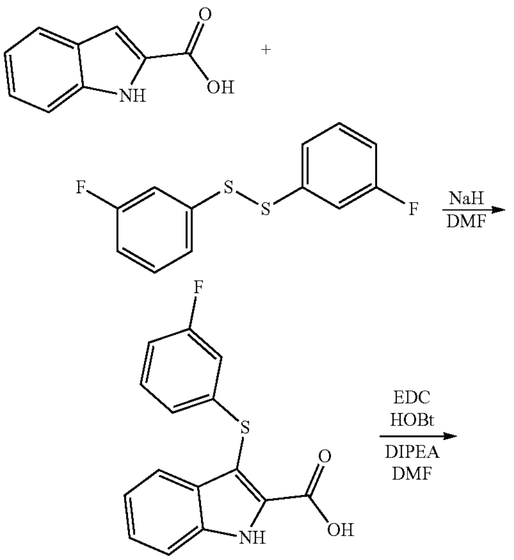

-continued

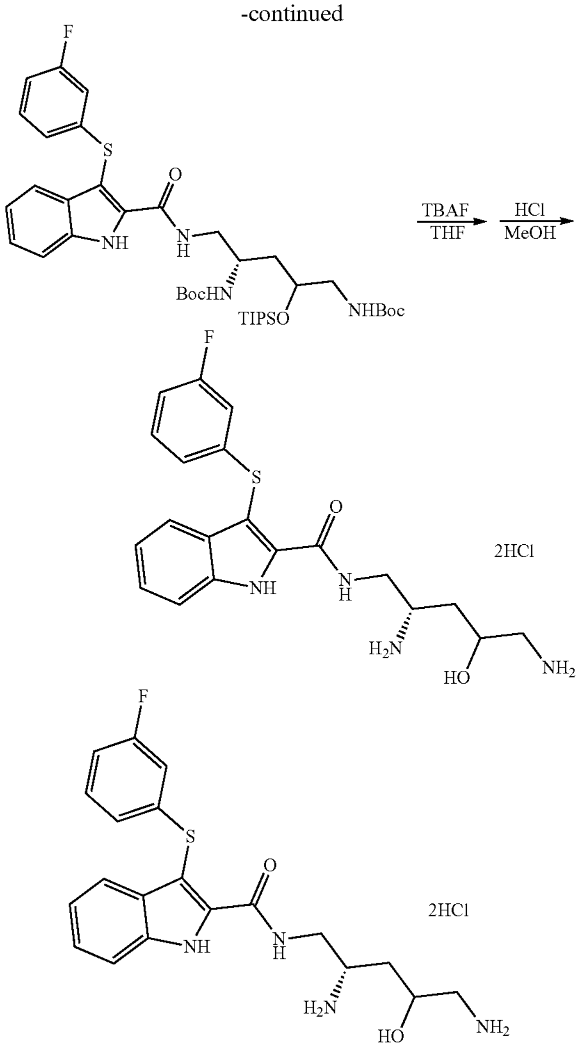

N-((2S)-2,5-diamino-4-hydroxypentyl)-3-((3-fluoro-phenyl)thio)-1H-indole-2-carboxamide hydrogen chloride salt To a solution of di-tert-butyl ((4S)-5-(3-((3-fluorophenyl) thio)-1H-indole-2-carboxamido)-2-((triisopropylsilyl)oxy) pentane-1,4-diyl)dicarbamate (52 mg, 0.07 mmol) in THE (2.0 mL) was added TBAF solution (1.0 M in THF, 0.5 mL, 0.5 mmol) at r.t. It was stirred for 1 hr and concentrated, then loaded on silica gel column chromatography and purified with 50-80% EtOAc in hexane to provide the alcohol as a white powder (36 mg, 87% yield). Then to a solution in MeOH (2 mL) HCl solution (4 M in dioxane, 1 mL, 4 mmol) was added. It was stirred at r.t. for 2 hrs, then solvent was removed in vacuo. The residue was dissolved in water and purified on a C18 column chromatography using 0-15% ethanol in water as eluents to provide the product as a white powder (21 mg, 74% yield). $^1$H NMR (300 MHz, $CD_3OD$) b 7.56 (t, J=8.4 Hz, 2H), 7.35 (m, 1H), 7.27 (m, 1H), 7.17 (m, 1H), 6.92 (m, 1H), 6.87 (m, 1H), 6.77 (m, 1H), 4.02 (m, 1H), 3.88 (m, 1H), 3.75 (m, 1H), 3.67 (m, 2H), 2.97 (m, 1H), 2.76 (m, 1H), 1.75 (t, J=6.0 Hz, 1H). MS (ESI): Calcd for $C_{20}H_{24}FN_4O_2S^+$ 403.15 $[M+H]^+$, found 403.00 $[M+H]^+$.

The requisite intermediates were prepared as follows:

Step 1)

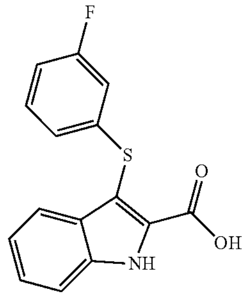 [SMILES: O=C(O)c1[nH]c2ccccc2c1Sc1cccc(F)c1]

3-((3-fluorophenyl)thio)-1H-indole-2-carboxylic acid

To a solution of DMF (20 mL) was added NaH (60% in mineral oil, 0.92 g, 23 mmol), then 1H-indole-2-carboxylic acid (1.61 g, 10 mmol) was added. After stirring at r.t. for 0.5 hr., 1,2-bis(3-fluorophenyl)disulfane (2.8 g, 11 mmol) was added. The mixture was heat at 110° C. for 6 hrs. under nitrogen. After cooling to r.t., it was diluted with EtOAc, treated with aqueous HCl solution, then the organic phase was washed with water, brine, and dried over anhydrous $Na_2SO_4$. The solvent was removed under vacuo and the residual brown oil was used for the next step of reaction without purification (2.0 g, 70% yield). $^1$H NMR (300 MHz, $CDCl_3$) b 9.82 (br s, 1H), 7.58 (d, J=8.4 Hz, 1H), 7.48 (m, 1H), 7.36 (m, 1H), 7.15 (m, 2H), 7.02 (m, 1H), 6.95 (m, 1H), 6.79 (m, 1H). MS (ESI): Calcd for $C_{15}H_{16}FNO_2S^+$ 287.05 $[M+H]^+$, found 287.00 $[M+H]^+$.

Step 2)

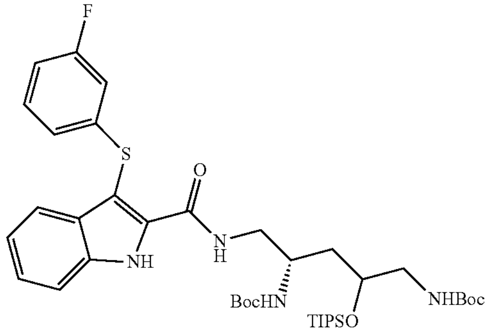

di-tert-butyl ((4S)-5-(3-((3-fluorophenyl)thio)-1H-indole-2-carboxamido)-2-((triisopropylsilyl)oxy) pentane-1,4-diyl)dicarbamate To a solution of 3-((3-fluorophenyl)thio)-1H-indole-2-carboxylic acid (29 mg, 0.1 mmol) in dry DMF (1.0 mL) was added DIPEA (0.035 mL, 0.2 mmol), HOBt (10 mg, 0.06 mmol) and EDC (24 mg, 0.12 mmol). The reaction mixture was stirred at r.t. and di-tert-butyl ((4S)-5-amino-2-((triisopropylsilyl)oxy)pentane-1,4-diyl)dicarbamate (Amine Intermediate B) (50 mg, 0.1 mmol) was added. The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel using 50-70% EtOAc in hexane as eluents to give the amide (56 mg, 74% yield) as a pale yellow powder.

Example 30. Preparation of 6-(4-fluorophenyl)-N-((2S)-2,5-diamino-4-hydroxypentyl)-1H-indole-2-carboxamide hydrogen chloride salt

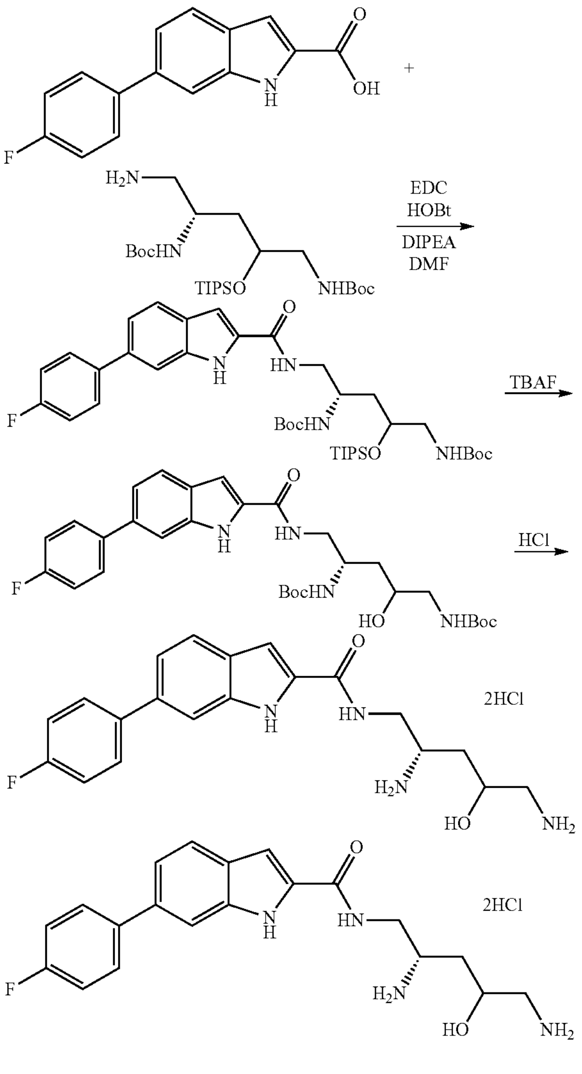

6-(4-fluorophenyl)-N-((2S)-2,5-diamino-4-hydroxypentyl)-1H-indole-2-carboxamide hydrogen chloride salt To a solution of di-tert-butyl ((4S)-5-(6-(4-fluorophenyl)-1H-indole-2-carboxamido)-2-hydroxypentane-1,4-diyl)dicarbamate (470 mg, 0.82 mmol) in MeOH (5 mL) HCl solution (4 M in dioxane, 1 mL, 4 mmol) was added. It was stirred at r.t. for 2 hrs, then solvent was removed in vacuo. The residue was dissolved in water and purified on a C18 column chromatography using 0-20% ethanol in water as eluents to provide the product as a white powder (336 mg, 92% yield). $^1H$ NMR (300 MHz, $CD_3OD$) δ 7.48 (m, 1H), 7.32 (m, 4H), 7.10 (m, 1H), 6.96 (m, 1H), 6.88 (m, 2H), 4.00 (m, 1H), 3.58 (m, 1H), 3.47 (m, 2H), 3.01 (m, 1H), 2.83 (m, 1H), 1.78 (m, 1H), 1.66 (m, 1H). $^{13}C$ NMR (75 MHz, $D_2O$) δ 164.1, 160.2, 137.2, 136.7, 136.3, 129.8, 128.2, 128.1, 126.3, 122.2, 119.9, 115.2, 114.9, 109.6, 105.2, 65.7, 50.7, 44.7, 41.2, 33.9. MS (ESI): Calcd for $C_{20}H_{24}FN_4O_2^+$ 371.18 $[M+H]^+$, found 371.00 $[M+H]^+$.

The requisite intermediates were prepared as follows:

Step 1)

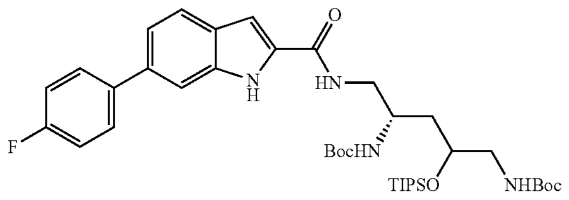

di-tert-butyl ((4S)-5-(6-(4-fluorophenyl)-1H-indole-2-carboxamido)-2-((triisopropylsilyl)oxy)pentane-1,4-diyl)dicarbamate To a solution of 6-(4-fluorophenyl)-1H-indole-2-carboxylic acid (385 mg, 1.5 mmol) in dry DMF (5 mL) was added DIPEA (0.51 mL, 3 mmol), HOBt (130 mg, 0.9 mmol) and EDC (380 mg, 2 mmol). The reaction mixture was stirred at r.t. and di-tert-butyl ((4S)-5-amino-2-((triisopropylsilyl)oxy)pentane-1,4-diyl)dicarbamate (Amine Intermediate B) (750 mg, 1.5 mmol) was added. The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel using 50-70% EtOAc in hexane as eluents to give the amide (950 mg, 87% yield) as a white powder. MS (ESI): Calcd for $C_{39}H_{59}FN_4O_6NaSi^+$749.42 $[M+H]^+$, found 749.35 $[M+Na]^+$.

Step 2)

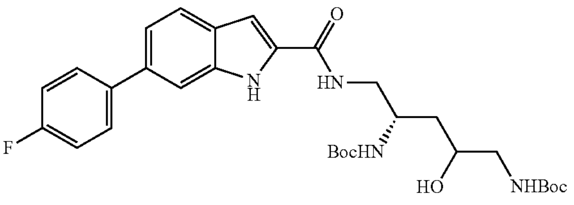 [SMILES: CC(C)(C)OC(=O)NCC(O)C[C@@H](CNC(=O)c1cc2ccc(-c3ccc(F)cc3)cc2[nH]1)NC(=O)OC(C)(C)C]

di-tert-butyl ((4S)-5-(6-(4-fluorophenyl)-1H-indole-2-carboxamido)-2-hydroxypentane-1,4-diyl)dicarbamate To a solution of di-tert-butyl ((4S)-5-(3-(4-fluorophenyl)-1H-indole-2-carboxamido)-2-((triisopropylsilyl)oxy)pentane-1,4-diyl)dicarbamate (930 mg, 1.28 mmol) in THE (20 mL) was added TBAF solution (1.0 M in THF, 4 mL, 4 mmol) at r.t. It was stirred for 1 hr and concentrated, then loaded on a silica gel column chromatography and purified with 50-80% EtOAc in hexane to provide the alcohol as a white powder (490 mg, 67% yield). $^{1}H$ NMR (300 MHz, DMSO-$d_6$) δ 11.13 (br s, 1H), 8.43 (br s, 1H), 8.14 (m, 1H), 8.08 (m, 3H), 7.75 (dd, J=8.1 Hz, 1.5 Hz, 1H), 7.57 (t, J=8.7 Hz, 2H), 7.48 (s, 1H), 6.56 (br d, 1H), 6.29 (br s, 1H), 4.72 (br, 1H), 4.41 (m, 1H), 4.28 (m, 1H), 3.98 (m, 2H), 3.62 (m, 1H), 3.54 (m, 1H), 3.46 (m, 1H), 2.12 (m, 1H), 2.06 (m, 1H), 1.81 (s, 18H). MS (ESI): Calcd for $C_{30}H_{40}FN_4O_6^+$ 571.29 $[M+H]^+$, found 571.25 $[M+H]^+$.

Example 31. Preparation of (R)—N-(2-amino-3-(2-aminoethoxy)propyl)-6-(4-fluorophenyl)-1H-indole-2-carboxamide hydrogen chloride salt

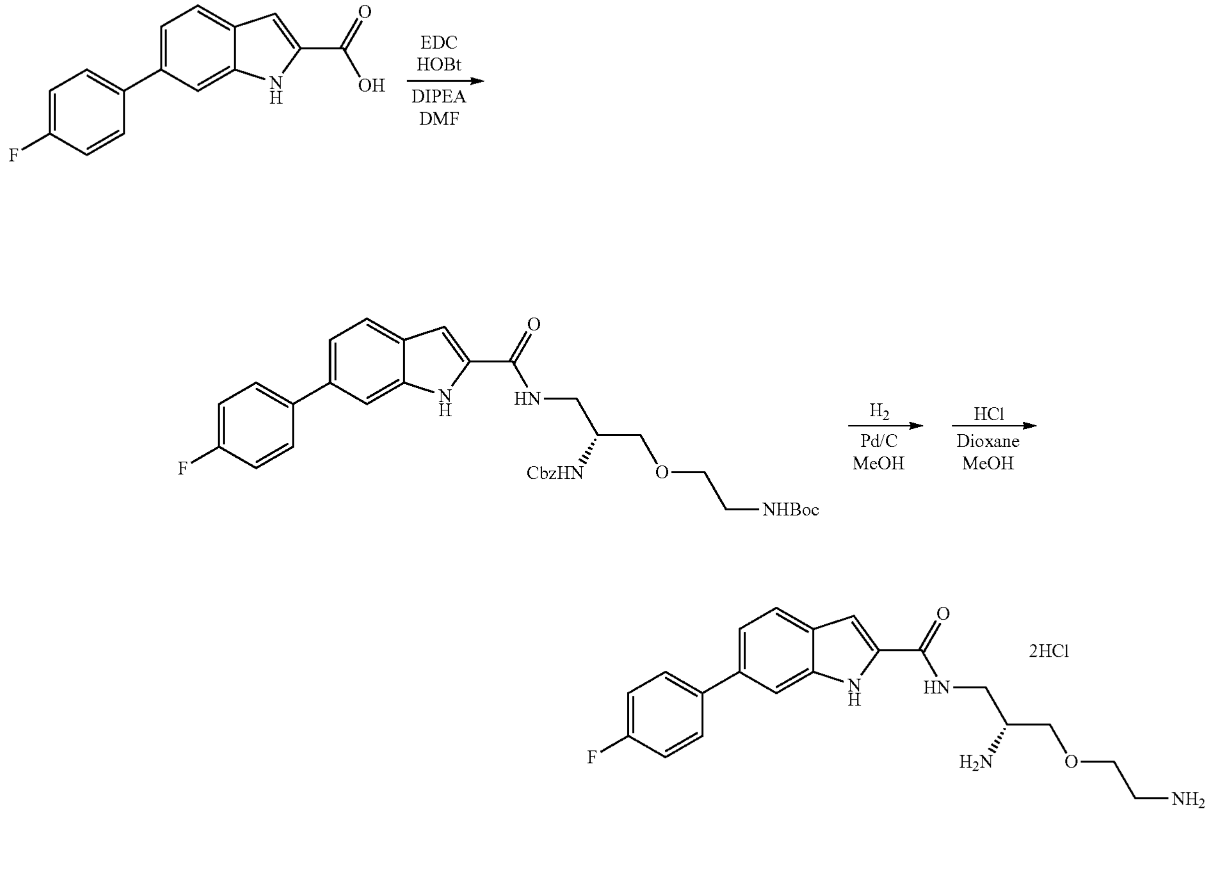

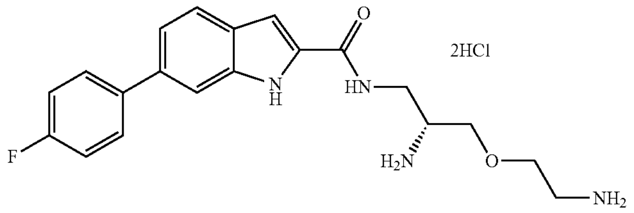

(R)—N-(2-amino-3-(2-aminoethoxy)propyl)-6-(4-fluorophenyl)-1H-indole-2-carboxamide hydrogen chloride salt To a solution tert-butyl (R)-(2-(2-(((benzyloxy)carbonyl)amino)-3-(6-(4-fluorophenyl)-1H-indole-2-carboxamido)propoxy)ethyl)carbamate (130 mg, 0.22 mmol) in MeOH (20 mL) was added Pd/C (10%, 50 mg, 0.05 mmol). Then it was stirred under $H_2$ (55 psi) overnight. It was filtered through a Celite pad and washed with methanol, then concentrated to provide the crude product as an off-white powder. MS (ESI): Calcd for $C_{25}H_{32}FN_4O_4^+$ 471.23 $[M+H]^+$, found 471.15 $[M+H]^+$. To a solution of tert-butyl (R)-(2-(2-amino-3-(6-(4-fliorophenyl)-1H-indole-2-carboxamido)propoxy)ethyl)carbamate in MeOH (5 mL) HCl solution (4 M in dioxane, 0.2 mL, 0.8 mmol) was added. It was stirred at r.t. until no starting material left, then solvent was removed in vacuo. The residue was dissolved in water and loaded on a C18 column chromatography and purified with 0-15% EtOH in water to give the desired product as a white powder (82 mg, 86% yield). $^{1}H$ NMR (300 MHz, $CD_3OD$) δ 8.77 (br 1H), 7.66 (m, 4H), 7.33 (d, J=8.4 Hz, 1H), 7.18 (m, 3H), 3.80 (m, 3H), 3.77 (m, 2H), 3.70 (m, 2H), 3.22 (m, 2H). MS (ESI): Calcd for $C_{20}H_{24}FN_4O_2^+$371.18 $[M+H]^+$, found 371.05 $[M+H]^+$.

The requisite intermediate was prepared as follow:

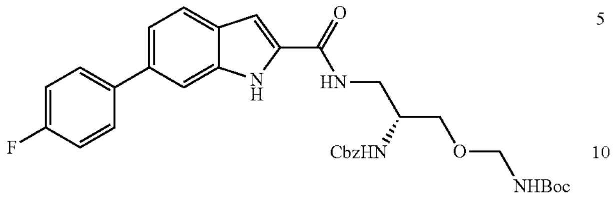

tert-butyl (R)-(2-(2-(((benzyloxy)carbonyl)amino)-3-(6-(4-fluorophenyl)-1H-indole-2-carboxamido)propoxy)ethyl)carbamate To a solution of 6-(4-fluorophenyl)-1H-indole-2-carboxylic acid (124 mg, 0.4 mmol) in dry DMF (2 mL) was added DIPEA (0.17 mL, 1 mmol), HOBt (42 mg, 0.3 mmol) and EDC (100 mg, 0.5 mmol). The reaction mixture was stirred at r.t. and benzyl (R)-(1-amino-3-(2-((tert-butoxycarbonyl)amino)ethoxy)propan-2-yl)carbamate (Amine Intermediate D) (148 mg, 0.4 mmol) was added. The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel to give the product (136 mg, 56% yield) as a white powder. $^1$H NMR (300 MHz, $CDCl_3$) δ 9.27 (br s, 1H), 7.71 (m, 1H), 7.57 (m, 2H), 7.55 (m, 1H), 7.24-7.36 (m, 5H), 7.14 (m, 3H), 7.05 (m, 1H), 6.19 (br s, 1H), 5.80 (br s, 1H), 5.12 (s, 2H), 4.93 (br, 1H), 3.64 (m, 1H), 3.47-3.61 (m, 4H), 3.45 (m, 2H), 3.29 (m, 2H), 1.47 (s, 9H). MS (ESI): Calcd for $C_{33}H_{38}FN_4O_6^+$ 605.28 $[M+H]^+$, found 605.20 $[M+H]^+$.

Example 32. Preparation of (R)—N-(2-amino-3-(2-aminoethoxy)propyl)-6-phenyl-1H-indole-2-carboxamide hydrogen chloride salt

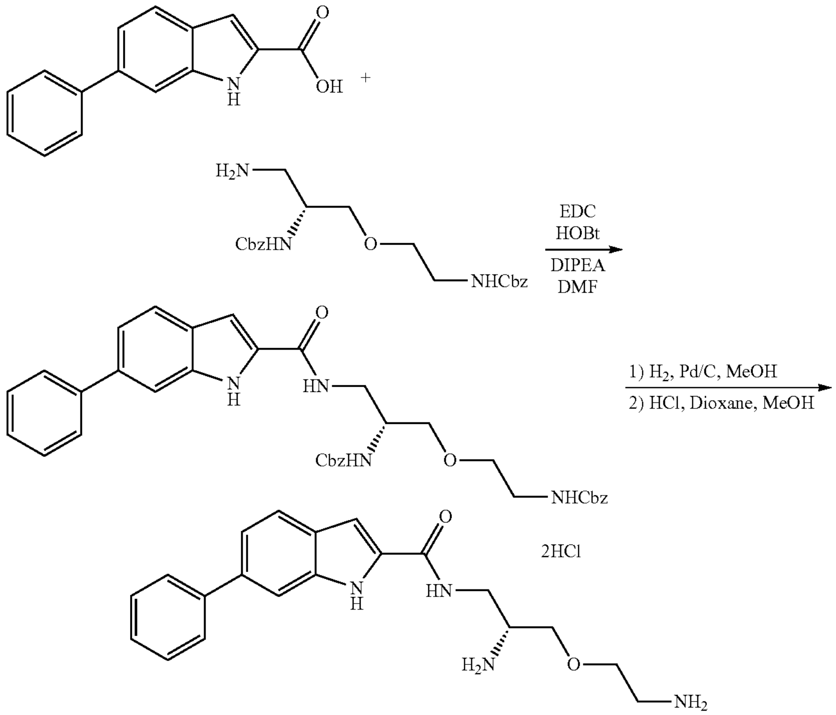

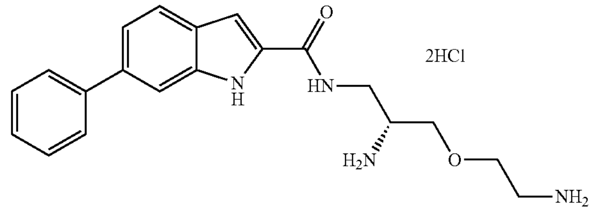

(R)—N-(2-amino-3-(2-aminoethoxy)propyl)-6-phenyl-1H-indole-2-carboxamide hydrogen chloride salt To a solution of benzyl (R)-(2-(2-(((benzyloxy)carbonyl)amino)-3-(6-phenyl-1H-indole-2-carboxamido)propoxy)ethyl)carbamate (245 mg, 0.48 mmol) in MeOH (20 mL) was added Pd/C (10%, 50 mg, 0.05 mmol). Then it was stirred under $H_2$ (50 psi) overnight. It was filtered through a Celite pad and washed with methanol, then concentrated. To the solution was added HCl solution (4 M in dioxane, 0.5 mL, 2.0 mmol), then solvent was removed in vacuo. The residue was dissolved in water and purified on C18 column with 0-15% acetonitrile in water to give a white powder (135 mg, 80% yield). $^1$H NMR (300 MHz, $D_2O$) δ 7.79 (m, 2H), 7.74 (m, 2H), 7.51 (m, 3H), 7.41 (t, J=7.2 Hz, 1H), 7.14 (m, 1H), 3.83 (m, 1H), 3.78 (m, 3H), 3.71 (m, 3H), 3.21 (t, J=5.1 Hz, 2H). MS (ESI): Calcd for $C_{20}H_{25}N_4O_2^+$ 353.20 $[M+H]^+$, found 352.95 $[M+H]^+$.

The requisite intermediate was prepared as follow:

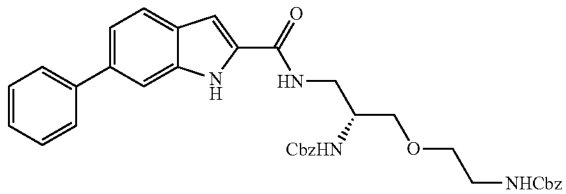 [SMILES: O=C(NCCOC[C@@H](CNC(=O)c1cc2ccc(-c3ccccc3)cc2[nH]1)NC(=O)OCc1ccccc1)OCc1ccccc1]

benzyl (R)-(2-(2-(((benzyloxy)carbonyl)amino)-3-(6-phenyl-1H-indole-2-carboxamido)propoxy)ethyl) carbamate To a solution of 6-phenyl-1H-indole-2-carboxylic acid (119 mg, 0.5 mmol) in dry DMF (3 mL) was added EDC (120 mg, 0.6 mmol) and HOBt (50 mg, 0.3 mmol). The reaction mixture was stirred at r.t. and DIPEA (0.17 mL, 1 mmol) was added followed by benzyl (R)-(1-amino-3-(2-(((benzyloxy)carbonyl)amino)ethoxy)propan-2-yl)carbamate (Amine Intermediate G) (201 mg, 0.5 mmol). The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel to give the product (251 mg, 81% yield) as a white powder. $^1H$ NMR (300 MHz, $CDCl_3$) δ 9.23 (br d, 1H), 7.71 (d, J=8.4 Hz, 1H), 7.64 (m, 2H), 7.48 (m, 2H), 7.42 (m, 2H), 7.35 (m, 1H) 7.27-7.33 (m, 10H), 6.98 (s, 1H), 5.74 (br s, 1H), 5.46 (br t, 1H), 5.12 (m, 2H), 5.11 (m, 2H), 3.97 (m, 1H), 3.76 (m, 1H), 3.64 (m, 1H), 3.55 (m, 4H), 3.42 (m, 2H). MS (ESI): Calcd for $C_{36}H_{37}N_4O_6^+$ 621.27 $[M+H]^+$, found 621.20 $[M+H]^+$.

Example 33. Preparation of (R)—N-(2-amino-3-(2-aminoethoxy)propyl)-4-(4-fluorophenyl)-3-methyl-1H-indole-2-carb oxamide hydrogen chloride salt

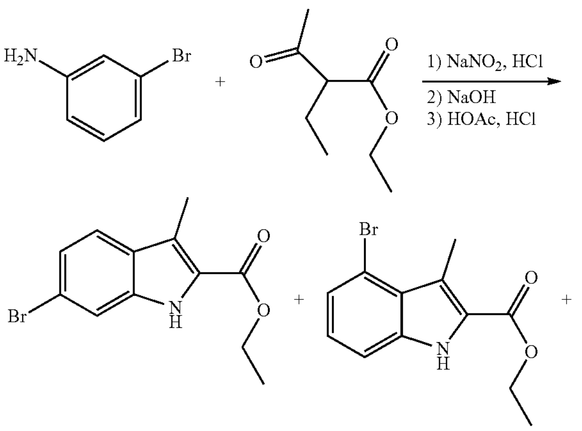

-continued

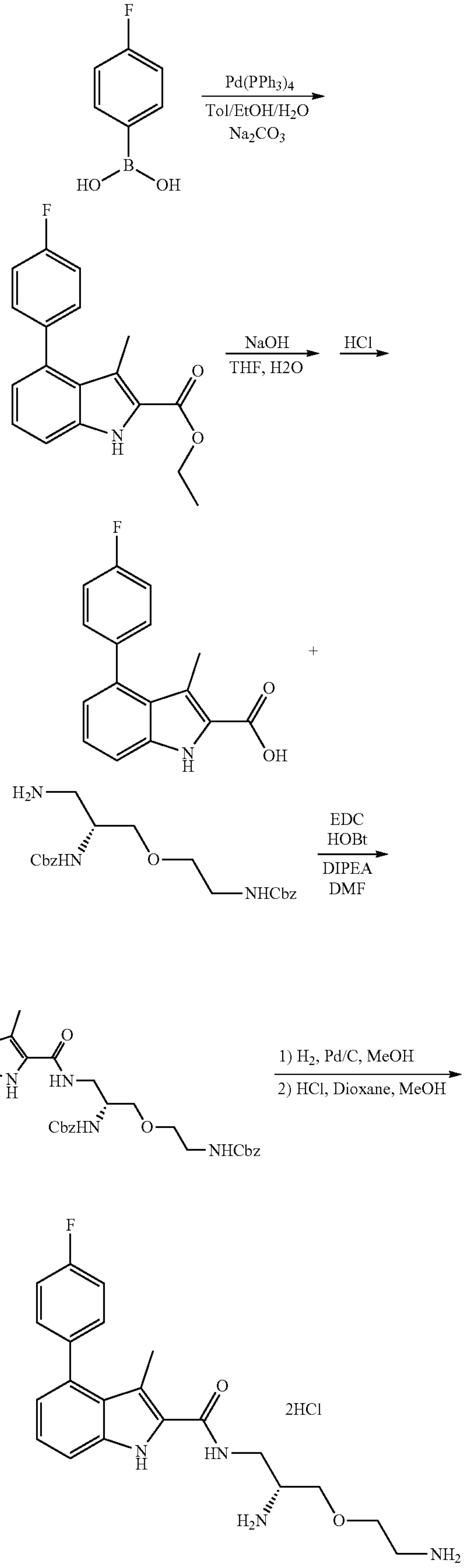

-continued

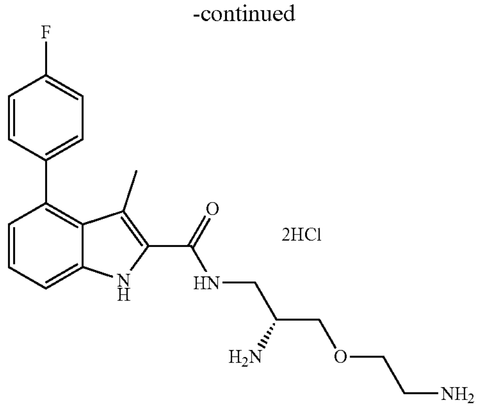

(R)—N-(2-amino-3-(2-aminoethoxy)propyl)-4-(4-fluorophenyl)-3-methyl-1H-indole-2-carboxamide hydrogen chloride salt To a solution of benzyl (R)-(2-(2-(((benzyloxy)carbonyl) amino)-3-(4-(4-fluorophenyl)-3-methyl-1H-indole-2-carboxamido)propoxy)ethyl)carbamate (310 mg, 0.48 mmol) in MeOH (20 mL) was added Pd/C (10%, 50 mg, 0.05 mmol). Then it was stirred under $H_2$ (50 psi) overnight. It was filtered through a Celite pad and washed with methanol, then concentrated. To the solution was added HCl solution (4 M in dioxane, 0.5 mL, 2.0 mmol), then solvent was removed in vacuo. The residue was dissolved in water and purified on C18 column with 0-15% acetonitrile in water to give a white powder (153 mg, 79% yield). $^1H$ NMR (300 MHz, $CD_3OD$) δ 7.41 (m, 1H), 7.38 (m, 2H), 7.27 (dd, J 6.9 Hz, 8.4 Hz, 1H), 7.16 (m, 2H), 6.88 (dd, J=0.9 Hz, 6.9 Hz, 1H), 3.80 (m, 3H), 3.78 (m, 2H), 3.66 (m, 2H), 3.20 (t, J=4.8 Hz, 2H), 2.09 (s, 3H). MS (ESI): Calcd for $C_{21}H_{26}FN_4O_2^+$ 385.20 $[M+H]^+$, found 385.00 $[M+H]^+$.

The requisite intermediates were prepared as follows:

Step 1)

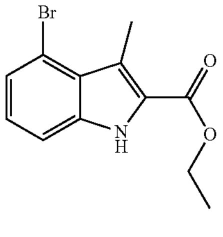 [SMILES: CCOC(=O)c1[nH]c2cccc(Br)c2c1C]

ethyl 4-bromo-3-methyl-1H-indole-2-carboxylate

To a suspension of 3-bromoaniline (11.8 g, 62.8 mmol) in water (28 mL) was added conc. HCl (35% in $H_2O$, 15.4 mL) at 0° C., then $NaNO_2$ (4.8 g, 69.2 mmol) was added by portions. The reaction mixture was stirred at 0° C. for 20 minutes, then ethyl-2-ethylacetate (12 g, 76 mmol) in EtOAc (60 mL) was added dropwise at same temperature. After 30 minutes, the pH of the reaction mixture was adjusted to 7-8 by adding 4.4 g of NaOAc and 7.3 g of NaOH, then it was continued to stir for 3 hours at room temperature. It was stirred at 50° C. overnight. After cooled to room temperature, the reaction mixture was separated, and the aqueous layer was extracted with EtOAc (3×40 mL). The combined organic layer was washed with water, brine and dried over $Na_2SO_4$. Solvent was removed and the residue was purified by column chromatography on silica gel to give two isomers. The first isomer ethyl 6-bromo-3-methyl-1H-indole-2-carboxylate was got as a pale brown powder (1.4 g, 7.9%)$^1H$ NMR (300 MHz, $CDCl_3$) δ 8.96 (br s, 1H), 7.50-7.73 (m, 2H), 7.22-7.26 (m, 1H), 4.42 (q, J=7.2 Hz, 2H), 2.56 (s, 3H), 1.43 (t, J=7.2 Hz, 3H). The second isomer ethyl 4-bromo-3-methyl-1H-indole-2-carboxylate was got as a pale brown powder (1.1 g, 6.2%). $^1H$ NMR (300 MHz, $CDCl_3$) δ 8.75 (br s, 1H), 7.26-7.32 (m, 2H), 7.20 (t, J=7.5 Hz, 1H), 4.42 (q, J=7.2 Hz, 2H), 2.92 (s, 3H), 1.44 (t, J=7.2 Hz, 3H).

Step 2)

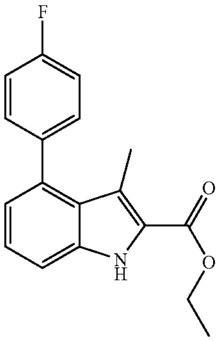 [SMILES: CCOC(=O)c1[nH]c2cccc(-c3ccc(F)cc3)c2c1C]

ethyl 4-(4-fluorophenyl)-3-methyl-1H-indole-2-carboxylate

The mixture of ethyl 4-bromo-3-methyl-1H-indole-2-carboxylate (565 mg, 2.0 mmol) and (4-fluorophenyl)boronic acid (350 mg, 2.5 mmol) in a mixture of toluene, ethanol and saturated $Na_2CO_3$ solution (20/5/5 mL) was degassed and $Pd(dppf)Cl_2$ (70 mg, 0.1 mmol) was added. The reaction mixture was heated at 100° C. overnight, it was extracted with EtOAc and washed with brine and dried over $Na_2SO_4$, then concentrated. It was purified by column chromatography on silica gel with 0-20% EtOAc in hexane as eluents to give the product (510 mg, 86% yield) as an off-white powder. $^1H$ NMR (300 MHz, $CDCl_3$) δ 8.79 (br s, 1H), 7.36 (m, 3H), 7.29 (m, 1H), 7.11 (t, J=8.7 Hz, 2H), 6.94 (dd, J=1.2 Hz, 6.9 Hz, 1H), 4.40 (q, J=7.2 Hz, 2H), 2.14 (s, 3H), 1.40 (t, J=7.2 Hz, 3H). MS (ESI): Calcd for $C_{18}H_{17}FNO_2^+$ 298.12 $[M+H]^+$, found 297.95 $[M+H]^+$.

Step 3)

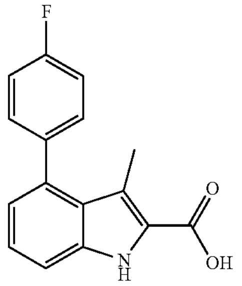 [SMILES: Cc1c(C(=O)O)[nH]c2cccc(-c3ccc(F)cc3)c12]

4-(4-fluorophenyl)-3-methyl-1H-indole-2-carboxylic acid

To a solution of ethyl 4-(4-fluorophenyl)-3-methyl-1H-indole-2-carboxylate (350 mg, 1.18 mmol) in THE (10 mL) and EtOH (5 mL) was added NaOH solution (1 M, 10 mL). It was heated at 50° C. until no starting material left. Solvents were removed in vacuo and the residue was diluted with water, then acidified with HCl solution. The precipitate was collected and washed with water. It was dried to provide the acid as a pale brown powder (250 mg, 79% yield) which was used for next step reaction without further purification. Calcd for $C_{16}H_{13}FNO_2^+$ 270.09 [M+H]$^+$, found 269.90 [M+H]$^+$.

Step 4)

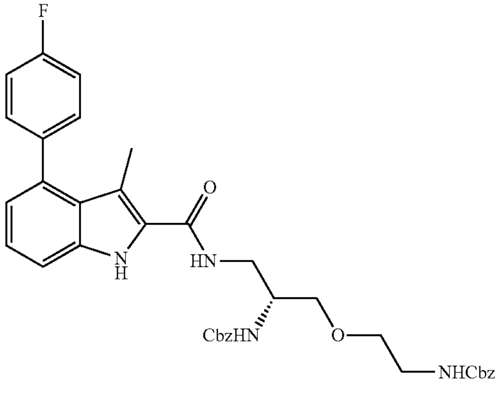 [SMILES: Cc1c(C(=O)NC[C@H](COCCNC(=O)OCc2ccccc2)NC(=O)OCc2ccccc2)[nH]c2cccc(-c3ccc(F)cc3)c12]

benzyl (R)-(2-(2-(((benzyloxy)carbonyl)amino)-3-(4-(4-fluorophenyl)-3-methyl-1H-indole-2-carboxamido)propoxy)ethyl)carbamate To a solution of 3-methyl-4-(4-fluoro-phenyl)-1H-indole-2-carboxylic acid (135 mg, 0.5 mmol) in dry DMF (3 mL) was added EDC (120 mg, 0.6 mmol) and HOBt (50 mg, 0.3 mmol). The reaction mixture was stirred at r.t. and DIPEA (0.17 mL, 1 mmol) was added followed by benzyl (R)-(1-amino-3-(2-(((benzyloxy)carbonyl)amino)ethoxy)propan-2-yl)carbamate (Amine Intermediate G) (201 mg, 0.5 mmol). The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel to give the product (314 mg, 96% yield) as a colorless oil. $^1$H NMR (300 MHz, $CDCl_3$) δ 9.37 (br s, 1H), 7.35 (m, 2H), 7.31 (m, 6H), 7.27 (m, 4H), 7.24 (m, 2H), 7.11 (t, J=8.7 Hz, 2H), 6.91 (m, 1H), 6.71 (br, s, 1H), 5.72 (br s, 1H), 5.57 (br s, 1H), 5.09 (m, 2H), 5.06 (m, 2H), 3.96 (m, 1H), 3.80 (m, 1H), 3.62 (m, 1H), 3.54 (m, 4H), 3.38 (m, 2H), 2.05 (s, 3H). MS (ESI): Calcd for $C_{37}H_{38}FN_4O_6^+$ 653.27 [M+H]$^+$, found 653.25 [M+H]$^+$.

Example 34. Preparation of N—((R)-2-amino-3-(((S)-2,5-diaminopentyl)oxy)propyl)-3-(4-fluorophenyl)-1H-indole-2-carboxamide hydrogen chloride salt

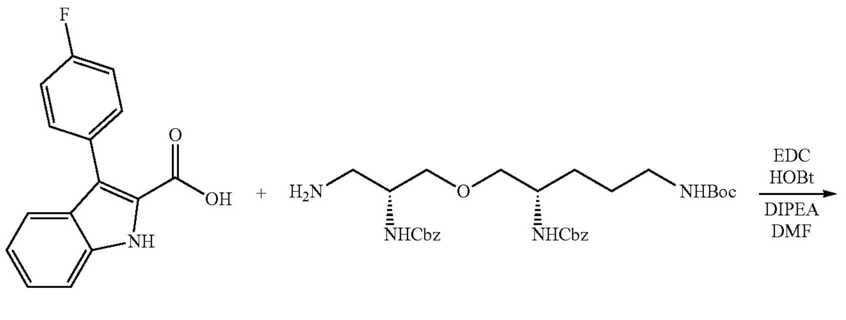

-continued

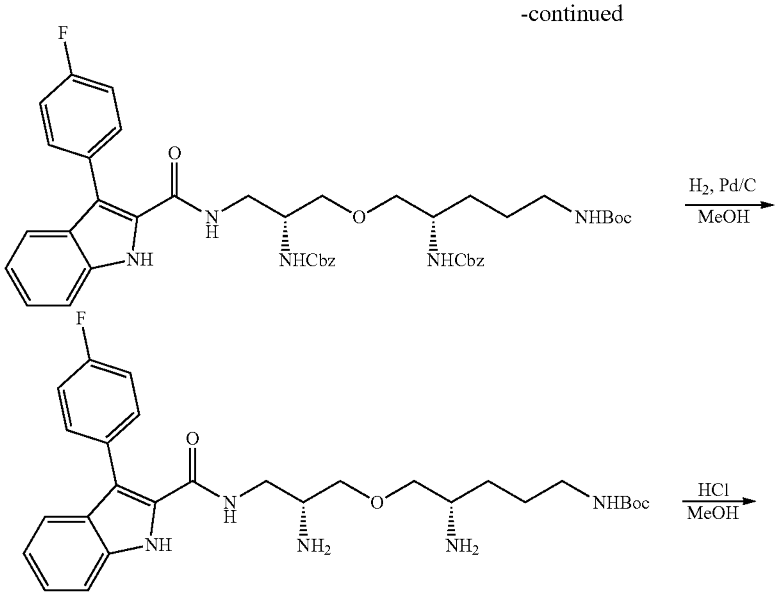

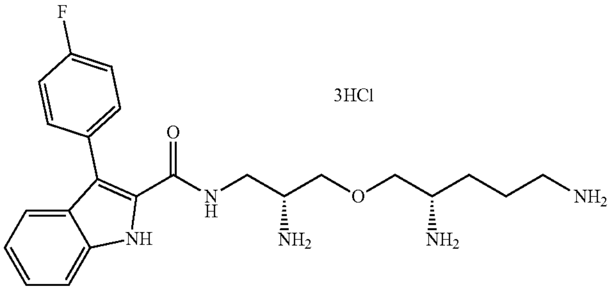

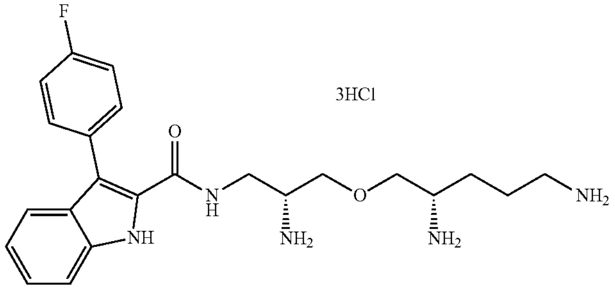

N—((R)-2-amino-3-(((S)-2,5-diaminopentyl)oxy)propyl)-3-(4-fluorophenyl)-1H-indole-2-carboxamide hydrogen chloride salt To a solution of tert-butyl ((S)-4-amino-5-((R)-2-amino-3-(3-(4-fluorophenyl)-1H indole-2-carboxamido)propoxy)pentyl)carbamate (15 mg, 0.03 mmol) in MeOH (2 mL) HCl solution (4 M in dioxane, 0.1 mL, 0.4 mmol) was added. It was stirred at r.t. for 1 hrs, then solvent was removed in vacuo. The residue was dissolved in water and purified on a C18 column chromatography using water as eluent to give the product as a white powder (4 mg, 27% yield). $^{1}H$ NMR (300 MHz, $CD_3OD$) δ 7.67 (m, 1H), 7.56 (m, 2H), 7.59 (m, 1H), 7.32 (m, 3H), 7.13 (m, 1H), 3.77 (m, 3H), 3.74 (m, 2H), 3.52 (m, 3H), 2.97 (m, 2H), 1.78 (m, 4H). MS (ESI): Calcd for $C_{23}H_{31}FN_5O_2^+$428.25 $[M+H]^+$, found 428.15 $[M+H]^+$.

The requisite intermediates were prepared as follows:

Step 1)

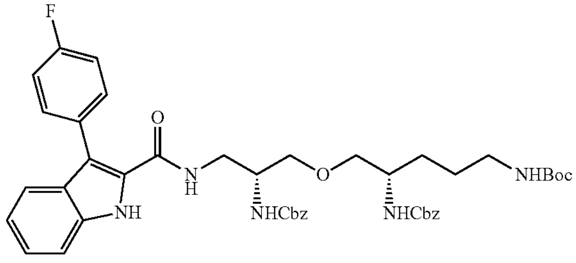 [SMILES: CC(C)(C)OC(=O)NCCC[C@@H](COC[C@@H](CNC(=O)c1[nH]c2ccccc2c1-c1ccc(F)cc1)NC(=O)OCc1ccccc1)NC(=O)OCc1ccccc1]

benzyl tert-butyl ((S)-5-((R)-2-(((benzyloxy)carbonyl)amino)-3-(3-(4-fluorophenyl)-1H-indole-2-carboxamido)propoxy)pentane-1,4-diyl)dicarbamate To a solution of 3-(4-fluorophenyl)-1H-indole-2-carboxylic acid (26 mg, 0.1 mmol) in dry DMF (1 mL) was added DIPEA (0.034 mL, 0.2 mmol), HOBt (10 mg, 0.06 mmol) and EDC (24 mg, 0.12 mmol). The reaction mixture was stirred at r.t. and benzyl tert-butyl ((S)-5-((R)-3-amino-2-(((benzyloxy)carbonyl)amino)propoxy)pentane-1,4-diyl)dicarbamate (Amine Intermediate H) (56 mg, 0.1 mmol) was added. The reaction mixture was stirred at r.t. overnight. It was extracted with EtOAc and washed with water and brine. The organic layer was dried over anhydrous sodium sulfate and filtered. The filtrate was concentrated and purified by column chromatography on silica gel to give the product (48 mg, 60% yield) as a white powder. MS (ESI): Calcd for $C_{44}H_{51}FN_5O_8^+$ 796.36 [M+H]$^+$, found 796.35 [M+H]$^+$ Step 2)

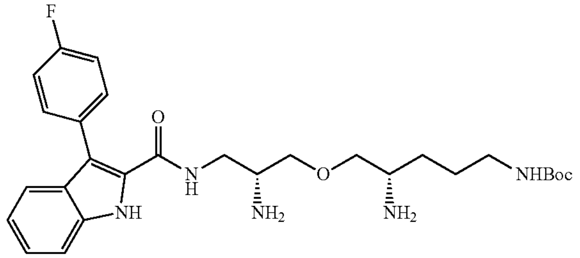 [SMILES: CC(C)(C)OC(=O)NCCC[C@H](N)COC[C@H](N)CNC(=O)c1[nH]c2ccccc2c1-c1ccc(F)cc1]

tert-butyl ((S)-4-amino-5-((R)-2-amino-3-(3-(4-fluorophenyl)-1H-indole-2-carboxamido)propoxy)pentyl)carbamate To a solution benzyl tert-butyl ((5)-5-((R)-2-(((benzyloxy)carbonyl)amino)-3-(3-(4-fluorophenyl)-1H-indole-2-carboxamido)propoxy)pentane-1,4-diyl)dicarbamate (46 mg, 0.058 mmol) in MeOH (10 mL) was added Pd/C (10%, 10 mg, 0.01 mmol). Then it was stirred under $H_2$ (50 psi) overnight. It was filtered through a Celite pad and washed with methanol, then concentrated to provide the crude product which was purified by column chromatography on silica gel to give the amine as an off-white powder (16 mg, 52% yield). MS (ESI): Calcd for $C_{28}H_{39}FN_5O_4^+$ 528.30 [M+H]$^+$, found 528.20 [M+H]$^+$.

Example 35. Preparation of N-((2R)-2,4-diamino-3-hydroxybutyl)-3-(4-fluorophenyl)-1H-indole-2-carboxamide

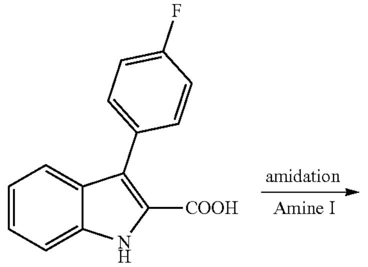

-continued

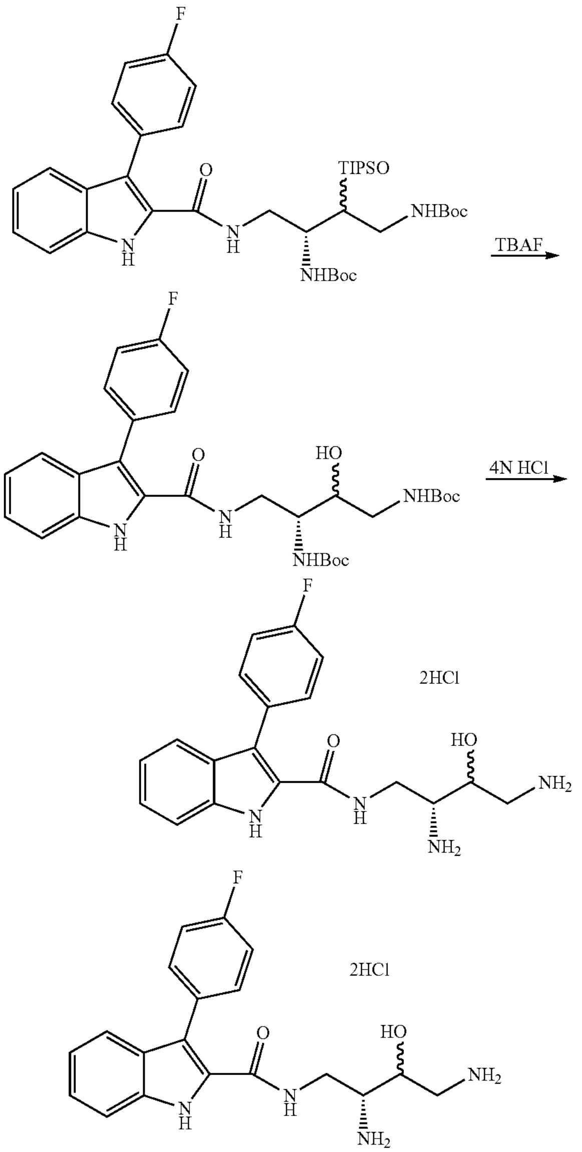

N-((2R)-2,4-diamino-3-hydroxybutyl)-3-(4-fluorophenyl)-1H-indole-2-carboxamide

To a solution of di-tert-butyl ((3R)-4-(3-(4-fluorophenyl)-1H-indole-2-carboxamido)-2-hydroxybutane-1,3-diyl)dicarbamate (18 mg, 0.03 mmol) in 1 mL of methanol was added 0.2 mL of HCl (4N in dioxane, 0.8 mmol). Reaction mixture was stirred at 50° C. for 30 minutes then solvents were removed by rotovapor. Residue was washed with small amount of ethyl ether and dried. Product was collected as gray solid powder, 7.4 mg, 53%. $^1H$ NMR (300 MHz, $D_2O$) δ 7.36-7.46 (m, 3H), 7.24 (t, J=7.8 Hz, 1H), 7.16 (t, J=9.0 Hz, 1H), 7.05 (t, J=7.2 Hz, 1H), 3.99-4.03 (m, 1H), 3.37-3.54 (m, 3H), 3.05 (dd, $J_1$=3.0 Hz, $J_2$=13.5 Hz, 1H), 2.89 (dd, $J_1$=11.1 Hz, $J_2$=12.9 Hz, 1H); MS: Calcd for $C_{19}H_{22}FN_4O_2^+$ 357.17 [M+H$^+$], found 357.00 [M+H]

The requisite intermediates were prepared as follows:

Step 1)

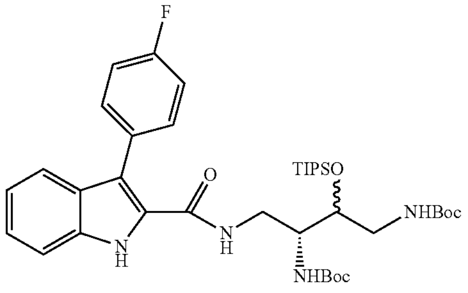

di-tert-butyl ((3R)-4-(3-(4-fluorophenyl)-1H-indole-2-carboxamido)-2-((triisopropylsilyl)oxy)butane-1,3-diyl)dicarbamate To a solution of (S)-di-tert-butyl (4-amino-2-((triisopropylsilyl)oxy)butane-1,3-diyl)dicarbamate (Amine intermediate I) (34 mg, 0.07 mmol) in 1 mL of DMF was added 3-(4-fluorophenyl)-1H-indole-2-carboxylic acid (35 mg, 0.08 mmol, 1.2 eq), 1-ethyl-3-(3-dimethylaminopropyl) carbodiimide (EDCI, 16.5 mg, 0.1 mmol, 1.5 eq), hydroxybenzotriazole (HOBt, 1.0 mg, 10 mol % cat.) and N,N-diisopropylethylamine (DIPEA, 13.8 mg, 0.13 umol, 1.5 eq). Resulting reaction mixture was stirred at room temperature overnight then diluted with 5 mL of water and stirred for 30 minutes. Solid was filtered and washed with small amount of water then dissolved in 3 mL of dichloromethane, washed with small amount of brine and dried. After solvent removed, crude product was used to next step without further purification.

Step 2)

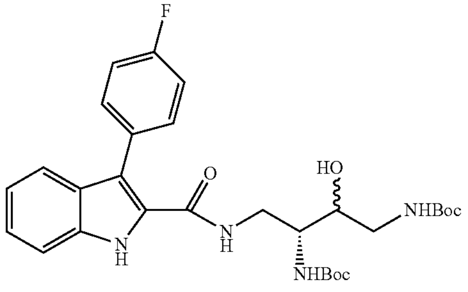 [SMILES: CC(C)(C)OC(=O)NCC(O)[C@@H](CNC(=O)c1[nH]c2ccccc2c1-c1ccc(F)cc1)NC(=O)OC(C)(C)C]

di-tert-butyl ((3R)-4-(3-(4-fluorophenyl)-1H-indole-2-carboxamido)-2-hydroxybutane-1,3-diyl)dicarbamate To a solution of 60 mg of di-tert-butyl ((3R)-4-(3-(4-fluorophenyl)-1H-indole-2-carboxamido)-2-((triisopropylsilyl)oxy)butane-1,3-diyl)dicarbamate (0.08 mmol) in 2 mL of THE was added 0.2 mL of TBAF solution (1.0 M/THF, 0.2 mmol) at 0° C. with stirring. Resulting reaction mixture was stirred at room temperature for 1 hour then diluted with 10 mL of EtOAc. The mixture was continuously washed with 0.5 N HCl, water, aq. Sat. $NaHCO_3$, brine then dried over $Na_2SO_4$. Solvent removed and residue was purified on column to give 38.5 mg product as white solid, 82%. 1H NMR (300 MHz, CDCl3) δ 9.58 (s, 1H), 7.42-7.51 (m, 4H), 7.23-7.36 (m, 3H), 7.16 (t, J=8.1 Hz, 1H), 6.35 (br s, 1H), 5.46 (br s, 1H), 5.20 (d, J=7.2 Hz, 1H), 4.56 (br s, 1H), 3.72-3.84 (m, 1H), 3.46-3.63 (m, 2H), 3.32-3.46 (m, 2H), 2.91-3.03 (m, 1H), 1.42 (s, 9H), 1.40 (s, 9H); MS: Calcd for $C_{29}H_{38}FN_4O_6^+$557.27 [M+H$^+$], found 557.00 [M+H]$^+$.

Example 36. Preparation of N-(((2R,4S)-4-(aminomethyl)-3-oxopyrrolidin-2-yl)methyl)-3-(4-fluorophenyl)-1H-indole-2-carboxamide

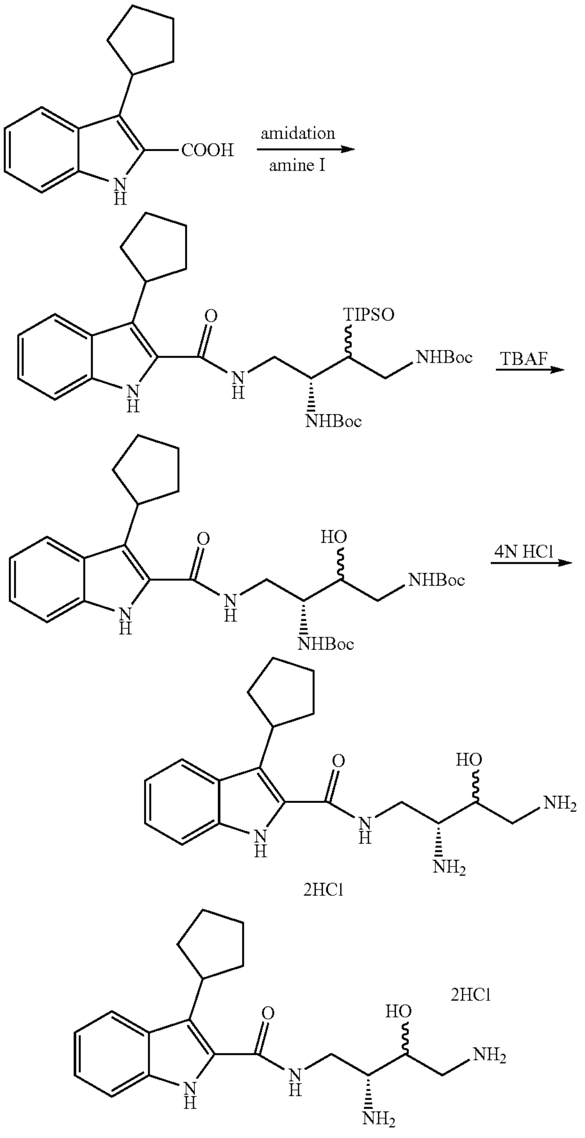

3-cyclopentyl-N-((2R)-2,4-diamino-3-hydroxybutyl)-1H-indole-2-carboxamide

To a solution of di-tert-butyl ((3R)-4-(3-cyclopentyl-1H-indole-2-carboxamido)-2-hydroxybutane-1,3-diyl)dicarbamate (11 mg, 0.02 mmol) in 1 mL of methanol was added 0.2 mL of HCl (4N in dioxane, 0.8 mmol). Reaction mixture was stirred at 50° C. for 30 minutes then solvents were removed by rotovapor. Residue was washed with small amount of ethyl ether and dried. Product was collected as gray solid powder, 6.9 mg, 82%. $^1$H NMR (300 MHz, $D_2O$) δ 7.75 (d, J=8.1 Hz, 1H), 7.39 (d, J=9.0 Hz, 1H), 7.23 (t, J=8.4 Hz, 1H), 7.05 (t, J=7.2 Hz, 1H), 4.13 (d, J=11.1 Hz, 1H), 3.53-3.71 (m, 4H), 3.19-3.24 (m, 1H), 3.03-3.09 (m, 1H) 1.83-1.92 (m, 6H), 1.62 (br s, 2H); MS: Calcd for $C_{18}H_{26}N_4O_2^+$ 331.21 [M+H$^+$], found 331.00 [M+H]$^+$ The requisite intermediates were prepared as follows:

Step 1)

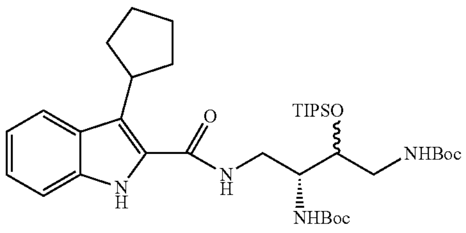

di-tert-butyl ((3R)-4-(3-cyclopentyl-1H-indole-2-carboxamido)-2-((triisopropylsilyl)oxy)butane-1,3-diyl)dicarbamate To a solution of di-tert-butyl ((3R)-4-(3-cyclopentyl-1H-indole-2-carboxamido)-2-((triisopropylsilyl)oxy)butane-1,3-diyl)dicarbamate (Amine intermediate I) (40 mg, 0.175 mmol) in 1 mL of DMF was added 3-(4-fluorophenyl)-1H-indole-2-carboxylic acid (86 mg, 0.2 mmol, 1.2 eq), 1-ethyl-3-(3-dimethylaminopropyl) carbodiimide (EDCI, 41 mg, 0.26 mmol, 1.5 eq), hydroxybenzotriazole (HOBt, 2.5 mg, 10 mol % cat.) and N,N-diisopropylethylamine (DIPEA, 28 mg, 0.26 mmol, 1.5 eq). Resulting reaction mixture was stirred at room temperature overnight then diluted with 5 mL of water and stirred for 30 minutes. Solid was filtered and washed with small amount of water then dissolved in 3 mL of dichloromethane, washed with small amount of brine and dried. After solvent removed, residue was used to next step without further purification.

Step 2)

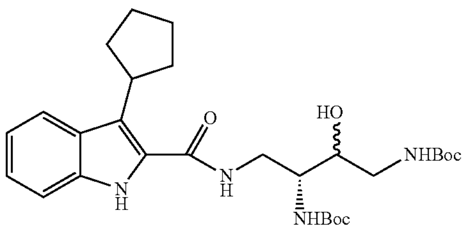 [SMILES: CC(C)(C)OC(=O)NCC(O)[C@@H](CNC(=O)c1[nH]c2ccccc2c1C1CCCC1)NC(=O)OC(C)(C)C]

di-tert-butyl ((3R)-4-(3-cyclopentyl-1H-indole-2-carboxamido)-2-hydroxybutane-1,3-diyl)dicarbamate To a solution of 42 mg of di-tert-butyl ((3R)-4-(3-cyclopentyl-1H-indole-2-carboxamido)-2-hydroxybutane-1,3-diyl)dicarbamate (0.06 mmol) in 2 mL of THE was added 0.2 mL of TBAF solution (1.0 M/THF, 0.2 mmol) at 0° C. with stirring. Resulting reaction mixture was stirred at room temperature for 1 hour then diluted with 10 mL of EtOAc. The mixture was continuously washed with 0.5 N HCl, water, aq. Sat. $NaHCO_3$, brine then dried over $Na_2SO_4$. Solvent removed and residue was purified on column to give 12 mg product as white solid, 37%. 1H NMR (300 MHz, $CDCl_3$) δ 9.37 (br s, 1H), 7.23 (d, J=8.1 Hz, 1H), 7.34 (d, J=8.1 Hz, 1H), 7.26 (t, J=14.1 Hz, 1H), 7.07 (t, J=7.5 Hz, 1H), 5.80 (br s, 1H), 5.51 (br s, 1H), 3.66-3.92 (m, 3H), 3.54-3.66 (m, 2H), 3.02-3.08 (m, 1H), 2.01-2.14 (m, 3H), 1.87-2.01 (m, 3H), 1.66-1.87 (m, 3H), 1.44 (s, 9H), 1.35 (s, 9H); MS: Calcd for $C_{28}H_{43}N_4O_6^+$ 543.31 [M+H$^+$], found 543.00 [M+H]$^+$.

Example 37. Description of General Test Methods

Intrinsic MIC Assays

MIC assays were conducted in accordance with Clinical and Laboratory Standards Institute (CLSI) guidelines for broth microdilution. A 96-well plate containing cation-adjusted Mueller-Hinton (CAMH broth with 2-fold serial dilution of compounds was inoculated with log-phase bacterial at 5×10$^5$ CFU/mL. The final volume in each well was 100 μL. Each compound was tested in duplicate. The microtiter plates were incubated in an aerobic environment for 18 hours at 37° C. Then the bacterial growth was tested by reading the plate with a VersaMax plate reader (Molecular Devices, Inc.) at 600 nm. The MIC was defined as the lowest compound concentration that inhibited 90% of bacteria growth.

The intrinsic MIC of the experimental EPIs was tested with the method described. The 2-fold serial dilution begins with 100 μg/mL of tested compound in the first column of the 96-well plates. The following Gram-negative bacterial strain was included in these assays: *Pseudomonas aeruginosa* ATCC 27853.

Bacterial EPI Assays

The EPI assay for the purposes of these studies represents a MIC assay in which the MIC of the antibiotic against the bacteria is tested in the presence of an experimental efflux pump inhibitor (EPI). The highest concentration of the EPI present in the assay typically is ½ of the intrinsic MIC of the compound. If the intrinsic MIC of the EPI is greater than 100 μg/mL, the EPI assay was tested with 50 μg/mL. Using serial dilutions of the EPI, its enhancement of antibiotic activity was then evaluated. The relative EPI activity was decided by comparing the MIC of the antibiotic in the presence of the EPI compound with the intrinsic MIC of the antibiotic alone.

Example 38. Standard EPI Assays

The impact of the EPIs on the MIC values of three test antibiotics (levofloxacin, ceftazidime and doxycycline) against *P. aeruginosa* ATCC 27853 were evaluated using our standard EPI assay. All three antibiotics levofloxacin, ceftazidime and doxycycline are known substrates of efflux pumps in *P. aeruginosa*, and are thus well-suited to be test antibiotics to assay for EPI activity.

In our standard EPI assay, the MIC of the test antibiotic is determined in the absence and presence of sub-inhibitory concentrations of the EPI. For an example, as the intrinsic MIC of Example 4 against *P. aeruginosa* ATCC 27853 is greater than 100 μg/mL, we used 6.25 μg/mL of the Example 4 in the standard EPI assay. The MIC of levofloxacin against *P. aeruginosa* ATCC 27853 in the absence of EPI is 1

μg/mL. In the presence of 6.25 μg/mL of the Example 4, the MIC of levofloxacin was markedly reduced to 0.032 μg/mL, a 32-fold reduction relative to the MIC of levofloxacin in the absence of EPI (1 μg/mL). Similarly, the MIC of ceftazidime against *P. aeruginosa* ATCC 27853 in the absence of EPI is 2 μg/mL. In the presence of 6.25 μg/mL of the Example 4, the MIC of ceftazidime was reduced to 0.5 μg/mL, a 4-fold reduction. For doxycycline, in the presence of 6.25 μg/mL of Example 4, the MIC is reduced 32-fold (1 μg/mL vs. 32 μg/mL without the EPI). For all the examples in Table 1, the potentiation activities are determined at 6.25 μg/mL.

Example 39. Fluorescent-Based Cellular Assay for Efflux Inhibition

The impact of potential EPI compounds on the activity of efflux pumps was also evaluated with a fluorescence-based cellular assay that measures the efflux of Ethidium Bromide (EtBr), a known substrate of Gram-negative bacterial efflux pumps. When bound to intracellular bacterial DNA, EtBr fluoresces brightly, while the unbound fluorophore outside the bacterial cell exhibits little or no fluorescence. Thus, the efflux of EtBr from inside to outside the bacterial cell is associated with a substantive decrease in fluorescence.

Specifically, for this cellular assay, *P. aeruginosa* ATCC 27853 bacterial cells are grown overnight in CAMH broth. Bacteria are harvested from the overnight culture by centrifugation, and the cell pellet washed with phosphate-buffered containing 1 mM $MgCl_2$ (PBSM). The washed cell pellets are resuspended in PBSM to achieve a final OD at 600 nm of 1.0. Carbonyl cyanide 3-chlorophenylhydrazone (CCCP) is added to the bacterial suspension at a final concentration 50 μM, along with the addition of EtBr at a final concentration of 200 μM. The cells are then incubated in the dark at 37° C. for 50 minutes to allow for the depletion of ATP by the CCCP, which negatively impacts cellular efflux pump activity and thus results in the concomitant accumulation of ethidium bromide inside the cells. After the 50-minute incubation, the bacteria are spun down, and the supernatant discarded to remove extracellular CCCP and EtBr. The bacterial pellet is resuspended in an equal volume of PBSM, and 200 μL of the bacterial suspension added to wells of a black, flat-bottom 96-well plate containing test EPI compounds at concentrations ranging from 0.031-0.25-fold MIC, or an equivalent volume of the vehicle (DMSO) alone. The plates are pre-incubated at 37° C. for 5 minutes. EtBr efflux is initiated by addition of glucose (100 mM) to reenergizes the efflux pumps. A Spectramax iD5 fluorescent plate reader (Molecular Devices, Inc., Sunnyvale, CA) is used to monitor the fluorescence of each well at 37° C. once per minute for 240 minutes. The excitation and emission wavelengths were set at 510 and 610 nm, respectively.

In our EtBr efflux assay, our EPIs increase the level of accumulation of ethidium bromide inside the cell in a concentration-dependent manner suggesting that efflux pump inhibition is their mechanism of action.

Example 40. The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| | mg/tablet |
|---|---|
| (i) Tablet 1 | |
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/mL |
|---|---|
| (iv) Injection 1 (1 mg/mL) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/mL) | |
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

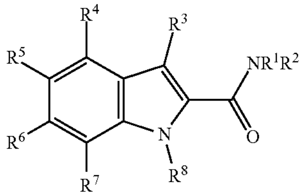

I wherein:

$R^1$ is:

(a) $(C_1-C_{14})$alkyl wherein the $(C_1-C_{14})$alkyl is substituted with one or more —$NR^{a1}R^{b1}$ groups, and wherein the $(C_1-C_{14})$alkyl is substituted with one or more groups independently selected from the group consisting of —OH, —$OR^c$, —CN, $NO_2$, —$B(OH)_2$, —$SO_2R^d$, —$CO_2R^e$, —OC(═O)—$NR^{a2}R^{b2}$, and —O(C═O)—$(C_1-C_6)$alkyl-$NR^{a2}R^{b2}$, and wherein the $(C_1-C_{14})$alkyl is optionally substituted independently with one or more halo, $(C_1-C_4)$alkyl or $(C_3-C_7)$carbocyclyl; or (b) 4-7 membered monocyclic heterocyclyl-$(C_1-C_6)$alkyl- wherein the 4-7 membered monocyclic heterocyclyl-$(C_1-C_6)$alkyl- is substituted independently with one or more $Z^1$ or $Z^2$, and wherein the 4-7 membered monocyclic heterocyclyl-$(C_1-C_6)$alkyl- is substituted independently with one or more oxo, $Z^3$, or $Z^4$, and wherein the 4-7 membered monocyclic heterocyclyl-$(C_1-C_6)$alkyl- is optionally substituted independently with one or more halo, $(C_1-C_4)$alkyl, or $(C_3-C_7)$carbocyclyl;

$R^2$ is hydrogen, $(C_1-C_4)$alkyl, or $(C_3-C_7)$carbocyclyl;

$R^3$ is hydrogen, halo, $(C_1-C_4)$alkyl, $(C_1-C_4)$haloalkyl, $(C_1-C_4)$alkoxy, $(C_1-C_4)$haloalkoxy, —OH, —X—$(C_3-C_7)$carbocyclyl, —X-aryl, —X-heterocyclyl, or —X-heteroaryl, wherein the —X—$(C_3-C_7)$carbocyclyl, —X-aryl, —X-heterocyclyl, or —X-heteroaryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy;

$R^4$ is hydrogen, halo, $(C_1-C_4)$alkyl, $(C_1-C_4)$haloalkyl, $(C_1-C_4)$alkoxy, $(C_1-C_4)$haloalkoxy, —OH, X-aryl, —X-heterocyclyl, or —X-heteroaryl, wherein the —X—$(C_3-C_7)$carbocyclyl, —X-aryl, —X-heterocyclyl, or —X-heteroaryl is independently optionally substituted with one or more groups independently selected from the group consisting of halo, —OH, —$NO_2$, —CN, $(C_1-C_4)$alkyl, $(C_1-C_4)$haloalkyl, $(C_1-C_6)$alkoxy, and $(C_1-C_4)$haloalkoxy;

$R^5$ is hydrogen, halo, $(C_1-C_4)$alkyl, $(C_1-C_4)$haloalkyl, $(C_1-C_4)$alkoxy, $(C_1-C_4)$haloalkoxy, —OH, X-aryl, —X-heterocyclyl, or —X-heteroaryl, wherein the —X—$(C_3-C_7)$carbocyclyl, —X-aryl, —X-heterocyclyl, or —X-heteroaryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy;

$R^6$ is hydrogen, halo, $(C_1-C_4)$alkyl, $(C_1-C_4)$haloalkyl, $(C_1-C_4)$alkoxy, $(C_1-C_4)$haloalkoxy, —OH, X-aryl, —X-heterocyclyl, or —X-heteroaryl, wherein the —X—$(C_3-C_7)$carbocyclyl, —X-aryl, —X-heterocyclyl, or —X-heteroaryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy;

$R^7$ is hydrogen, halo, $(C_1-C_4)$alkyl, $(C_1-C_4)$haloalkyl, $(C_1-C_4)$alkoxy, $(C_1-C_4)$haloalkoxy, —OH, X-aryl, —X-heterocyclyl, or —X-heteroaryl, wherein the ~X-$(C_3-C_7)$carbocyclyl, —X-aryl, —X-heterocyclyl, or —X-heteroaryl is independently optionally substituted with one or more groups independently selected from the group consisting of halo, —OH, —$NO_2$, —CN, $(C_1-C_4)$alkyl, $(C_1-C_4)$haloalkyl, $(C_1-C_4)$alkoxy, and $(C_1-C_4)$haloalkoxy;

$R^8$ is hydrogen, $(C_1-C_4)$alkyl, or $(C_3-C_7)$carbocyclyl;

each X is independently absent, —$(C_1-C_6)$alkyl-, —O—, —S—, —S(═O)—, —$S(═O)_2$, or —$NR^f$—;

$Z^1$ is —$NR^{d1}R^{b1}$, each $Z^2$ is independently —$(C_1-C_6)$alkyl substituted with one or more $Z^1$, wherein the —$(C_1-C_6)$alkyl is optionally substituted independently with one or more halo or $(C_3-C_7)$carbocyclyl;

each $Z^3$ is independently —OH, —ORE, —CN, $NO_2$, —$B(OH)_2$, —$SO_2R^d$, —$CO_2R^e$, —OC(═O)—$NR^{a2}R^{b2}$ and —O(C═O)—$(C_1-C_6)$alkyl-$NR^{a2}R^{b2}$, each $Z^4$ is independently —$(C_1-C_6)$alkyl substituted with one or more $Z^3$, wherein the —$(C_1-C_6)$alkyl is optionally substituted independently with one or more halo or $(C_3-C_7)$carbocyclyl;

each $R^{a1}$ and $R^{b1}$ is independently hydrogen, $(C_1-C_6)$alkyl or $(C_3-C_7)$carbocyclyl;

each $R^{a2}$ and $R^{b2}$ is independently hydrogen, $(C_1-C_6)$alkyl, or $(C_3-C_7)$carbocyclyl; and each $R^{a3}$ and $R^{b3}$ is independently hydrogen, $(C_1-C_6)$alkyl, or $(C_3-C_7)$carbocyclyl;

each $R^c$ is independently $(C_1-C_6)$alkyl, wherein the $(C_1-C_6)$alkyl is optionally substituted independently with one or more —$NR^{a3}R^{b3}$, OH, $(C_1-C_6)$alkoxy, or $(C_1-C_6)$haloalkoxy;

each $R^d$ is independently $(C_1-C_6)$alkyl or $(C_3-C_7)$carbocyclyl;

each $R^e$ is independently hydrogen, $(C_1-C_6)$alkyl, or $(C_3-C_7)$carbocyclyl; and each $R^f$ is independently hydrogen, $(C_1-C_6)$alkyl, or $(C_3-C_7)$carbocyclyl;

or a salt thereof.

2. The compound of claim 1 wherein:

$R^1$ is:

(a) $(C_1-C_{14})$alkyl wherein the $(C_1-C_{14})$alkyl is substituted with one or more —$NR^{a1}R^{b1}$ groups, and wherein the $(C_1-C_{14})$alkyl is substituted with one or more groups independently selected from the group consisting of —OH, —ORE, —CN, —$B(OH)_2$, —$SO_2R^d$, —$CO_2R^e$, OC(═O)—$NR^{a2}R^{b2}$, and —O(C═O)—$(C_1-C_6)$alkyl-$NR^{a2}R^{b2}$, and wherein the $(C_1-C_{14})$alkyl is optionally substituted independently with one or more halo, $(C_1-C_4)$alkyl or $(C_3-C_7)$carbocyclyl;

of (b) 4-7 membered monocyclic heterocyclyl-($C_1$-$C_6$) alkyl- wherein the 4-7 membered monocyclic heterocyclyl-($C_1$-$C_6$)alkyl- is substituted independently with one or more $Z^1$ or $Z^2$, and wherein the 4-7 membered monocyclic heterocyclyl-($C_1$-$C_6$)alkyl- is substituted independently with one or more oxo, $Z^3$, or $Z^4$, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl;

$R^2$ is hydrogen, ($C_1$-$C_4$)alkyl, or ($C_3$-$C_7$)carbocyclyl;

$R^3$ is —X—($C_3$-$C_7$)carbocyclyl, —X-aryl, —X-heterocyclyl, or —X-heteroaryl wherein the —X—($C_3$-$C_7$)carbocyclyl, —X-aryl, —X-heterocyclyl, or —X-heteroaryl is independently optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^7$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, or —OH;

$R^8$ is hydrogen, ($C_1$-$C_4$)alkyl, or ($C_3$-$C_7$)carbocyclyl;

each X is independently absent, —($C_1$-$C_6$)alkyl-, —O—, —S—, —S(═O)—, —S(═O)$_2$—, or —$NR^f$;

$Z^1$ is —$NR_{a1}R^{b1}$, each $Z^2$ is independently —($C_1$-$C_6$)alkyl substituted with one or more $Z^1$, wherein the —($C_1$-$C_6$)alkyl is optionally substituted independently with one or more halo or ($C_3$-$C_7$)carbocyclyl;

each $Z^3$ is independently —OH, —ORG, —CN, —$B(OH)_2$, ~$SO_2R^d$, —$CO_2R^e$, —OC(═O)—$NR^{a2}R^{b2}$ and —O(C═O)—($C_1$-$C_6$)alkyl-$NR^{a2}R^{b2}$, each $Z^4$ is independently —($C_1$-$C_6$)alkyl substituted with one or more $Z^3$, wherein the —($C_1$-$C_6$)alkyl is optionally substituted independently with one or more halo or ($C_3$-$C_7$)carbocyclyl;

each $R^{a1}$ and $R^{b1}$ is independently hydrogen, ($C_1$-$C_6$)alkyl or ($C_3$-$C_7$)carbocyclyl;

each $R^{a2}$ and $R^{b2}$ is independently hydrogen, ($C_1$-$C_6$) alkyl, or ($C_3$-$C_7$)carbocyclyl; and each $R^{a3}$ and $R^{b3}$ is independently hydrogen, ($C_1$-$C_6$) alkyl, or ($C_3$-$C_7$)carbocyclyl;

each $R^c$ is independently ($C_1$-$C_6$)alkyl, wherein the ($C_1$-$C_6$)alkyl is optionally substituted independently with one or more —$NR^{d3}R_{b3}$, OH, ($C_1$-$C_6$)alkoxy, or ($C_1$-$C_6$)haloalkoxy;

each $R^d$ is independently ($C_1$-$C_6$)alkyl or ($C_3$-$C_7$)carbocyclyl;

each $R^e$ is independently hydrogen, ($C_1$-$C_6$)alkyl, or ($C_3$-$C_7$)carbocyclyl; and each $R^f$ is independently hydrogen, ($C_1$-$C_6$)alkyl, or ($C_3$-$C_7$)carbocyclyl;

or a salt thereof.

3. The compound or salt of claim 1, wherein $R^2$ is hydrogen.

4. The compound or salt of claim 1 is hydrogen.

5. The compound or salt of claim 1, wherein the compound of formula I is a compound of formula Ia:

Ia

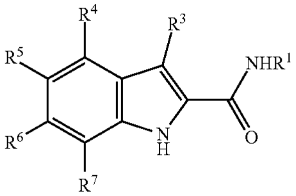

or a salt thereof.

6. The compound or salt of claim 1, wherein $R^4$ is hydrogen, halo, or aryl, wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

7. The compound or salt of claim 1, wherein $R^6$ is hydrogen, halo, or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

8. The compound or salt of claim 1, wherein $R^5$ is hydrogen or halo.

9. The compound or salt of claim 1, wherein $R^7$ is hydrogen, halo, or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

10. The compound or salt of claim 1, wherein $R^3$ is hydrogen, ($C_1$-$C_4$)alkyl, —X—($C_3$-$C_7$)carbocyclyl or —X-aryl, wherein the —X—($C_3$-$C_7$)carbocyclyl or —X-aryl is independently optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

11. The compound or salt of claim 1, wherein $R^3$ is hydrogen, ($C_1$-$C_4$)alkyl, ($C_4$-$C_7$)carbocyclyl or phenyl, wherein the ($C_3$-$C_7$)carbocyclyl or phenyl is independently optionally substituted with one or more groups independently selected from the group consisting of halo and —CN.

12. The compound or salt of claim 1, wherein $R^1$ is:

(a) ($C_2$-$C_7$)alkyl wherein the ($C_2$-$C_7$)alkyl is substituted with one or more —$NR^{a1}R^{b1}$ groups, and wherein the ($C_2$-$C_7$)alkyl is substituted with one or more groups independently selected from the group consisting of —OH, —ORE, —CN, —$B(OH)_2$, —$SO_2R^d$, —$CO_2R^e$, —OC(═O)—$NR^{a2}R^{b2}$, and —O(C—O)—($C_1$-$C_6$)alkyl-$NR^{a2}R^{b2}$, and wherein the ($C_2$-$C_7$)alkyl is optionally substituted independently with one or more halo, ($C_1$-$C_4$)alkyl or ($C_3$-$C_7$)carbocyclyl;

of (b) 4-7 membered monocyclic heterocyclyl-($C_1$-$C_2$) alkyl- wherein the 4-7 membered monocyclic heterocyclyl-($C_1$-$C_2$)alkyl- is substituted independently with one or more $Z^1$ or $Z^2$, and wherein the 4-7 membered monocyclic heterocyclyl-($C_1$-$C_1$)alkyl- is substituted independently with one or more oxo, $Z^3$, or $Z^4$, and wherein the 4-7 membered monocyclic heterocyclyl-($C_1$-$C_6$)alkyl- is optionally substituted independently with one or more halo, ($C_1$-$C_4$)alkyl, or ($C_3$-$C_7$)carbocyclyl.

13. The compound or salt of claim 1, wherein $R^1$ is $(C_2-C_7)$alkyl wherein the $(C_2-C_7)$alkyl is substituted with one or more —$NR^{a1}R^{b1}$ groups, and wherein the $(C_2-C_7)$ alkyl is substituted with one or more groups independently selected from the group consisting of —OH, —ORE, —CN, —$B(OH)_2$, —$SO_2R^d$, —$CO_2R^e$, —OC(═O)—$NR^{a2}R^{b2}$, and —O(C═O)—$(C_1-C_6)$alkyl-$NR^{a2}R^{b2}$, and wherein the $(C_2-C_7)$alkyl is optionally substituted independently with one or more halo, $(C_1-C_4)$alkyl or $(C_3-C_7)$carbocyclyl.

14. The compound or salt of claim 1, wherein $R^1$ is 4-7 membered monocyclic heterocyclyl-$(C_1-C_7)$alkyl- wherein the 4-7 membered monocyclic heterocyclyl-$(C_1-C_2)$alkyl- is substituted independently with one or more $Z^1$ or $Z^2$, and wherein the 4-7 membered monocyclic heterocyclyl-($C_1$-CD)alkyl- is substituted independently with one or more oxo, $Z^3$, or $Z^4$, and wherein the 4-7 membered monocyclic heterocyclyl-$(C_1-C_6)$alkyl- is optionally substituted independently with one or more halo, $(C_1-C_4)$alkyl, or $(C_3-C_7)$ carbocyclyl.

15. The compound or salt of claim 1, wherein $R^1$ is:

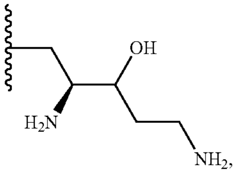
,
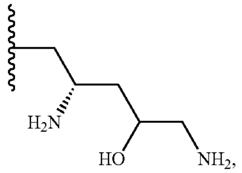
,
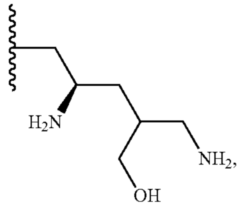
,
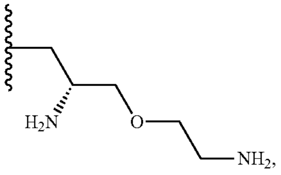
,
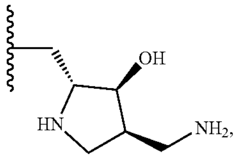
,
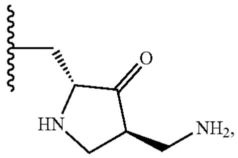
,
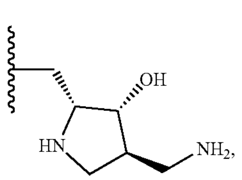
,
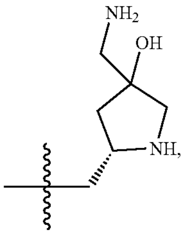
,
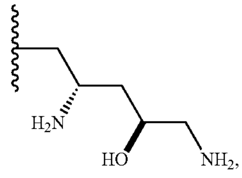
,
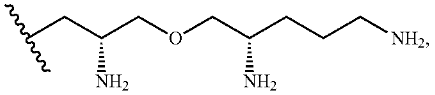
, -continued

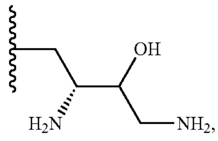
, or
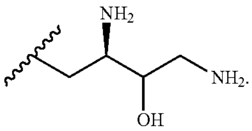
.

16. The compound of claim 1 that is:

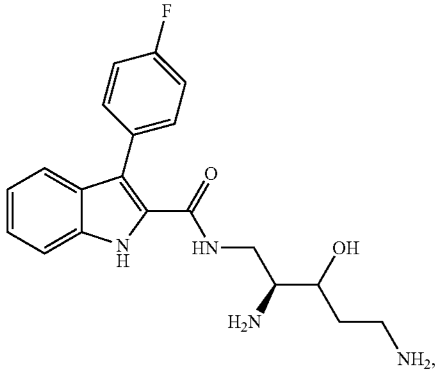
,
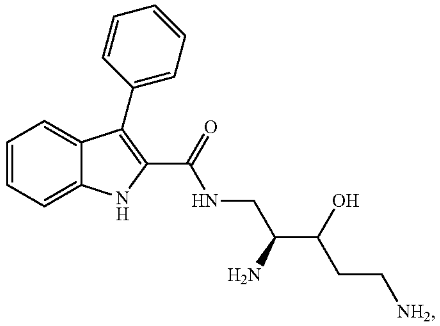
,
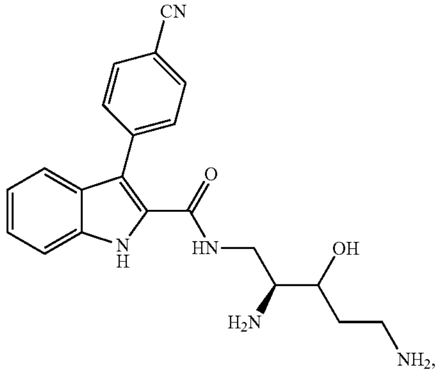
,
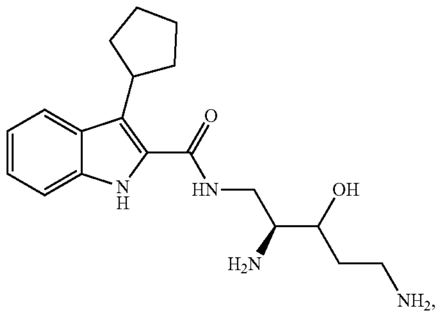
,

-continued
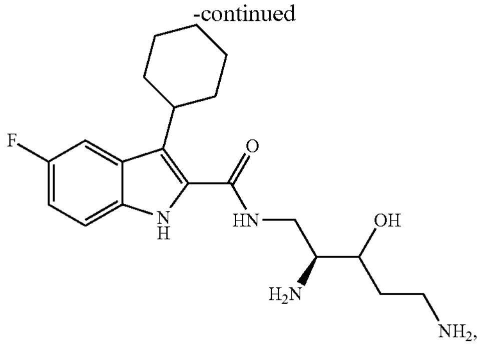
,
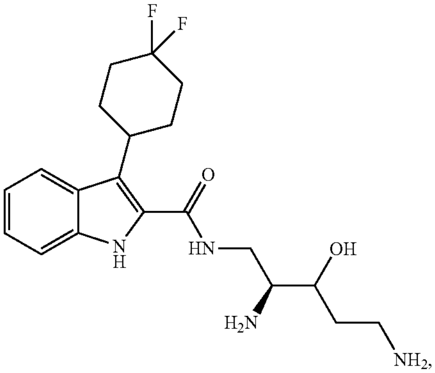
,
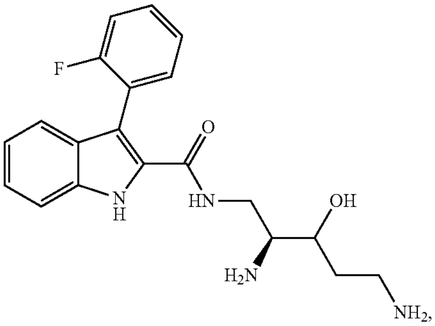
,
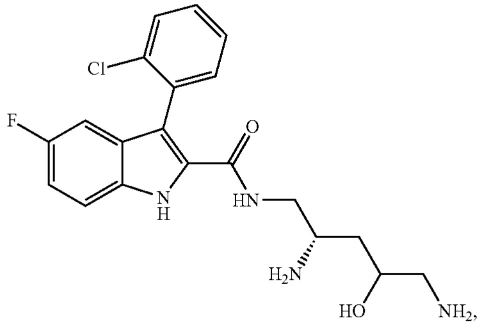
,
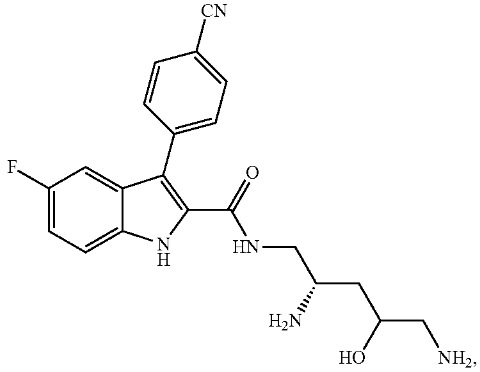
,
-continued
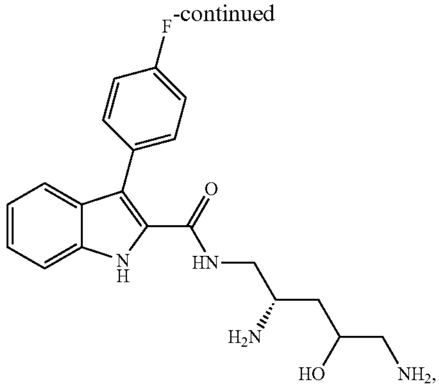
,
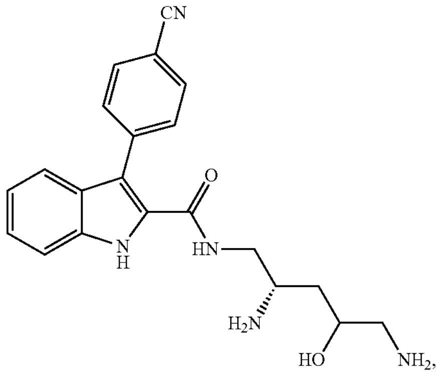
,
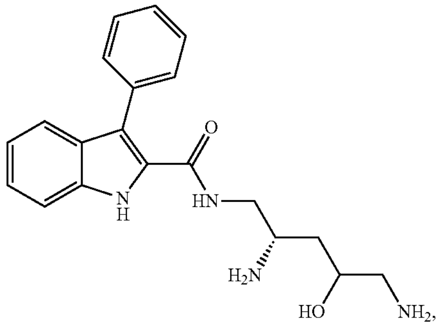
,
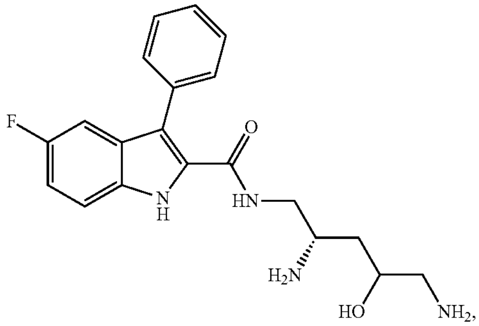
, -continued
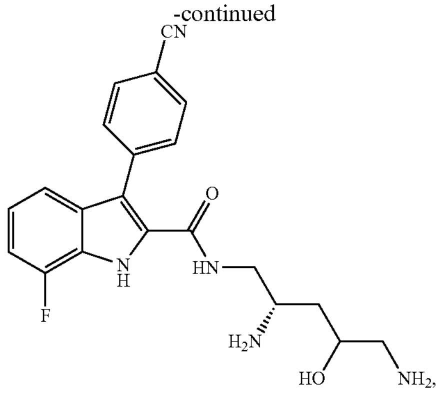
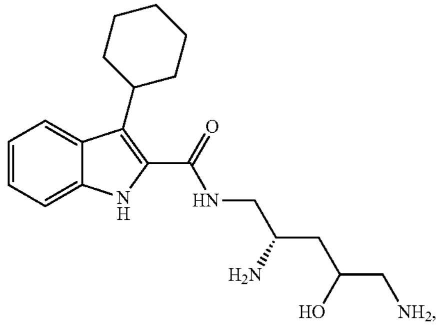
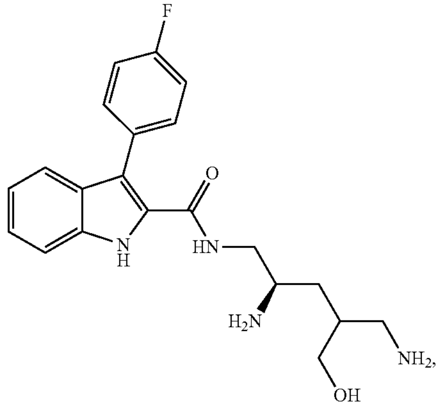
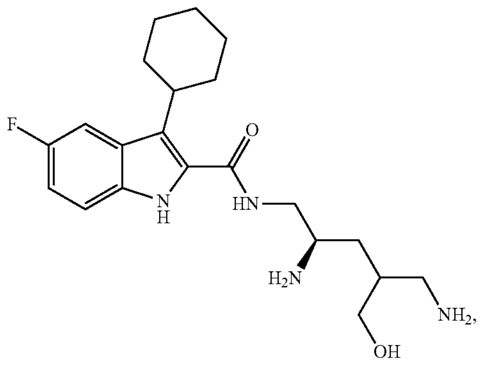
-continued
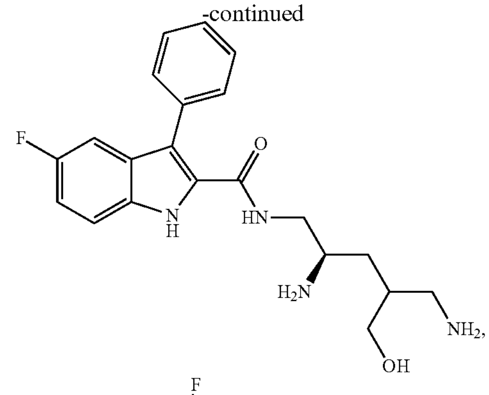
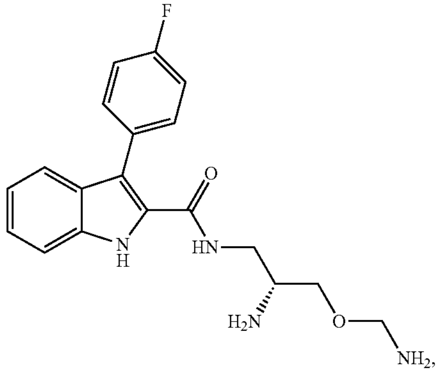
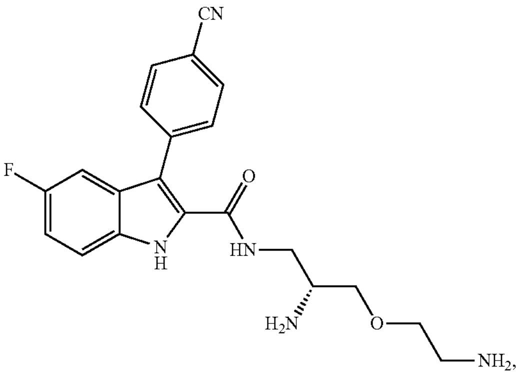
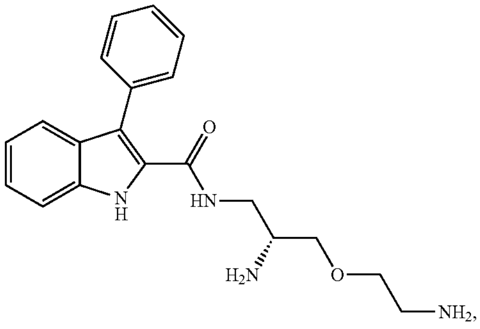

-continued
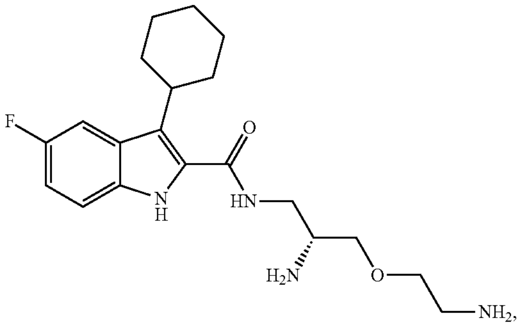
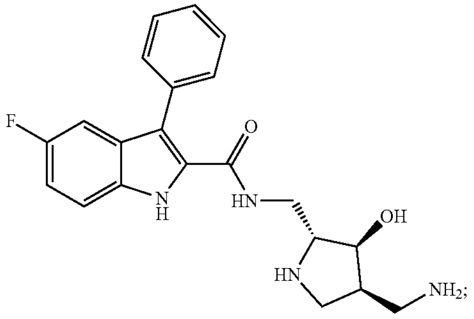
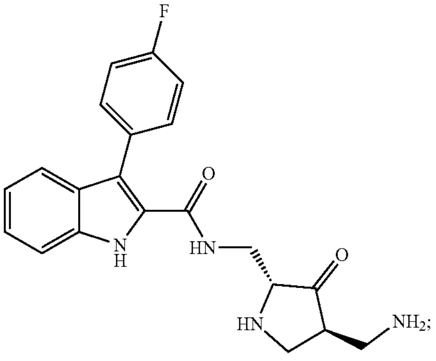
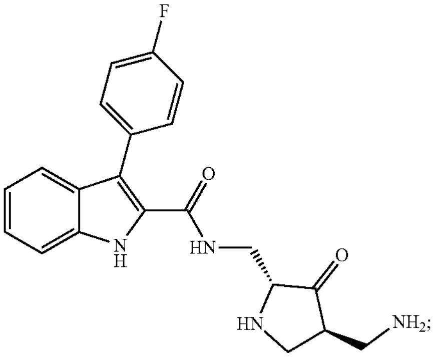
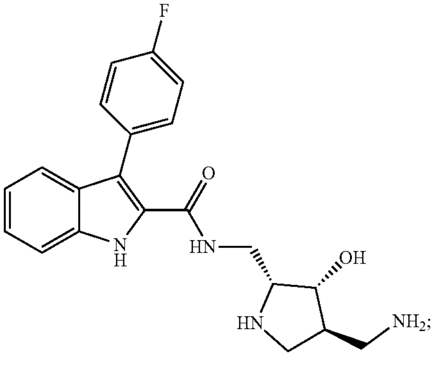
-continued
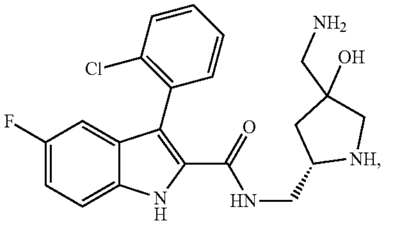
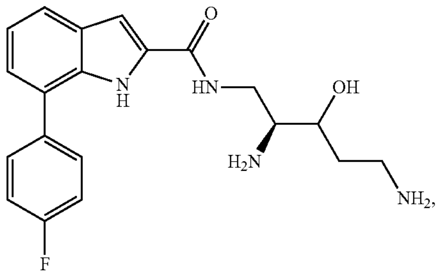
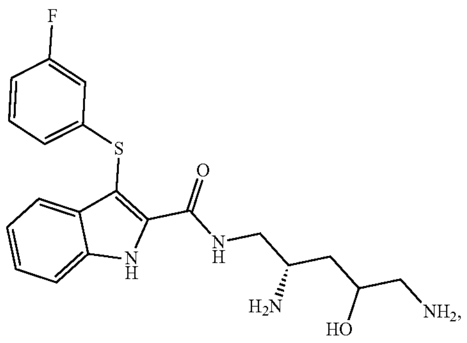
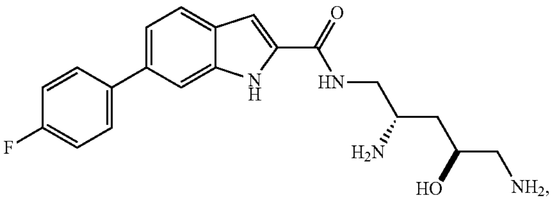
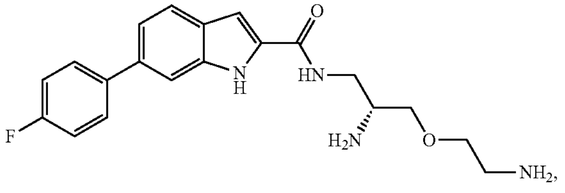
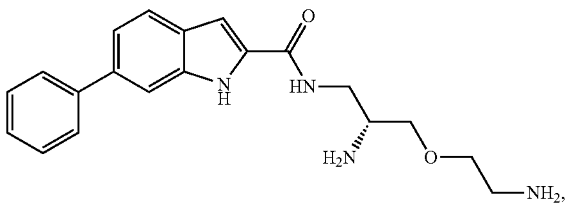

-continued

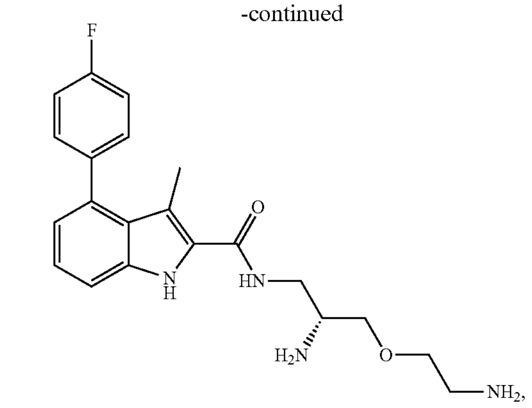

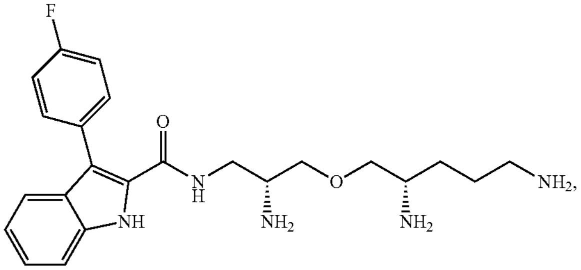

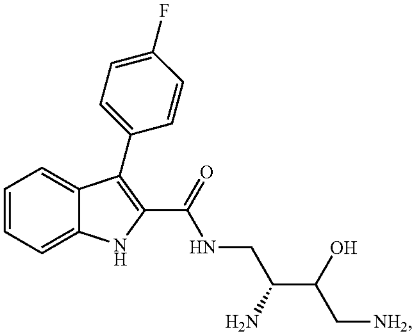

or

-continued

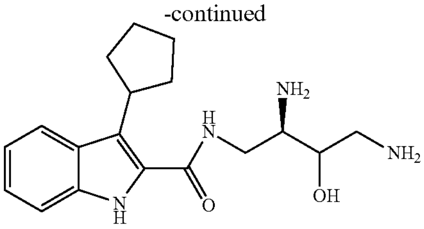

or a salt thereof.

17. A pharmaceutical composition comprising a compound as described in claim 1 or a pharmaceutically acceptable salt thereof, and a pharmaceutically acceptable excipient.

18. A pharmaceutical composition comprising a compound as described in claim 1 or a pharmaceutically acceptable salt thereof, one or more antibacterial agents and a pharmaceutically acceptable excipient.

19. A method of inhibiting a bacterial efflux pump in an animal comprising administering to the animal a compound as described in claim 1 or a pharmaceutically acceptable salt thereof.

20. A method of treating or preventing a bacterial infection in an animal comprising co-administering to the animal a compound as described in claim 1 or a pharmaceutically acceptable salt thereof and one or more antibacterial agents.

* * * * *